United States Patent
Al-Shayeb et al.

(10) Patent No.: US 12,351,818 B2
(45) Date of Patent: Jul. 8, 2025

(54) GENE-MODIFYING ENDONUCLEASES

(71) Applicant: Amber Bio Inc., San Francisco, CA (US)

(72) Inventors: Basem Al-Shayeb, San Francisco, CA (US); Jacob Borrajo, San Francisco, CA (US); Mohammad Kamyab Javanmardi, San Francisco, CA (US); Kushagra Sharma, San Francisco, CA (US)

(73) Assignee: Amber Bio Inc., San Francisco, CA (US)

( * ) Notice: Subject to any disclaimer, the term of this patent is extended or adjusted under 35 U.S.C. 154(b) by 0 days.

(21) Appl. No.: 18/518,831

(22) Filed: Nov. 24, 2023

(65) Prior Publication Data

US 2024/0344087 A1    Oct. 17, 2024

Related U.S. Application Data

(60) Provisional application No. 63/504,721, filed on May 26, 2023, provisional application No. 63/500,779, filed on May 8, 2023, provisional application No. 63/386,784, filed on Dec. 9, 2022, provisional application No. 63/384,937, filed on Nov. 23, 2022.

(51) Int. Cl.
| | | |
|---|---|---|
| *C12N 15/00* | (2006.01) | |
| *C12N 9/22* | (2006.01) | |
| *C12N 15/11* | (2006.01) | |
| *C12N 15/90* | (2006.01) | |

(52) U.S. Cl.
CPC ............ *C12N 15/907* (2013.01); *C12N 9/22* (2013.01); *C12N 15/11* (2013.01); *C12N 15/111* (2013.01); *C12N 2310/20* (2017.05)

(58) Field of Classification Search
None
See application file for complete search history.

(56) References Cited

U.S. PATENT DOCUMENTS

| | | |
|---|---|---|
| 11,060,115 B2 | 7/2021 | Severinov et al. |
| 11,377,646 B2 | 7/2022 | Doudna et al. |
| 11,421,250 B2 | 8/2022 | Severinov et al. |
| 11,530,398 B2 | 12/2022 | Doudna et al. |
| 11,578,313 B2 | 2/2023 | Doudna et al. |
| 11,685,909 B2 | 6/2023 | Doudna et al. |
| 11,739,309 B2 | 8/2023 | Doudna et al. |
| 11,767,528 B2 | 9/2023 | Borrajo |
| 2019/0275081 A1 | 9/2019 | Odunsi et al. |
| 2023/0058054 A1* | 2/2023 | Wang .................. C12N 15/907 |
| 2024/0035031 A1 | 2/2024 | Borrajo |

FOREIGN PATENT DOCUMENTS

| | | |
|---|---|---|
| WO | WO 2000/009734 A2 | 2/2000 |
| WO | WO 2010/012472 A1 | 2/2010 |
| WO | WO 2011/042556 A1 | 4/2011 |
| WO | WO 2013/025461 A1 | 2/2013 |
| WO | WO 2016/205764 A1 | 12/2016 |
| WO | WO 2017219027 A1 | 12/2017 |
| WO | WO 2018/071663 A1 | 4/2018 |
| WO | WO 2018170333 A1 | 9/2018 |
| WO | WO 2018191388 A1 | 10/2018 |
| WO | WO 2019005866 A1 | 1/2019 |
| WO | WO 2019006471 A2 | 1/2019 |
| WO | WO 2019/040664 A1 | 2/2019 |
| WO | WO 2020/156575 A1 | 8/2020 |
| WO | WO 2020160150 A1 | 8/2020 |
| WO | WO/2020/181101 A1 | 9/2020 |
| WO | WO/2020/181102 A1 | 9/2020 |
| WO | WO 2020214973 A1 | 10/2020 |
| WO | WO 2021/034717 A1 | 2/2021 |
| WO | WO 2021055874 A1 | 3/2021 |
| WO | WO 2021/076656 A1 | 4/2021 |
| WO | WO/2021/133829 A1 | 7/2021 |
| WO | WO/2021/216512 A1 | 10/2021 |
| WO | WO/2022/055998 A1 | 3/2022 |
| WO | WO 2022/140572 A1 | 6/2022 |
| WO | WO 2022/173770 A1 | 8/2022 |
| WO | WO 2022/183027 A1 | 9/2022 |
| WO | WO/2023/039346 A1 | 3/2023 |
| WO | WO/2023/039373 A2 | 3/2023 |
| WO | WO 2023064895 A1 | 4/2023 |
| WO | WO/2023/201203 A2 | 10/2023 |
| WO | WO/2023/220566 A1 | 11/2023 |
| WO | WO/2023/250384 A2 | 12/2023 |

OTHER PUBLICATIONS

Guo et al., PNAS, 2004, 101:9205 (Year: 2004).*
Coady et al. "Restoration of SMN function: delivery of a trans-splicing RNA re-directs SMN2 pre-mRNA splicing." Molecular Therapy 15.8 (2007): 1471-1478.
Koonin, Eugene V., Kira S. Makarova, and Feng Zhang. "Diversity, classification and evolution of CRISPR-Cas systems." Current opinion in microbiology 37 (2017): 67-78.
Haroon Butt et al., Efficient CRISPR/Cas9-Mediated Genome Editing Using a Chimeric Single-Guide RNA Molecule, Frontiers in Plant Science, vol. 8, Aug. 24, 2017.
Silvana Konermann et al., Transcriptome Engineering with RNA-Targeting Type VI_D CRISPR Effectors, Cell, vol. 173, No. 3, Apr. 19, 2018, pp. 665-676.
International Search Report & Written Opinion PCT Applcation No. PCT/US2023/081037, dated Apr. 2, 2024, 17 pages.

(Continued)

*Primary Examiner* — Arthur S Leonard
(74) *Attorney, Agent, or Firm* — Morgan, Lewis & Bockius LLP

(57) ABSTRACT

The disclosure relates to compositions and methods that modify target nucleic acids, as well as methods of detecting nucleic acids. Various compositions are described herein, including compositions comprising endonucleases, endonuclease systems, and chimeric proteins having the endonuclease and a nucleic-acid modulating domain or a nucleic acid modifying domain.

18 Claims, 40 Drawing Sheets

Specification includes a Sequence Listing.

(56) References Cited

OTHER PUBLICATIONS

Slaymaker, et al., "High-resolution structure of Cas13b and biochemical characterization of RNA targeting and cleavage", Cell Rep. Mar. 2, 20196; 26(13): 3741-3751.e5.
Zhang, et al., "Structural basis for the RNA-guided ribonuclease activity of CRISPR-Cas13d", Cell. Sep. 20, 2018; 175(1): 212-223. e17.

* cited by examiner

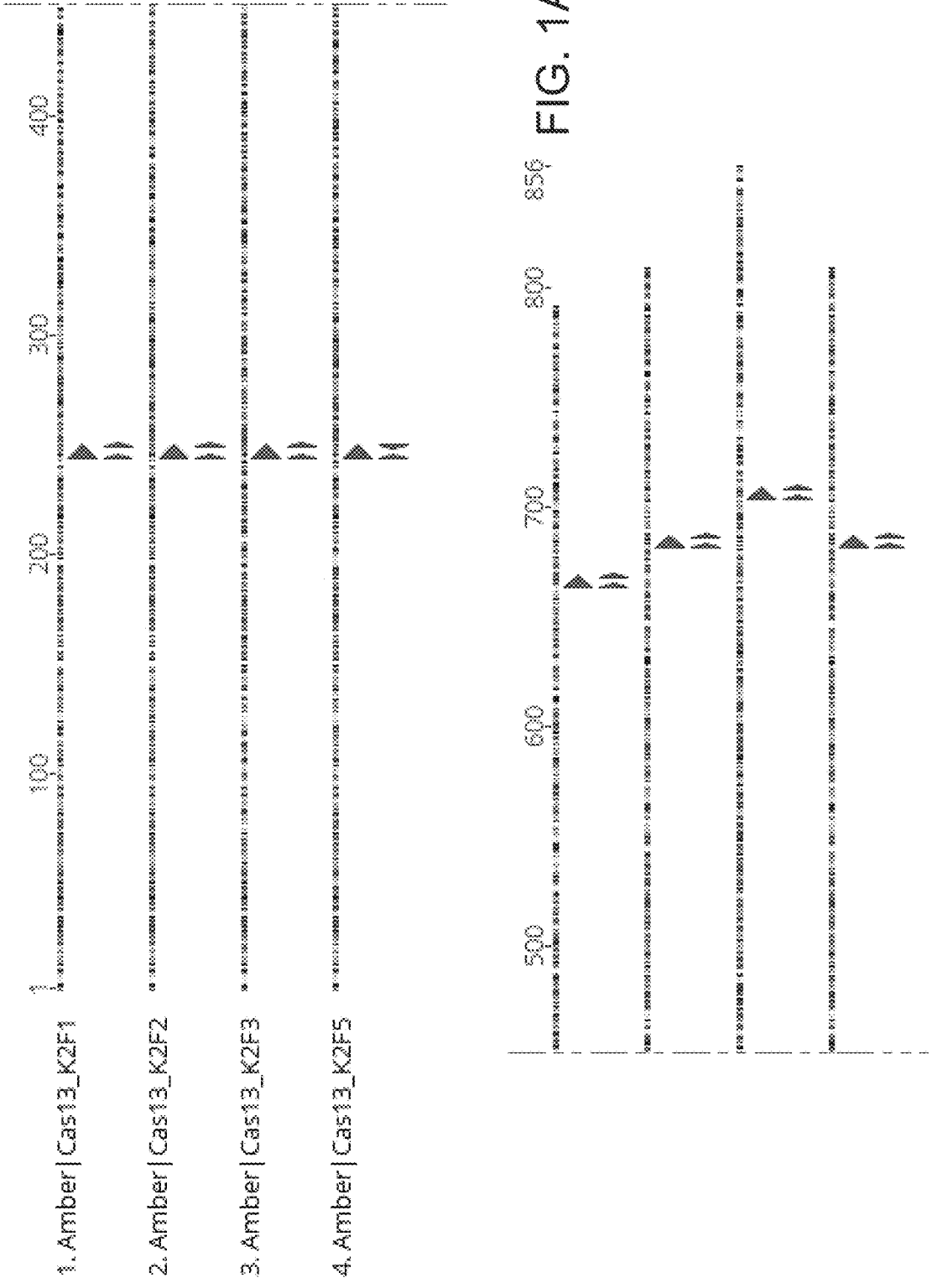

FIG. 5

| | Cas13X.1 | Cas13bt9 | Cas13bt2 | Cas13bt1 | Cas13bt8 | Cas13X.2 | Cas13bt9 | Cas13bt11 | Cas13bt5 | Cas13bt10 |
|---|---|---|---|---|---|---|---|---|---|---|
| Cas13X.1 | | 99.5 | 39.8 | 38.3 | 37.4 | 37.4 | 37.8 | 38 | 31.8 | 29 |
| Cas13bt9 | 99.5 | | 39.3 | 37.8 | 36.9 | 36.9 | 37.4 | 37.5 | 31.3 | 28.6 |
| Cas13bt2 | 39.8 | 39.3 | | 69.3 | 62.5 | 62.5 | 43.8 | 43.3 | 36.8 | 28.9 |
| Cas13bt1 | 38.3 | 37.8 | 69.3 | | 63 | 63 | 43.2 | 42.7 | 35.5 | 29.9 |
| Cas13bt8 | 37.4 | 36.9 | 62.5 | 63 | | 100 | 49.2 | 48.7 | 36.3 | 29.9 |
| Cas13X.2 | 37.4 | 36.9 | 62.5 | 63 | 100 | | 49.2 | 48.7 | 36.3 | 29.9 |
| Cas13bt9 | 37.8 | 37.4 | 43.8 | 43.2 | 49.2 | 49.2 | | 97.8 | 33.1 | 28.7 |
| Cas13bt11 | 38 | 37.5 | 43.3 | 42.7 | 48.7 | 48.7 | 97.8 | | 33.2 | 29.2 |
| Cas13bt5 | 31.8 | 31.3 | 36.8 | 35.5 | 36.3 | 36.3 | 33.1 | 33.2 | | 29.1 |
| Cas13bt10 | 29 | 28.6 | 28.9 | 29.9 | 29.9 | 29.9 | 28.7 | 29.2 | 29.1 | |
| Cas13bt15 | 21.9 | 21.4 | 23.3 | 22.2 | 23.5 | 23.5 | 22.6 | 22.5 | 22.2 | 21.2 |
| Cas13bt7 | 19.9 | 19.5 | 21.6 | 21.4 | 21.7 | 21.7 | 22.7 | 22.5 | 20.6 | 20.5 |
| Cas13bt6 | 13.8 | 13.3 | 14.2 | 14.1 | 14.1 | 14.1 | 12.5 | 12.6 | 12.2 | 13.5 |
| Cas13bt14 | 13.6 | 13.2 | 14.6 | 14.5 | 14.6 | 14.6 | 13 | 13.1 | 12.1 | 14 |
| Cas13Y.3 | 13.6 | 13.2 | 14.6 | 14.5 | 14.6 | 14.6 | 13 | 13.1 | 12.1 | 14 |
| Cas13bt12 | 14.4 | 13.9 | 15.3 | 14.6 | 14.7 | 14.7 | 12.9 | 12.9 | 12.5 | 14 |
| Cas13Y.1 | 14.4 | 13.9 | 15.3 | 14.6 | 14.7 | 14.7 | 12.9 | 12.9 | 12.5 | 14 |
| Cas13bt4 | 14.1 | 13.6 | 14.7 | 14.8 | 14.9 | 14.9 | 13.3 | 13.5 | 12.2 | 13 |
| Cas13bt16 | 14.3 | 13.8 | 14.7 | 14.7 | 14.9 | 14.9 | 13.7 | 13.8 | 11.7 | 13.9 |
| Cas13Y.5 | 13.9 | 13.4 | 15.6 | 15.9 | 15.8 | 15.8 | 14 | 14.1 | 13.6 | 15 |
| Cas13Y.4 | 13 | 12.5 | 14.9 | 15.5 | 14.8 | 14.8 | 13.3 | 13.2 | 12.5 | 13.7 |
| Amber\|Cas13_K2F1 | 9 | 8.7 | 8.4 | 9.2 | 8.6 | 8.6 | 8.4 | 8.3 | 9.4 | 9.1 |
| Amber\|Cas13_K2F2 | 9.1 | 8.9 | 8.7 | 9.8 | 8.6 | 8.6 | 8.4 | 8.3 | 9.9 | 8.9 |
| Amber\|Cas13_K2F5 | 9.5 | 9.3 | 9.6 | 9.9 | 9.5 | 9.5 | 9.3 | 9.1 | 10.1 | 8.8 |
| Amber\|Cas13_K2F3 | 9.4 | 9.4 | 8.9 | 9.1 | 9.2 | 9.2 | 8.6 | 8.4 | 8.3 | 8.4 |

PREVIOUSLY REPORTED SYSTEMS

FIG. 5 (CONT.)

| Cas13bt15 | Cas13bt7 | Cas13bt6 | Cas13bt14 | Cas13Y.3 | Cas13bt12 | Cas13Y.1 | Cas13bt4 | Cas13bt16 | Cas13Y.5 | Cas13Y.4 |
|---|---|---|---|---|---|---|---|---|---|---|
| 21.9 | 19.9 | 13.8 | 13.6 | 13.6 | 14.4 | 14.4 | 14.1 | 14.3 | 13.9 | 13 |
| 21.4 | 19.5 | 13.3 | 13.2 | 13.2 | 13.9 | 13.9 | 13.6 | 13.8 | 13.4 | 12.5 |
| 23.3 | 21.6 | 14.2 | 14.6 | 14.6 | 15.3 | 15.3 | 14.7 | 14.7 | 15.6 | 14.9 |
| 22.2 | 21.4 | 14.1 | 14.5 | 14.5 | 14.6 | 14.6 | 14.8 | 14.7 | 15.9 | 15.5 |
| 23.5 | 21.7 | 14.1 | 14.6 | 14.6 | 14.7 | 14.7 | 14.9 | 14.9 | 15.8 | 14.8 |
| 23.5 | 21.7 | 14.1 | 14.6 | 14.6 | 14.7 | 14.7 | 14.9 | 14.9 | 15.8 | 14.8 |
| 22.6 | 22.7 | 12.5 | 13 | 13 | 12.9 | 12.9 | 13.3 | 13.7 | 14 | 13.3 |
| 22.5 | 22.5 | 12.6 | 13.1 | 13.1 | 12.9 | 12.9 | 13.5 | 13.8 | 14.1 | 13.2 |
| 22.2 | 20.6 | 12.2 | 12.1 | 12.1 | 12.5 | 12.5 | 12.2 | 11.7 | 13.6 | 12.5 |
| 21.2 | 20.5 | 13.5 | 14 | 14 | 14 | 14 | 13 | 13.9 | 15 | 13.7 |
| 44.8 | 44.8 | 12 | 12.1 | 12.1 | 13.3 | 13.3 | 12.3 | 12.2 | 10.8 | 12.8 |
| 12 | 12.1 | 12.1 | 12.2 | 12.2 | 13.3 | 13.3 | 12.4 | 12.7 | 12.3 | 13.5 |
| 12.1 | 12.2 | 87.2 | 87.2 | 87.2 | 78.1 | 78.1 | 77 | 73.2 | 63.8 | 62.1 |
| 12.1 | 12.2 | 87.2 | 100 | 100 | 78.1 | 78.1 | 76.9 | 76.6 | 65 | 62.7 |
| 13.3 | 13.3 | 78.1 | 78.1 | 78.1 | 78.1 | 78.1 | 76.9 | 76.8 | 65 | 62.7 |
| 13.3 | 13.3 | 78.1 | 78.1 | 78.1 | 100 | 100 | 80.6 | 72.7 | 64.5 | 62.5 |
| 12.3 | 12.4 | 77 | 76.9 | 76.9 | 80.6 | 80.6 | 80.6 | 72.7 | 64.5 | 62.5 |
| 12.2 | 12.7 | 73.2 | 76.8 | 76.8 | 72.7 | 72.7 | 72.3 | 64.5 | 64.8 | 60.7 |
| 11.8 | 12.3 | 63.8 | 65 | 65 | 64.5 | 64.5 | 64.8 | 61.4 | 64.5 | 61.4 |
| 12.8 | 13.5 | 62.1 | 62.7 | 62.7 | 62.5 | 62.5 | 60.7 | 61.4 | 64.9 | 64.9 |
| 7.9 | 8.3 | 7.9 | 7.4 | 7.4 | 7.7 | 7.7 | 8 | 7.8 | 8.3 | 8 |
| 8.5 | 8.3 | 7.9 | 7.6 | 7.6 | 7.7 | 7.7 | 8.3 | 7.8 | 8.4 | 8.3 |
| 8.6 | 8.9 | 7.9 | 7.9 | 7.9 | 7.9 | 7.9 | 8.4 | 7.9 | 7.7 | 8 |
| 8.1 | 8.3 | 7.9 | 7.4 | 7.4 | 7.7 | 7.7 | 7.6 | 7.5 | 7.6 | 7.2 |

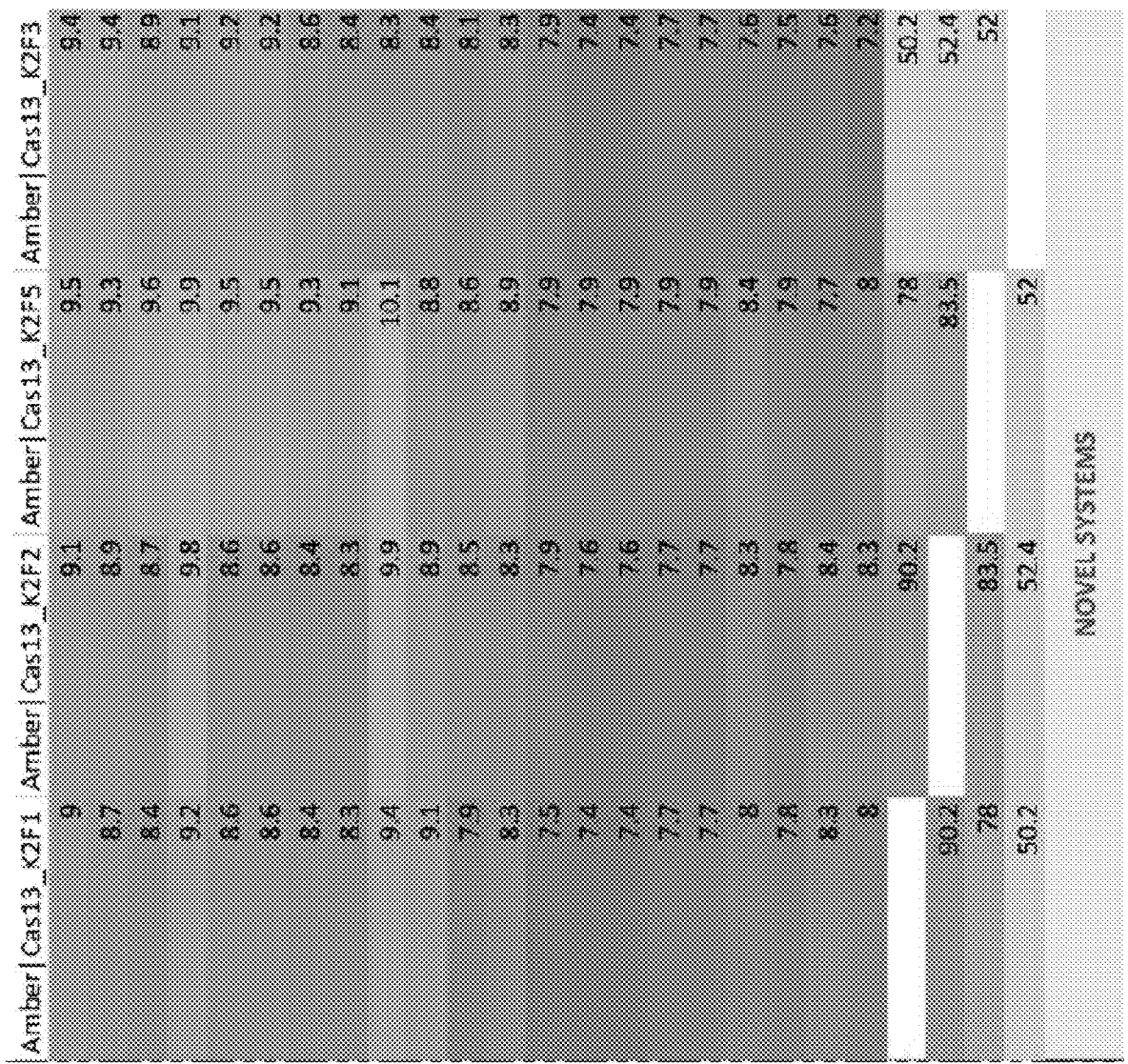

FIG. 10B RNA Knockdown

FIG. 10D SE3 Testing

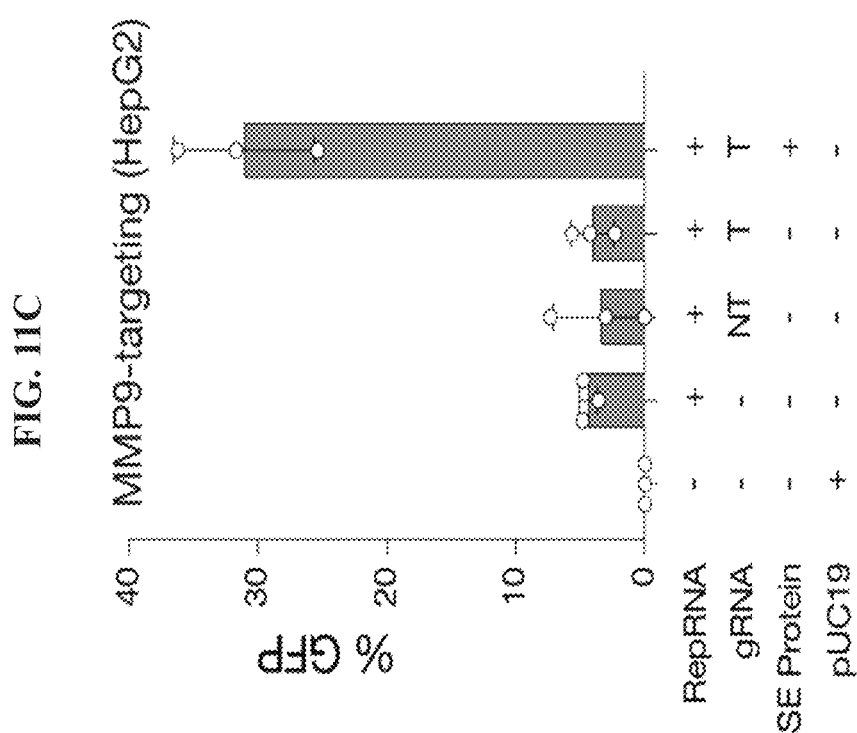

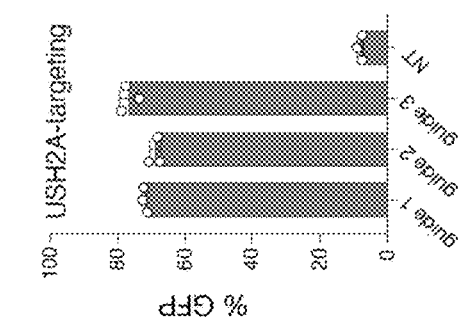
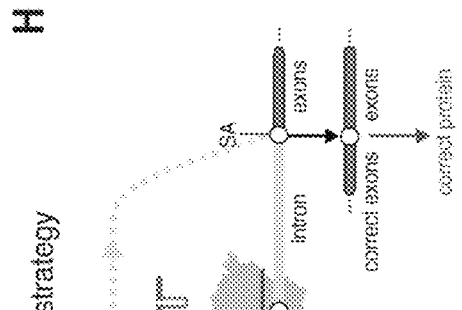
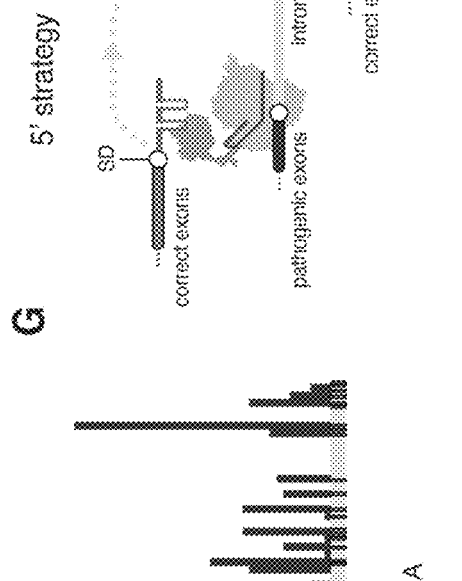
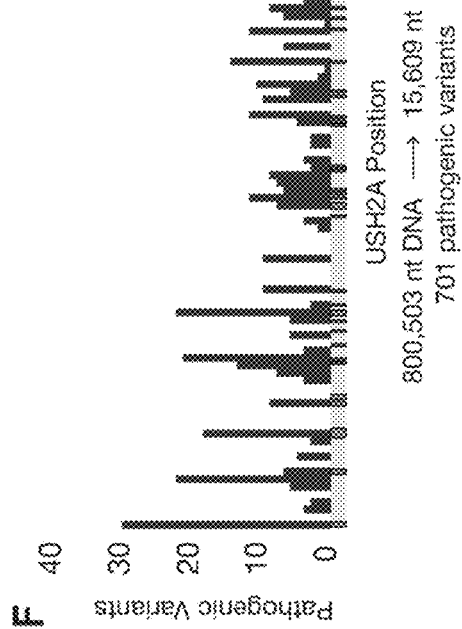
FIG. 11D
FIG. 11E
FIG. 11F

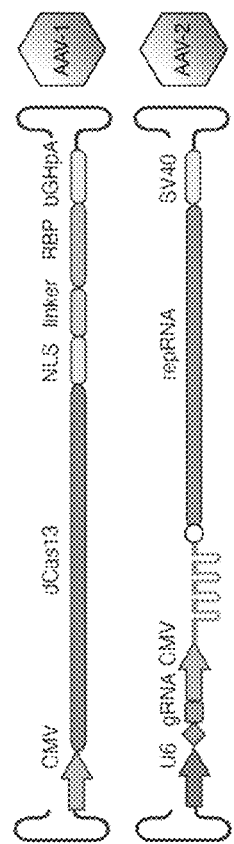
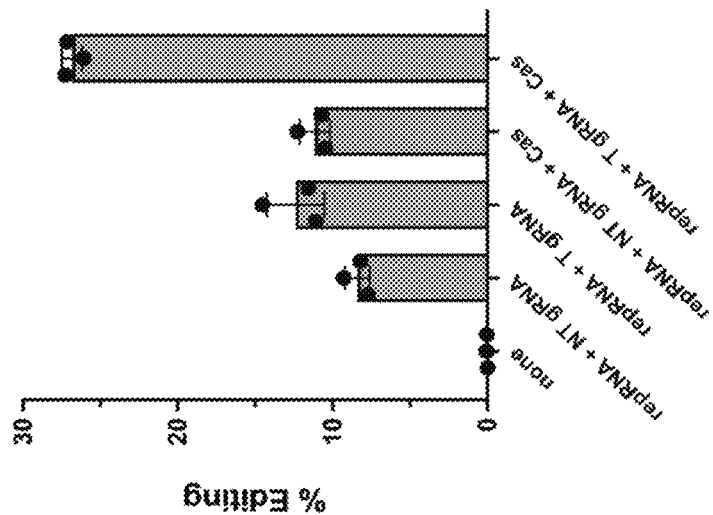
FIG. 15A
FIG. 15B

```
                                      SEQUENCE LISTING

Sequence total quantity: 105
SEQ ID NO: 1             moltype = AA   length = 791
FEATURE                  Location/Qualifiers
REGION                   1..791
                         note = Synthetic Sequence
source                   1..791
                         mol_type = protein
                         organism = synthetic construct
SEQUENCE: 1
MIKKPSNRHA LPKVIISEVN SEKILEFKIK YEKLARLDRF EVKAMHYEGK EIVFDEVLVN     60
GGLIDVEYED EHKTLFVKVG EKSYSIRGQK VGGKQRLLEN RVSKTKVLLE LSDGVPDKNA    120
KLRKSRTERE LIVVENIKLY SQIVGKEVST TKEIYLTKRF LSYRSDLLFY YSFVDNFFKV    180
AGNEKELWKI NFDDASSAQF MGYVPFMVND NLKNDNAYLK DYVSDNEQIK DDLKKVQTMF    240
STLRHALLHF NYEFLNLLIE NIDKLNIDAK KEFIDEEKIK LFGENLSLAK VYRLYSDICV    300
NRVGFNKFIN SMLIKDGVEN QALKAEFDRK FFGKAYTIDI HSNQAYKRIY NEHKKLVIKV    360
STLKDGQAIR RGNKKISELK EQMKSMTKKN SLARLECKMR LAFGFLYGEY NNYNTFKNNF    420
DTNIKNSQFD VNDVEKSKAY FLSTYERRKP RTSEKLEKVA KNIERLELKT VIANDPLLKF    480
ILLMFAFMPQ ELKGEFLGFV KKYYHDVHSI DDDTKEQEQD VVEAMSTSLK LKILGRNIRS    540
LTLFKYALSS QVNYNSTYNL FYVEGNRYGK IYKKLGISHN QEEFDKTLVV PLLRYYSALF    600
KLMNDFEIYS LAKANPTAVS LQELVDDERS PYKQGRFYNF REVLKQVYLL SDNELTHCKI    660
RITRNKIAHF ITEDLLGKPL LGEIKLNLQR KDMVSFMEAR GNIKELLDYD AINDFRMKVI    720
HLRTKMRVNS DKLQTMMDLL SNPKTPNDFY NVYKVKGVEI INKHLLEVLA QTAEERSIEK    780
QIREGNEKYA L                                                        791

SEQ ID NO: 2             moltype = AA   length = 809
FEATURE                  Location/Qualifiers
REGION                   1..809
                         note = Synthetic Sequence
source                   1..809
                         mol_type = protein
                         organism = synthetic construct
SEQUENCE: 2
MIKKPSNRHA LPKVIISEVN SEKILEFKIK YEKLARLDRF EVKAMHYEGK EIVFDEVLVN     60
GGLIDVEYHD EHKTLFVKVG EKSYSIRGQK VGGKQRLLEN RVSKTKVLLE LSDGVEDNKG    120
NLRKSKTERE LIVAENIKLY SQIVGREVST TKEIYLTKRF LSYRSDLLFY YSFVDNFFKV    180
AGNEKELWKI NFDDASSAQF MGYVPFMVND NLKNDNAYLK DYVSDNEQIK DDLKKVQTMF    240
STLRHALLHF NYEFFEKLFN GEDVGFDFDI GFLNLLIENI DKLNIDAKKE FIDDEKIKLF    300
GENLSLAKVY RLYSDICVNR VGFNKFINSM LIKDGVENQL KAEFDRKFG GKAYTVDIHS    360
NQAYKRIYNE HKKLVIKVST LKDGQAIRRG NKKISELKEQ MKSMTKKNSL ARLECKMRLA    420
FGFLYGEYNN YNAFKNNFDT HIKNSQFDVN DVEKSKAYFL STYERRKPRT SEKLEKVAKN    480
IESLELKTVI ANDPLLKFIL LMFVFMPQEL KGEFLGFVKK YYHDVHSIDD DTKEQEEDVV    540
EAMSTSLKLK ILGRNIRSLT LFKYALSSQV NYNSTDNLFY VEGNRYGKIY KKLGISHNQE    600
EFDKTLTVPL FRYYSALFKL MNDFEIYSLA KANPMAVSLQ ELVDDETSPY KQGDYFNFNK    660
MLREIYGLTN DEIKSGKVVF MRNKIAHFDT EVLLSKPLLG QTKMNLQRKD IVSFIEARGN    720
IKELLGYDAI NDFRMKVIHL RTKMRVYSDK LQTMMDLLRS AKTPNDFYNV YKVKGVESIN    780
KYLLEVLAQT AEERSIEKQI KEGNEKYDL                                     809

SEQ ID NO: 3             moltype = AA   length = 855
FEATURE                  Location/Qualifiers
REGION                   1..855
                         note = Synthetic Sequence
source                   1..855
                         mol_type = protein
                         organism = synthetic construct
SEQUENCE: 3
MDKHPSNRYA LPKVIISEVD HERILEFKVK YEKLARLDRF EVKAMHYDGA EIVFDEVVAN     60
GGLIEVEYQD NNKTITINLN GKKYTINGRK VGGKRRLLED RISRGKVCLE LHDKIPDEKG    120
NLRSSRTERE LITFDSTKLY SQIIGRDVAS TKEIYLIKRF LAYRSDLLFY YGFIDNFFKV    180
AGNKRELWKI DFSGDKNQEL IKYFNFTIND KLKNDKGYLK EYTANDEQIK KDLQNTKEVF    240
TALRHALMHF EYDFFEKLFN NEEIETLSKI HDIELLNTMI NKLDKLNIDT RKEYIDDEKI    300
TVFGEEISLK TLYGLYAHTA INRVAFNKLI NRFMVENGTE NEALKKYFNS KAEGGIAYEI    360
DIHQNSEYKQ LYIQHKDLVS KLSALSDGDE IADTNKKISE LKVKMKAITK ANSLKRLEHK    420
LRLTFGFIYT EYQDYNAFKN NFDTDIKSGR FIPKDSEGKR RGFDHRELDQ LKRYYDATFA    480
DKKPQTKETF DEIDKQIDQL SLKNLIGDDT LLKVILLIYI FLPREIKGEF LGFVKKYYHD    540
TKHIEEDTKD KDEGFDDTFP VGLKLKVLDK NIRALSVLKH SLSYQAKYNK KEEKKEQFYE    600
AGNRHGRFYK KLGISHNQEE FDKSVYAPLL RYHAALFKLL NDFEIYSLAQ HIEGKETLAQ    660
QIEKPQFSQY EHYNFRKMLS KTYPKSAERG ALDNDAFDTV INMRNDIAHL SHEPLFECPL    720
DGKKSYKLKQ GKRTNTINVK PLPISRKMIV DFISSQSDMK KTLGYDAVND LTMKIIQLRT    780
RLKVYADKSE TIKTLVDAAK TPNDFYHIYK VKGVEAINRH LLEVIGETKD EKRIRKRIES    840
GNAIAGRTPA DSQEN                                                    855
```

```
SEQ ID NO: 4              moltype = AA  length = 809
FEATURE                   Location/Qualifiers
REGION                    1..809
                          note = Synthetic Sequence
source                    1..809
                          mol_type = protein
                          organism = synthetic construct
SEQUENCE: 4
MIKKPSNRHA LPKVIISEVN SDNILEFKIK YEKLARLDKI EVKAMHYDNR NIVFDEVIVN    60
DGLIELEYRD DHKRLFVKVG DKSYGITGQK VGGKQRLLEN RVSKTKVQLE LTDGVLDNKG   120
KHRISRTERE LIVATNIALY NQIIGREVKT TKEIYLIKRF LGYRSDLLFY YAFVDNFFKV   180
ADNEKELWKI DFDANNSTQL IKYISYIVND NLKNDNAYLK EYVSNVEQIK EDLKKVQTIF   240
SKLRHALLHF NYDFFEKLFN GKDVGFDFDI DFLNLLIENI DKLNIDAKKE FIDDEKIKLF   300
GENLSLAKVY RLYSDICVNR VGFNKFINAM LIKDGVENQA LKEAFDNKLG RKAYTIDIHS   360
NQEYKGLYNR HKKLVIELST LKNGQAIRKK NAEIAKLKEQ MNEMTKKNSL SRLEHKLRLA   420
FGFMYAEYNN HKAFKNNFDT DIKNSKFSEN DVEKFKAYFL STYEGRKRRT SEKLEKVAKN   480
IESLKLKTLI ANDPLLKFIL LMFVFMPQEL KGEFLGFVKK YYHDIHSIDE DSKEQENTVL   540
ELMPTSLKLK ILGRNIRSLT LFKYALSSQV NYNSSDELFY VEGNRYGKIY KKLGISHNQE   600
EFDKTLVVPL FRYYSALFKL MNDFEIYSLA QANPRVLSLQ ELVDDTTSPY KQGDYYNFKK   660
MLTEIYGVTN DEVNEGKVVF MRNKIAHFET KILLSKPLLG QTKLNLQRKD IVSFIEARGD   720
IKELLGYDAI NDFRMKVIHL RTKMKVYADK LQTMMDLLRN VKTPNDFYNV YKVKGVESIN   780
KHLLEVLAQT DQERTIEKQM VEGNKKYKL                                    809

SEQ ID NO: 5              moltype = RNA  length = 66
FEATURE                   Location/Qualifiers
variation                 37..66
                          note = n is a, c, g, or u
source                    1..66
                          mol_type = other RNA
                          organism = synthetic construct
SEQUENCE: 5
gttggaatat aaccccgttt gtaggggtaa taaaacnnnn nnnnnnnnnn nnnnnnnnnn    60
nnnnnn                                                               66

SEQ ID NO: 6              moltype = AA  length = 775
FEATURE                   Location/Qualifiers
REGION                    1..775
                          note = Synthetic Sequence
source                    1..775
                          mol_type = protein
                          organism = synthetic construct
SEQUENCE: 6
MAQVSKQTSK KRELSIDEYQ GARKWCFTIA FNKALVNRDK NDGLFVESLL RHEKYSKHDW    60
YDEDTRALIK CSTQAANAKA EALRNYFSHY RHSPGCLTFT AEDELRTIME RAYERAIFEC   120
RRRETEVIIE FPSLFEGDRI TTAGVVFFVS FFVERRVLDR LYGAVSGLKK NEGQYKLTRK   180
ALSMYCLKDS RFTKAWDKRV LLFRDILAQL GRIPAEAYEY YHGEQGDKKR ANDNEGTNPK   240
RHKDKFIEFA LHYLEAQHSE ICFGRRHIVR EEAGAGDEHK KHRTKGKVVV DFSKKDEDQS   300
YYISKNNVIV RIDKNAGPRS YRMGLNELKY LVLLSLQGKG DDAIAKLYRY RQHVENILDV   360
VKVTDKDNHV FLPRFVLEQH GIGRKAFKQR IDGRVKHVRG VWEKKKAATN EMTLHEKARD   420
ILQYVNENCT RSFNPGEYNR LLVCLVGKDV ENFQAGLKYL QLAERIDGRV YSIFAQTSTI   480
NEMHQVVCDQ ILNRLCRIGD QKLYDYVGLG KKDEIDYKQK VAWFKEHISI RRGFLRKKFW   540
YDSKKGFAKL VEEHLESGGG QRDVGLDKKY YHIDAIGRFE GANPALYETL ARDRLCLMMA   600
QYFLGSVRKE LGNKIVWSND SIELPVEGSV GNEKSIVFSV SDYGKLYVLD DAEFLGRICE   660
YFMPHEKGKI RYHTVYEKGF RAYNDLQKKC VEAVLAFEEK VVKAKKMSEK EGAHYIDFRE   720
ILAQTMCKEA EKTAVNKVRR AFFHHHLKFV IDEFGLFSDV MKKYGIEKEW KFPVK        775

SEQ ID NO: 7              moltype = AA  length = 777
FEATURE                   Location/Qualifiers
REGION                    1..777
                          note = Synthetic Sequence
source                    1..777
                          mol_type = protein
                          organism = synthetic construct
SEQUENCE: 7
GGMAQVSKQT SKKRELSIDE YQGARKWCFT IAFNKALVNR DKNDGLFVES LLRHEKYSKH    60
DWYDEDTRAL IKCSTQAANA KAEALANYFS AYRHSPGCLT FTAEDELRTI MERAYERAIF   120
ECRRRETEVI IEFPSLFEGD RITTAGVVFF VSFPFVERRVL DRLYGAVSGL KKNEGQYKLT   180
RKALSMYCLK DSRFTKAWDK RVLLFRDILA QLGRIPAEAY EYYHGEQGDK KRANDNEGTN   240
PKRHKDKFIE FALHYLEAQH SEICFGRRHI VREEAGAGDE HKKHRTKGKV VVDFSKKDED   300
QSYYISKNNV IVRIDKNAGP RSYRMGLNEL KYLVLLSLQG KGDDAIAKLY RYRQHVENIL   360
DVVKVTDKDN HVFLPRFVLE QHGIGRKAFK QRIDGRVKHV RGVWEKKKAA TNEMTLHEKA   420
RDILQYVNEN CTRSFNPGEY NRLLVCLVGK DVENFQAGLK RLQLAERIDG RVYSIFAQTS   480
TINEMHQVVC DQILNRLCRI GDQKLYDYVG LGKKDEIDYK QKVAWFKEHI SIRRGFLRKK   540
FWYDSKKGFA KLVEEHLESG GGQRDVGLDK KYYHIDAIGR FEGANPALYE TLARDRLCLM   600
MAQYFLGSVR KELGNKIVWS NDSIELPVEG SVGNEKSIVF SVSDYGKLYV LDDAEFLGRI   660
CEYFMPHEKG KIRYHTVYEK GFRAYNDLQK KCVEAVLAFE EKVVKAKKMS EKEGAHYIDF   720
REILAQTMCK EAEKTAVNKV ARAFFAHHLK FVIDEFGLFS DVMKKYGIEK EWKFPVK      777
```

| SEQ ID NO: 8 | moltype = AA length = 802 |
| --- | --- |
| FEATURE | Location/Qualifiers |
| REGION | 1..802 |
| | note = Synthetic Sequence |
| source | 1..802 |
| | mol_type = protein |
| | organism = synthetic construct |

SEQUENCE: 8

```
MQVENIKKGS SQGMYSIEQY EGAKKWCFAI VLNRAQTNLQ GNPKLFEETL TRFERIRKED   60
WFDQETKKLI YAKQEQNEVE EEIQKAADEK LRDLRNYFSH YFHTPDCLIF TQNDPVRIIM  120
EKAYEKARFE QAKKEQEDIS IEFGELFEEN GRITSAGVVF FASFFAERRF LNRLMGYVQG  180
FTRTEGEYKI TRDVFSTYCL RDSYSVKTPD HDAVMFRDIL GYLSRVPSES YQRIKESQMR  240
SETQLSERKT DKFILFALNY LEDYGLEDLA DYTACFARTR IKREQDENTD GKEQKPHRKK  300
PRVEIHFERA EGDPFYIKHN NVILRTQKKG AQTYIFRMGV YELKYLVLLS LLGKGAEAVK  360
RIDRYVHSLR NQLPHIEKKS TEEIEGYVRF LPRFVRSHLG LLGVDDEKKI KARVDYVKAK  420
WLEKKEKSRE LQLHRKGRDI LRYINERCER PLNIDEYNRI LELLVTKHLD GFYRELEELK  480
KTRRIDKNIV CNLSRHKSVN ALHEKVCDLV VQELESLGRE ELKEYVGLIP KEEKEVSFEE  540
KTDRVVKQPV IYKGFLRNEF FRESRKSFAR LVEEAVREKG EVYDVPLGGE YYEIVSLDTF  600
DKDNKRLYET LAMDRLLLMI ARQYHLSLNK ELAKRAQQIE WKKEDGEEVI IFTLKNPAQP  660
EQSCSVRFSL RDYTKLYVMD DAEFLARLCD YFLPKDEEQI DYHRLYTQGM NRYTNLQREG  720
IEAILELEKK TIGPEQPRPP KNYIPFSEIM DKSAYNEDDQ KALRRVRNAL LHHNLNFARA  780
DFKRFCGIMK REGIEKRWSL AV                                          802
```

| SEQ ID NO: 9 | moltype = AA length = 804 |
| --- | --- |
| FEATURE | Location/Qualifiers |
| REGION | 1..804 |
| | note = Synthetic Sequence |
| source | 1..804 |
| | mol_type = protein |
| | organism = synthetic construct |

SEQUENCE: 9

```
MEFENIKKTS NKEVYSIEQY EGEKKWCFAI VLNRAQTNLE ENPKLFEQTL TRFEKIMKQD   60
WFNEETKKLI YEKEEENKVK EEIQIAASER LKNLRNYFSH YLHAPDCLIF NRNDTIRIIM  120
EKAYERSRFE AKKKQQEDIS IEFPELFEEE DKITSAGVVF FVSFFIERRF LNRLMGYVQG  180
FRKTEGEYNI TRQVFSKYCL KDSYSVQAQD HDAVMFRDIL GYLSRVPTEI YQHIKLTRKR  240
SQDQLSERKT DKFILFALKY LEDYGLKDLA DYTACFARSK IKRENEDTKE TDGNKHKFHR  300
EKPVVEIHFD KEKQDQFYIK RNNVILKAQK KGGQSNVFRM GVYELKYLVL LSLLGKAEEA  360
IQRIDRYISS LKKQLPYLDK ISNEEIQKSI NFLPRFVSR LGLLQVDDEK RLKTRLEYVK  420
AKWTDKKEGS RKLELHRKGR DILRYINERC DRPLSRKEYN NILKFIVNKD FAGFYNELEE  480
LKRTRRLDKN IIQKLSGHTT LNALHERVCD LVLQELGSLQ SENLKEYIGL IPKEEKEVTF  540
REKVDRILEQ PVVYKGFLRY EFFKEDKKSF ARLVEEAIKT KWSDFDIPLG EEYYNIPSLD  600
RFDRTNKKLY ETLAMDRLCL MMARQYYLRL NEKLAEKAQH IYWKKEDGRE VIIFKFQNPK  660
EQKKSFSIRF SILDYTKMYV MDDPEFLSRL WEYFIPKEAK EIDYHKHYAR AFDKYNLQK  720
EGIDAILKLE GRIIERRKIK PAKNYIEFQE IMNRSGYNND QQVALKRVRN ALLHYNLFE  780
REHLKRFYGV VKREGIEKKW SLIV                                        804
```

| SEQ ID NO: 10 | moltype = AA length = 805 |
| --- | --- |
| FEATURE | Location/Qualifiers |
| REGION | 1..805 |
| | note = Synthetic Sequence |
| source | 1..805 |
| | mol_type = protein |
| | organism = synthetic construct |

SEQUENCE: 10

```
MKVENIKEKS KKAMYLINHY EGPKKWCFAI VLNRACDNYE DNPHLFSKSL LEFEKTSRKD   60
WFDEETRELV EQADTEIQPN PNLKPNTTAN RKLKDIRNYF SHHYHKNECL YFKNDDPIRC  120
IMEAAYEKSK IYIKGKQIEQ SDIPLPELFE SSGWITPAGI LLLASFFVER GILHRLMGNI  180
GGFKDNRGEY GLTHDIFTTY CLKGSYSIRA QDHDAVMFRD ILGYLSRVPT ESFQRIKPPQ  240
IRKEGQLSER KTDKFITFAL NYLEDYGLKD LEGCKACFAR SKIVREQENV ESINDKEYKP  300
HENKKKVEIH FDQSKEDRFY INRNNVILKI QKKDGHSNIV RMGVYELKYL VLMSLVGKAK  360
EAVEKIDNYI QDLRDQLPYI EGKNKEEIKE YVRFFPRFIR SHLGLLQIND EEKIKARLDY  420
VKTKWLDKKE KSKELELHKK GRDILRYINE RCDRELNRNV YNRILELLVS KDLTGFYREL  480
EELKRTRRID KNIVQNLSGQ KTINALHEKV CDLVLKEIES LDTENLRKYL GLIPKEEKEV  540
TFKEKVDRIL KQPVIYKGFL RYQFFKDDKK SFVLLVEDAL KEKGGGCDVP LGKEYYKIVS  600
LDKYDKENKT LCETLAMDRL CLMMARQYYL SLNAKLAQEA QQIEWKKEDS IELIIFTLKN  660
PDQSKQSFSI RFSVRDFTKL YVTDDPEFLA RLCSYFFPVE KEIEYHKLYS EGINKYTNLQ  720
KEGIEAILEL EKKLIERNRI QSAKNYLSFN EIMNKSGYNK DEQDDLKKVR NSLLHYKLIF  780
EKEHLKKFYE VMRGEGIEKK WSLIV                                       805
```

| SEQ ID NO: 11 | moltype = AA length = 805 |
| --- | --- |
| FEATURE | Location/Qualifiers |
| REGION | 1..805 |
| | note = Synthetic Sequence |
| source | 1..805 |
| | mol_type = protein |
| | organism = synthetic construct |

SEQUENCE: 11

```
MKVENIKEKS KKAMYLINHY EGPKKWCFAI VLNRACDNYE DNPHLFSKSL LEFEKTSRKD   60
WFDEETRELV EQADTEIQPN PNLKPNTTAN RKLKDIRNYF SHHYHKNECL YFKNDDPIRC  120
```

```
IMEAAYEKSK IYIKGKQIEQ SDIPLPELFE SSGWITPAGI LLLASFFVER GILHRLMGNI   180
GGFKDNRGEY GLTHDIFTTY CLKGSYSIRA QDHDAVMFRD ILGYLSRVPT ESFQRIKQPQ   240
IRKEGQLSER KTDKFITFAL NYLEDYGLKD LEGCKACFAR SKIVREQENV ESINDKEYKP   300
HENKKKVEIH FDQSKEDRFY INRNNVILKI QKKDGHSNIV RMGVYELKYL VLMSLVGKAK   360
EAVEKIDNYI QDLRDQLPYI EGKNKEEIKE YVRFFPRFIR SHLGLLQIND EEKIKARLDY   420
VKTKWLDKKE KSKELELHKK GRDILRYINE RCDRELNRNV YNRILELLVS KDLTGFYREL   480
EELKRTRRID KNIVQNLSGQ KTINALHEKV CDLVLKEIES LDTENLRKYL GLIPKEEKEV   540
TFKEKVDRIL KQPVIYKGFL RYQFFKDDKK SFVLLVEDAL KEKGGGCDVP LGKEYYKIVS   600
LDKYDKENKT LCETLAMDRL CLMMARQYYL SLNAKLAQEA QQIEWKKEDS IELIIFTLKL   660
PDQSKQSFSI RFSVRDFTKL YVTDDPEFLA RLCSYFFPVE KEIEYHKLYS EGINKYTNLQ   720
KEGIEAILEL EKKLIERNRI QSAKNYLSFN EIMNKSGYNK DEQDDLKKVR NSLLHYKLIF   780
EKEHLKKFYE VMRGEGIEKK WSLIV                                        805

SEQ ID NO: 12              moltype = AA  length = 838
FEATURE                    Location/Qualifiers
REGION                     1..838
                           note = Synthetic Sequence
source                     1..838
                           mol_type = protein
                           organism = synthetic construct
SEQUENCE: 12
MQFENIKDTG QKPIYSIDQY EGAKKWCFAI VLNRACDNYE DNPQLFSESL LRFEEVNRRD    60
WFDKDIRDLI KKADTEDQIE PKRKPNTPVN RRLHDIRNYF SHSRHQDDCL YFKNDDPMRC   120
IMEAAYEKAK IHIKGRQTEQ SDIPLPELFD ANNKITSAGV LFLASFFVER GILHRLMGNI   180
GGFKDNRGKY GLTHDIFTTY CLKDSYSIHA SDPKVVLFRD IAGYLSLVAC EYYPTYLSKI   240
PKENAGGKSS DEEKYAERKT DKFILFALKY LEEFVLPSLK DDYLVDIGRI DIIREESKET   300
EEKDEQYKPH PNQGKVKVVF DSINKELPYY INHNTVILRI QKNGVMAYSC KIGVNDLKYL   360
LLLCLQGKTD KALDAIYNYL HSMQDPPEVV KIGATDKLFQ GLPEFILKQS GIKVQDKNKE   420
KAARIKYIRD KWEKKKSESA DIELHRKGRD ILRYVNWHCE TPLGTEKYDQ LLVLLVNKNF   480
AGFGDELNQL KRTEIISKDI FEKLSGFKTI NTLHQKVCNL VLEELSFFEK SNPEKLEEYI   540
GLIRKPAPEN NPPPEYKEKV RRFVEQPMIY KGFLRDQFFV NKDQDGKKLK EQKTFAKLVE   600
ETLGQNADVP LGKDFYYVPN IEKDEKKNRF HKDNAVLYET LALDRLCAMM ARKCLTQINK   660
NLAEKSEEID WRNEDGKDFI YLKLVKSDRP QETFKIRFKV NDFAKLYVMD DPDFLGGLMK   720
HFFPQEHSIE YHKLYRNGIE RYTDRQKDGI EAILRLEDSV IRQKGMKPKP AKNYISFSEI   780
MAQTDYPEHD QKVLNKVRRA LLHYHLKFEP ADYNRFVDIM KKDKFWDGER KNEESRGK    838

SEQ ID NO: 13              moltype = AA  length = 838
FEATURE                    Location/Qualifiers
REGION                     1..838
                           note = Synthetic Sequence
source                     1..838
                           mol_type = protein
                           organism = synthetic construct
SEQUENCE: 13
MQFENIKDTG QKPIYSIDQY EGAKKWCFAI VLNRACDNYE DNPQLFSESL LRFEEVNRRD    60
WFDKDIRDLI KKADTEDQIE PKRKPNTPVN RRLHDIRNYF SHSRHQDDCL YFKNDDPMRC   120
IMEAAYEKAK IHIKGRQTEQ SDIPLPELFD ANNKITSAGV LFLASFFVER GILHRLMGNI   180
GGFKDNRGKY GLTHDIFTTY CLKDSYSIHA SDPKVVLFRD IAGYLSLVAC EYYPTYLSKI   240
PKENAGEKSS DEEKYAERKT DKFILFALKY LEEFVLPSLK DDYLVDIGRI DIIREESKET   300
EEKDEQYKPH PNQGKVKVVF DSINKELPYY INHNTVILRI QKNGVMAYSC KIGVNDLKYL   360
LLLCLQGKTD KALDAIYNYL HSMQDPPEVV KIGATDKLFQ GLPEFILKQS GIKVQDKNKE   420
KAARIKYIRD KWEKKKSESA DMELHRKGRD ILRYVNWHCE TPLGTEKYDQ LLVLLVNKNF   480
VVFGDELNQL KRTEIISKDI LEKLSGFQTI NTLHQKVCNL VLEELSSLEK NDPGKLAEHI   540
GLVRKPAPEN NPPPEYKEKV RRFVEQPMIY KGFLRDQFFV NKDQDGKKLK EQKTFAKLVE   600
ETLGQNADVP LGKDFYYVPN IEKDEKKNRF HKDNAVLYET LALDRLCAMM ARKCLTQINK   660
NLAEKSEEID WRNEDGKDFI YLKLVKSDRP QETFKIRFKV NDFAKLYVMD DPDFLGGLMK   720
HFFPQEHSIE YHKLYRNGIE RYTDRQKDGI EAILRLEDSV IRQKGMKPKP AKNYISFSEI   780
MAQTDYPEHD QKVLNKVRRA VLHYHLKFEP ADYNRFVDIM KKNKFWDGER KNESRGR     838

SEQ ID NO: 14              moltype = AA  length = 905
FEATURE                    Location/Qualifiers
REGION                     1..905
                           note = Synthetic Sequence
source                     1..905
                           mol_type = protein
                           organism = synthetic construct
SEQUENCE: 14
MNPVDIKEAS KKAVYYIDQY KGDKKWCFAI VLNRAYDNLE DNPNLLNESL LRFENISLMS    60
WFDFQEDEKQ MRDSVFQGYE NINKAEQKKE IKLKPDIQKA VVKRLEDLRN YFSHRLHTDD   120
CLTFLKEDPI RFILEKAYEK AKLVHLGRET QESKDFSVPL FEDDKITTAG VILFASFFVE   180
MRILIRVLGL KDVRGFTLTE GKFNLTRKAI CHYALPDSYS IKTPRDTKLF RDILGYLSRM   240
PSESYDHYFP EAKKKAEEGE KDKEGEGKDK ENKEPQWSKR NTDKFMVFAM RYLEDFQPDV   300
FRICFARQDI QQPQREKDQE RKPHKQKGKR KLQFPPENLQE ARDNPAVRYF IRQNNIDIQI   360
QKNNQKIHCR MGLNELKYLI LLCLKGQGGE AIEAIYNEAG QVGNKLPHLA KMRKEGFQDY   420
QKWMPGFVLN HHGLMPEGPN RKEPVAARVG YIRQKWERKR DGSKEARLDS KARDILQYIN   480
ECGQEYALQQ DRERKGTLNI DKYRKIHDFL VNKNIEAFRQ ELDGLKVDEK VREDLKKRQT   540
VNDLHQRVCN LMIRKLEDLQ QSGDLEQLKC YIGLAPAWEY RDEDQTGKEQ KEQRFENKVK   600
NLKPMLYRGF LRERFFAEYR SKENKRNFAD LVEDVRQKKG EGDVPDLIY YQIEGDTQEI   660
QVANKKLTET LARDRLCLLI GREYLEQLNR TLSQNAIEER HGPKRKYFIK TEWSKEPVQM   720
```

```
GDGKERMRDV IICRIRENPE DENPLCSIRF AVKHWTKLYV MDDPFFLSDV HSYFLSKSNE    780
IDYHTLNQKG ICQYTNLQAD CMVNILKLEK KVFERVTKRD IDKEKDIKKL INEINNKLQH    840
LPAKKEDNRV PFLLVCEAAL EKGILKEKSE IDVVSMVRNS AFHYQLYFSK SEKETFDRIM    900
RREGI                                                                905

SEQ ID NO: 15             moltype = AA  length = 900
FEATURE                   Location/Qualifiers
REGION                    1..900
                          note = Synthetic Sequence
source                    1..900
                          mol_type = protein
                          organism = synthetic construct
SEQUENCE: 15
MQTATQEQKQ KQSIYSILNY QGQRKWCFAI VLNRALDNIN PKRETETGKY KNKELFYKSL     60
LRFEGIKKQP WFDETKAEKE NVTAKEIIDS KDKAAELLLN LRNYFSHNYH TEKCLYFGTE    120
SQHKQIRLIM EAAYERAKAE LTGRRTGQEI SAEAEKDKDG NIKKYKLSDV PWPPLFDEKD    180
IITTAGVVFF ASFFTEAGQI FRLMNWINGL KRNDDKFNIT RRALSFYSLP DSYAEAIAEY    240
EVEEDGASRT IRYKAKIFKD ILNYLRRIPS ETYKLYHSGE ENKISGKKEE KGEDENTPVE    300
RKTDKFAEFA MRYLEDFEGV RFARYRINTK TRENEVFFDE DELKKLIDKK GVPEQEKDKK    360
FEDYRYYYVK NNAILKTEKG SIRIGINELK YFVLLSLDKM GQQAKEKINS FLSKFTGDNL    420
GNREFIKANI EELPPFILKK FDPLAEDKEK RIEKRVDYLI RKWKRKKEDY EKMRINDKVG    480
GILRYVNENL KPGKKLNAEG YKYLQKLLTM ERFSEFEKEI NKFEDERESR LKRGALSEIE    540
RLKSIDKMFL KVCSIVLKKL ESLEGDELAG YIGLKKQPLT DEKAAENQEY DNVLQRYIET    600
KIALPKGTLR DLYLKTGGKN NFSDAVEDVL EKKKLDFDIE LDKKYYDYEI DKRKEAPKDR    660
EGLKTARKLR ETMAKDRLCL LTGMKFYENI REDLNIRWER RVGKNVIYAD IYKKGDKTKK    720
LFTLKFSEKD YVKMYVIDNT DFLRQVWEKF VKGKEGQEVN YHEFYQKGIQ KGLGDFQRDV    780
ALKVLKFEET VVEKNAGTGL PVSGINNKLS GIIKNRGREM KSDFNKHRDV FVSNDTICKA    840
FFDDADDIER VKKIRNSAFH YNADFEDEDY TGFNKIMDRE GIKIKEIDGK KQEGKQRKRF    900

SEQ ID NO: 16             moltype = AA  length = 866
FEATURE                   Location/Qualifiers
REGION                    1..866
                          note = Synthetic Sequence
source                    1..866
                          mol_type = protein
                          organism = synthetic construct
SEQUENCE: 16
MAVDYSLKNE WYREINKSCF TVALNVAYDN CKAKGHENLL REAQRSKGGI TNEQIKNVQT     60
EIKTRLEDIR SHFSHFYHDE KSLIFEKDNI VKDFLESAYE KAQSSVIGST RQSDYKGVVP    120
PLFEPHDGMI TAAGVVFLAS FFCHRSNVYR MLGAVKGFKH TGKEELSDGA KRDYGFTRRL    180
MAHYSLRDSY VIKAEETKSF RDLLGYLSRV PQQAVDWLNE HNQLSEDEKK EFLNQKPSDE    240
ESQEQSKTEN TDRQADRMPR RSLRKTDKFI LFAAKFIEDW AQKEKMDVTF ARYQKTVTED    300
ENKNQDGKQV RDVLKYEKD TKKLNPDFDY KWTYYIRNNH AIIQIKPDEY KQAVSARISE    360
NELKYLVLLI FQGKGWEAIK KIGDYIFHIG NKIKIGRFDH NEERRMPSFL KNPPADIIGE    420
MVENRLKYIR DELNKVIETI KKEEPQNNKW LLYGKKISI ILKFISDSIS DIKKRPDVNE     480
YNTLRDMLQK LDFDNFYERL KSYVSEGRIE QTLYDEIKGI KDISTLCIKI CELRLAALEE    540
LEKEGGDDLN KYIGLAVQEK HKNYDDSNTP QKKAERFLES QFSVGKNFLR ETFYDEYIKN    600
RKSLYEIIKE KITGITPLNE NRWYLMDKNP KEFESKDSKI IRGLCNIYIQ DILCMKIALW    660
YYENLSPSYK NKLKWDFIGQ GFGYDRYKLS YKTDCGITIE FKLADLNRLD IIEKPKMIEN    720
ICHSFILEKD VKKQTISWHE FRQDGIAKYR KLQKEVVEAV FEFENSLKIP DKNWLTQGYV    780
PPFNKNKRFED KGFSTFILEE AVRKGKIKSD DKEPLRKVRT DFFHEQFDST DAERRIFDKY   840
MPAKHDGKNK GGKMQEKQEK SYTRRI                                         866

SEQ ID NO: 17             moltype = AA  length = 871
FEATURE                   Location/Qualifiers
REGION                    1..871
                          note = Synthetic Sequence
source                    1..871
                          mol_type = protein
                          organism = synthetic construct
SEQUENCE: 17
MEKYLIKNFE GINKSKFTVA LNIANDNCKN KGIQELLKEA QRSKGGITDT QITEVQEHIK     60
ERLNSVRNYF SHCYHEKKPL YFEANDPVKI FLEETFAKAV ENLQGRFLSD KYKLTVPPLF    120
EPNQNNTITA AGVIFLASFF CHRSYVYRML GGIPGFKRSD KKKWGDGQKI DYGFTRKLMS    180
FYSLRDSYSV NVQENKELTA FRDILGYLAR VPGQAIDWLI EKGKLTKEEG KQPFYLGEQSE   240
EREEKAKKEE IKYALRKTDK FMLFAVRFIE DWAEQERIKV EFARYEKMTI VNENKQDEK     300
EERKVKFVSD EPTAAGWTYY IRNNHAIIKI IPDDKKKKAV SARISENELK YLVLTIIDGN    360
GKNAIAYIGD YIFRTARQIE NKSYNAESEK YAPAFVRGGQ KKSVDKRIKY IRDEIQQVIN    420
DIEAEQEKQK NEQDAPAENR TWLIYKGKKI SIILRYVNDN IAEYKKRLSV TEYNELRGYL    480
QQLDFINFHR KLAEYQHHGR LPNGFAESIN KFQDLSKLCI EVCERQKKKL QEMAAKGGIE    540
LEQYIGLAPK EENQEQNKYA TKANNFIKVW LSIPENFLRQ KFYDKFCKQQ ECKNKGSDKP    600
DNTSVPQRKY FIAIIREKNI RPIHADKYYL LGQNPKDYER PDGKIIRQLC DVYCKDGLCM    660
AMAKWYYENR LGKFKDLIEW QTGDDKQQHG YAGHTLEYQA TEKIKIRFKL ADFTRLDIIE    720
PPERVKNICR QWETELLKKT RDGTISWYDF KLNGLEPYRQ WQGYAVADIF WFEESLKINE    780
TQWQGRTHMP FNFEKDKPLW CNILDEAVKQ NKIEKQDTQA LRRVRHDCFH EEFLANYEQL    840
KIFKNLISDK AKDAKPKDKK SRKNEQKYGK R                                   871

SEQ ID NO: 18             moltype = AA  length = 789
FEATURE                   Location/Qualifiers
```

```
REGION                  1..789
                        note = Synthetic Sequence
source                  1..789
                        mol_type = protein
                        organism = synthetic construct
SEQUENCE: 18
MENIKLEKQK AAFYFNQAEL NLKAIEGNIF DKGRRKTLFD NPKILSKVEN FIFNFKDVTK   60
NAKGEIDCLL SKLMELRNFY SHYVHKPDVK ELSKGEKPLL ERYYQIAIEA TGSENVKLEI  120
IENDKWLTDA GVLLFLCMFL KKSQANKLIS GISGFKRNDT FGQPRRNLFN YPFSVRERYKV  180
VPDMQKHFLL FVLVNHLSEQ DDYIEKAQQP YNIGEGLFFH RIASTFLNVS GILRNMEFYT  240
YQSKRLKEQR GELKREKDIF TWEEPFQGNS YFEINGHKGV IGEDELKELC YALLSYNKSK  300
YAVEQIEKFL KGFGEVKSEQ EIRDSDILNE SYFPTNYFAE SNIGSIKEKI LNRLGKTDDS  360
YKKTGTKIKP YDMMKEVMEF INNSLPADEK LKRKDYRRYL KMVRIWDSEK DNIKREFESK  420
EWSKYFSSNF WMAKNLERVY GLAREKNAEL FNKLKAVVEK MDEREFEKYR QINSAEDLAS  480
LRRLANDYGV KWEEKDWQEY SGQIKKQISD RQKLTIMKQR ITAELKKKHG IENLNLRITI  540
DSNKSRKAVL NRIAVPRGFV KEHILGWQGS EKVSKKTREA KCKILLSKEY EELSKQFFQT  600
RNYDKMTQVN SLYEKNKLIA FMAVYLMGQL NIRFDKPTRL NELEKAEVDF KISDKVTAKI  660
PFSQYPSLVY AMSSKYADSV GSYKFENDEK NKPFLGKIDI IEKQRMEFIK EVLGFEEYLF  720
EKKIIDKSKF ADTATHISFR EICDELIQKG WDENKLTNLK DARNAALHGE IPAETSFREA  780
KPLINGLKK                                                          789

SEQ ID NO: 19           moltype = AA  length = 792
FEATURE                 Location/Qualifiers
REGION                  1..792
                        note = Synthetic Sequence
source                  1..792
                        mol_type = protein
                        organism = synthetic construct
SEQUENCE: 19
MSPDFIKLEK QEAAFYFNQT ELNLKAIESN IFDKQQRVIL LNNPQILAKV GDFIFNFRDV   60
TKNAKGEIDC LLLKLRELRN FYSHYVYTDD VKILSNGERP LLEKYYQFAI EATGSENVKL  120
EIIESNNRLT EAGVLFFLCM FLKKSQANKL ISGISGFKRN DPTGQPRRNL FTYFSVREGY  180
KVVPDMQKHF LLFVLVNHLS GQDDYIEKAQ KPYDIGEGLF FHRIASTFLN ISGILRNMEF  240
YIYQSKRLKE QQGELKREKD IFPWIEPFQG NSYFEINGNK GIIGEDELKE LCYALLVAGK  300
DVRAVEGKIT QFLEKFKNAD NAQQVEKDEM LDRNNFPANY FAESNIGSIK EKILNRLGKT  360
DDSYNKTGTK IKPYDMMKEV MEFINNSLPA DEKLKRKDYR RYLKMVRIWD SEKDNIKREF  420
ESKEWSKYFS SDFWMAKNLE RVYGLAREKN AELFNKLKAV VEKMDEREFE KYRLINSAED  480
LASLRRLAKD FGLKWEEKDW QEYSGQIKKQ ISDRQKLTIM KQRITAELKK KHGIENLNLR  540
ITIDSNKSRK AVLNRIAVPR GFVKEHILGW QGSEKVSKKT REAKCKILLS KEYEELSKQF  600
FQTRNYDKMT QVNGLYEKNK LLAFMVVYLM ERLNILLNKP TELNELEKAE VDFKISDKVM  660
AKIPFSQYPS LVYAMSSKYA DSVGSYKFEN DEKNKPFLGK IDTIEKQRME FIKEVLGFEE  720
YLFEKKIIDK SEFADTATHI SFDEICNELI KKGWDKDKLT KLKDARNAAL HGEIPAETSF  780
REAKPLINGL KK                                                      792

SEQ ID NO: 20           moltype = AA  length = 792
FEATURE                 Location/Qualifiers
REGION                  1..792
                        note = Synthetic Sequence
source                  1..792
                        mol_type = protein
                        organism = synthetic construct
SEQUENCE: 20
MSPDFIKLEK QEAAFYFNQT ELNLKAIESN IFDKQQRVIL LNNPQILAKV GDFIFNFRDV   60
TKNAKGEIDC LLLKLRELRN FYSHYVYTDD VKILSNGERP LLEKYYQFAI EATGSENVKL  120
EIIESNNRLT EAGVLFFLCM FLKKSQANKL ISGISGFKRN DPTGQPRRNL FTYFSVREGY  180
KVVPDMQKHF LLFVLVNHLS GQDDYIEKAQ KPYDIGEGLF FHRIASTFLN ISGILRNMEF  240
YIYQSKRLKE QQGELKREKD IFPWIEPFQG NSYFEINGNK GIIGEDELKE LCYALLVAGK  300
DVRAVEGKIT QFLEKFKNAD NAQQVEKDEM LDRNNFPANY FAESNIGSIK EKILNRLGKT  360
DDSYNKTGTK IKPYDMMKEV MEFINNSLPA DEKLKRKDYR RYLKMVRIWD SEKDNIKREF  420
ESKEWSKYFS SDFWMAKNLE RVYGLAREKN AELFNKLKAV VEKMDEREFE KYRLINSAED  480
LASLRRLAKD FGLKWEEKDW QEYSGQIKKQ ISDRQKLTIM KQRITAELKK KHGIENLNLR  540
ITIDSNKSRK AVLNRIAVPR GFVKEHILGW QGSEKVSKKT REAKCKILLS KEYEELSKQF  600
FQTRNYDKMT QVNGLYEKNK LLAFMVVYLM ERLNILLNKP TELNELEKAE VDFKISDKVM  660
AKIPFSQYPS LVYAMSSKYA DSVGSYKFEN DEKNKPFLGK IDTIEKQRME FIKEVLGFEE  720
YLFEKKIIDK SEFADTATHI SFDEICNELI KKGWDKDKLT KLKDARNAAL HGEIPAETSF  780
REAKPLINGL KK                                                      792

SEQ ID NO: 21           moltype = AA  length = 790
FEATURE                 Location/Qualifiers
REGION                  1..790
                        note = Synthetic Sequence
source                  1..790
                        mol_type = protein
                        organism = synthetic construct
SEQUENCE: 21
MNGIELKKEE AAFYFNQAEL NLKAIEDNIF DKERRKTLLN NPQILAKMEN FIFNFRDVTK   60
NAKGEIDCLL LKLRELRNFY SHYVHKRDVR ELSKGEKPIL EKYYQFAIES TGSENVKLEI  120
IENDAWLADA GVLFFLCIFL KKSQANKLIS GISGFKRNDD TGQPRRNLFT YFSIREGYKV  180
VPEMQKHFLL FSLVNHLSNQ DDYIEKAHQP YDIGEGLFFH RIASTFLNIS GILRNMKFYT  240
```

```
YQSKRLVEQR GELKREKDIF AWEEPFQGNS YFEINGHKGV IGEDELKELC YAFLIGNQDA    300
NKVEGRITQF LEKFRNANSV QQVKDDEMLK PEYFPANYFA ESGVGRIKDR VLNRLNKAIK    360
SNKAKKGEII AYDKMREVMA FINNSLPVDE KLKPKDYKRY LGMVRFWDRE KDNIKREFET    420
KEWSKYLPSN FWTAKNLERV YGLAREKNAE LFNKLKADVE KMDERELEKY QKINDAKDLA    480
NLRRLASDFG VKWEEKDWDE YSGQIKKQIT DSQKLTIMKQ RITAGLKKKH GIENLNLRIT    540
IDINKSRKAV LNRIAIPRGF VKRHILGWQE SEKVSKKIRE AECEILLSKE YEELSKQFFQ    600
SKDYDKMTRI NGLYEKNKLI ALMAVYLMGQ LRILFKEHTK LDDITKTTVD FKISDKVTVK    660
IPFSNYPSLV YTMSSKYVDN IGNYGFSNKD KDKPILGKID VIEKQRMEFI KEVLGFEKYL    720
FDDKIIDKSK FADTATHISF AEIVEELVEK GWDKDRLTKL KDARNKALHG EILTGTSFDE    780
TKSLINELKK                                                            790

SEQ ID NO: 22             moltype = AA length = 790
FEATURE                   Location/Qualifiers
REGION                    1..790
                          note = Synthetic Sequence
source                    1..790
                          mol_type = protein
                          organism = synthetic construct
SEQUENCE: 22
MNGIELKKEE AAFYFNQAEL NLKAIEDNIF DKERRKTLLN NPQILAKMEN FIFNFRDVTK    60
NAKGEIDCLL LKLRELRNFY SHYVHKRDVR ELSKGEKPIL EKYYQFAIES TGSENVKLEI   120
IENDAWLADA GVLFFLCIFL KKSQANKLIS GISGFKRNDD TGQPRRNLFT YFSIREGYKV   180
VPEMQKHFLL FSLVNHLSNQ DDYIEKAHQP YDIGEGLFFH RIASTFLNIS GILRNMKFYT   240
YQSKRLVEQR GELKREKDIF AWEEPFQGNS YFEINGHKGV IGEDELKELC YAFLIGNQDA   300
NKVEGRITQF LEKFRNANSV QQVKDDEMLK PEYFPANYFA ESGVGRIKDR VLNRLNKAIK   360
SNKAKKGEII AYDKMREVMA FINNSLPVDE KLKPKDYKRY LGMVRFWDRE KDNIKREFET   420
KEWSKYLPSN FWTAKNLERV YGLAREKNAE LFNKLKADVE KMDERELEKY QKINDAKDLA   480
NLRRLASDFG VKWEEKDWDE YSGQIKKQIT DSQKLTIMKQ RITAGLKKKH GIENLNLRIT   540
IDINKSRKAV LNRIAIPRGF VKRHILGWQE SEKVSKKIRE AECEILLSKE YEELSKQFFQ   600
SKDYDKMTRI NGLYEKNKLI ALMAVYLMGQ LRILFKEHTK LDDITKTTVD FKISDKVTVK   660
IPFSNYPSLV YTMSSKYVDN IGNYGFSNKD KDKPILGKID VIEKQRMEFI KEVLGFEKYL   720
FDDKIIDKSK FADTATHISF AEIVEELVEK GWDKDRLTKL KDARNKALHG EILTGTSFDE   780
TKSLINELKK                                                           790

SEQ ID NO: 23             moltype = AA length = 797
FEATURE                   Location/Qualifiers
REGION                    1..797
                          note = Synthetic Sequence
source                    1..797
                          mol_type = protein
                          organism = synthetic construct
SEQUENCE: 23
MSGIELKKEE AAFYFNQAEL NLKAIEVSIF DEGRRKTLLN NPKILAKVEN FIFNSEDVTK    60
NAKGEIDCLL SKLMELRNFY SHYVHKPDVK ELSKGEKPIL EKYYQFAIDA TASADVKLEI   120
IENDTWLTDA GVLLLLCMFL KKSQANKLIG GISGFKRNDP TGQPRRNLFT YYSVREGYKV   180
VPEMQKHFLL FALVNHLSNQ DDYIEKAQQP YDIGEGLFFH RIASTFLDIS GILRNMKFYT   240
YQSKRLKEQR GELKREKDSF EWIEPFQGNS YFSVDGQKGV IGEDELKELC YALLIGKQDA   300
NKVEGRITQF LKKFKNADDA QKVSDDEMLD RGNFPASYFA ERRVGSIKDK ILSSLEQAIK   360
SYKTSGADVK AYNKMKEVME FINNSLPVDE KLKRKDYKRY LGMVRLWGSE RDNIKREFEA   420
KGWSKYFTSG FWMAKNLERV YGLAREKNAE LFNKLKTAVE KMDEREFVKY QQINDAKDLA   480
SLRQLANDFG VNWEEKDWEK YSGQIKKQIT DSQKLTIMKQ RITAGLKRKH GIENLNLRIT   540
IDSSKSRKAV LNRIAIPRGF VKKHILDWQG SEKVPKKIRE AKCKILLSKE YEELSRQFYK   600
VKDYDKMTQI NSLYEKNKLI ALMAVYLMEQ LRIQLKEHTE LRNLDKTTVD FRISDKVTEK   660
IPFSQYPSLV YAMSREYADN VDNYKFSEED KKKLDKIKKN LFLGKIDIIE KQRMEFIKEV   720
LGFEEYLFDD KIIDRSKFAD TATHISFGEI VGELIGKGWD KDKLTKLEYA RNKALHGEIP   780
EATSFNEAKQ LINELKK                                                   797

SEQ ID NO: 24             moltype = AA length = 792
FEATURE                   Location/Qualifiers
REGION                    1..792
                          note = Synthetic Sequence
source                    1..792
                          mol_type = protein
                          organism = synthetic construct
SEQUENCE: 24
MSPDFIKLEK QEAAFYFNQT ELNLKAIESN ILDKQQRMIL LNNPRILAKV GNFIFNFRDV    60
TKNAKGEIDC LLFKLEELRN FYSHYVHTDN VKELSNGEKP LLERYYQIAI QATRSEDVKF   120
ELFETRNENK ITDAGVLFFL CMFLKKSQAN KLISGISGFK RNDPTGQPRR NLFTYFSARE   180
GYKALPDMQK HFLLFTLVNY LSNQDEYISE LKQYGEIGQG AFFNRIASTF LNISGISGNT   240
KFYSYQSKRI KEQRGELNSE KDSFEWIEPF QGNSYFEING HKGVIGEDEL KELCYALLVA   300
KQDINAVEGK IMQFLKKFRN TGNLQQVKDD EMLEIEYFPA SYFNESKKED IKKEILGRLD   360
KKIRSCSAKA EKAYDKMKEV MEFINNSLPA EEKLKRKDYR RYLKMVRFWS REKGNIEREF   420
RTKEWSKYFS SDFWRKNNLE DVYKLATQKN AELFKNLKAA AEKMGETEFE KYQQINDVKD   480
LASLRRLTQD FGLKWEEKDW EEYSEQIKKQ ITDRQKLTIM KQRVTAELKK KYGIENLNLR   540
ITIDSNKSRK AVLNRIAIPR GFVKKHILGW QGSEKISKNI REAECEILLS KKYEELSRQF   600
FEAGNFDKLT QINGLYEKNK LTAFMSVYLM GRLNIQLNKH TELGNLKKTE VDFKISDKVT   660
EKIPFSQYPS LVYAMSREKY VDNVDKYKFSH QDKKKPFLGK IDSIEKERIE FIKEVLDFEE   720
YLFKNKVIDK SKFSDTATHI SFKEICDEMG KKGCNRNKLT ELNNARNAAL HGEIPSETSF   780
REAKPLINEL KK                                                        792
```

```
SEQ ID NO: 25          moltype = AA   length = 803
FEATURE                Location/Qualifiers
REGION                 1..803
                       note = Synthetic Sequence
source                 1..803
                       mol_type = protein
                       organism = synthetic construct
SEQUENCE: 25
MNAIELKKEE AAFYFNQARL NISGLDEIIE KQLPHIGSNR ENAKKTVDMI LDNPEVLKKM   60
ENYVFNSRDI AKNARGELEA LLLKLVELRN FYSHYVHKDD VKTLSYGEKP LLDKYYEIAI  120
EATGSKDVRL EIIDDKNKLT DAGVLFLLCM FLKKSEANKL ISSIRGFKRN DKEGQPRRNL  180
FTYYSVREGY KVVPDMQKHF LLFTLVNHLS NQDEYISNLR PNQEIGQGGF FHRIASKFLS  240
DSGILHSMKF YTYRSKRLTE QRGELKPKKD HFTWIEPFQG NSYFSVQGQK GVIGEEQLKE  300
LCYVLLVARE DFRAVEGKVT QFLKKFQNAN NVQQVEKDEV LEKEYFPANY FENRDVGRVK  360
DKILNRLKKI TESYKAKGRE VKAYDKMKEV MEFINNCLPT DENLKLKDYR RYLKMVRFWG  420
REKENIKREF DSKKWERFLP RELWQKRNLE DAYQLAKEKN TELFNKLKTT VERMNELEFE  480
KYQQINDAKD LANLRQLARD FGVKWEEKDW QEYSGQIKKQ ITDRQKLTIM KQRITAALKK  540
KQGIENLNLR ITTDTNKSRK VVLNRIALPK GFVRKHILKT DIKISKQIRQ SQCPIILSNN  600
YMKLAKEFFE ERNFDKMTQI NGLFEKNVLI AFMIVYLMEQ LNLRLGKNTE LSNLKKTEVN  660
FTITDKVTEK VQISQYPSLV FAINREYVDG ISGYKLPPKK PKEPPYTFFE KIDAIEKERM  720
EPIKQVLGFE EHLFEKNVID KTRFTDTATH ISFNEICDEL IKKGWDENKI IKLKDARNAA  780
LHGKIPEDTS FDEAKVLINE LKK                                         803

SEQ ID NO: 26          moltype = AA   length = 811
FEATURE                Location/Qualifiers
REGION                 1..811
                       note = Synthetic Sequence
source                 1..811
                       mol_type = protein
                       organism = synthetic construct
SEQUENCE: 26
MTKSLLLWRY LIMNIIKLKK EEAAFYFNQT ILNLSGLDEI IEKQIPHIIS NKENAKKVID   60
KIFNNRLLLK SVENYIYNFK DVAKNARTEI EAILLKLVEL RNFYSHYVHN DTVKILSNGE  120
KPILEKYYQI AIEATGSKNV KLVIIENNNC LTDSGVLFLL CMFLKKSQAN KLISSVSGFK  180
RNDKEGQPRR NLFTYYSVRE GYKVVPDMQK HFLLFALVNH LSEQDDHIEK QQQSDELGKG  240
LFFHRIASTF LNESGIFNKM QFYTYQSNRL KEKRGELKHE KDTFTWIEPF QGNSYFTLNG  300
HKGVISEDQL KELCYTILIE KQNVDSLEGK IIQFLKKFQN KVSSKQQVDED ELLKREYFPA  360
NYFGRAGTGT LKEKILNRLD KRMDPTSKVT DKAYDKMIEV MEFINMCLPS DEKLRQKDYR  420
RYLKMVRFWN KEKHNIKREF DSKKWTRFLP TELWNKRNLE EAYQLARKEN KKKLEDMRNQ  480
VRSLKENDLE KYQQINYVND LENLRLLSQE LGVKWQEKDW VEYSGQIKKQ ISDNQKLTIM  540
KQRITAELKK MHGIENLNLR ISIDTNKSRQ TVMNRIALPK GFVKNHIQQN SSEKISKRIR  600
EDYCKIELSG KYEELSRQFF DKKNFDKMTL INGLCEKNKL IAFMVIYLLE RLGFELKEKT  660
KLGELKQTRM TYKISDKVKE DIPLSYYPKL VYAMNRKYVD NIDSYAFAAY ESKKAILDKV  720
DIIEKQRMEF IKQVLCFEEY IFENRIIEKS KFNDEETHIS FTQIHDELIK KGRDTEKLSK  780
LKHARNKALH GEIPDGTSFE KAKLLINEIK K                                 811

SEQ ID NO: 27          moltype = AA   length = 1000
FEATURE                Location/Qualifiers
REGION                 1..1000
                       note = Synthetic Sequence
source                 1..1000
                       mol_type = protein
                       organism = synthetic construct
SEQUENCE: 27
MSPKKKRKVE ASIEKKKSFA KGMGVKSTLV SGSKVYMTTF AEGSDARLEK IVEGDSIRSV   60
NEGEAFSAEM ADKNAGYKIG NAKFSHPKGY AVVANNPLYT GPVQQDMLGL KETLEKRYFG  120
ESADGNDNIC IQVIHNILDI EKILAEYITN AAYAVNNISG LDKDIIGFGK FSTVYTYDEF  180
KDPEHHRAAF NNNDKLINAI KAQYDEFDNF LDNPRLGYFG QAFFSKEGRN YIINYGNECY  240
DILALLSGLR HWVVHNNEEE SRISRTWLYN LDKNLDNEYI STLNYLYDRI TNELTNSFSK  300
NSAANVNYIA ETLGINPAEF AEQYFRFSIM KEQKNLGFNI TKLREVMLDR KDMSEIRKNH  360
KVFDSIRTKV YTMMDFVIYR YYIEEDAKVA AANKSLPDNE KSLSEKDIFV INLRGSFNDD  420
QKDALYYDEA NRIWRKLENI MHNIKEFRGN KTREYKKKDA PRLPRILPAG RDVSAFSKLN  480
YALTMFLDGK EINDLLTTLI NKFDNIQSFL KVMPLIGVNA KFVEEYAFFK DSAKIADELR  540
LIKSFARMGE PIADARRAMY IDAIRILGTN LSYDELKALA DTFSLDENGN KLKKGKHGMR  600
NFIINNVISN KRFHYLIRYG DPAHLHEIAK NEAVVKFVLG RIADIQKKQG QNGKNQIDRY  660
YETCIGKDKG KSVSEKVDAL TKIITGMNYD QFDKKRSVIE DTGRENAERE KFKKIISLYL  720
TVIYHILKNI VNINARYVIG FHCVERDAQL YKEKGYDINL KKLEEKGFSS VTKLCAGIDE  780
TAPDKRKDVE KEMAERAKES IDSLESANPK LYANYIKYSD EKKAEEFTRQ INREKAKTAL  840
NAYLRNTKWN VIIREDLLRI DNKTCTLFRN KAVHLEVARY VHAYINDIAE VNSYFQLYHY  900
IMQRIIMNER YEKSSGKVSE YFDAVNDEKK YNDRLLKLLC VPFGYCIPRF KNLSIEALFD  960
RNEAAKFDKE KKKVSGNSGS GPKKKRKVAA AYPYDVPDYA                       1000

SEQ ID NO: 28          moltype = DNA   length = 36
FEATURE                Location/Qualifiers
source                 1..36
                       mol_type = other DNA
                       organism = synthetic construct
SEQUENCE: 28
```

```
gttagaatat aacccctgttt gtagggtaa taaaac                          36

SEQ ID NO: 29           moltype = DNA   length = 36
FEATURE                 Location/Qualifiers
source                  1..36
                        mol_type = other DNA
                        organism = synthetic construct
SEQUENCE: 29
gttagaatat aacccctgttt gtagggtaa taaaac                          36

SEQ ID NO: 30           moltype = DNA   length = 36
FEATURE                 Location/Qualifiers
source                  1..36
                        mol_type = other DNA
                        organism = synthetic construct
SEQUENCE: 30
gttggaatat aaccccgttt gtagggtaa taaaac                           36

SEQ ID NO: 31           moltype = DNA   length = 36
FEATURE                 Location/Qualifiers
source                  1..36
                        mol_type = other DNA
                        organism = synthetic construct
SEQUENCE: 31
gttagaatat aacccctgttt gtagggtaa taaaac                          36

SEQ ID NO: 32           moltype = AA    length = 6
FEATURE                 Location/Qualifiers
VARIANT                 4
                        note = X is any naturally occurring amino acid
source                  1..6
                        mol_type = protein
                        organism = synthetic construct
SEQUENCE: 32
KKRXKR                                                            6

SEQ ID NO: 33           moltype = AA    length = 7
FEATURE                 Location/Qualifiers
VARIANT                 5
                        note = X is any naturally occurring amino acid
source                  1..7
                        mol_type = protein
                        organism = synthetic construct
SEQUENCE: 33
KRKRXKR                                                           7

SEQ ID NO: 34           moltype = AA    length = 9
FEATURE                 Location/Qualifiers
REGION                  1..9
                        note = Synthetic Sequence
source                  1..9
                        mol_type = protein
                        organism = synthetic construct
SEQUENCE: 34
PAAKRVKLD                                                         9

SEQ ID NO: 35           moltype = AA    length = 16
FEATURE                 Location/Qualifiers
REGION                  1..16
                        note = Synthetic Sequence
source                  1..16
                        mol_type = protein
                        organism = synthetic construct
SEQUENCE: 35
KRPAATKKAG QAKKKK                                                16

SEQ ID NO: 36           moltype = AA    length = 7
FEATURE                 Location/Qualifiers
source                  1..7
                        mol_type = protein
                        organism = synthetic construct
SEQUENCE: 36
PKKKRKV                                                           7

SEQ ID NO: 37           moltype = AA    length = 24
FEATURE                 Location/Qualifiers
REGION                  1..24
                        note = Synthetic Sequence
source                  1..24
```

```
                         mol_type = protein
                         organism = synthetic construct
SEQUENCE: 37
DPKKKRKVDP KKKRKVDPKK KRKV                                            24

SEQ ID NO: 38            moltype = AA   length = 16
FEATURE                  Location/Qualifiers
REGION                   1..16
                         note = Synthetic Sequence
source                   1..16
                         mol_type = protein
                         organism = synthetic construct
SEQUENCE: 38
RQIKIWFQNR RMKWKK                                                     16

SEQ ID NO: 39            moltype = AA   length = 187
FEATURE                  Location/Qualifiers
REGION                   1..187
                         note = Synthetic Sequence
source                   1..187
                         mol_type = protein
                         organism = synthetic construct
SEQUENCE: 39
MDPHIFTSNF NNGIGRHKTY LCYEVERLDN GTSVKMDQHR GFLHNQAKNL LCGFYGRHAE      60
LRFLDLVPSL QLDPAQIYRV TWFISWSPCF SWGCAGEVRA FLQENTHVRL RIFAARIYDY     120
DPLYKEALQM LRDAGAQVSI MTYDEFKHCW DTFVDHQGCP FQPWDGLDEH SQALSGRLRA     180
ILQNQGN                                                              187

SEQ ID NO: 40            moltype = AA   length = 190
FEATURE                  Location/Qualifiers
REGION                   1..190
                         note = Synthetic Sequence
source                   1..190
                         mol_type = protein
                         organism = synthetic construct
SEQUENCE: 40
MDPDTFTFNF NNDPLVLRRR QTYLCYEVER LDNGTWVLMD QHMGFLCNEA KNLLCGFYGR      60
HAELRFLDLV PSLQLDPAQI YRVTWFISWS PCFSWGCAGE VRAFLQENTH VRLRIFAARI     120
YDYDPLYKEA LQMLRDAGAQ VSIMTYDEFE YCWDTFVYRQ GCPFQPWDGL EEHSQALSGR     180
LRAILQNQGN                                                           190

SEQ ID NO: 41            moltype = AA   length = 236
FEATURE                  Location/Qualifiers
REGION                   1..236
                         note = Synthetic Sequence
source                   1..236
                         mol_type = protein
                         organism = synthetic construct
SEQUENCE: 41
MTSEKGPSTG DPTLRRRIEP WEFDVFYDPR ELRKEACLLY EIKWGMSRKI WRSSGKNTTN      60
HVEVNFIKKF TSERDFHPSM SCSITWFLSW SPCWECSQAI REFLSRHPGV TLVIYVARLF     120
WHMDQQNRQG LRDLVNSGVT IQIMRASEYY HCWRNFVNYP PGDEAHWPQY PPLWMMLYAL     180
ELHCIILSLP PCLKISRRWQ NHLTFFRLHL QNCHYQTIPP HILLATGLIH PSVAWR         236

SEQ ID NO: 42            moltype = AA   length = 190
FEATURE                  Location/Qualifiers
REGION                   1..190
                         note = Synthetic Sequence
source                   1..190
                         mol_type = protein
                         organism = synthetic construct
SEQUENCE: 42
MNPQIRNPMK AMYPGTFYFQ FKNLWEANDR NETWLCFTVE GIKRRSVVSW KTGVFRNQVD      60
SETHCHAERC FLSWFCDDIL SPNTKYQVTW YTSWSPCPDC AGEVAEFLAR HSNVNLTIFT     120
ARLYYFQYPC YQEGLRSLSQ EGVAVEIMDY EDFKYCWENF VYNDNEPFKP WKGLKTNFRL     180
LKRRLRESLQ                                                           190

SEQ ID NO: 43            moltype = AA   length = 386
FEATURE                  Location/Qualifiers
REGION                   1..386
                         note = Synthetic Sequence
source                   1..386
                         mol_type = protein
                         organism = synthetic construct
SEQUENCE: 43
MNPQIRNPME RMYRDTFYDN FENEPILYGR SYTWLCYEVK IKRGRSNLLW DTGVFRGPVL      60
PKRQSNHRQE VYFRFENHAE MCFLSWFCGN RLPANRRFQI TWFVSWNPCL PCVVKVTKFL     120
AEHPNVTLTI SAARLYYYRD RDWRWVLLRL HKAGARVKIM DYEDFAYCWE NFVCNEGQPF     180
MPWYKFDDNY ASLHRTLKEI LRNPMEAMYP HIFYFHFKNL LKACGRNESW LCFTMEVTKH     240
```

```
HSAVFRKRGV FRNQVDPETH CHAERCFLSW FCDDILSPNT NYEVTWYTSW SPCPECAGEV    300
AEFLARHSNV NLTIFTARLC YFWDTDYQEG LCSLSQEGAS VKIMGYKDFV SCWKNFVYSD    360
DEPFKPWKGL QTNFRLLKRR LREILQ                                        386

SEQ ID NO: 44           moltype = AA  length = 373
FEATURE                 Location/Qualifiers
REGION                  1..373
                        note = Synthetic Sequence
source                  1..373
                        mol_type = protein
                        organism = synthetic construct
SEQUENCE: 44
MKPHFRNTVE RMYRDTFSYN FYNRPILSRR NTVWLCYEVK TKGPSRPRLD AKIFRGQVYS     60
QPEHHAEMCF LSWFCGNQLP AYKCFQITWF VSWTPCPDCV AKLAEFLAEH PNVTLTISAA    120
RLYYYWERDY RRALCRLSQA GARVKIMDDE EFAYCWENFV YSEGQPFMPW YKFDDNYAFL    180
HRTLKEILRN PMEAMYPHIF YFHFKNLRKA YGRNESWLCF TMEVVKHHSP VSWKRGVFRN    240
QVDPETHCHA ERCFLSWFCD DILSPNTNYE VTWYTSWSPC PECAGEVAEF LARHSNVNLT    300
IFTARLYYFW DTDYQEGLRS LSQEGASVEI MGYKDFKYCW ENFVYNDDEP FKPWKGLKYN    360
FLFLDSKLQE ILE                                                      373

SEQ ID NO: 45           moltype = AA  length = 384
FEATURE                 Location/Qualifiers
REGION                  1..384
                        note = Synthetic Sequence
source                  1..384
                        mol_type = protein
                        organism = synthetic construct
SEQUENCE: 45
MKPHFRNTVE RMYRDTFSYN FYNRPILSRR NTVWLCYEVK TKGPSRPPLD AKIFRGQVYS     60
ELKYHPEMRF FHWFSKWRKL HRDQEYEVTW YISWSPCTKC TRDMATFLAE DPKVTLTIFV    120
ARLYYFWDPD YQEALRSLCQ KRDGPRATMK IMNYDEFQHC WSKFVYSQRE LFEPWNNLPK    180
YYILLHIMLG EILRHSMDPP TFTFNFNNEP WVRGRHETYL CYEVERMHND TWVLLNQRRG    240
FLCNQAPHKH GFLEGRHAEL CFLDVIPFWK LDLDQDYRVT CFTSWSPCFS CAQEMAKFIS    300
KNKHVSLCIF TARIYDDQGR CQEGLRTLAE AGAKISIMTY SEFKHCWDTF VDHQGCPFQP    360
WDGLDEHSQD LSGRLRAILQ NQEN                                          384

SEQ ID NO: 46           moltype = AA  length = 183
FEATURE                 Location/Qualifiers
REGION                  1..183
                        note = Synthetic Sequence
source                  1..183
                        mol_type = protein
                        organism = synthetic construct
SEQUENCE: 46
MALLTAETFR LQFNNKRRLR RPYYPRKALL CYQLTPQNGS TPTRGYFENK KKCHAEICFI     60
NEIKSMGLDE TQCYQVTCYL TWSPCSSCAW ELVDFIKAHD HLNLGIFASR LYYHWCKPQQ    120
KGLRLLCGSQ VPVEVMGFPE FADCWENFVD HEKPLSFNPY KMLEELDKNS RAIKRRLERI    180
KQS                                                                 183

SEQ ID NO: 47           moltype = AA  length = 16
FEATURE                 Location/Qualifiers
VARIANT                 5
                        note = X is any naturally occurring amino acid
source                  1..16
                        mol_type = protein
                        organism = synthetic construct
SEQUENCE: 47
SGGSXTENSG GSSGGS                                                    16

SEQ ID NO: 48           moltype = AA  length = 166
FEATURE                 Location/Qualifiers
REGION                  1..166
                        note = Synthetic Sequence
source                  1..166
                        mol_type = protein
                        organism = synthetic construct
SEQUENCE: 48
SEVEFSHEYW MRHALTLAKR ARDEREVPVG AVLVLNNRVI GEGWNRAIGL HDPTAHAEIM     60
ALRQGGLVMQ NYRLIDATLY VTFEPCVMCA GAMIHSRIGR VVFGVRNAKT GAAGSLMDVL    120
HYPGMNHRVE ITEGILADEC AALLCYFFRM PRQVFNAQKK AQSSTD                   166

SEQ ID NO: 49           moltype = AA  length = 167
FEATURE                 Location/Qualifiers
REGION                  1..167
                        note = Synthetic Sequence
source                  1..167
                        mol_type = protein
                        organism = synthetic construct
SEQUENCE: 49
```

```
MSEVEFSHEY WMRHALTLAK RAWDEREVPV GAVLVLNNRV IGEGWNRSIG LHDPTAHAEI    60
MALRQGGLVM QNYRLIDATL YVTFEPCVMC AGAMIHSRIG RVVFGVRNAK TGAAGSLMDV   120
LHYPGMNHRV EITEGILADE CAALLCYFFR MRRQVFNAQK KAQSSTD                167

SEQ ID NO: 50           moltype = AA   length = 167
FEATURE                 Location/Qualifiers
REGION                  1..167
                        note = Synthetic Sequence
source                  1..167
                        mol_type = protein
                        organism = synthetic construct
SEQUENCE: 50
MSEVEFSHEY WMRHALTLAK RALDEREVPV GAVLVLNNRV IGEGWNRAIG LHDPTAHAEI    60
MALRQGGLVM QNYRLIDATL YVTFEPCVMC AGAMIHSRIG RVVFGVRNAK TGAAGSLMDV   120
LHYPGMNHRV EITEGILADE CNALLCYFFR MRRQVFNAQK KAQSSTD                167

SEQ ID NO: 51           moltype = AA   length = 167
FEATURE                 Location/Qualifiers
REGION                  1..167
                        note = Synthetic Sequence
source                  1..167
                        mol_type = protein
                        organism = synthetic construct
SEQUENCE: 51
MSEVEFSHEY WMRHALTLAK RALDEREVPV GAVLVLNNRV IGEGWNRAIG LHDPTAHAEI    60
MALRQGGLVM QNYRLIDATL YVTFEPCVMC AGAMIHSRIG RVVFGVRNAK TGAAGSLMDV   120
LHYPGMNHRV EITEGILADE CNALLCYFFR MPRQVFNAQK KAQSSTD                167

SEQ ID NO: 52           moltype = AA   length = 167
FEATURE                 Location/Qualifiers
REGION                  1..167
                        note = Synthetic Sequence
source                  1..167
                        mol_type = protein
                        organism = synthetic construct
SEQUENCE: 52
MSEVEFSHEY WMRHALTLAK RARDEREVPV GAVLVLNNRV IGEGWNRAIG LHDPTAHAEI    60
MALRQGGLVM QNYRLIDATL YVTFEPCVMC AGAMIHSRIG RVVFGVRNSK RGAAGSLMNV   120
LNYPGMNHRV EITEGILADE CAALLCDFYR MPRQVFNAQK KAQSSIN                167

SEQ ID NO: 53           moltype = AA   length = 1226
FEATURE                 Location/Qualifiers
REGION                  1..1226
                        note = Synthetic Sequence
source                  1..1226
                        mol_type = protein
                        organism = synthetic construct
SEQUENCE: 53
MNPRQGYSLS GYYTHPFQGY EHRQLRYQQP GPGSSPSSFL LKQIEFLKGQ LPEAPVIGKQ    60
TPSLPPSLPG LRPRFPVLLA SSTRGRQVDI RGVPRGVHLR SQGLQRGFQH PSPRGRSLPQ   120
RGVDCLSSHF QELSIYQDQE QRILKFLEEL GEGKATTAHD LSGKLGTPKK EINRVLYSLA   180
KKGKLQKEAG TPPLWKIAVS TQAWNQHSGV VRPDGHSQGA PNSDPSLEPE DRNSTSVSED   240
LLEPFIAVSA QAWNQHSGVV RPDSHSQGSP NSDPGLEPED SNSTSALEDP LEFLDMAEIK   300
EKICDYLFNV SDSSALNLAK NIGLTKARDI NAVLIDMERQ GDVYRQGTTP PIWHLTDKKR   360
ERMQIKRNTN SVPETAPAAI PETKRNAEFL TCNIPTSNAS NNMVTTEKVE NGQEPVIKLE   420
NRQEARPEPA RLKPPVHYNG PSKAGYVDFE NGQWATDDIP DDLNSIRAAP GEFRAIMEMP   480
SFYSHGLPRC SPYKKLTECQ LKNPISGLLE YAQFASQTCE FNMIEQSGPP HEPRFKFQVV   540
INGREFPPAE AGSKKVAKQD AAMKAMTILL EEAKAKDSGK SEESSHYSTE KESEKTAESQ   600
TPTPSATSFF SGKSPVTTLL ECMHKLGNSC EFRLLSKEGP AHEPKFQYCV AVGAQTFPSV   660
SAPSKKVAKQ MAAEEAMKAL HGEATNSMAS DNQPEGMISE SLDNLESMMP NKVRKIGELV   720
RYLNTNPVGG LLEYARSHGF AAEFKLVDQS GPPHEPKFVY QAKVGGRWFP AVCAHSKKQG   780
KQEAADAALR VLIGENEKAE RMGFTEVTPV TGASLRRTML LLSRSPEAQP KTLPLTGSTF   840
HDQIAMLSHR CFNTLTNSFQ PSLLGRKILA AIIMKKDSED MGVVVSLGTG NRCVKGDSLS   900
LKGETVNDCH AEIISRRGFI RFLYSELMKY NSQTAKDSIF EPAKGGEKLQ IKKTVSFHLY   960
ISTAPCGDGA LFDKSCSDRA MESTESRHYP VFENPKQGKL RTKVENGEGT IPVESSDIVP  1020
TWDGIRLGER LRTMSCSDKI LRWNVLGLQG ALLTHFLQPI YLKSVTLGYL FSQGHLTRAI  1080
CCRVTRDGSA FEDGLRHPFI VNHPKVGRVS IYDSKRQSGK TKETSVNWCL ADGYDLEILD  1140
GTRGTVDGPR NELSRVSKKN IFLLFKKLCS FRYRRDLLRL SYGEAKKAAR DYETAKNYFK  1200
KGLKDMGYGN WISKPQEEKN FYLCPV                                      1226

SEQ ID NO: 54           moltype = AA   length = 701
FEATURE                 Location/Qualifiers
REGION                  1..701
                        note = Synthetic Sequence
source                  1..701
                        mol_type = protein
                        organism = synthetic construct
SEQUENCE: 54
MDIEDEENMS SSSTDVKENR NLDNVSPKDG STPGPGEGSQ LSNGGGGGPG RKRPLEEGSN    60
```

```
GHSKYRLKKR  RKTPGPVLPK  NALMQLNEIK  PGLQYTLLSQ  TGPVHAPLFV  MSVEVNGQVF   120
EGSGPTKKKA  KLHAAEKALR  SFVQFPNASE  AHLAMGRTLS  VNTDFTSDQA  DFPDTLFNGF   180
ETPDKAEPPF  YVGSNGDDSF  SSSGDLSLSA  SPVPASLAQP  PLPVLPPFPP  PSGKNPVMIL   240
NELRPGLKYD  FLSESGESHA  KSFVMSVVVD  GQFFEGSGRN  KKLAKARAAQ  SALAAIFNLH   300
LDQTPSRQPI  PSEGLQLHLP  QVLADAVSRL  VLGKFGDLTD  NFSSPHARRK  VLAGVVMTTG   360
TDVKDAKVIS  VSTGTKCING  EYMSDRGLAL  NDCHAEIISR  RSLLRFLYTQ  LELYLNNKDD   420
QKRSIFQKSE  RGGFRLKENV  QFHLYISTSP  CGDARIFSPH  EPILEEPADR  HPNRKARGQL   480
RTKIESGEGT  IPVRSNASIQ  TWDGVLQGER  LLTMSCSDKI  ARWNVVGIQG  SLLSIFVEPI   540
YFSSIILGSL  YHGDHLSRAM  YQRISNIEDL  PPLYTLNKPL  LSGISNAEAR  QPGKAPNFSV   600
NWTVGDSAIE  VINATTGKDE  LGRASRLCKH  ALYCRWMRVH  GKVPSHLLRS  KITKPNVYHE   660
SKLAAKEYQA  AKARLFTAFI  KAGLGAWVEK  PTEQDQFSLT  P                        701

SEQ ID NO: 55               moltype = AA  length = 677
FEATURE                     Location/Qualifiers
REGION                      1..677
                            note = Synthetic Sequence
source                      1..677
                            mol_type = protein
                            organism = synthetic construct
SEQUENCE: 55
TLNIEDEYRL  HETSKEPDVS  LGSTWLSDFP  QAWAETGGMG  LAVRQAPLII  PLKATSTPVS    60
IKQYPMSQEA  RLGIKPHIQR  LLDQGILVPC  QSPWNTPLFD  VKKPGTNDYR  PVQDLREVNK   120
RVEDIHPTVP  NPYNLLSGLP  PSHQWYTVLD  LKDAFFCLRL  HPTSQPLFAF  EWRDPEMGIS   180
GQLTWTRLPQ  GFKNSPTLFD  EALHRDLADF  RIQHPDLILL  QYVDDLLLAA  TSELDCQQGT   240
RALLQTLGNL  GYRASAKKAQ  ICQKQVKYLG  YLLKEGQRWL  TEARKETVMG  QPTPKTPRQL   300
REFLGTAGFC  RLWIPGFAEM  AAPLYPLTKT  GTLFNWGPDQ  QKAYQEIKQA  LLTAPALGLP   360
DLTKPFELFV  DEKQGYAKGV  LTQKLGPWRR  PVAYLSKKLD  PVAAGWPPCL  RMVAAIAVLT   420
KDAGKLTMGQ  PLVILAPHAV  EALVKQPPDR  WLSNARMTHY  QALLLDTDRV  QFGPVVALNP   480
ATLLPLPEEG  LQHNCLDILA  EAHGTRPDLT  DQPLPDADHT  WYTDGSSLLQ  EGQRKAGAAV   540
TTETEVIWAK  ALPAGTSAQR  AELIALTQAL  KMAEGKKLNV  YTDSRYAFAT  AHIHGEIYRR   600
RGLLTSEGKE  IKNKDEILAL  LKALFLPKRL  SIIHCPGHQK  GHSAEARGNR  MADQAARKAA   660
ITETPDTSTL  LIENSSP                                                     677

SEQ ID NO: 56               moltype = AA  length = 560
FEATURE                     Location/Qualifiers
VARIANT                     229
                            note = X is any naturally occurring amino acid
source                      1..560
                            mol_type = protein
                            organism = synthetic construct
SEQUENCE: 56
APFLERPDWD  YTTQAGRNHL  VHYRQLLLAG  LQNAGRSPTN  LAKVKGITQG  PNESPSAFLE    60
RLKEAYRRYT  PYDPEDPGQE  TNVSMSFIWQ  SAPDIGRKLG  RLEDLKSKTL  GDLVREAEKI   120
FNKRETPEER  EERIRRETEE  KEERRRTVDE  QKEKERDRRR  HREMSKLLAT  VVIGQEQDRQ   180
EGERKRPQLD  KDQCAYCKEK  GHWAKDCPKK  PRGPRGPRPQ  TSLLTLGDXG  GQGQDPPPEP   240
RITLKVGGQP  VTFLVDTGAQ  HSVLTQNPGP  LSDKSAWVQG  ATGGKRYRWT  TDRKVHLATG   300
KVTHSFLHVP  DCPYPLLGRD  LLTKLKAQIH  FEGSGAQVVG  PMGQPLQVLT  LNIEDEYRLH   360
ETSKEPDVSL  GFTWLSDFPQ  AWAESGGMGL  AVRQAPLIIP  LKATSTPVSI  KQYPMSQEAR   420
LGIKPHIQRL  LDQGILVPCQ  SPWNTPLLPV  KKPGTNDYRP  VQDLREVNKR  VEDIHPTVPN   480
PYNLLSGLPP  SHQWYTVLDL  KDAFFCLRLH  PTSQPLFAFE  WRDPEMGISG  QLTWTRLPQG   540
FKNSPTLFDE  ALHRDLADFR                                                  560

SEQ ID NO: 57               moltype = AA  length = 215
FEATURE                     Location/Qualifiers
REGION                      1..215
                            note = Synthetic Sequence
source                      1..215
                            mol_type = protein
                            organism = synthetic construct
SEQUENCE: 57
MYRRHLKHSR  VKNLFKFVSA  KMNTVFTVES  ALEFDTCFHL  EYSPSVKFYE  AQPEGFYYEF    60
AGRQCPYTPD  FRLVDQNDSV  SFLEIKPSDK  VADPDFLHRF  PLKQQRAIEL  SSPLKLVTEK   120
QIRIDPILGN  LKLLHRYSGF  QSFTPLHMQL  LGLVQKLGRV  SLLRLSDSID  APPEEVLASA   180
LSLIARGIMQ  SDLTVQKIGI  SSFVWAGGHS  GIDHG                               215

SEQ ID NO: 58               moltype = AA  length = 624
FEATURE                     Location/Qualifiers
REGION                      1..624
                            note = Synthetic Sequence
source                      1..624
                            mol_type = protein
                            organism = synthetic construct
SEQUENCE: 58
MDKHNGGLFE  DEFVIPQPST  STSPIDAIQA  VLPATVDSFP  YVLKVEALHR  RDYILWVEKN    60
LAGGWTEKNL  TPLLADAALV  LPPPTPNWRT  LARWRKIYIQ  HGRKLVSLIP  KHQAKGNARS   120
RLPPSDELFF  EQAVHRYLVG  EQPSIASAFQ  LYSDSIRIEN  LGVVENSIKT  ISYMAFYNRI   180
KKLPAYQVMK  SRKGSYIADV  EFKAIASHKP  PSRIMERVEI  DHTPLDLLLL  DDDLLVPLGR   240
PSLTLLIDAY  SHCVVGFNLN  FNQPSYESVR  NALLSSISKK  DYVKNKYPSI  EHEWPCYGKP   300
ETLVVDNGVE  FWSASLAQSC  LELGINIQYN  PVRKPWLKPM  IERMFGIINR  KLLEPIPGKT   360
```

```
                                     -continued

FSNIQEKGDY  DPQKDAVMRF  STFLEIFHHW  VIDVYHYEPD  SRYRYIPIIS  WQHGNKDAPP   420
APIIGDDLTK  LEVILSLSLH  CTHRRGGIQR  YHLRYDSDEL  ASYRMNYPDQ  TRGKRKVLVK   480
LNPRDISYVY  VFLEDLGSYI  RVPCIDPIGY  TKGLSLQEHQ  INVKLHRDFI  NEQMDVVSLS   540
KARIYLNDRI  KNELIEVRRN  IRQRNVKGVN  KIAKYRNVGS  HAETSIVHEL  NHPATNEVIS   600
KMESASQPEH  CDDWDNFTSG  LEPY                                             624

SEQ ID NO: 59           moltype = AA  length = 335
FEATURE                 Location/Qualifiers
REGION                  1..335
                        note = Synthetic Sequence
source                  1..335
                        mol_type = protein
                        organism = synthetic construct
SEQUENCE: 59
MDLSCHDADK  LRSFIECYVE  TPLLRAIQED  FDRLRFNKQF  AGEPQCMLLT  GDTGTGKSSL    60
IRHYAAKHPE  QVRHGFIHKP  LLVSRIPSRP  TLESTMVELL  KDLGQFGSSD  RIHKSSAESL   120
TEALIKCLKR  CETELIIIDA  FQELIENKTR  EKRNQIANRL  KYISETAKIP  IVLVGMPWAT   180
KIAEEPQWSS  RLLIRRSIPY  FKLSDDRENF  IRLIMGLANR  MPFETQARLE  TKHTIYALFA   240
ACYGSLRALK  QLLDESVKQA  LAAHAETLKH  EHIAVAYALF  YPDQVNPFLQ  PIDEIKACEV   300
KQYSRYEIDA  AGKEEVLNPL  QFTDKIPISQ  LLKKR                                335

SEQ ID NO: 60           moltype = AA  length = 167
FEATURE                 Location/Qualifiers
REGION                  1..167
                        note = Synthetic Sequence
source                  1..167
                        mol_type = protein
                        organism = synthetic construct
SEQUENCE: 60
MIEAPDVKPW  LFLIKPYEGE  SLSHFLGRFR  RANHLSASGL  GTLAGIGAIV  ARWERFHFNP    60
RPSQQELEAI  ASVVEVDAQR  LAQMLPPAGV  GMQHEPIRLC  GACYAESPCH  RIEWQYKSVW   120
KCDRHQLKIL  AKCPNCQAPF  KMPALWEDGC  CHRCRMPFAE  MAKLQKV                  167

SEQ ID NO: 61           moltype = AA  length = 10
FEATURE                 Location/Qualifiers
REGION                  1..10
                        note = Synthetic Sequence
source                  1..10
                        mol_type = protein
                        organism = synthetic construct
SEQUENCE: 61
GGSGGSGGSG                                                                10

SEQ ID NO: 62           moltype = AA  length = 16
FEATURE                 Location/Qualifiers
REGION                  1..16
                        note = Synthetic Sequence
source                  1..16
                        mol_type = protein
                        organism = synthetic construct
SEQUENCE: 62
GGSGGSGGGG  SGGGGS                                                        16

SEQ ID NO: 63           moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 63
GGGGS                                                                      5

SEQ ID NO: 64           moltype =     length =
SEQUENCE: 64
000

SEQ ID NO: 65           moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 65
GGGGS                                                                      5

SEQ ID NO: 66           moltype = AA  length = 8
FEATURE                 Location/Qualifiers
```

-continued

```
source                   1..8
                         mol_type = protein
                         organism = synthetic construct
SEQUENCE: 66
GGGGGGGG                                                                 8

SEQ ID NO: 67            moltype = AA   length = 6
FEATURE                  Location/Qualifiers
REGION                   1..6
                         note = Synthetic Sequence
source                   1..6
                         mol_type = protein
                         organism = synthetic construct
SEQUENCE: 67
GGGGGG                                                                   6

SEQ ID NO: 68            moltype = AA   length = 5
FEATURE                  Location/Qualifiers
REGION                   1..5
                         note = Synthetic Sequence
source                   1..5
                         mol_type = protein
                         organism = synthetic construct
SEQUENCE: 68
EAAAK                                                                    5

SEQ ID NO: 69            moltype = AA   length = 7
FEATURE                  Location/Qualifiers
REGION                   1..7
                         note = Synthetic Sequence
source                   1..7
                         mol_type = protein
                         organism = synthetic construct
SEQUENCE: 69
AEAAAKA                                                                  7

SEQ ID NO: 70            moltype = AA   length = 12
FEATURE                  Location/Qualifiers
REGION                   1..12
                         note = Synthetic Sequence
source                   1..12
                         mol_type = protein
                         organism = synthetic construct
SEQUENCE: 70
AEAAAKEAAA KA                                                           12

SEQ ID NO: 71            moltype = AA   length = 16
FEATURE                  Location/Qualifiers
REGION                   1..16
                         note = Synthetic Sequence
source                   1..16
                         mol_type = protein
                         organism = synthetic construct
SEQUENCE: 71
AEAAAKALEA EAAAKA                                                       16

SEQ ID NO: 72            moltype = AA   length = 5
FEATURE                  Location/Qualifiers
REGION                   1..5
                         note = Synthetic Sequence
source                   1..5
                         mol_type = protein
                         organism = synthetic construct
SEQUENCE: 72
PAPAP                                                                    5

SEQ ID NO: 73            moltype = AA   length = 18
FEATURE                  Location/Qualifiers
REGION                   1..18
                         note = Synthetic Sequence
source                   1..18
                         mol_type = protein
                         organism = synthetic construct
SEQUENCE: 73
KESGSVSSEQ LAQFRSLD                                                     18

SEQ ID NO: 74            moltype = AA   length = 14
FEATURE                  Location/Qualifiers
REGION                   1..14
```

```
                        note = Synthetic Sequence
source                  1..14
                        mol_type = protein
                        organism = synthetic construct
SEQUENCE: 74
EGKSSGSGSE SKST                                                     14

SEQ ID NO: 75           moltype = AA  length = 12
FEATURE                 Location/Qualifiers
REGION                  1..12
                        note = Synthetic Sequence
source                  1..12
                        mol_type = protein
                        organism = synthetic construct
SEQUENCE: 75
GSAGSAAGSG EF                                                       12

SEQ ID NO: 76           moltype = DNA  length = 82
FEATURE                 Location/Qualifiers
source                  1..82
                        mol_type = other DNA
                        organism = synthetic construct
SEQUENCE: 76
cgccccattg acgcaaatgg gcggtaggcg tgtacggtgg gaggtctata taagcagagc   60
tggtttagtg aaccgtcaga tc                                            82

SEQ ID NO: 77           moltype = AA  length = 22
FEATURE                 Location/Qualifiers
REGION                  1..22
                        note = Synthetic Sequence
source                  1..22
                        mol_type = protein
                        organism = synthetic construct
SEQUENCE: 77
GSGPKKKRKV AAAYPYDVPD YA                                            22

SEQ ID NO: 78           moltype = AA  length = 12
FEATURE                 Location/Qualifiers
REGION                  1..12
                        note = Synthetic Sequence
source                  1..12
                        mol_type = protein
                        organism = synthetic construct
SEQUENCE: 78
MSPKKKRKVE AS                                                       12

SEQ ID NO: 79           moltype = AA  length = 234
FEATURE                 Location/Qualifiers
REGION                  1..234
                        note = Synthetic Sequence
source                  1..234
                        mol_type = protein
                        organism = synthetic construct
SEQUENCE: 79
CAGCTCACAG ACATGATAAG ATACATTGAT GAGTTTGGAC AAACCACAAC TAGAATGCAG   60
TGAAAAAAAT GCTTTATTTG TGAAATTTGT GATGCTATTG CTTTATTTGT AACCATTATA  120
AGCTGCAATA AACAAGTTAA CAACAACAAT TGCATTCATT TTATGTTTCA GGTTCAGGGG  180
GAGGTGTGGG AGGTTTTTTA AAGCAAGTAA AACCTCTACA AATGTGGTAT TGGC        234

SEQ ID NO: 80           moltype = AA  length = 782
FEATURE                 Location/Qualifiers
source                  1..782
                        mol_type = protein
                        organism = synthetic construct
SEQUENCE: 80
MESNKNPSNR HSLPKVIISD VDKDNILEFK VKYEKLGRLD KFKIVSMKYE DRDIVFRDIV   60
SSDKSLEFSL ANSNREIIVN LDNKKYTIRG QRVDNNEEKA KKVQLILTDN IKDENGAIRE  120
TLTERELIDN SDSIYSKIAG RKINSSKDIY LIKRYLAYRS NLQFFYNPID KPFKIVDNKE  180
LWNIEFGNKH IEYFKFLIND NIKNANGYLY SYLQDNRRVK NDLYKTKDIF SKLRHALMHF  240
DYEFFDKLFN NENLELDLNI EFLNLTIQNI DKLNIDTKKS YIGNQKIKIY SEEIKLDELY  300
NLYNTISINR LGFNRLINSF FMQDGLENRK LKEFFNEEAN SEEIYFVDIH QNRDYKKLYI  360
KHKNFVAKLY GNRDGKSIAK LNRDISNIKK QMQEITDKNS TLRLEYKLRV AFGFIYTNYK  420
NYRHFKNSFD NDLKSGRFNN IDLSQIIEYY KNSYTNKDVL IRVTIKKIDK LNLNALIKDD  480
NLLKIILLIF TFIPNELKGK FLGFIKRYYH DIKHIDEDSK EELEFNDGLS TSLKLKILHK  540
NIRKLTILKY SLATESKYNK KDNYYYEDGH KTKRFLSSLG VSHNIEEFDK TIYTPFFKYY  600
SAMYKLINDF EIFALTQFDS SANLKEITMK EELKQDNEYN FKILLRETNL YDENIVKLRN  660
KISHIDGEFL FSNPLNRRIN ISSMREKITN FIDSKNIKKI LGYDALNDLS MKIIQQKTKL  720
EANANKDEKI NELIKNAQKA NDYYSIYKLK AIEGINKRLL KIIGETKQEK YIKDKIIKGN  780
NK                                                                 782
```

```
SEQ ID NO: 81            moltype = AA  length = 782
FEATURE                  Location/Qualifiers
source                   1..782
                         mol_type = protein
                         organism = synthetic construct
SEQUENCE: 81
MESNKNPSNR HSLPKVIISD VDKDNILEFK VKYEKLGRLD KFKIVSMKYE DRDIVFRDIV    60
SSDKSLEFSL ANSNREIIVN LDNKKYTIRG QRVDNNEEKA KKVQLILTDN IKDENGAIRE   120
TLTERELIDN SDSIYSKIAG RKINSSKDIY LIKRYLAYRS NLQFFYNFID KFFKIVDNKE   180
LWNIEFGNKH IEYFKPLIND NIKNANGYLY SYLQDNRRVK NDLYKTKDIF SKLRHALMHF   240
DYEFFDKLFN NENLELDLNI EFLNLTIQNI DKLNIDTKKS YIGNQKIKIY SEEIKLDELY   300
NLYNTISINR LGFNRLINSF FMQDGLENRK LKEFFNEEAN SEEIYFVDIH QNRDYKKLYI   360
KHKNFVAKLY GNRDGKTIAR LNRDISNIKK QMQEITDKNS TLRLEYKLRV AFGFIYTNYK   420
NYMHFENSFD NDLKSGRFNN IDLSKIIEYY KNSYTNKDVR IRVTIKKIDK LNLNALIKDD   480
NLLKIILLIF TFIPNELKGE FLGFIKRYYH DIKHIDEDSK EELEFNDGLS TSLKLKILHK   540
NIRKLTILKY SLATESKYNK KDNYYYEDGH KTKRFLSSLG VSHNIEEFDK TIYTPFFKYY   600
SAMYKLINDF EIFALTQFDS SANLKEITMK EELKQDNEYN FKILLRETNL YDENIVKLRN   660
KISHIDGEFL FSNPLNRRIN ISSMREKITN FIDSKNIKKI LGYDALNDLS MKIIQQKTKL   720
EANANKDEKI NELIKNAQKA NDYYSIYKLK AIEGINKRLL KIIGETKQEK YIKDKIIKGN   780
NK                                                                 782

SEQ ID NO: 82            moltype = AA  length = 782
FEATURE                  Location/Qualifiers
source                   1..782
                         mol_type = protein
                         organism = synthetic construct
SEQUENCE: 82
MESNKNPSNR HSLPKVIISD VDKDNILEFK VKYEKLGRLD KFKIVSMKYE DRDIVFRDIV    60
SSDKSLEFSL ANSNREIIVN LDNKKYTIRG QRVDNNEEKA KKVQLILTDN IKDENGAIRE   120
TLTERELIDN SDSIYSKIAG RKINSSKDIY LIKRYLAYRS NLQFFYNFID KFFKIVDNKE   180
LWNIEFDNKH IEYFKPLIND NIKNANGYLY SYLQDNRRVK NDLYKTKDIF SKLRHALMHF   240
DYEFFDKLFN NENLELDLNI EFLNFTIQNI DKLNIDTKKS YIGNQKIKIY SEEIKLDELY   300
NLYNTISINR LGFNRLINSF FMQDGLENRE LKKFFNEEAN SEEIYFVDIH QNRDYKKLYI   360
KHKNFVAKLY GNRDGKSIAK LNRDISNIKK QMQEITDKNS TLRLEYKLRV AFGFIYTNYK   420
NYRHFKNSFD NDLKSGRFNN IDLSKIIEYY KNSCTNKDVR IRVTIKKIDK LNLNALIKDD   480
NLLKIILLIF TFIPNELKGE FLGFIKRYYH DIKHIDEDSK EELEFNDGLS KSLKLKILHK   540
NIRKLTILKY SLATESKYNK KDNYYYEDGH KTKRFLSSLG VSHNIEEFDK TIYTPFFKYY   600
SAMYKLINDF EIFALTQFDS SANLKEITMK EELKQDNEYN FKILLRETNL YDENIVKLRN   660
KISHIDGEFL FSNPLNRRIN ISSMREKITN FIDSKNIKKI LGYDALNDLS MKIIQQKTKL   720
EANANKDEKI NELIKNAQKA NDYYSIYKLK AIEGINKRLL KIIGETKQEK YIKDKIIKGN   780
NK                                                                 782

SEQ ID NO: 83            moltype = AA  length = 804
FEATURE                  Location/Qualifiers
source                   1..804
                         mol_type = protein
                         organism = synthetic construct
SEQUENCE: 83
MTKKPANRHA LPKVIISEVD SEKILEFKIK YEKLARLDRV EVKAMHYEGK SIVFDEVVVN    60
GGLIDVEYQD DHKTLFVKVG EKSYSIRGQK VGGKQRLREE RVSQVKVQLE LTDGSSERVS   120
RTERELIVAD NIKLYSQIVG REVKTTKEIY LAKRFLGYRS DLLFYYGFVD NFFKVAGNEK   180
ELWKIDFEAS ESSQLLAYIP YMVNDNLKNN DAYLKDYIAN EEQIKSDLKK VQTIFSELRH   240
ALLHFNYDFF EKLFNGEDVG FDFDIEFLNL LIANIDKLNI DAKKEFITDE KIKLFGENLS   300
LAKVYKLYSD ICVNRVGFNK FINSMLIKDG LENQALKSEF DRKQGHKAYY IDIHSNEEYK   360
RLYNRHKALV IKVSTLRDGQ KIRKGNAEIS EFKKQMNSMT TKNSLSHLEH KMRLAFGFMY   420
GEYNHYNAFK NGFDTDVKNR KFDETDVSKS KAYFLSTYER QKPRTREKLE RVAKDIESLK   480
LETLIAHDPL LKFILLMFAF MPREIKGEFL GFVKKYYHDV HSIEVDIIEQ ELDVVESMST   540
SLKLKNLGRN IRSLTLFKYA LSAKVNYNGS DESPFYEEGNR YGKIYKKLGI SHNQEEFDKT   600
LVVPLFRYYS ALFKLMNDFE IYSLAKANPT ALNLQMLVDD ETSPYKQGNY YNFNKMLREV   660
HGVTNDEIKN GQAVFMRNKI AHFDTEVLLS KPLLGQTKMN LQRKIIIEFI KARGEMREIL   720
GYDAINDFRM KVVHLRTKMK VYSDKLQTMM DLLRSAKTPN DFYNVYKVKG VESINKQLLE   780
VLAETAEERS IEKQICEGNM KYNS                                         804

SEQ ID NO: 84            moltype = AA  length = 806
FEATURE                  Location/Qualifiers
source                   1..806
                         mol_type = protein
                         organism = synthetic construct
SEQUENCE: 84
MSKNPSNRNS LPKVIINKVD ENIILEFKIK YEKLARLDRF EVRSMRYDGD GRIIFDEVVA    60
NGGLLDVGYE DDNKTIVVKI ENKAYKIYGK KVGGKKRLNG KISKAKVQLI LTDNIRKNAN   120
DTHRQSLTER ELIDKNEIDL YSKIAEREIS STKDIYLVKR FLAYRSDLLL YYAFVNDYVK   180
VKGNKEEFWK TPIDDKIIDY FIYTINDTLK NKEGYLEKYI VDRDQIKKDL EKTKRIFSHL   240
RHKLMHYDFR FFTDLFDGKD VDIKVDNSTQ KISELLDIKF LNIVIEELEK LNIDAKKEFI   300
DDEKIPLFRQ EIELKKLYSI YAHTAINRVA FNKLINSFLI KDGIENKELK EYFNAQNQGK   360
ESYYIDIHQN KEYKKLYIEH KDLLAKLSAT KNGKEIAKIN RELADKKEQM KQITKANSLK   420
RLEYKLRLAF GFIYTEYKDY ETFKNSFDTD TKNQFKDAID NAKIIEYFEA TNKAKKIEKL   480
EEIILKGIDKL SLKTLIQDDI LLKFLLLFFT FLPQEIKGEF LGFIRKYYHD ITSLDEDTKD   540
```

-continued

```
KDDEITELSR SLKLKIFAKN IRKLSILKHS LSYQIKYNKK ESSYYEVGNA FNKMFKKQAI  600
SHNLEEFGKS IYLPMLKYYS ALYKLINDFE IYALYKDMDT SETLSQQVDK QEYERNEYFN  660
FETLLRKKFG NDIEKVLVTY RNKIAHLDFN FLYDKPINKF ISLYKSRDKI VNYIKNHDTQ  720
AVLKYDAVND FVMKVIQQRS KLKVYADKEQ TIESMIQNAQ NPNDFYNIYK VKAVENINQH  780
LLKVIGYTDS EKAIEEKIRA GNISKS                                      806

SEQ ID NO: 85           moltype = AA  length = 843
FEATURE                 Location/Qualifiers
source                  1..843
                        mol_type = protein
                        organism = synthetic construct
SEQUENCE: 85
MLKKPVNRYA LPKVIISEVN HEDILEFKIK YEKLGRLDRV AVKKMHYEKE NIVFDEVDVN   60
GGLIEVMYKD EHQILLVQAG GKSYSIRGKK IGGKQRKRED RVSQVKIQLE LTDGVLDKNE  120
KYRVSQTERE LIVNDNIKIY SQIVGKEVKT TKEIYLIKRF LGYRSDLLFY YGFVDNFFKV  180
VGNKTELWKI NFQDTKNEKL IEYFKFSIND KLKNDETYLK VYSSDNQNIE EDLTKVKNNF  240
SKLRRALMHF DYGFFEKLFN DEDVGFDLDI MFLNVIIKNL DKNIDTRKE FIDDEKIKIF   300
GEELSLKHLY GMYAHIAINR VAFNKLINSF MMQDGVENRS LKEYFNKRAK DGVAYEVDIH  360
QNSQYKELYK QHKNLVSKVS ALSDGVAIAK MNDEIYTLKE KMKQITKPNS LKRLEHKLRL  420
AFGFIYSEYK DYDDFKNNFN DHIIDGRFVP KDEEGKRRAF DSRELARLQG YYDVTLQNKK  480
PQTKEKLGEV SKKIDSLSLA TLIDDDKLLL FILLMFTFMP QELKGEFLGF VKKYYHDTKH  540
IEEDSKDKDK DFADGLSVGL RLKVLDKNIR NLSILKHSLS LQTKYNKKDN YFYEDGNVHG  600
RFFKSLGISH NQEEFSKSVY APLLKYYSAL YKLINDFEIY TLAQYITTEY PTLSKVIDSE  660
KPFHLRWDNRS KELVPSDDYV FSTLTNKTYD HEKVKELNFI RNKISHFNSK ELFEIPLQGY  720
QMKGKKKLPF FLSKKREEII DEIELQKDIQ KTLGYDAIND FNMKMVQLYT KLKVYANKEE  780
TIEKMLEEAT TPNDFYNYVK VKGVETINKH LLDVIGETER EKFIRIQIEV NNKRVSNENL  840
DKL                                                               843

SEQ ID NO: 86           moltype = AA  length = 876
FEATURE                 Location/Qualifiers
source                  1..876
                        mol_type = protein
                        organism = synthetic construct
SEQUENCE: 86
MSKKPANRHA LPKVIISEVD SEKILEFKIK YEKLARLDRV EVKAMHYEGK SIVFDEVVVN   60
GGLIDVEYQD NHKTLFVKVG EKSYSIRGKK VGGKQRLREE RVSQVKVQLE LSDGSSERVS  120
RTERELIVNE NIKLYSQIVG REVKTTKEIY LAKRFLGYRS DLLFYYGFVD NFFKEAKLFN  180
ARKNPIELWS EEFYVNDKLS NYTKFMFNDN LKNSESYLKE YIKNNEKENQ KIKNDLESAR  240
DIFATLRHNL MHFNYSFFER LFKGKDVKIK NLQTKKFESL SNVLRNIEFL NKVIQSIDKL  300
NIDTRKEFID KEKIKLFNED LDLQQLYGFF AHTAINRVAF NKLINSFIIK DGIENEQLKE  360
YFNQRVDGTA YEIDIHQNRE YKELYKKHKN LVSKVSTLSD GKEIAKGNSE ISALKEQMNK  420
ITKANSLKRL EYKLRLAFGF IYTEYGSYKA FVSRFNEDTK RKKIKNVEFE KIGFEKQKEY  480
FKSTFEPLKS KKKDNLEKLI QEYEKLSLND LIENDTFLKV ILLLFIFMPK EVKGDFLGFI  540
KKYYHDTKYI EEDTKEKDEG FTNTLPIGLK LKIVERNIAK LSVLKHSLSL KVKYNRGQYE  600
EDNTYRKVFK KLNISHNQEE FHKSMFSPLL RYYASLYKLI NDFEIYTLSH YITDKYSTLN  660
KVIASKQFHY RYVWNRKENK GELVKTDNYT FSTLLSKKYE HKNSQEISEM RNKISHFDEK  720
ILFKFPLEEV NSFFKGKGKN KKEEPVKSLV EKREEIISLM EKQTFKDQIL GYDAINDFRM  780
KTVQFQTKLK EDSKKKEETI KKMIAEAKIP NDFYNIYKVK GVESINKHLL KIIGQTDKEW  840
KIEGDILDGN FKIACKNQRL EEKQQRAKNK QNLDKL                           876

SEQ ID NO: 87           moltype = AA  length = 919
FEATURE                 Location/Qualifiers
source                  1..919
                        mol_type = protein
                        organism = synthetic construct
SEQUENCE: 87
MIKNPSNRHS LPKVIISEVD HEKILEFKIK YEKLARLDRF EVKAMHYEGK EIVFDEVLVN   60
GGLIEVEYQD DNKTLFVKVG EKSYRICGER IGGNYIVTEY KDKNEPKSKK HFRLIEKDGK  120
YFKPNGEEVT KNIRKSSVKV LLTLTDGVED NNGKLRKSRT ERELIVADNI KLYSQIVGRE  180
VTTTKEIYLV KRFLGYRSDL LFYYGFVNNF FHVAGKREEL WKIDFDTLPS NSPLLEYFKF  240
TINDEKYLKS YSSDIQQIKK DLQNNKYIFL VNGEDIEIKA ENYNIKPLSE LLNIEFLNIQ  300
IKKDLQNSEY IFSALRHALM HFDYDFFVRL FNGEDIEIKA KNGNKKPLSE LLNIEFLNIM  360
IENIDKLNID TRKEFIDDDD VPIKLFGEEM KPKNLYGLYA HTAINRVAFN KLINSFMMEN  420
GVENQALKSY FDQKAGGVAY EVDIHQNSNY KKLYVKHKNL VSKVSTLSDG QEIAKVNAKI  480
SELKEQMKKI TKANSLKRLE HKFRLAFGFV YSEYKDYEAF KNNFDTDIKK GKFVPKDKEG  540
KRRAFDHREL EQLKGYFDST FKSKKPNTKE KLGELSKSTG KLSLKALIGD DMFLKFILLM  600
FTFMPQELKG EFLGFVKKYY HDTKHIEEDT KDRDDGFSNE RPMGLKLKVL DKNIRSLSIL  660
KHSLSFQTKY NKKDKSFYED GNVHGKFYKK LGISHNQEEF NKSVYAPLFK YYSALSKLIN  720
DFEIYSLTQH VVGSETLAQQ VRRKFIKKG YYNFGNLLKK TDSIIRSSRD NDIFYAVIDM  780
RNTISHLSVE PMFDYPLNGK KFYKLYENKV ICVDPLKSRK MIIDFIKRQT EMKKTLGYDA  840
VNDFTMKMVQ LQTKLKVYAN KEKTIEKMKE EAQTPNDYYN IYKVKGVEAI NQYLLEIIGE  900
TDDEALIRKL INRGNSINP                                             919

SEQ ID NO: 88           moltype = AA  length = 846
FEATURE                 Location/Qualifiers
source                  1..846
                        mol_type = protein
                        organism = synthetic construct
SEQUENCE: 88
```

```
MKKIKNPSNR NSLPSIIISR FDDKNIYELK VKYEKLARLD KLEIEDMSLD EESTLLFKKV   60
KFNGIEIEIK NQKLLEFDSY IISGKKQTNT TGKTIISLLK EGKKVTYNVT KKDGKYYKNG  120
KEFIIPQNAN KLPDRLINDK FIITIEDKVR DEDTKRKKET QRDILSDDTI ETYKRISSYK  180
SIKSEDIYTI KRYITFKSDM MFFYTFVDDF FNPIKKQDLW KVKFGEVENL GKFIEFTLND  240
TLKNPKGILE TYCKDLKTVQ ADFAKINTIF SKIRHSLVPF DFVFIDKLLS NQKIEEFDFD  300
IKLLNDVIDK TQDLYYEAKK EFIEDEKITI LDEKDMEIKK LYTFFSKIDI KQPAFNKLIN  360
SFIIKDGIEN IELKTYIKEK YKSEYFIDIH ANKEYKKIYN EHKKLVGENQ FLQLNPKENG  420
QKIKELNDQV EEYKKQMKTI TEANSLKRLE FKLRLAFGFI KVEYGRFDTF KNSFDEDIKK  480
GKFKEISFEK IKGYLDKTYA KEQFFNYGSN KKTKKPYSIL DDIENETLKE LVQNDNLLKV  540
ILLFYIFTPK ELKGEFLGFI KKFYHDTKNI TKDTKDEEKE LENLKLETPL KLKILEKNLK  600
KITIFNYSIF SNINFDTTNK RFYAEGNRFN RIYKKLNISH NQDEFDKSLF APLLQYYMNL  660
YKLIGDFEIY LLLKFDNKKD LSELSNDERL KFRGYYNFTT LLSKWFQFDP KRDKKYEKVL  720
RLRNTISHQD INNMIINFEK STILSQRENI VQLIEEQNDL KEILKYDAVN DFTMKTIQLL  780
KSIEIQSDKS KTINELLSNK DISANDFYNI YKVKGVEMIK KELFNRLGKR EIEKKIEEEI  840
AKSTIC                                                            846

SEQ ID NO: 89         moltype = AA  length = 822
FEATURE               Location/Qualifiers
source                1..822
                      mol_type = protein
                      organism = synthetic construct
SEQUENCE: 89
MEKIKKPSNR NSIPSIIISD YDASKIKEIK VKYLKLARLD KITIQDMEIV DNIVEFKKIL   60
LNGTEHTIID NKKIEFDNYE ITGCIKPSNK RRDGKISQAK YVVTITIDKYL RDNEKEKRFK  120
STERELPNDI LLSRYKQISG FDTLTSKDIY KIKRYIDFKN EMLFYFQPIE EFFNPLLPKG  180
KNFYDLNIEQ NKDKVAKFIV YRLNDDFKNQ SLNSYIQKTD TIKYDFIKVQ KILNDFRHAL  240
AHFDFEFIQK FFDNQLDKTR FDINTISLIK TLLQKKEGKH YQEKNNYIDD NDTLTIFDDK  300
DSKFSKLHNF YTKISQKKPA FNKLINSFLS QDGIPNEEFK RYLATKKLDF FEDIHSNKEY  360
KEIYINHKNQ VIEKQKEESQ EKPDGQKLKN FNDELQKLKD KMNTITKQNS LNRLEVKLRL  420
APGFIANEYN YNFKNFNDNF TLDVKNEQKI KAFKNSSNEK LKEYFESTFE AKQFFYYGKN  480
KNIFNSIENE TLEELVKESP LLQIITFLYL FIPKELQGEF VGFILEIYHH TKNISSDTKE  540
DEISIEDAQN SFSLKLKILA KNLRGLQLFN YSLSHNTLYN NKQDFFYEKG NRWQNIYKNF  600
QISHNQDEFD IHLVIPVIKY YINLNKLIGD FEIYALLKYA DQNSITEKLS DITKRDDLKF  660
KGHYNFSTLL NRTFGISVYS DKNPISIQNI KQIRNDIAHQ NIENMLKAFE NSEIFAQREE  720
IVNYLQTEHQ MQEILHYNPI NDFTMKTVQY LKSLSVHSQK EGKIADIHKK DNLVPNDYYL  780
IYKLKAIEIL KQKVIEAIGE TKDEKKIKNA IAKEEQIKKG NN                     822

SEQ ID NO: 90         moltype = DNA  length = 36
FEATURE               Location/Qualifiers
source                1..36
                      mol_type = other DNA
                      organism = synthetic construct
SEQUENCE: 90
gttagaatat accccatttt gtatggggat taaaac                             36

SEQ ID NO: 91         moltype = DNA  length = 36
FEATURE               Location/Qualifiers
source                1..36
                      mol_type = other DNA
                      organism = synthetic construct
SEQUENCE: 91
gttggaatat agccctgttt gtagggtaa taaaac                              36

SEQ ID NO: 92         moltype = DNA  length = 36
FEATURE               Location/Qualifiers
source                1..36
                      mol_type = other DNA
                      organism = synthetic construct
SEQUENCE: 92
gatggaatat aaccccgttt gtagggtaa taaaac                              36

SEQ ID NO: 93         moltype = DNA  length = 39
FEATURE               Location/Qualifiers
source                1..39
                      mol_type = other DNA
                      organism = synthetic construct
SEQUENCE: 93
agtagaatat aaccctgata ttagtagggg taataaaac                          39

SEQ ID NO: 94         moltype = DNA  length = 36
FEATURE               Location/Qualifiers
source                1..36
                      mol_type = other DNA
                      organism = synthetic construct
SEQUENCE: 94
agtagaatat aaccctgtta gtagggtaa taaaac                              36

SEQ ID NO: 95         moltype = DNA  length = 37
FEATURE               Location/Qualifiers
```

```
SEQ ID NO: 95              moltype = DNA  length = 37
FEATURE                    Location/Qualifiers
source                     1..37
                           mol_type = other DNA
                           organism = synthetic construct
SEQUENCE: 95
tattgactat acccctgatt tgtaggggta aaagaga                              37

SEQ ID NO: 96              moltype = DNA  length = 37
FEATURE                    Location/Qualifiers
source                     1..37
                           mol_type = other DNA
                           organism = synthetic construct
SEQUENCE: 96
tattgactat acccctgatt tgtaggggta aaaaac                               37

SEQ ID NO: 97              moltype = DNA  length = 36
FEATURE                    Location/Qualifiers
source                     1..36
                           mol_type = other DNA
                           organism = synthetic construct
SEQUENCE: 97
gtcagactat accctcgttt gtaggggaa taaaac                                36

SEQ ID NO: 98              moltype =     length =
SEQUENCE: 98
000

SEQ ID NO: 99              moltype =     length =
SEQUENCE: 99
000

SEQ ID NO: 100             moltype =     length =
SEQUENCE: 100
000

SEQ ID NO: 101             moltype =     length =
SEQUENCE: 101
000

SEQ ID NO: 102             moltype = AA  length = 12
FEATURE                    Location/Qualifiers
source                     1..12
                           mol_type = protein
                           organism = synthetic construct
SEQUENCE: 102
MSPKKKRKVE AS                                                         12

SEQ ID NO: 103             moltype = AA  length = 22
FEATURE                    Location/Qualifiers
source                     1..22
                           mol_type = protein
                           organism = synthetic construct
SEQUENCE: 103
GSGPKKKRKV AAAYPYDVPD YA                                              22

SEQ ID NO: 104             moltype = DNA  length = 82
FEATURE                    Location/Qualifiers
source                     1..82
                           mol_type = other DNA
                           organism = synthetic construct
SEQUENCE: 104
cgccccattg acgcaaatgg gcggtaggcg tgtacggtgg gaggtctata taagcagagc     60
tggtttagtg aaccgtcaga tc                                              82

SEQ ID NO: 105             moltype = DNA  length = 234
FEATURE                    Location/Qualifiers
source                     1..234
                           mol_type = other DNA
                           organism = synthetic construct
SEQUENCE: 105
cagctcacag acatgataag atacattgat gagtttggac aaaccacaac tagaatgcag     60
tgaaaaaaat gctttatttg tgaaatttgt gatgctattg cttttatttgt aaccattata   120
agctgcaata aacaagttaa caacaacaat tgcattcatt ttatgtttca ggttcagggg    180
gaggtgtggg aggttttta aagcaagtaa aacctctaca aatgtggtat tggc            234
```

GENE-MODIFYING ENDONUCLEASES

CROSS-REFERENCE TO RELATED APPLICATIONS

This application claims priority to U.S. Provisional Application No. 63/384,937, filed on Nov. 23, 2022, U.S. Provisional Application No. 63/386,784, filed Dec. 9, 2022, U.S. Provisional Application No. 63/500,779, filed May 8, 2023, and U.S. Provisional Application No. 63/504,721, filed May 26, 2023, the entire contents which are incorporated herein in their entireties.

FIELD

The disclosure relates to compositions, systems, and methods that modify target RNA, as well as methods of detecting a nucleic acid.

DESCRIPTION OF THE TEXT FILE SUBMITTED ELECTRONICALLY

The instant application contains a sequence listing, which has been submitted in XML format via EFS-Web. The contents of the XML copy named "AMR-006US/134241-5006_Sequence Listing," which was created on Nov. 24, 2023 and is 150,000 bytes in size, the contents of which are incorporated herein by reference in their entirety.

BACKGROUND

Bacterial adaptive immune systems employ CRISPRs (clustered regularly interspaced short palindromic repeats) and CRISPR-associated (Cas) proteins for RNA-guided nucleic acid cleavage. The CRISPR-Cas systems thereby confer adaptive immunity in bacteria and archaea via RNA-guided nucleic acid interference. To provide anti-viral immunity, processed CRISPR array transcripts (crRNAs) assemble with Cas protein-containing surveillance complexes that recognize nucleic acids bearing sequence complementarity to the virus derived segment of the crRNAs, known as the spacer.

CRISPR-Cas tools have been widely used for gene editing, gene activation, gene inactivation, protein imaging, and beyond. For example, the RNA-guided endonucleases of the CRISPR-Cas9 system, including the most widely used Cas9 from *Streptococcus pyogenes* (SpCas9), can be used as a gene-editing tool in certain organisms. Although many current Cas9 polypeptides are capable of high-efficiency gene modifications, limitations remain due to off-target activities, such as the undesirable production of modifications within the genome at sites other than the desired target. Further, current endonuclease may be restricted in use due to protospacer adjacent motif (PAM) specificities and packaging constraints for delivery of system components.

Accordingly, there is a need for new gene engineering technologies, e.g., for therapy and/or diagnosis.

SUMMARY

Therefore, the present disclosure provides, in aspects, a composition comprising an endonuclease comprising a sequence, optionally comprising a higher eukaryotes and prokaryotes nucleotide-binding domain (HEPN) domain, or a fragment or variant thereof, having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) identity to any one of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises at least two HEPN domains, or fragments or variants thereof.

Additionally, the present disclosure provides, in aspects, a composition comprising an endonuclease comprising a sequence, optionally comprising one or more higher eukaryotes and prokaryotes nucleotide-binding domain (HEPN) domains, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) identity to any one of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises a fragment or variant of a HEPN domain. In embodiments, the sequence comprises at least two HEPN domains, or fragments or variants thereof.

In aspects, the present disclosure provides a composition comprising a nucleic acid encoding an endonuclease comprising a sequence, optionally comprising one or more HEPN domains, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%%, or at least about 97%, or at least about 98%, or at least about 99%) identity to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises at least one HEPN domain, or fragments or variants thereof. In embodiments, the sequence comprises at least two HEPN domains, or fragments or variants thereof.

In aspects, the present disclosure provides a composition comprising a nuclease system, comprising (a) an endonuclease comprising a sequence, optionally comprising a HEPN domain, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications); and (b) an RNA molecule comprising a sequence complementary to one strand of a target nucleic acid molecule. In embodiments, the sequence comprises at least one HEPN domain, or fragments or variants thereof. In embodiments, the sequence comprises at least two HEPN domains, or fragments or variants thereof.

In embodiments, the composition further comprises one or more donor polynucleotides and/or is suitable for introducing one or more donor polynucleotides into a target nucleic acid molecule.

In embodiments, the endonuclease is suitable for introducing one or more excisions into a target nucleic acid molecule.

In aspects, the present disclosure provides a composition comprising a chimeric protein comprising: an endonuclease comprising a sequence, optionally comprising a HEPN domain, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications); and a nucleic acid-modulating domain or a nucleic acid-modifying domain, or nucleic acid-interacting/binding domain, comprising a sequence comprising a catalytic domain, or a fragment or variant thereof, wherein (a) and (b) do not naturally occur together in a same reading frame. In embodiments, the sequence comprises at least one HEPN domain, or fragments or variants thereof. In embodiments, the sequence comprises at least two HEPN domains, or fragments or variants thereof. In embodiments, the nucleic acid-modulating domain or a nucleic acid-modifying domain is a nucleic acid-interacting domain, e.g. selected from MCP, lambdaN, PP7, QBeta, SLBP, and TBP/TAR. In embodiments, the endonuclease reduces or enhances collateral activity for nucleic acid detection.

In aspects, the present disclosure provides a composition comprising a complex comprising chimeric protein and an RNA molecule, wherein the chimeric protein comprises an endonuclease comprising a sequence, optionally comprising one or more HEPN domains, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications); and a nucleic acid-modulating domain or a nucleic acid-modifying domain comprising a sequence comprising a catalytic domain, or a fragment or variant thereof, wherein (a) and (b) do not naturally occur together in a same reading frame and the RNA molecule comprises a sequence complementary to one strand of a target nucleic acid molecule.

In embodiments, the sequence comprises at least one HEPN domain, or fragments or variants thereof. In embodiments, the sequence comprises at least two HEPN domains, or fragments or variants thereof. In embodiments, the nucleic acid-modulating domain or the nucleic acid-modifying domain has one or more of nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, debranching activity, transesterification activity, photolyase activity and glycosylase activity. In embodiments, the nucleic acid-modulating domain or the nucleic acid-modifying domain is a Methyltransferase-like Protein 3 (METTL3) methyltransferase domain, a METTL3: Methyltransferase-like Protein 1 (METTL1) fusion, or a fragment or variant thereof.

In embodiments, the nucleic acid-modulating domain or the nucleic acid-modifying domain is selected from a deaminase, reverse transcriptase, transposase, integrase, and recombinase. In embodiments, the deaminase is a cytidine or cytosine deaminase, or a fragment or variant thereof. In embodiments, the cytidine or cytosine deaminase is selected from activation-induced cytidine deaminase (AID), cytidine deaminase 1 (CDA1), and apolipoprotein B mRNA-editing complex (APOBEC), or a fragment or variant thereof. In embodiments, the APOBEC is selected from A3A, AB3, APOBEC1, APOBEC3C, APOBEC3D, APOBEC3F, APOBEC3G, and APOBEC3H, or a fragment or variant thereof. In embodiments, the APOBEC has an amino acid sequence of one of SEQ ID NO: 39 [A3A], SEQ ID NO: 40 [AB3], SEQ ID NO: 41 [APOBEC1], SEQ ID NO: 42 [APOBEC3C], SEQ ID NO: 43 [APOBEC3D], SEQ ID NO: 44 [APOBEC3F], SEQ ID NO: 45 [APOBEC3G], and SEQ ID NO: 46 [APOBEC3H], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the deaminase is a DNA-specific adenine or adenosine deaminase, or a fragment or variant thereof. In embodiments, the DNA-specific adenine or adenosine deaminase is selected from tRNA-specific adenosine deaminase 7.10 (TadA 7.10), tRNA-specific adenosine deaminase 6.3 (TadA 6.3), tRNA-specific adenosine deaminase 7.8 (TadA 7.8), tRNA-specific adenosine deaminase 7.9 (TadA 7.9), and tRNA-specific adenosine deaminase 8e (TadA8e (TadA-8e V106W)) or a fragment or variant thereof. In embodiments, the TadA has an amino acid sequence of one of SEQ ID NO: 48 [TadA 7.10], SEQ ID NO: 49 [TadA 6.3], SEQ ID NO: 50 [TadA 7.8], SEQ ID NO: 51 [TadA 7.9], and SEQ ID NO: 52 [TadA 8e], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the deaminase is a RNA-specific adenine or adenosine deaminase, or a fragment or variant thereof. In embodiments, the RNA-specific adenine or adenosine deaminase is an adenosine deaminases acting on RNA (ADAR) enzyme, or a fragment or variant thereof. In embodiments, the ADAR is selected from ADAR1, ADAR2, and ADAR3, or a fragment or variant thereof. In embodiments, the ADAR has an amino acid sequence of one of SEQ ID NO: 53 [ADAR1] and SEQ ID NO: 54 [ADAR2] or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, and as a non-limiting example, the catalytic deaminase domain of ADAR1 comprises amino acids 833-1226 of SEQ ID NO: 53. As another non-limiting example the catalytic deaminase domain of ADAR2 comprises amino acids 299-701 of SEQ ID NO: 54.

In embodiments, the deaminase further comprises a nuclear localization signal. In embodiments, the endonuclease further comprises a uracil glycosylase inhibitor (UGI), or a fragment or variant thereof. In embodiments, the RNA molecule is a guide RNA (gRNA). In embodiments, the gRNA comprises a sequence that interacts with the endonuclease. In embodiments, the endonuclease forms a complex with the gRNA.

In embodiments, the composition is suitable for base editing. In embodiments, the composition is suitable for DNA base editing. In embodiments, the composition is suitable for RNA base editing. In embodiments, the composition is suitable for catalyzing C>T nucleotide conversions or A>G nucleotide conversions in a target nucleic acid.

In embodiments, the composition comprises both an adenosine deaminase and a cytidine deaminase.

In embodiments, the composition is suitable for dual base editing.

In embodiments, the reverse transcriptase is Moloney murine leukemia virus reverse transcriptase (M-MLV RT) or M-MLV RT(D200N/L603W/T330P/T306K/W313F), or a fragment or variant thereof. In embodiments, the M-MLV RT has an amino acid sequence of SEQ ID NO: 55 [M-MLV RT] or SEQ ID NO 56 [M-MLV RT(D200N/L603W/T330P/T306K/W313F)] or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the composition further comprises a dominant negative human MutL homolog (MLH1). In embodiments, the composition is suitable for use with a dominant negative MLH1.

In embodiments, the RNA molecule is or comprises a prime editing guide RNA (pegRNA). In embodiments, the endonuclease forms a complex with the pegRNA. In embodiments, the pegRNA serves as a template for transcription of a new DNA sequence. In embodiments, the pegRNA binds to a DNA strand opposite from a typical gRNA binding site. In embodiments, the pegRNA comprises a gRNA containing a primer binding site (PBS) and a reverse transcriptase (RT) template sequence. In embodiments, the RNA molecule is or comprises a gRNA. In embodiments, the gRNA comprises a sequence that interacts with the endonuclease.

In embodiments, the endonuclease forms a complex with the gRNA. In embodiments, the composition comprises both a gRNA and a pegRNA.

In embodiments, the composition is suitable for prime editing.

In embodiments, the transposase is selected from Tn1, Tn2, Tn3, Tn5, Tn7, Tn9, Tn10, Tn552, Tn903, Tn1000/Gamma-delta, Tn/O, tnsA, tnsB, tnsC, tniQ, IS10, ISS, IS911, Minos, Sleeping beauty, piggyBac, Tol2, Mos1, Himar1, Hermes, Tol2, Minos, Tel, P-element, MuA, Ty1, Chapaev, transib, Tc1/mariner, and Tc3 donor DNA system.

In embodiments, the transposase is a transposon 7-like (Tn7-like) transposon system, or a fragment or variant thereof. In embodiments, the transposase is one or more of transposon 7 protein A (TnsA), transposon 7 protein B (Tns B), transposon 7 protein C (Tns C), and transposition of integron protein Q (TniQ), or a fragment or variant thereof. In embodiments, the Tn7-like transposon system is derived from *Vibrio cholerae* Tn6677.

In embodiments, the transposase has an amino acid sequence of one or more of SEQ ID NO: 57 [TnsA], SEQ ID NO: 58 [TnsB], SEQ ID NO: 59 [TnsC], and SEQ ID NO: 60 [TniQ], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the integrase is a serine-recombinase, or a fragment or variant thereof.

In embodiments, the serine-recombinase is Bxb1, or a fragment or variant thereof. In embodiments, the recombinase is a Gin invertase or Tn3 resolvase, or a fragment or variant thereof.

In embodiments, the nucleic acid-modulating domain or the nucleic acid-modifying domain comprises one or more modifications, (e.g., without limitation, mutations) to reduce activity relative to an unmutated form.

In embodiments, the nucleic acid-modulating domain or the nucleic acid-modifying domain comprises one or more modifications, (e.g., without limitation, mutations) to increase activity relative to an unmutated form.

In embodiments, the sequence of (a) is disposed at the N-terminus of the chimeric protein and the sequence of (b) is disposed at the C-terminus of the chimeric protein.

In embodiments, the sequence of (a) is disposed at the C-terminus of the chimeric protein and the sequence of (b) is disposed at the N-terminus of the chimeric protein.

In embodiments, the composition further comprises a linker that joins the sequence of (a) and the sequence of (b). In embodiments, the linker is between about 4 and about 40 amino acids, or about 10 and about 40 amino acids, or about 20 and about 40 amino acids, or about 30 and about 40 amino acids, or about 4 and about 30 amino acids, or about 4 and about 20 amino acids, or about 4 and about 10 amino acids, or about 5 amino acids, or about 10 amino acids, or about 15 amino acids, or about 20 amino acids, or about 25 amino acids, or about 30 amino acids, or about 35 amino acids, or about 40 amino acids. In embodiments, the linker is substantially comprised of glycine and serine residues. In embodiments, the linker is $(GGS)_n$, wherein n is 1, or 2, or 3, or 4, or 5. In embodiments, the linker is GGSGGSGGSG (SEQ ID NO: 61), GGSGGSGGGGSGGGS (SEQ ID NO: 62), GGGGS (SEQ ID NO: 63), GGS (SEQ ID NO: 64), $(GGGGS)_n$(n=1-4) (SEQ ID NO: 65), $(Gly)_8$ (SEQ ID NO: 66), $(Gly)_6$ (SEQ ID NO: 67), $(EAAAK)_n$(n=1-3) (SEQ ID NO: 68), $A(EAAAK)_nA$ (n=2-5) (SEQ ID NO: 69), AEAAAKEAAAKA (SEQ ID NO: 70), $A(EAAAK)_4ALEA$ $(EAAAK)_4A$ (SEQ ID NO: 71), PAPAP (SEQ ID NO: 72), KESGSVSSEQLAQFRSLD (SEQ ID NO: 73), EGKSSGSGSESKST (SEQ ID NO: 74), and GSAGSAAGSGEF (SEQ ID NO: 75), or a variant thereof, wherein the variant comprises about 1, or about 2, or about 3, or about 4, or about 5 mutations, the mutations selected from substitutions or deletions.

In embodiments, the endonuclease is suitable for creating a double stranded break in a nucleic acid. In embodiments, the endonuclease is suitable for creating a nick in a nucleic acid. In embodiments, the endonuclease is suitable for nucleic acid modification by homology-directed repair (HDR). In embodiments, the endonuclease is suitable for nucleic acid modification by non-homologous end joining (NHEJ). In embodiments, the endonuclease recognizes a PAM. In embodiments, the endonuclease recognizes a plurality of PAMs. In embodiments, the endonuclease comprises one or more modifications, (e.g., without limitation, mutations) to reduce catalytic activity relative to an unmutated form. In embodiments, the endonuclease comprises one or more modifications, (e.g., without limitation, mutations) to render the endonuclease substantially catalytically inactive relative to an unmutated form. In embodiments, the endonuclease comprises one or more modifications, (e.g., without limitation, modifications, (e.g., without limitation, mutations) to increase catalytic activity relative to an unmutated form. In embodiments, the endonuclease comprises one or more modifications, (e.g., without limitation, mutations) to render the endonuclease substantially catalytically hyperactive relative to an unmutated form. In embodiments, the endonuclease has nickase activity. In embodiments, the endonuclease comprises one or more modifications, (e.g., without limitation, mutations) to produce nickase activity. In embodiments, the endonuclease has collateral cleavage activity. In embodiments, the endonuclease comprises one or more modifications, (e.g., without limitation, mutations) to produce collateral cleavage activity. In embodiments, the endonuclease has at least about 75% identity to one or more of SEQ ID NOs: 1-4, and/or SEQ ID NOs: 80-89. In embodiments, the endonuclease has at least about 80% identity to one or more of SEQ ID NOs: 1-4, and/or SEQ ID NOs: 80-89. In embodiments, the endonuclease has at least about 85% identity to one or more of SEQ ID NOs: 1-4, and/or SEQ ID NOs: 80-89.

In embodiments, the endonuclease has at least about 90% identity to one or more of SEQ ID NOs: 1-4, and/or SEQ ID NOs: 80-89. In embodiments, the endonuclease has at least about 95% identity to one or more of SEQ ID NOs: 1-4, and/or SEQ ID NOs: 80-89. In embodiments, the endonuclease has at least about 97% identity to one or more of SEQ ID NOs: 1-4, and/or SEQ ID NOs: 80-89. In embodiments, the endonuclease has at least about 99% identity to one or more of SEQ ID NOs: 1-4, and/or SEQ ID NOs: 80-89.

In embodiments, the endonuclease has about 1 to about 15 amino acid modifications. In embodiments, the endonuclease has about 1 to about 10 amino acid modifications. In embodiments, the endonuclease has about 1 to about 5 amino acid modifications. In embodiments, the endonuclease has about 1, or about 2, or about 3, or about 4, or about 5, or about 10, or about 15, or about 20 amino acid modifications. In embodiments, the amino acid modifications are selected from substitutions and deletions.

In embodiments, the endonuclease (or chimeric protein) comprises a domain from a different endonuclease. In embodiments, the different endonuclease is a Cas endonuclease. In embodiments, the domain is a PAM-interacting domain. In embodiments, the target nucleic acid is or comprises single-stranded RNA (ssRNA). In embodiments, the target nucleic acid is or comprises double-stranded RNA (dsRNA). In embodiments, the target nucleic acid is or comprises single-stranded DNA (ssDNA). In embodiments, the target nucleic acid is or comprises double-stranded DNA (dsDNA). In embodiments, the target nucleic acid is about 2 to about 6 nucleotides upstream of a PAM sequence. In embodiments, the RNA molecule is or comprises a guide ribonucleic structure configured to form a complex with the endonuclease.

In embodiments, the guide ribonucleic structure (i) comprises (a) a CRISPR RNA (crRNA) suitable for hybridizing to a target nucleic acid molecule and/or (b) a transactivating CRISPR RNA (tracrRNA) suitable for interacting with the endonuclease or (ii) lacks a (a) a crRNA suitable for hybridizing to a target nucleic acid molecule and/or (b) a tracrRNA suitable for interacting with the endonuclease.

In embodiments, the RNA molecule is or comprises a gRNA. In embodiments, the gRNA comprises a sequence that interacts with the endonuclease. In embodiments, the endonuclease forms a complex with the gRNA.

In embodiments, the RNA molecule is or comprises the nucleic acid sequence of SEQ ID NOs: 1-4, and/or SEQ ID NOs: 80-89, or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the RNA molecule has perfect sequence complementarity to one strand of a target nucleic acid molecule. In embodiments, the RNA molecule has partial sequence complementarity to one strand of a target nucleic acid molecule.

In embodiments, the composition further comprises a viral vector. In embodiments, the viral vector is or comprises an AAV. In embodiments, the AAV is or comprises one or more of AAV1, AAV2, AAV3, AAV4, AAV5, AAV6, AAV7, AAV8, AAV9, AAV10, AAV11, AAV12, AAV13, AAV2/1, AAV2/5, AAV2/8, AAV2/9, AAV3/1, AAV3/5, AAV3/8, and AAV3/9. In embodiments, the composition further comprises a non-viral vector. In embodiments, the composition further comprises a lipid nanoparticle (LNP) liposomes, lipoplexes or polymeric nanoparticle. In embodiments, the LNP comprises one or more of ionizable lipids, amino lipids, anionic lipids, neutral lipids, amphipathic lipids, helper lipids, structural lipids, PEG lipids, and lipoids. In embodiments, the composition further comprises a virus-like particle (VLP).

In aspects, the present disclosure provides a nucleic acid encoding the endonuclease or chimeric protein of any one of the embodiments and/or aspects disclosed herein. In embodiments, the nucleic acid is or comprises a DNA molecule or an RNA molecule. In embodiments, the RNA is or comprises mRNA or modified mRNA (mmRNA). In embodiments, the DNA is or comprises a vector or plasmid. In embodiments, the nucleic acid comprises a codon optimized sequence. In embodiments, the nucleic acid comprises one or more modifications. In embodiments, the modifications are one or more of base modifications and backbone modifications.

In aspects, the present disclosure provides a viral vector comprising the nucleic acid of any one of the embodiments and/or aspects disclosed herein. In embodiments, the viral vector is or comprises an AAV. In embodiments, the AAV is or comprises one or more of AAV1, AAV2, AAV3, AAV4, AAV5, AAV6, AAV7, AAV8, AAV9, AAV10, AAV11, AAV12, AAV13, AAV2/1, AAV2/5, AAV2/8, AAV2/9, AAV3/1, AAV3/5, AAV3/8, and AAV3/9.

In aspects, the present disclosure provides a viral vector comprising the nucleic acid of any one of the embodiments and/or aspects disclosed herein. In embodiments, the viral vector is or comprises a VLP.

In embodiments, the endonuclease mediates a trans-splicing event.

In embodiments, the endonuclease mediates an exon skipping or exon inclusion event.

In aspects, the present disclosure provides a lipid nanoparticle comprising the nucleic acid of any one of the embodiments and/or aspects disclosed herein.

In aspects, the present disclosure provides a cell comprising a nucleic acid of any one of the embodiments and/or aspects disclosed herein, the viral vector of any one of the embodiments and/or aspects disclosed herein, or the lipid nanoparticle of any one of the embodiments and/or aspects disclosed herein.

In embodiments, the cell is a prokaryotic cell. In embodiments, the cell is a eukaryotic cell. In embodiments, the cell is a mammalian cell. In embodiments, the cell is a human cell. In embodiments, the cell is an immortalized cell. In embodiments, the cell is harvested from a subject.

In aspects, the present disclosure provides a pharmaceutical composition comprising the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, or the cell of any one of the embodiments and/or aspects disclosed herein, and a pharmaceutically acceptable carrier.

In aspects, the present disclosure provides a composition comprising an RNA molecule comprising a nucleic acid sequence of SEQ ID NOs: 1-4, and/or SEQ ID NOs: 80-89, or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the RNA molecule interacts with an endonuclease comprising a sequence comprising, optionally a HEPN domain, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises at least one HEPN domain, or fragments or variants thereof. In embodiments, the sequence comprises at least two HEPN domains, or fragments or variants thereof.

In embodiments, the RNA molecule comprises one or more modifications. In embodiments, the modifications are one or more of base modifications and backbone modifications. In embodiments, the RNA molecule comprises a sequence complementary to one strand of a target nucleic acid molecule. In embodiments, the RNA molecule has perfect sequence complementarity to one strand of a target nucleic acid molecule.

In embodiments, the RNA molecule has partial sequence complementarity to one strand of a target nucleic acid molecule.

In aspects, the present disclosure provides a composition comprising a nucleic acid encoding an endonuclease comprising a sequence, optionally comprising a HEPN domain, or a fragment or variant thereof, in conjunction with an RNA containing a repeat having at least about 70% identity to one or more of SEQ ID NOs: 28-31, and/or SEQ ID NOs: 90-97. In embodiments, the composition has least about 75%, or at least about 80%, or at least about 85%, or at least about 90%, or at least about 91%, or at least about 92%, or at least about 93%, or at least about 94%, or at least about 95%, or at least about 96%%, or at least about 97%, or at least about 98%, or at least about 99%) identity to SEQ ID NOs: 28-31, and/or SEQ ID NOs: 90-97, or has about 1 to about 20 nucleotide modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises at least one HEPN domain, or fragments or variants thereof. In embodiments, the sequence comprises at least two HEPN domains, or fragments or variants thereof.

In aspects, the present disclosure provides a kit comprising a container comprising the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein and with instructions for use in modulating and/or modifying a nucleic acid.

In aspects, the present disclosure provides a method of modulating and/or modifying a nucleic acid in a cell, comprising contacting the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In aspects, the present disclosure provides a method of modulating and/or modifying a nucleic acid in a subject in need thereof, comprising administering an effective amount of the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein to the subject.

In embodiments, the modulating and/or modifying is selected from one or more of cleaving, nicking, methylating, labeling, and mutating the nucleic acid. In embodiments, the modulating and/or modifying is selected from one or more of cleaving the nucleic acid; inserting a nucleic acid, editing the nucleic acid; modulating transcription from the nucleic acid; isolating the nucleic acid, binding the nucleic acid, and imaging the nucleic acid.

In aspects, the present disclosure provides a method of disrupting, correcting, and/or replacing a gene in a cell, comprising contacting the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In aspects, the present disclosure provides a method of disrupting, correcting, and/or replacing a gene in a subject in need thereof, comprising administering an effective amount of the composition of any one of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein to the subject.

In aspects, the present disclosure provides a method of treating, ameliorating or preventing a disease or disorder in a subject, comprising (a) contacting a cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein, and (b) administering an effective amount of the cell to the subject.

In aspects, the present disclosure provides a method of treating, ameliorating or preventing a disease or disorder in a subject, comprising administering an effective amount of the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein to the subject.

In embodiments, composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein for use in treating, ameliorating or preventing a patient with a disease or disorder.

In aspects, the present disclosure provides use of the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein in the manufacture of a medicament for the treating, ameliorating or preventing of a disease or disorder.

In aspects, the present disclosure provides a method of detecting and/or quantifying a nucleic acid in a sample, comprising contacting the sample with a composition of any one of the embodiments and/or aspects disclosed herein.

In embodiments, the nucleic acid is a target and/or reporter nucleic acid. In embodiments, the method comprises detection of a reporter signal, the reporter signal being generated upon endonuclease cleavage. In embodiments, the reporter signal is a fluorescent signal. In embodiments, the endonuclease has collateral cleavage activity.

In various embodiments, the composition disclosed herein, or the trans-splicing system disclosed herein, further comprises a repair RNA (repRNA) sequence, comprising: (a) one or more exons and/or introns; (b) a splice donor and/or splice acceptor, wherein the repRNA is suitable for trans-splicing. In embodiments, the trans-splicing system comprises a splice donor, a splice acceptor, and replaces an internal exon. In embodiments, the repRNA is operably linked to the RNA molecule comprising a sequence complementary to one strand of a target nucleic acid molecule or the gRNA.

In aspects, the present disclosure provides a system for targeting a nucleic acid for trans-splicing, the system comprising: (a) an endonuclease of any one of the embodiments disclosed herein, and optionally an RNA molecule comprising a sequence complementary to one strand of a target nucleic acid molecule; (b) an RNA-binding polypeptide that associates with the endonuclease; and (c) a repair RNA (repRNA) sequence, comprising: (i) one or more exons and/or introns; (ii) a splice donor and/or splice acceptor.

In embodiments, the RNA molecule is a gRNA.

In embodiments, the endonuclease is not linked, associated, and/or fused with an RNA binding protein.

In embodiments, the repRNA is not operably linked to one or more gRNAs. In embodiments, the repRNA is provided in trans to one or more gRNAs.

In embodiments, the repRNA further comprises a ribozyme site. In embodiments, the ribozyme site is a hairpin, hammerhead, hepatitis delta virus (HDV), Varkud satellite (VS), or glmS ribozyme site, or a variant thereof. In embodiments, the ribozyme site is a HDV ribozyme site. In embodiments, the ribozyme site is upstream of the one or more exons and/or introns of the repRNA.

In aspects, the present disclosure provides a system for targeting a nucleic acid for trans-splicing, the system comprising: (a) an endonuclease of any one of the embodiments disclosed herein and an RNA molecule comprising a sequence complementary to one strand of a target nucleic acid molecule; and (b) a repair RNA (repRNA) sequence, comprising: (i) one or more exons and/or introns; (ii) a splice donor and/or splice acceptor.

In embodiments, the RNA molecule is a gRNA. In embodiments, the endonuclease is not linked, associated, and/or fused with an RNA binding protein. In embodiments, the repRNA is operably linked to one or more gRNAs.

In embodiments, the composition comprises a gRNA, repRNA, and a Cas endonuclease operably linked to a single promoter or a bidirectional promoter.

In embodiments, the gRNA and repRNA are located on a first side of the bidirectional promoter, and the Cas endonuclease is located on a second side of the bidirectional promoter.

In embodiments, disclosed herein is a composition comprising an endonuclease and having an amino acid sequence of least 90%, or at least 95%, or at least 98%, or at least 99% identity to SEQ ID NO: 3. In embodiments, substitutions are made to SEQ ID NO: 3:

```
Met Asp Lys His Pro Ser Asn Arg Tyr Ala Leu Pro Lys Val Ile Ile Ser Glu Val

Asp His Glu Arg Ile Leu Glu Phe Lys Val Lys Tyr Glu Lys Leu Ala Arg Leu

Asp Arg Phe Glu Val Lys Ala Met His Tyr Asp Gly Ala Glu Ile Val Phe Asp

Glu Val Val Ala Asn Gly Gly Leu Ile Glu Val Glu Tyr Gln Asp Asn Asn Lys

Thr Ile Thr Ile Asn Leu Asn Gly Lys Lys Tyr Thr Ile Asn Gly Arg Lys Val Gly

Gly Lys Arg Arg Leu Leu Glu Asp Arg Ile Ser Arg Gly Lys Val Cys Leu Glu

Leu His Asp Lys Ile Pro Asp Glu Lys Gly Asn Leu Arg Ser Ser Arg Thr Glu

Arg Glu Leu Ile Thr Phe Asp Ser Thr Lys Leu Tyr Ser Gln Ile Ile Gly Arg Asp

Val Ala Ser Thr Lys Glu Ile Tyr Leu Ile Lys Arg Phe Leu Ala Tyr Arg Ser Asp

Leu Leu Phe Tyr Tyr Gly Phe Ile Asp Asn Phe Phe Lys Val Ala Gly Asn Lys

Arg Glu Leu Trp Lys Ile Asp Phe Ser Gly Asp Lys Asn Gln Glu Leu Ile Lys

Tyr Phe Asn Phe Thr Ile Asn Asp Lys Leu Lys Asn Asp Lys Gly Tyr Leu Lys

Glu Tyr Thr Ala Asn Asp Glu Gln Ile Lys Lys Asp Leu Gln Asn Thr Lys Glu

Val Phe Thr Ala Leu Arg His Ala Leu Met His Phe Glu Tyr Asp Phe Phe Glu

Lys Leu Phe Asn Asn Glu Glu Ile Glu Thr Leu Ser Lys Ile His Asp Ile Glu Leu

Leu Asn Thr Met Ile Asn Lys Leu Asp Lys Leu Asn Ile Asp Thr Arg Lys Glu

Tyr Ile Asp Asp Glu Lys Ile Thr Val Phe Gly Glu Ile Ser Leu Lys Thr Leu

Tyr Gly Leu Tyr Ala His Thr Ala Ile Asn Arg Val Ala Phe Asn Lys Leu Ile Asn

Arg Phe Met Val Glu Asn Gly Thr Glu Asn Glu Ala Leu Lys Lys Tyr Phe Asn

Ser Lys Ala Glu Gly Gly Ile Ala Tyr Glu Ile Asp Ile His Gln Asn Ser Glu Tyr

Lys Gln Leu Tyr Ile Gln His Lys Asp Leu Val Ser Lys Leu Ser Ala Leu Ser Asp

Gly Asp Glu Ile Ala Asp Thr Asn Lys Lys Ile Ser Glu Leu Lys Val Lys Met

Lys Ala Ile Thr Lys Ala Asn Ser Leu Lys Arg Leu Glu His Lys Leu Arg Leu

Thr Phe Gly Phe Ile Tyr Thr Glu Tyr Gln Asp Tyr Asn Ala Phe Lys Asn Asn

Phe Asp Thr Asp Ile Lys Ser Gly Arg Phe Ile Pro Lys Asp Ser Glu Gly Lys Arg

Arg Gly Phe Asp His Arg Glu Leu Asp Gln Leu Lys Arg Tyr Tyr Asp Ala Thr

Phe Ala Asp Lys Lys Pro Gln Thr Lys Glu Thr Phe Asp Glu Ile Asp Lys Gln

Ile Asp Gln Leu Ser Leu Lys Asn Leu Ile Gly Asp Asp Thr Leu Leu Lys Val

Ile Leu Leu Ile Tyr Ile Phe Leu Pro Arg Glu Ile Lys Gly Glu Phe Leu Gly Phe

Val Lys Lys Tyr Tyr His Asp Thr Lys His Ile Glu Glu Asp Thr Lys Asp Lys

Asp Glu Gly Phe Asp Thr Phe Pro Val Gly Leu Lys Leu Lys Val Leu Asp

Lys Asn Ile Arg Ala Leu Ser Val Leu Lys His Ser Leu Ser Tyr Gln Ala Lys Tyr

Asn Lys Lys Glu Glu Lys Lys Glu Gln Phe Tyr Glu Ala Gly Asn Arg His Gly

Arg Phe Tyr Lys Lys Leu Gly Ile Ser His Asn Gln Glu Glu Phe Asp Lys Ser

Val Tyr Ala Pro Leu Leu Arg Tyr His Ala Ala Leu Phe Lys Leu Leu Asn Asp
```

-continued

```
Phe Glu Ile Tyr Ser Leu Ala Gln His Ile Glu Gly Lys Glu Thr Leu Ala Gln Gln

Ile Glu Lys Pro Gln Phe Ser Gln Tyr Glu His Tyr Asn Phe Arg Lys Met Leu

Ser Lys Thr Tyr Pro Lys Ser Ala Glu Arg Gly Ala Leu Asp Asn Asp Ala Phe

Asp Thr Val Ile Asn Met Arg Asn Asp Ile Ala His Leu Ser His Glu Pro Leu Phe

Glu Cys Pro Leu Asp Gly Lys Lys Ser Tyr Lys Leu Lys Gln Gly Lys Arg Thr

Asn Thr Ile Asn Val Lys Pro Leu Pro Ile Ser Arg Lys Met Ile Val Asp Phe Ile

Ser Ser Gln Ser Asp Met Lys Lys Thr Leu Gly Tyr Asp Ala Val Asn Asp Leu

Thr Met Lys Ile Ile Gln Leu Arg Thr Arg Leu Lys Val Tyr Ala Asp Lys Ser Glu

Thr Ile Lys Thr Leu Val Asp Ala Ala Lys Thr Pro Asn Asp Phe Tyr His Ile Tyr

Lys Val Lys Gly Val Glu Ala Ile Asn Arg His Leu Leu Glu Val Ile Gly Glu Thr

Lys Asp Glu Lys Arg Ile Arg Lys Arg Ile Glu Ser Gly Asn Ala Ile Ala Gly Arg

Thr Pro Ala Asp Ser Gln Glu Asn
```

As described herein, substitutions may be made to this sequence to generate the inventive endonuclease (including, taking into account degeneracy of the genetic code).

In some embodiments, the endonuclease has one or more substitutions at positions corresponding to D38X, A59X, G172X, T236X, T319X, H375X, H419X, T424X, E529X, T541X, G562X, K564X, D569X, A586X, N641X, D642X, S647X, D721X, R779X, K13X, K566X, G554X, A35X, E110X, G314X, K114X, D498X, I86X, V57X, H249X, R704X of SEQ ID NO: 3, wherein the substitution is defined by X and wherein X is any amino acid. In some embodiments, X is an essential or non-essential amino acid.

In some embodiments, X is a hydrophilic or hydrophobic amino acid.

In some embodiments, X is a hydrophilic amino acid.

In some embodiments, X is a polar and positively charged hydrophilic amino acid. In some embodiments, X is selected from arginine (R) or lysine (K).

In some embodiments, X is a polar and neutral charged hydrophilic amino acid. In some embodiments, X is selected from asparagine (N), glutamine (Q), serine (S), threonine (T), proline (P), and cysteine (C).

In some embodiments, X is a polar and negatively charged hydrophilic amino acid. In some embodiments, X is selected from aspartate (D) or glutamate (E).

In some embodiments, wherein X is an aromatic, polar and positively charged hydrophilic amino acid. In some embodiments, wherein X is histidine (H).

In some embodiments, X is a hydrophobic amino acid.

In some embodiments, X is a hydrophobic, aliphatic amino acid. In some embodiments, X is selected from glycine (G), alanine (A), leucine (L), isoleucine (I), methionine (M), or valine (V).

In some embodiments, X is a hydrophobic, aromatic amino acid. In some embodiments, wherein X is selected from phenylalanine (F), tryptophan (W), or tyrosine (Y).

In some embodiments, the endonuclease of SEQ ID NO: 3 comprises one or more of the following substitutions:
  a hydrophilic residue other than aspartate (D) at a position corresponding to 38;
  a hydrophobic residue other than alanine (A) at a position corresponding to 59;
  a hydrophobic residue other than glycine (G) at a position corresponding to 172;
  a hydrophilic residue other than threonine (T) at a position corresponding to 236;
  a hydrophilic residue other than threonine (T) at a position corresponding to 319;
  a hydrophilic residue other than histidine (H) at a position corresponding to 375;
  a hydrophilic residue other than histidine (H) at a position corresponding to 419;
  a hydrophilic residue other than threonine (T) at a position corresponding to 424;
  a hydrophilic residue other than glutamate (E) at a position corresponding to 529;
  a hydrophilic residue other than threonine (T) at a position corresponding to 541;
  a hydrophobic residue other than glycine (G) at a position corresponding to 562;
  a hydrophilic residue other than lysine (K) at a position corresponding to 564;
  a hydrophilic residue other than aspartate (D) at a position corresponding to 569;
  a hydrophobic residue other than alanine (A) at a position corresponding to 586;
  a hydrophilic residue other than asparagine (N) at a position corresponding to 641;
  a hydrophilic residue other than aspartate (D) at a position corresponding to 642;
  a hydrophilic residue other than serine (S) at a position corresponding to 647;
  a hydrophilic residue other than aspartate (D) at a position corresponding to 721;
  a hydrophilic residue other than arginine (R) at a position corresponding to 779;
  a hydrophilic residue other than lysine (K) at a position corresponding to 13;
  a hydrophilic residue other than lysine (K) at a position corresponding to 566;
  a hydrophobic residue other than glycine (G) at a position corresponding to 554;
  a hydrophobic residue other than alanine (A) at a position corresponding to 35;
  a hydrophilic residue other than glutamate (E) at a position corresponding to 110;
  a hydrophobic residue other than glycine (G) at a position corresponding to 314;

a hydrophilic residue other than lysine (K) at a position corresponding to 114;
a hydrophilic residue other than aspartate (D) at a position corresponding to 498;
a hydrophobic residue other than isoleucine (I) at a position corresponding to 86;
a hydrophobic residue other than valine (V) at a position corresponding to 57;
a hydrophilic residue other than histidine (H) at a position corresponding to 249; and
a hydrophilic residue other than arginine (R) at a position corresponding to 704.

In some embodiments, the endonuclease of SEQ ID NO: 3 comprises D38F. In some embodiments, the endonuclease of SEQ ID NO: 3 comprises A59V. In some embodiments, the endonuclease of SEQ ID NO: 3 comprises G172L. In some embodiments, the endonuclease of SEQ ID NO: 3 comprises T236L. In some embodiments, the endonuclease of SEQ ID NO: 3 comprises T319I. In some embodiments, the endonuclease of SEQ ID NO: 3 comprises H375L. In some embodiments, the endonuclease of SEQ ID NO: 3 comprises H419Y. In some embodiments, the endonuclease of SEQ ID NO: 3 comprises T424F. In some embodiments, the endonuclease of SEQ ID NO: 3 comprises E529L. In some embodiments, the endonuclease of SEQ ID NO: 3 comprises T541L. In some embodiments, the endonuclease of SEQ ID NO: 3 comprises G562Y. In some embodiments, the endonuclease of SEQ ID NO: 3 comprises K564M. In some embodiments, the endonuclease of SEQ ID NO: 3 comprises D569L. In some embodiments, the endonuclease of SEQ ID NO: 3 comprises A586I. In some embodiments, the endonuclease of SEQ ID NO: 3 comprises N641F. In some embodiments, the endonuclease of SEQ ID NO: 3 comprises D642L. In some embodiments, the endonuclease of SEQ ID NO: 3 comprises S647L. In some embodiments, the endonuclease of SEQ ID NO: 3 comprises D721L. In some embodiments, the endonuclease of SEQ ID NO: 3 comprises R779I. In some embodiments, the endonuclease of SEQ ID NO: 3 comprises K13R. In some embodiments, the endonuclease of SEQ ID NO: 3 comprises K566R. In some embodiments, the endonuclease of SEQ ID NO: 3 comprises G554H. In some embodiments, the endonuclease of SEQ ID NO: 3 comprises A35N. In some embodiments, the endonuclease of SEQ ID NO: 3 comprises E110T. In some embodiments, the endonuclease of SEQ ID NO: 3 comprises G314Q. In some embodiments, the endonuclease of SEQ ID NO: 3 comprises K114P. In some embodiments, the endonuclease of SEQ ID NO: 3 comprises D498P. In some embodiments, the endonuclease of SEQ ID NO: 3 comprises I86P. In some embodiments, the endonuclease of SEQ ID NO: 3 comprises V57E. In some embodiments, the endonuclease of SEQ ID NO: 3 comprises H249W. In some embodiments, the endonuclease of SEQ ID NO: 3 comprises R704F.

In some embodiments, the endonuclease of SEQ ID NO: 3 comprises D38F and A59V. In some embodiments, the endonuclease of SEQ ID NO: 3 comprises D38F, A59V, and G172L. In some embodiments, the endonuclease of SEQ ID NO: 3 comprises D38F, A59V, G172L, and T236L. In some embodiments, the endonuclease of SEQ ID NO: 3 comprises D38F, A59V, G172L, T236L, and T319I. In some embodiments, the endonuclease of SEQ ID NO: 3 comprises D38F, A59V, G172L, T236L, T319I, and H375L. In some embodiments, the endonuclease of SEQ ID NO: 3 comprises D38F, A59V, G172L, T236L, T319I, H375L, and H419Y. In some embodiments, the endonuclease of SEQ ID NO: 3 comprises D38F, A59V, G172L, T236L, T319I, H375L, H419Y, and T424F. In some embodiments, the endonuclease of SEQ ID NO: 3 comprises D38F, A59V, G172L, T236L, T319I, H375L, H419Y, T424F, and E529L. In some embodiments, the endonuclease of SEQ ID NO: 3 comprises D38F, A59V, G172L, T236L, T319I, H375L, H419Y, T424F, E529L, and T541L. In some embodiments, the endonuclease of SEQ ID NO: 3 comprises D38F, A59V, G172L, T236L, T319I, H375L, H419Y, T424F, E529L, T541L, and G562X. In some embodiments, the endonuclease of SEQ ID NO: 3 comprises D38F, A59V, G172L, T236L, T319I, H375L, H419Y, T424F, E529L, T541L, G562X, and K564M. In some embodiments, the endonuclease of SEQ ID NO: 3 comprises D38F, A59V, G172L, T236L, T319I, H375L, H419Y, T424F, E529L, T541L, G562X, K564M, and D569L. In some embodiments, the endonuclease of SEQ ID NO: 3 comprises D38F, A59V, G172L, T236L, T319I, H375L, H419Y, T424F, E529L, T541L, G562X, K564M, D569L, and A586I. In some embodiments, the endonuclease of SEQ ID NO: 3 comprises D38F, A59V, G172L, T236L, T319I, H375L, H419Y, T424F, E529L, T541L, G562X, K564M, D569L, A586I, and N641F. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, and D642L. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, and S647L. In some embodiments, the endonuclease of SEQ ID NO: 3 comprises D38F, A59V, G172L, T236L, T319I, H375L, H419Y, T424F, E529L, T541L, G562X, aK564M, D569L, A586I, N641F, D642L, S647L, and D721L. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, and R779I. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, and K13R. In some embodiments, the endonuclease of SEQ ID NO: 3 comprises D38F, A59V, G172L, T236L, T319I, H375L, H419Y, T424F, E529L, T541L, G562X, aK564M, D569L, A586I, N641F, D642L, S647L, D721L, R779I, K13R, and K566R. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, and G554H. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, and A35N. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, and E110T. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, and G314Q. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, and K114P. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, and D498P. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, and I86P. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, and V57E. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, V57E, and H249W. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, V57E, H249W, and R704F.

In some embodiments, the disclosed herein are one or more (e.g. about 1, or about 2, or about 3, or about 4, or about 5, or about 6, or about 7, or about 8, or about 9, or about 10, or about 15, or about 20, or about 30) substitutions to SEQ ID NO: 3 or a sequence with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 3 (or about 70%, or about 75%, or about 80%, or about 85%, or about 90%, or about 95%, or about 96%, or about 97%, or about 98%, or about 99% identity to SEQ ID NO: 3). In various embodiments, one or more amino acids of SEQ ID NO: 3 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In illustrative embodiments, inventive substitutions include, but are not limited to one or more (e.g. about 1, or about 2, or about 3, or about 4, or about 5, or about 6, or about 7, or about 8, or about 9, or about 10, or about 15, or about 20, or about 30) substitutions to SEQ ID NO: 3, or a sequence with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 3: D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, V57E, H249W, and R704F.

The details of one or more examples of the disclosure are set forth in the description below. Other features or advantages of the present disclosure will be apparent from the following drawings, detailed description of several examples, and also from the appended claims. The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

DESCRIPTION OF THE DRAWINGS

FIG. 1A, FIG. 1B, FIG. 1C, and FIG. 1D are images showing the protein sizes of the Cas13K2F system for SEQ ID NO: 1 (Cas13K2F1), SEQ ID NO: 2 (Cas13K2F2), SEQ ID NO: 3 (Cas13K2F3), SEQ ID NO: 4 (Cas13K2F5), SEQ ID NO: 80 (Cas13K2F7), SEQ ID NO: 81 (Cas13K2F8), SEQ ID NO: 82 (Cas13K2F9), SEQ ID NO: 83 (Cas13K2F10), SEQ ID NO: 84 (Cas13K2F11), SEQ ID NO: 85 (Cas13K2F12), SEQ ID NO: 86 (Cas13K2F13), and SEQ ID NO: 87 (Cas13K2F14). The red or black arrows in FIG. 1 indicate the placement of the higher eukaryotes and prokaryotes nucleotide-binding (HEPN) domain in each protein.

FIG. 5 is a percent identity matrix of SEQ ID NO: 6 (Cas13X.1), SEQ ID NO: 7 (Cas13bt3), SEQ ID NO: 8 (Cas13bt2), SEQ ID NO: 9 (Cas13bt1), SEQ ID NO: 10 (Cas13bt8), SEQ ID NO: 11 (Cas13X.2), SEQ ID NO: 12 (Cas13bt9), SEQ ID NO: 13 (Cas13bt11), SEQ ID NO: 14 (Cas13bt5), SEQ ID NO: 15 (Cas13bt10), SEQ ID NO: 16 (Cas13bt15), SEQ ID NO: 17 (Cas13bt7), SEQ ID NO: 18 (Cas13bt6), SEQ ID NO: 19 (Cas13bt14), SEQ ID NO: 20 (Cas13Y.3), SEQ ID NO: 21 (Cas13bt12), SEQ ID NO: 22

(Cas13Y.1), SEQ ID NO: 23 (Cas13bt4), SEQ ID NO: 24 (Cas13bt16), SEQ ID NO: 25 (Cas13Y.5), and SEQ ID NO: 26 (Cas13Y.4).

Figure 6:
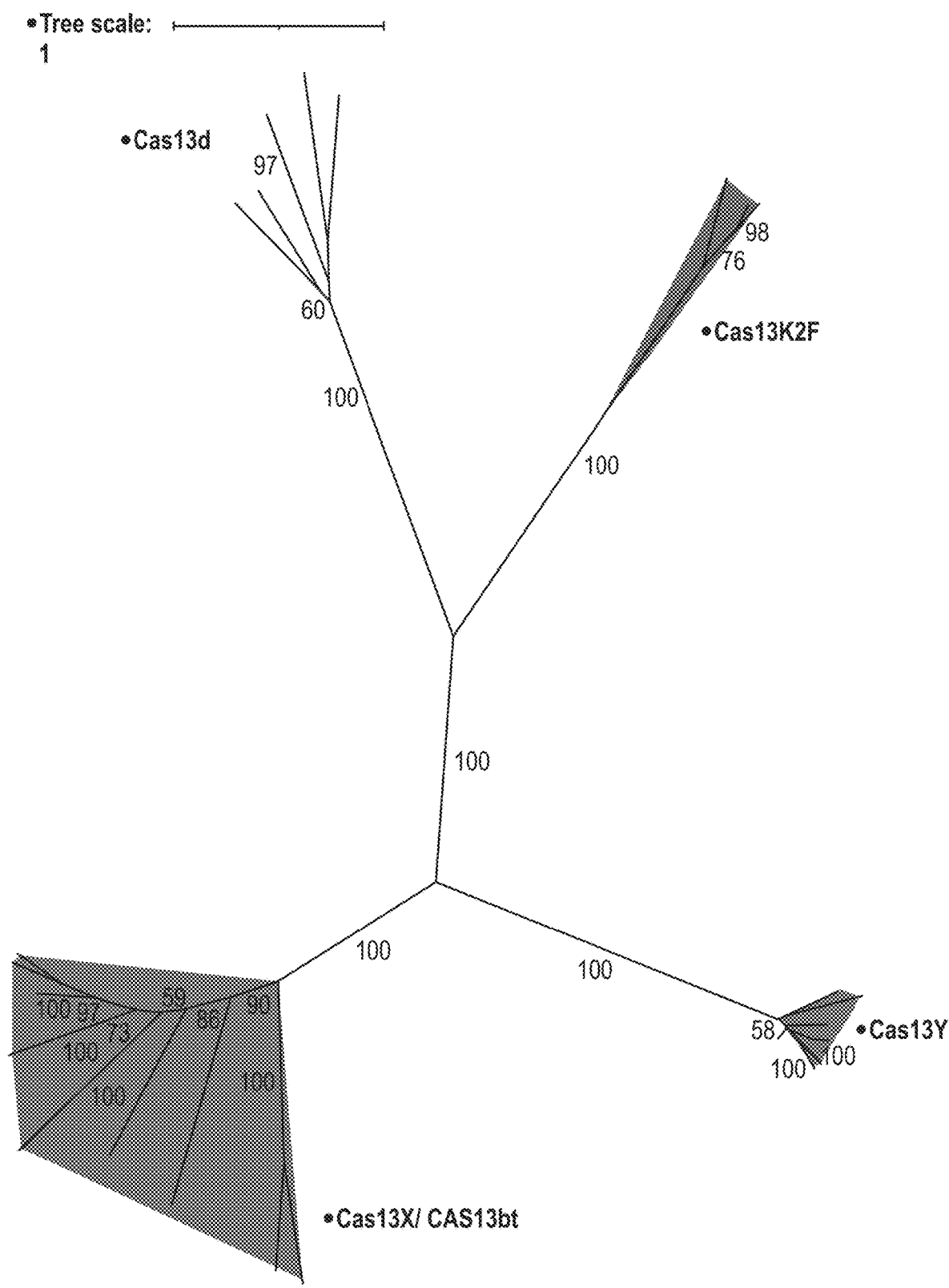

FIG. 6 is an image showing a maximum likelihood phylogenetic tree of SEQ ID NO: 6 (Cas13X.1), SEQ ID NO: 7 (Cas13bt3), SEQ ID NO: 8 (Cas13bt2), SEQ ID NO: 9 (Cas13bt1), SEQ ID NO: 10 (Cas13bt8), SEQ ID NO: 11 (Cas13X.2), SEQ ID NO: 12 (Cas13bt9), SEQ ID NO: 13 (Cas13bt11), SEQ ID NO: 14 (Cas13bt5), SEQ ID NO: 15 (Cas13bt10), SEQ ID NO: 16 (Cas13bt15), SEQ ID NO: 17 (Cas13bt7), SEQ ID NO: 18 (Cas13bt6), SEQ ID NO: 19 (Cas13bt14), SEQ ID NO: 20 (Cas13Y.3), SEQ ID NO: 21 (Cas13bt12), SEQ ID NO: 22 (Cas13Y.1), SEQ ID NO: 23 (Cas13bt4), SEQ ID NO: 24 (Cas13bt16), SEQ ID NO: 25 (Cas13Y.5), and SEQ ID NO: 26 (Cas13Y.4).

Figure 7A:
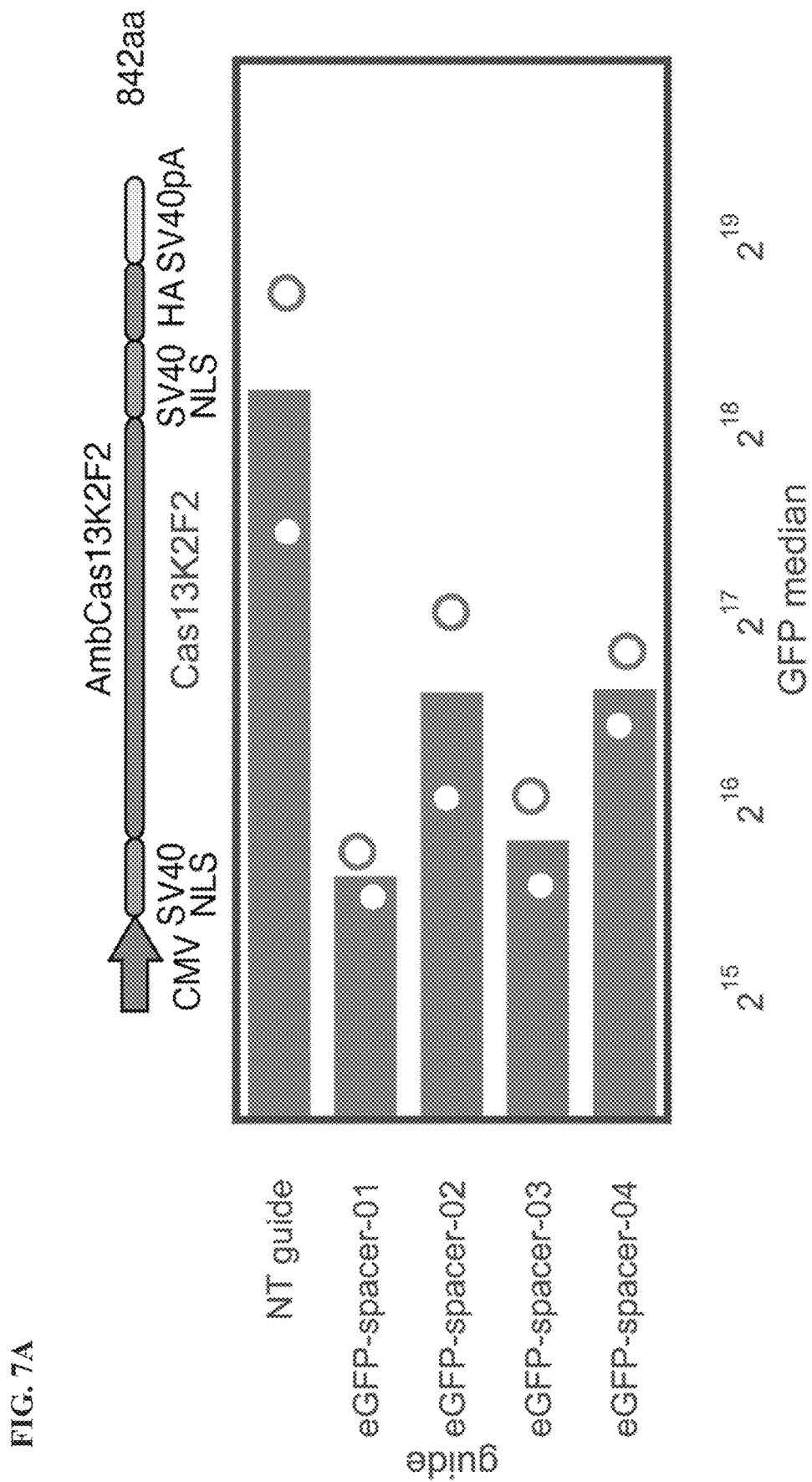
Figure 7B:
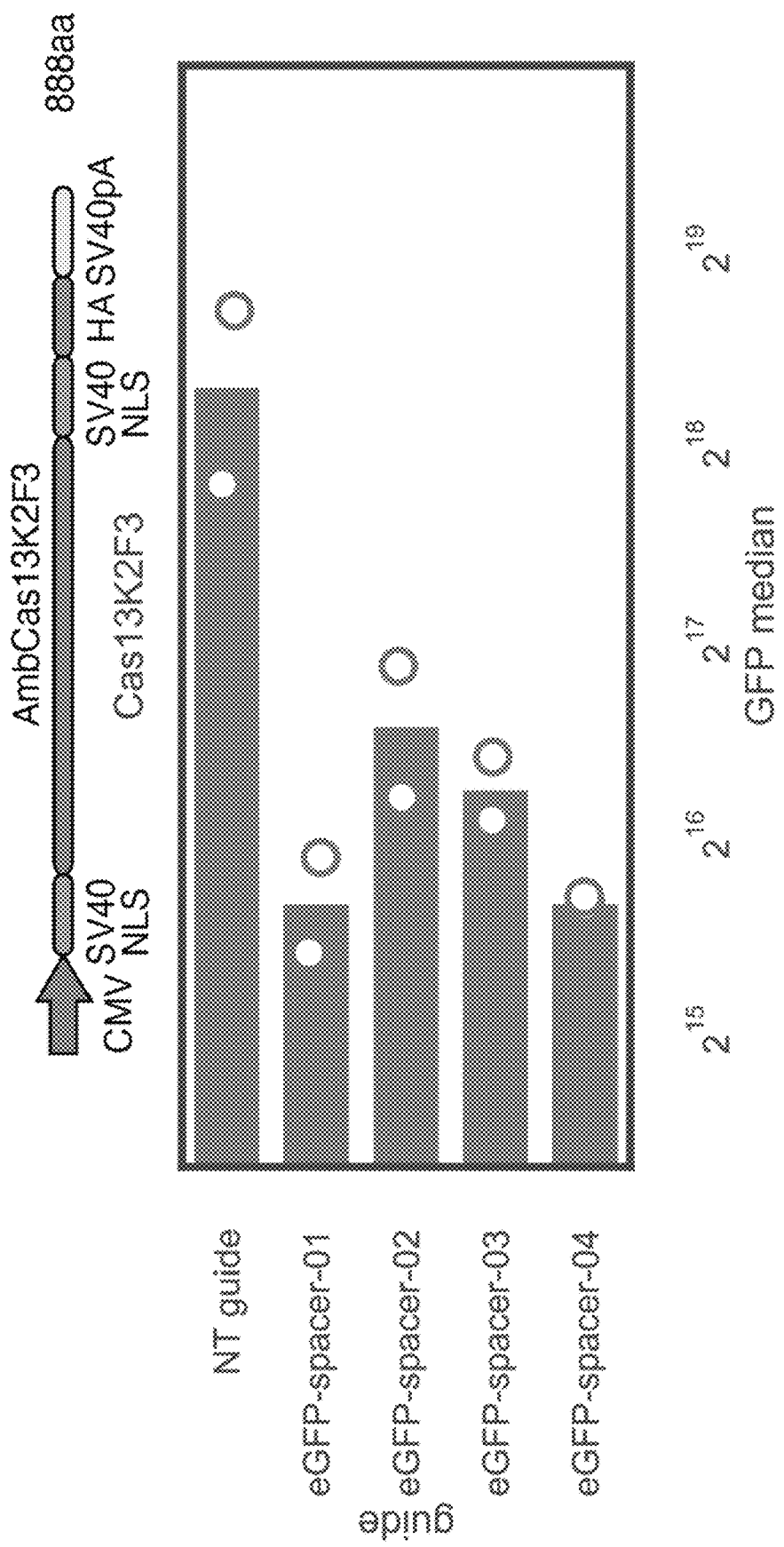
Figure 7C:
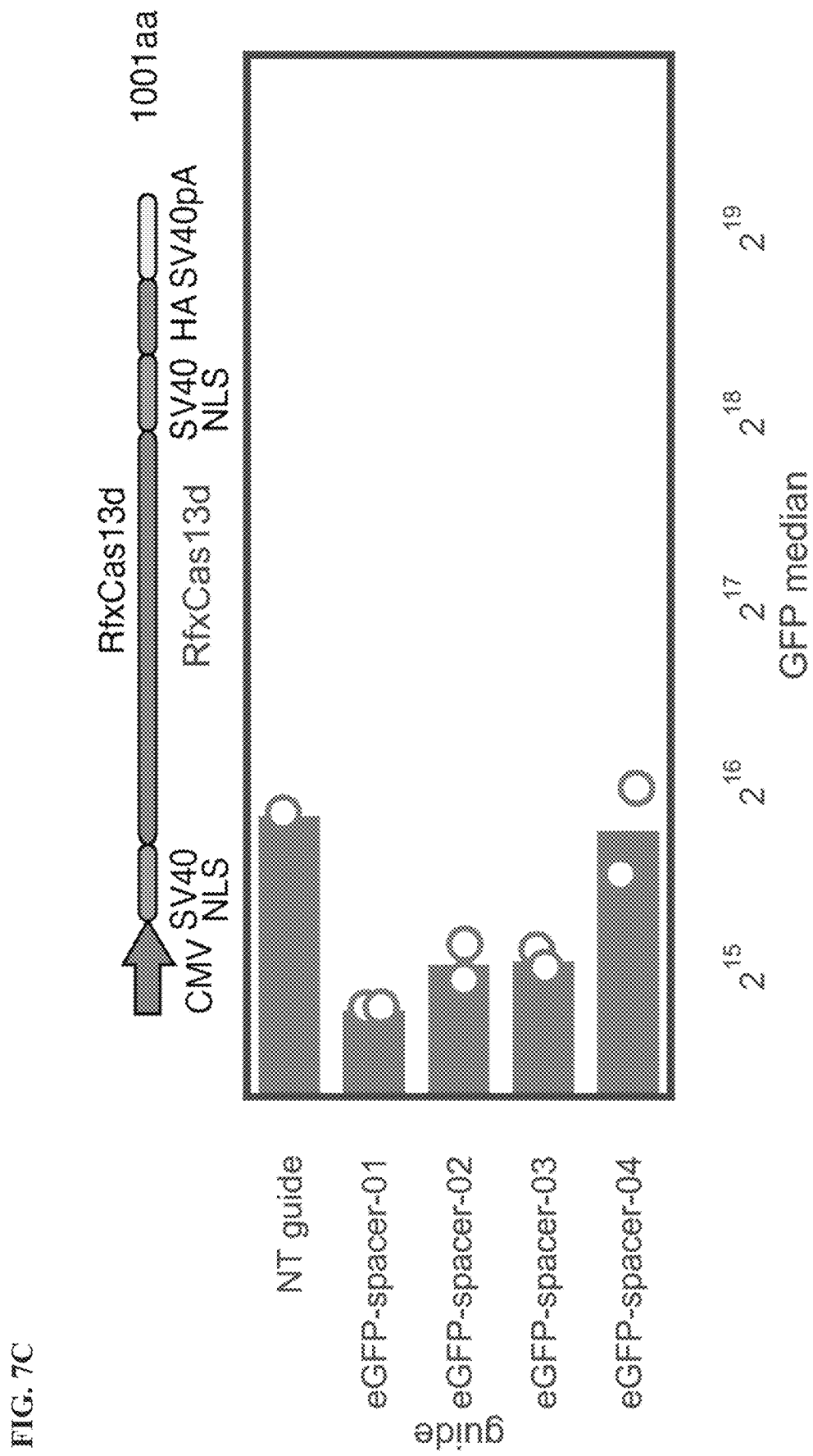

FIGS. 7A-7C each show results of RNA cleavage experiments for SEQ ID NO: 2 (FIG. 7A), SEQ ID NO: 3 (FIG. 7B), and SEQ ID NO: 27 (FIG. 7C).

Figure 8A:
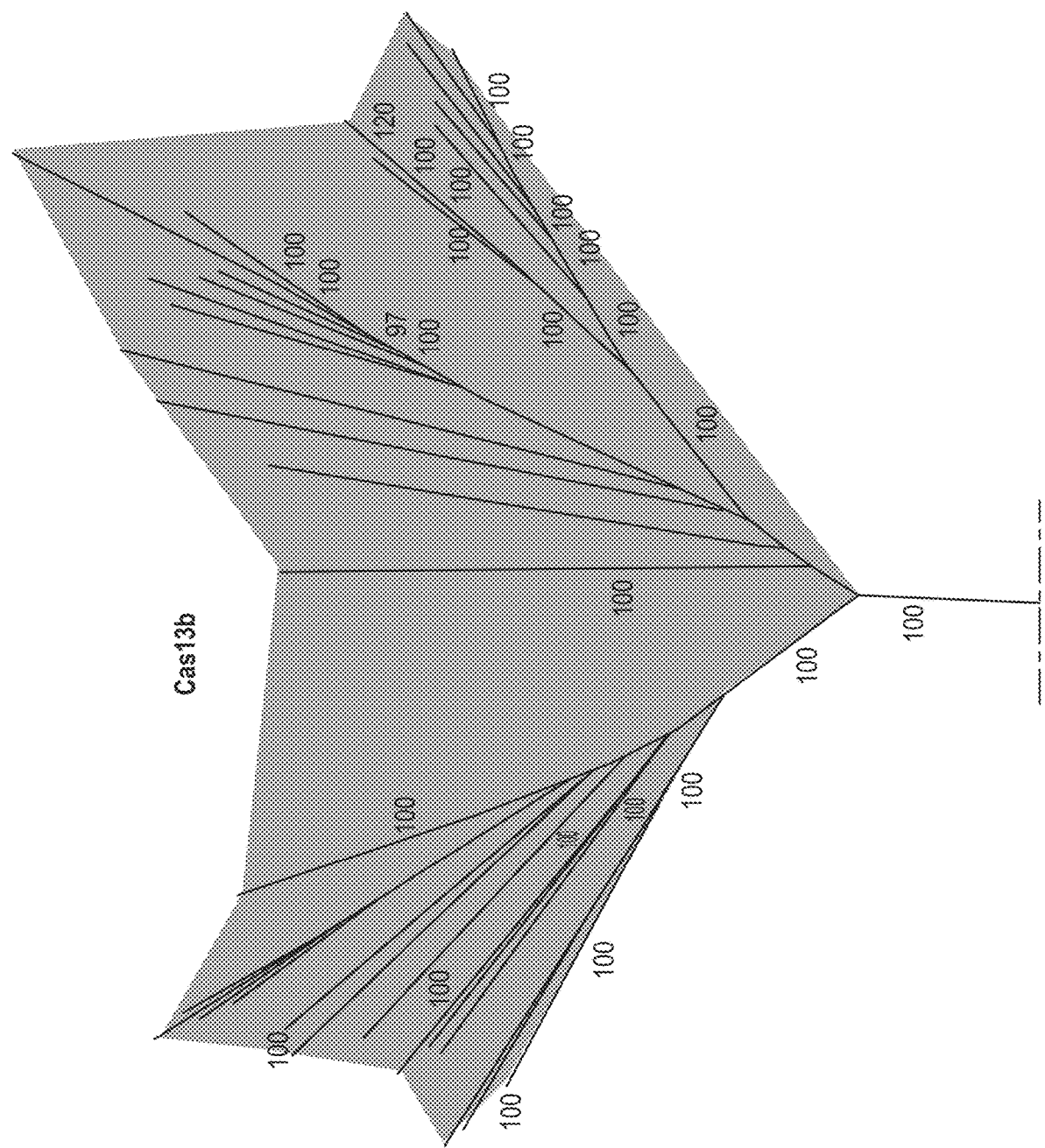
Figure 8A:
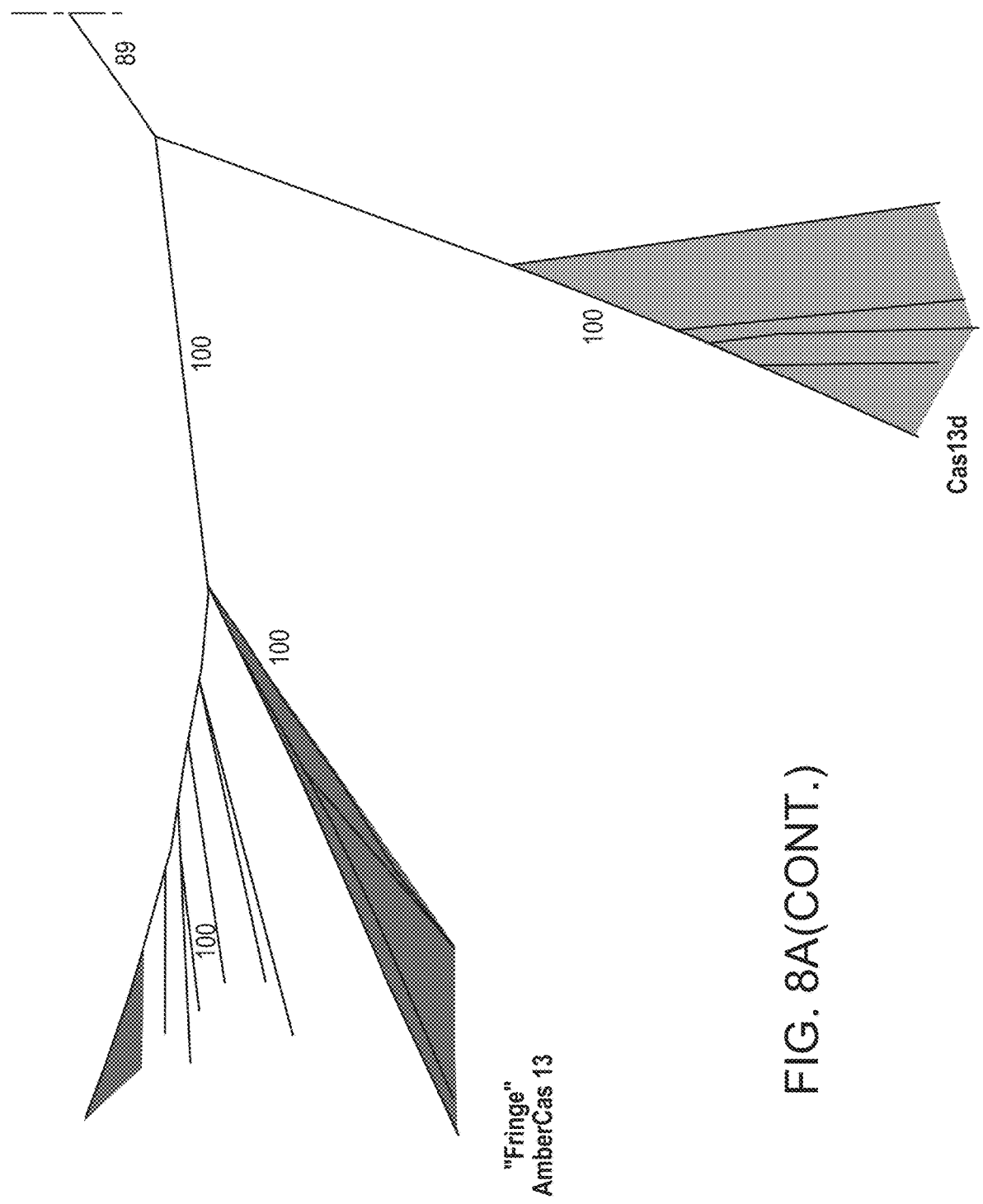
Figure 8A:
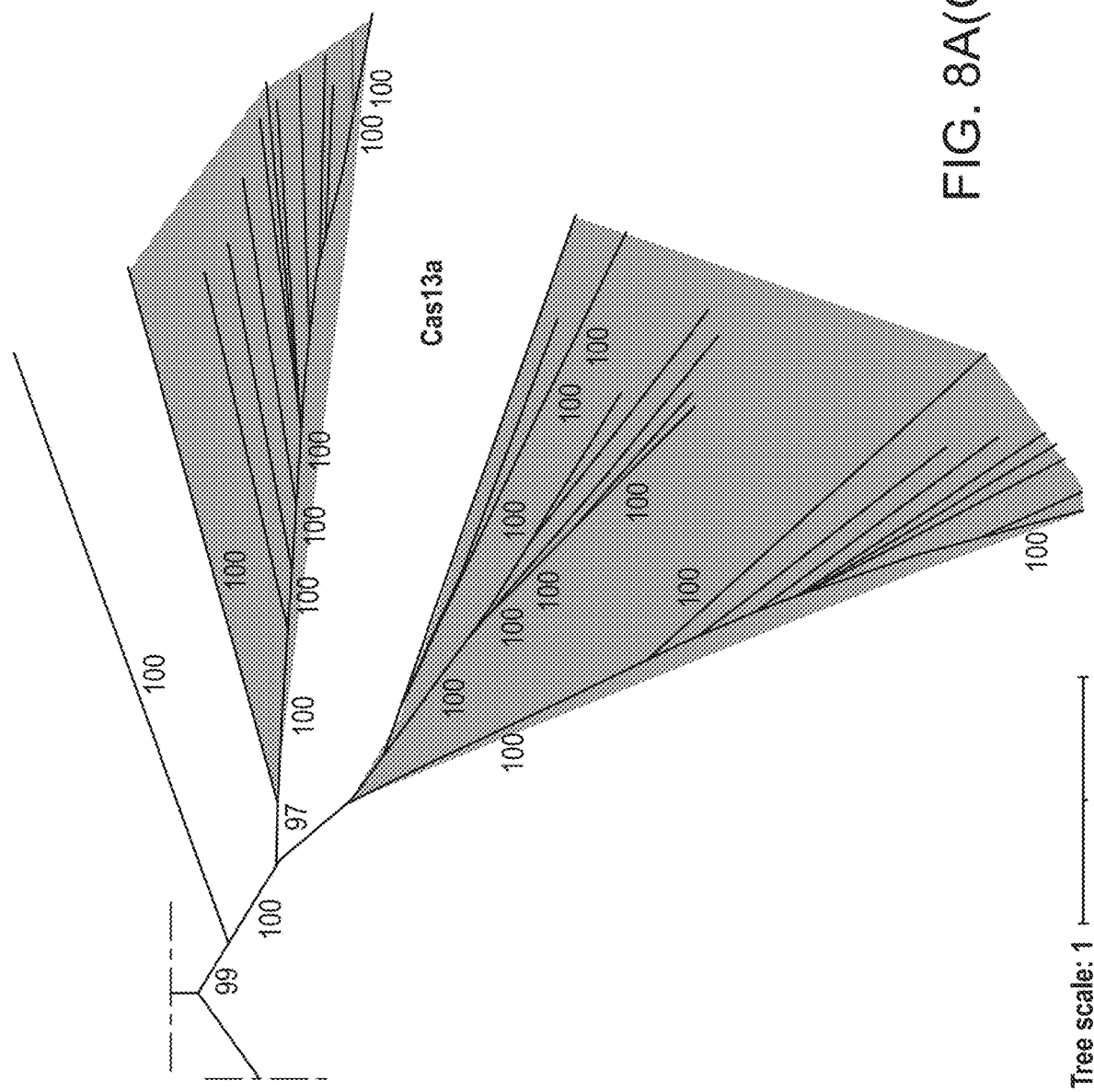

FIG. 8A is an image showing a maximum likelihood phylogenetic tree of Cas13, which has high divergence of Cas13, a clade which includes the Cas13K2F system, which is a fringe CRISPR-Cas13 family with <7% identity to previously characterized RNA-targeting systems.

Figure 8B:
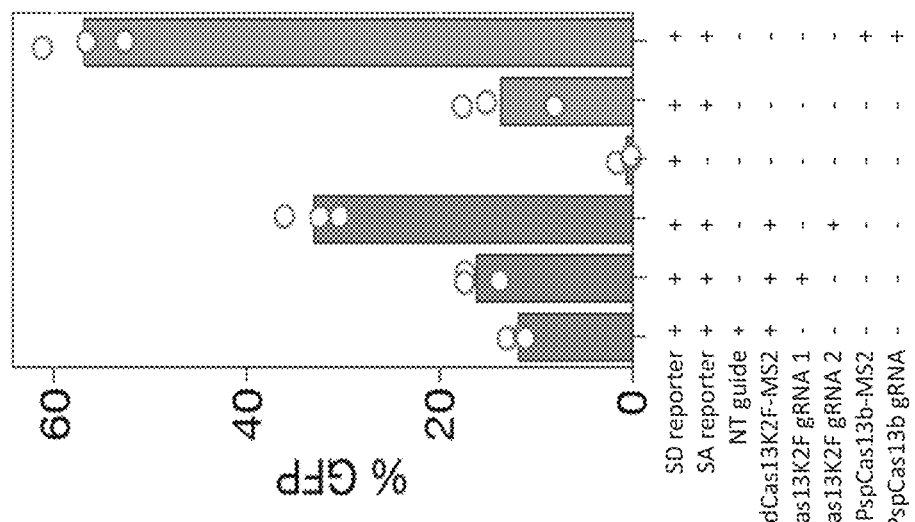

FIG. 8B is a graph showing the percent of GFP positive cells following transfection with an SD reporter encoding the 5'end of GFP, an SA reporter having MS2 stem loops and encoding the 3'end of GFP, and/or (i) a catalytically inactive Cas13K2F fused to a MS2 coat protein ("dCas13K2F-MS2") and gRNA targeting the SD reporter (Cas13K2F gRNA 1 or 2), or (ii) a catalytically inactive PspCas13 fused to a MS2 coat protein (dPspCas13b-MS2) and gRNA targeting the SD reporter (PspCas13b gRNA). Control cells were transfected with a non-targeting (NT) gRNA.

Figure 9:
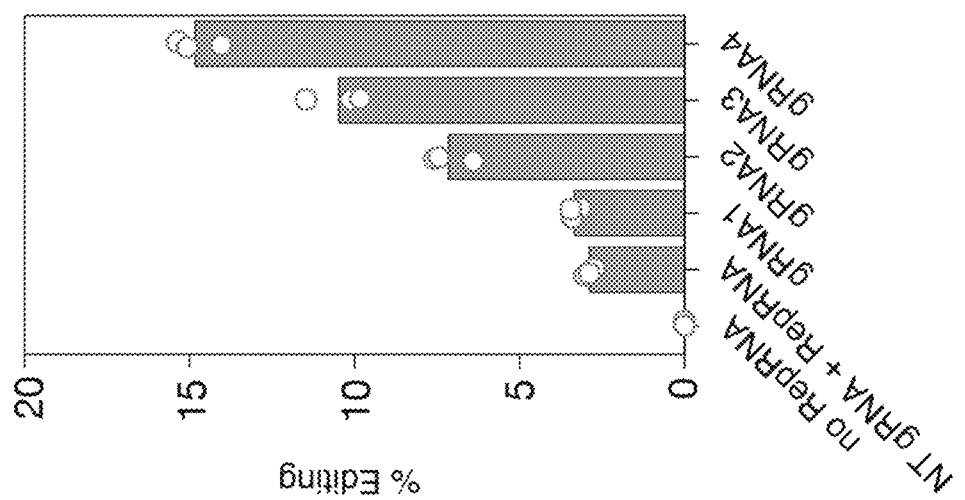

FIG. 9 is a graph showing the percent of GFP positive cells following transfection with (i) a target containing a sequence encoding the 5'end of GFP, a splice donor, a gene A intron, a splice acceptor, and a gene A exon, (ii) a template having two MS2 stem loops and a sequence encoding the 3'end of GFP, (iii) dCas13K2F fused to a MS2 coat protein (dCas13K2F-MS2) and gRNA directed to the target (gRNA12, gRNA2, gRNA18, or gRNA19). Control cells were transfected with a non-targeting (NT) gRNA or target only ("no RepRNA").

Figure 10A:
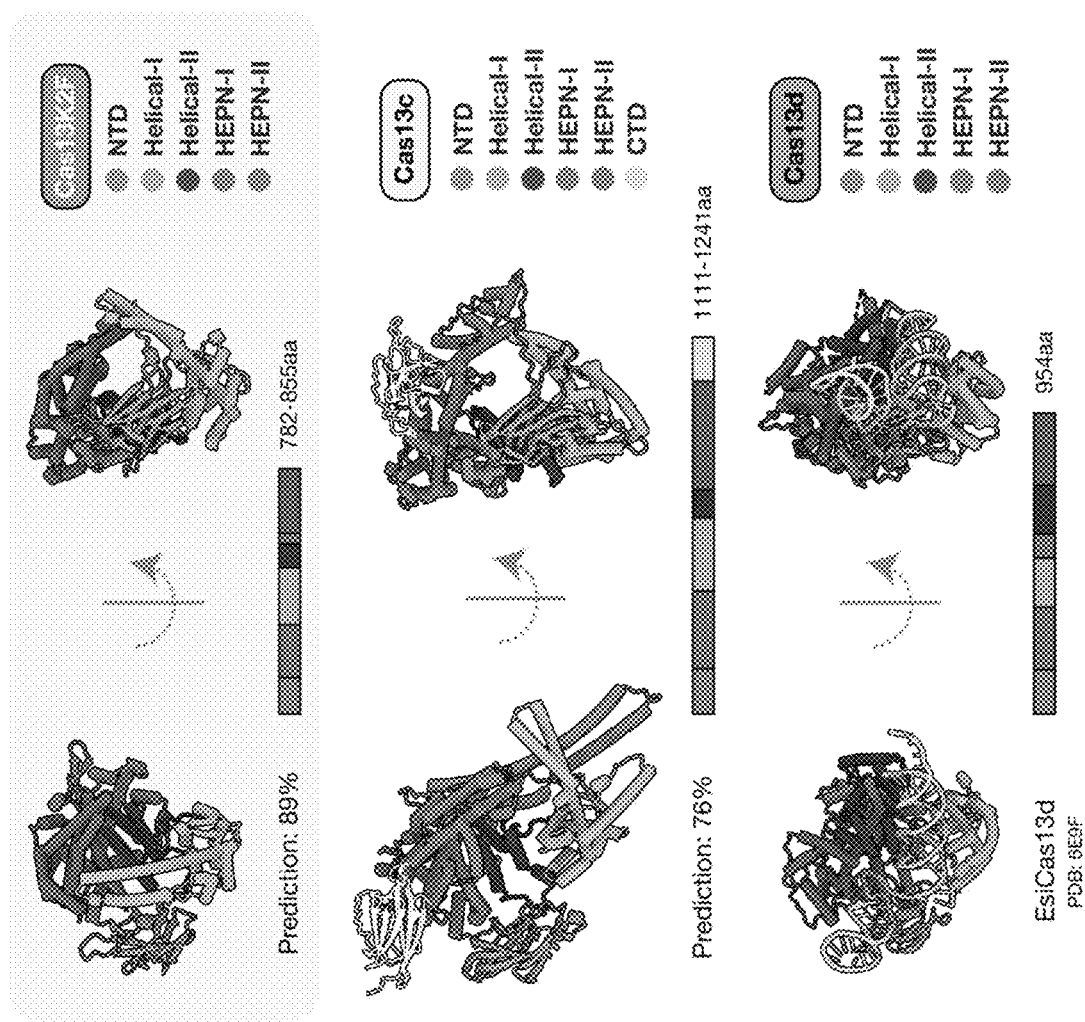
Figure 10C:
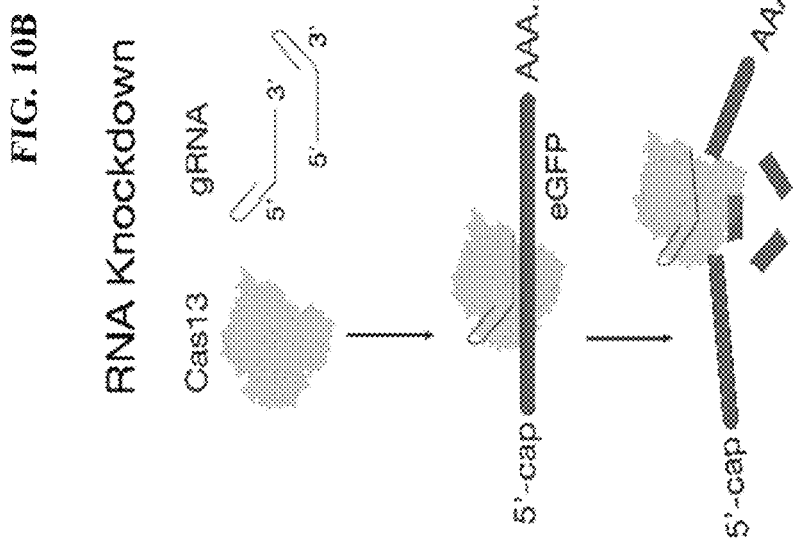
Figure 10C:
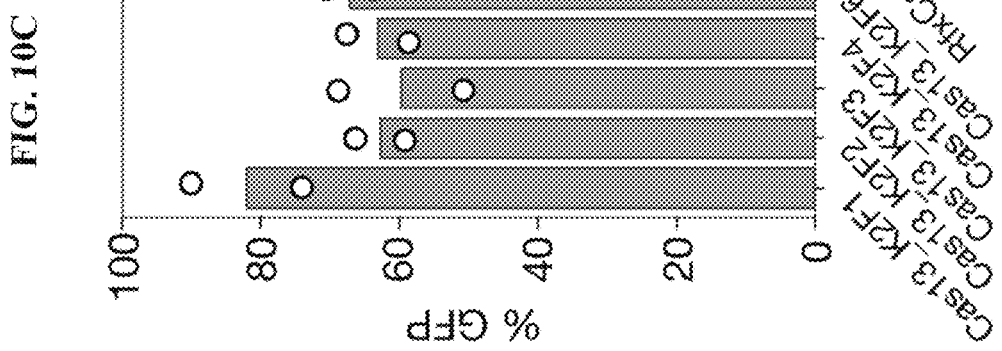
Figure 10C:
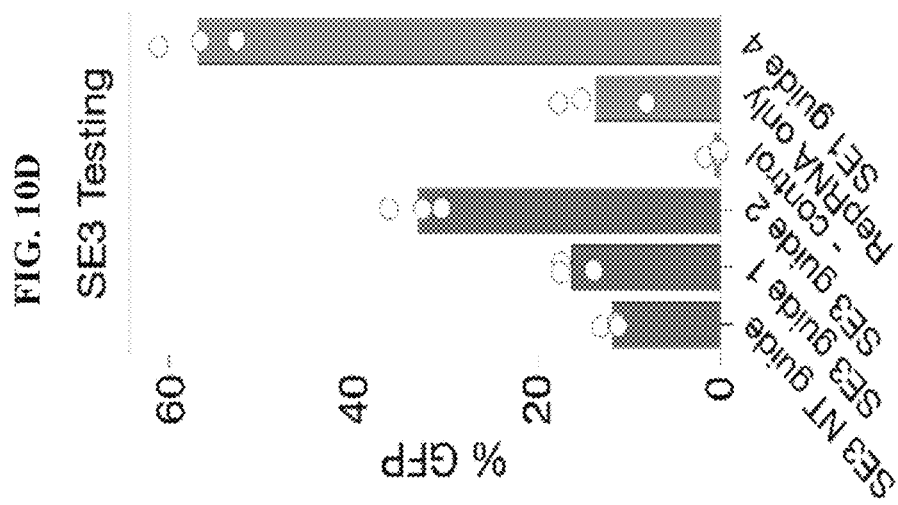

FIG. 10A is an image showing ColabFold-based predicted protein structures and domain organizations of Cas13e (used herein interchangeably with "Cas13K2F") and Cas13c representatives relative to EsiCas13d (PDB:6E9F). FIG. 10B is an image showing an RNA knockdown strategy to test the trans-splicing activity of Cas13e in mammalian cells. FIG. 10C is a graph showing the relative Cas13e GFP fluorescence (=MFI targeting crRNA/MFI nontargeting crRNA) of HEK293T-GFP cells transfected with plasmids expressing Cas13e or RfxCas13d, and GFP-targeting crRNA, measured by flow cytometry to show trans-splicing. Percent GFP detected in mammalian cells relative to non-targeting negative controls. In FIG. 10C, plasmids expressing Cas13e1 (used herein interchangeably with "Cas13K2F1"), Cas13e2 (used herein interchangeably with "Cas13K2F2"), Cas13e3 (used herein interchangeably with "Cas13K2F3"), Cas13e4 (used herein interchangeably with "Cas13K2F4"), and Cas13e5 (used herein interchangeably with "Cas13K2F5") are shown on the x-axis. FIG. 10D is a graph showing the validation of dCas13e activity as capable of trans-splicing in mammalian cells.

Figure 11A:
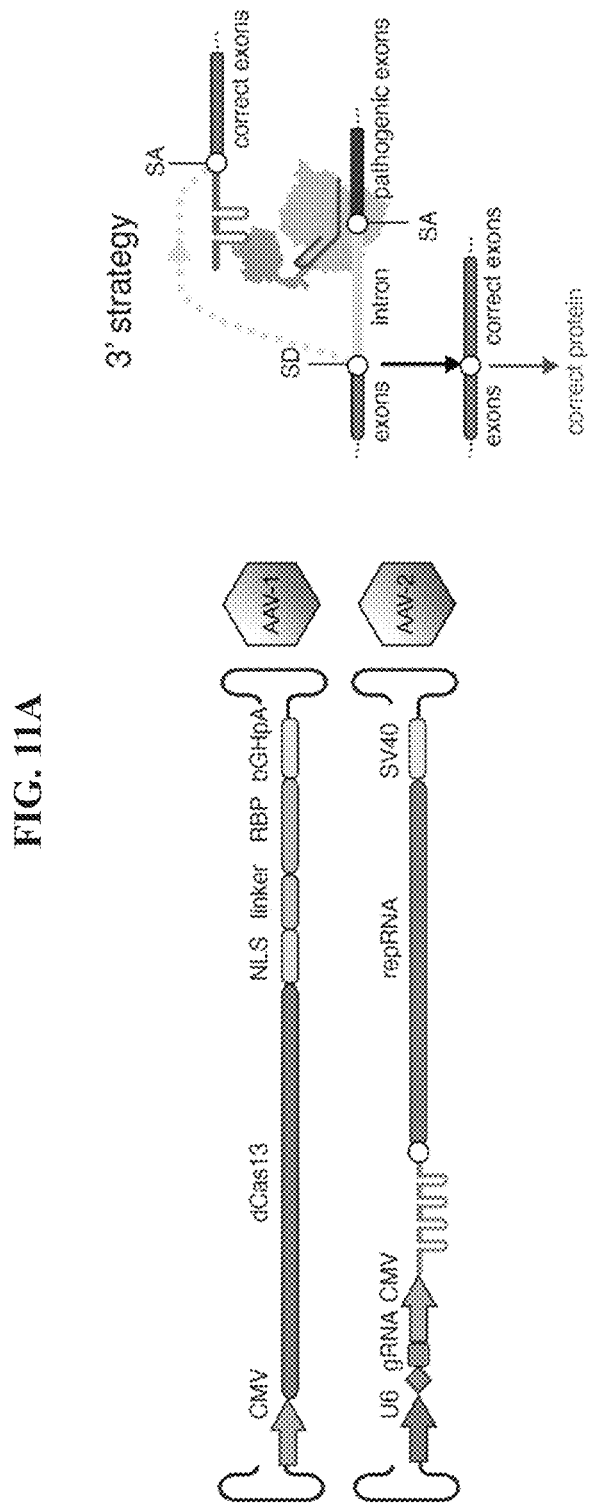
Figure 11B:
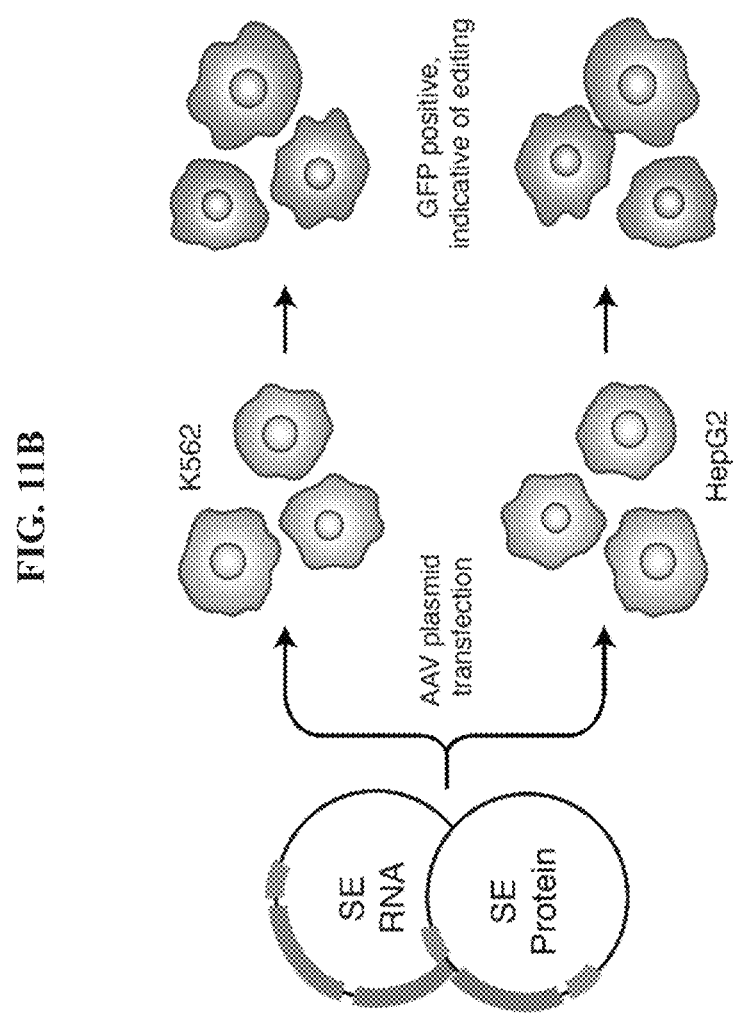

FIG. 11A is an image showing v1 SE3 AAVs and the strategy for RNA replacement at the 3' end. FIG. 11B is an image of experimental workflow for evaluating the performance of SE3 as AAV plasmids in alternative cell types. FIG. 11C is an image showing editing performance of SE3 with targeting (T) and non-targeting (NT) guides in HepG2 cell lines. FIG. 11D is a graph showing the number of pathogenic mutations, which are plotted in maroon (dark) per position in the USH2A gene, with exons shown in blue (grey color) and introns shown in light cream color (white color). Over 700 pathogenic variants occur throughout the full length. FIG. 11E is an image showing a non-limiting strategy for the correction of the 5' end of a target RNA. FIG. 11F is a graph showing 5' editing as applied to a USH2A reporter, with gRNAs targeting intron 12, vs a non-targeting guide where activity is driven by the presence of the repair RNA.

Figure 12:
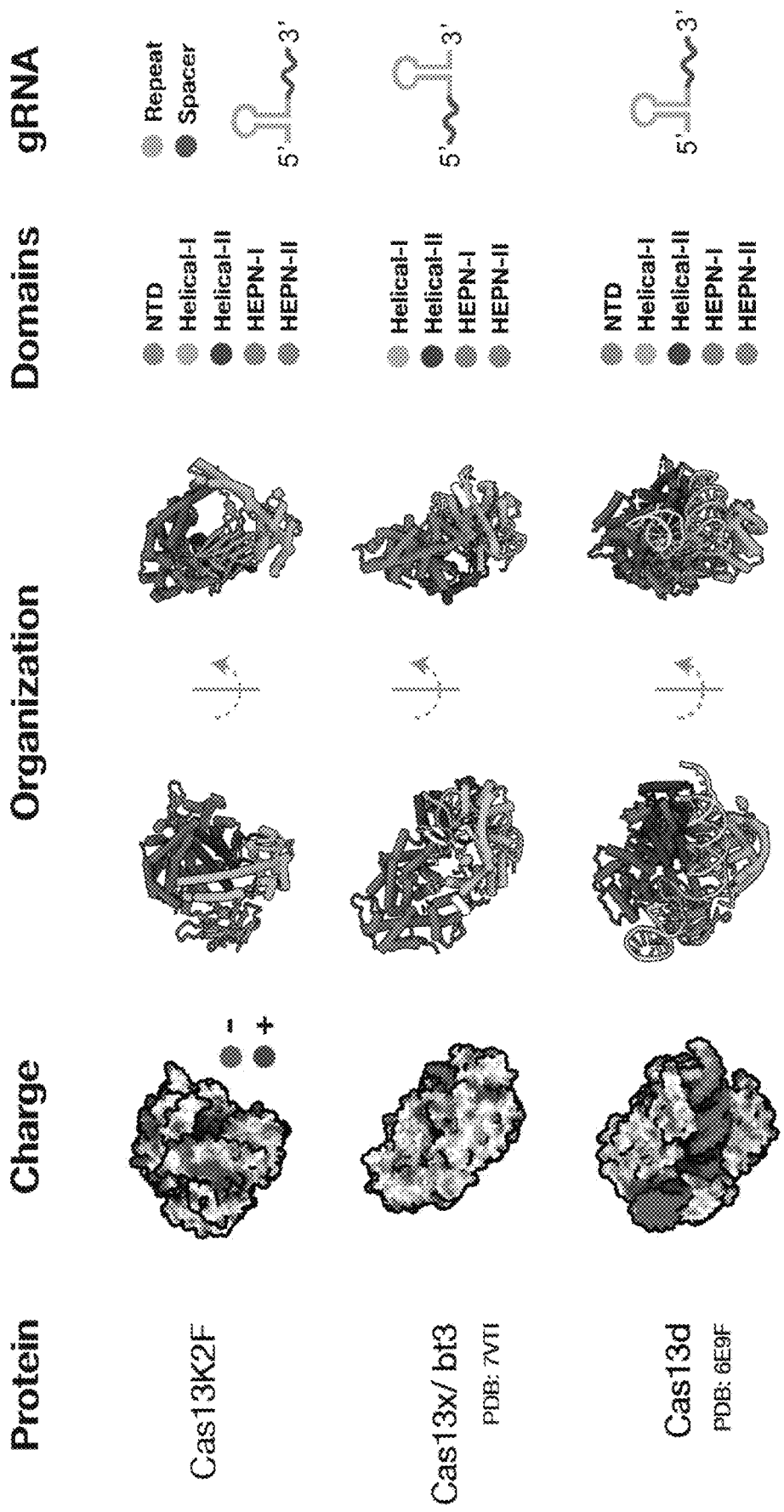
Figure 12:
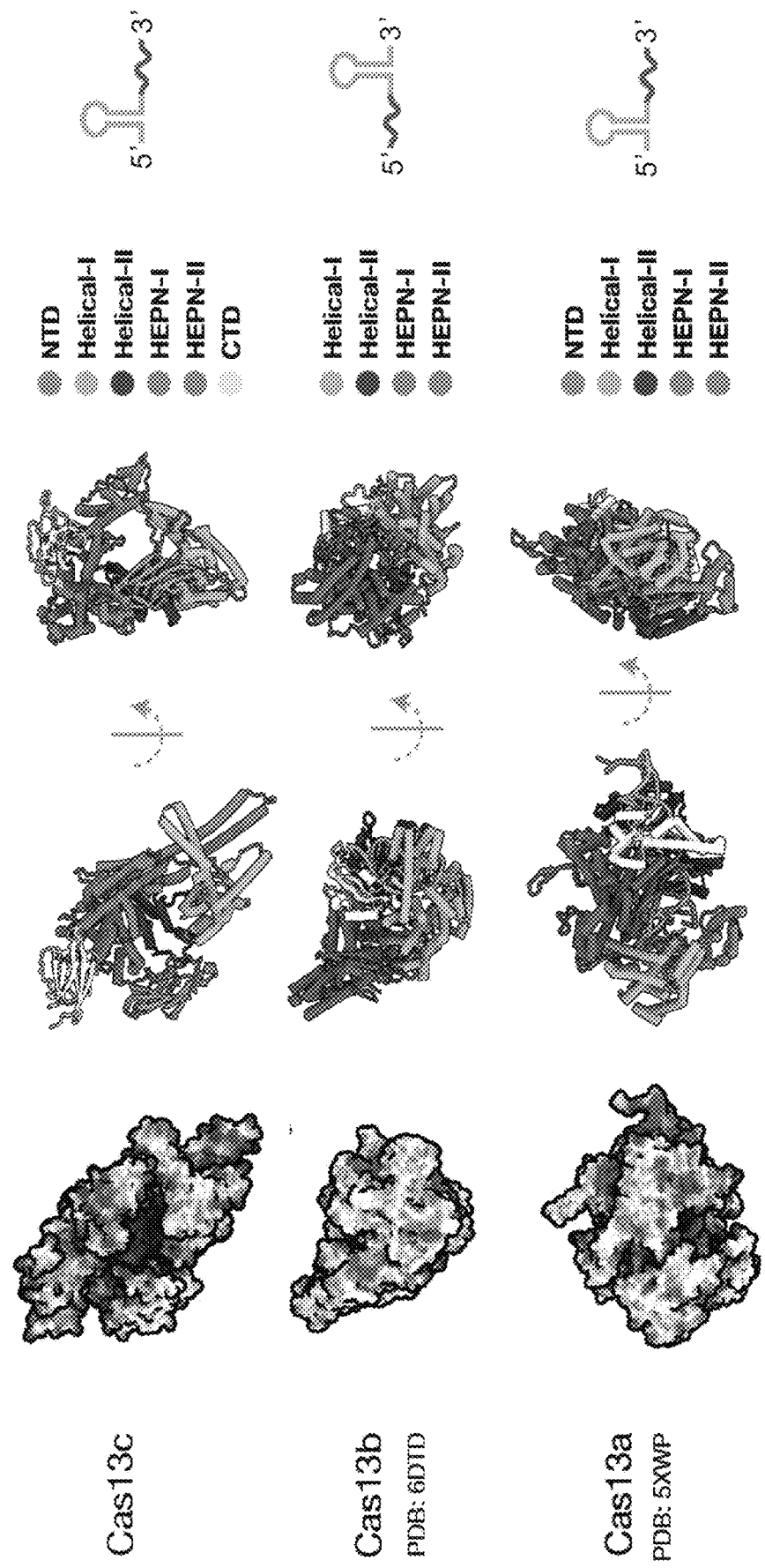

FIG. 12 is an image showing ColabFold-based predicted protein structures and domain organizations of different Cas13 family members. Cas13e is used herein interchangeably with "Cas13K2F".

Figure 13A:
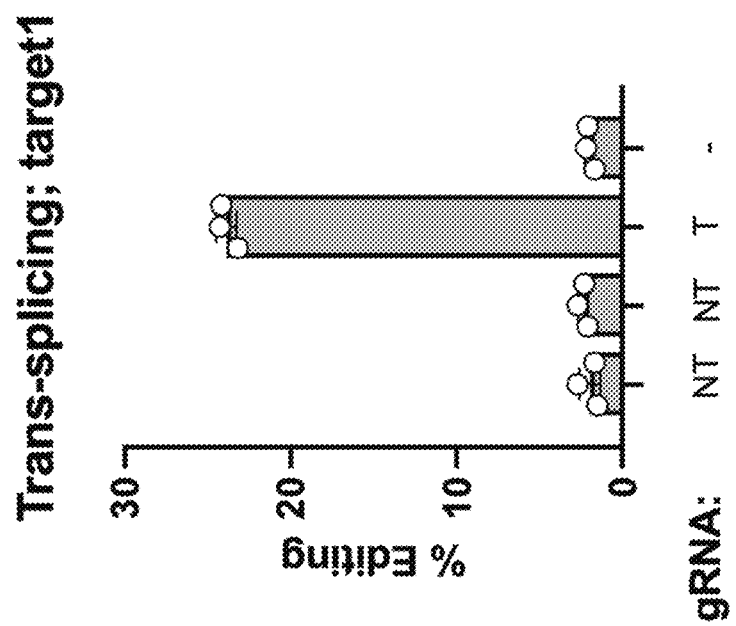
Figure 13B:
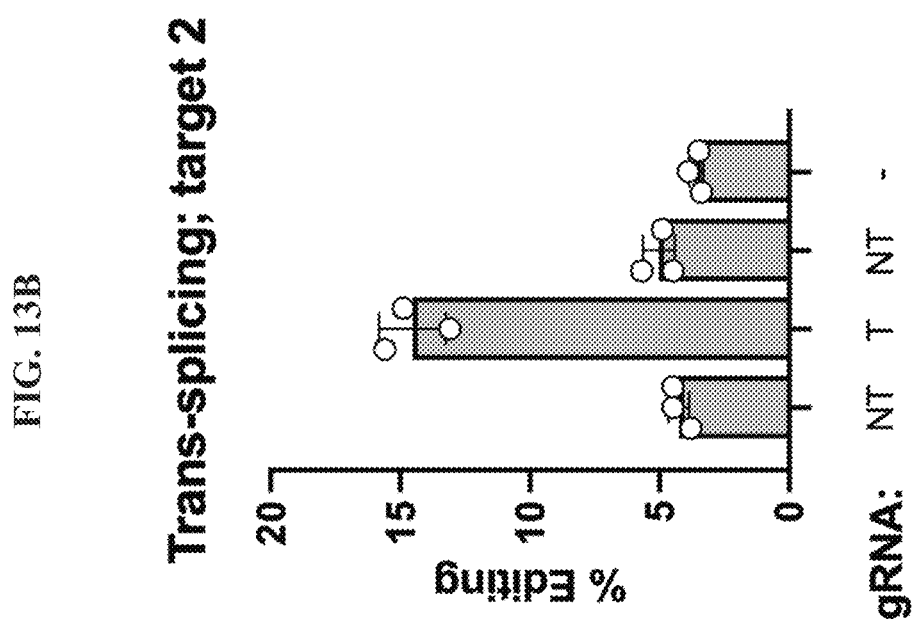

FIG. 13A and FIG. 13B are graphs showing Cas13K2F trans-splicing across two different RNA targets (MMP9 (FIG. 13A) and USH2A (FIG. 13B)) using PP7 (PCP) as the RNA binding partner (RBP) partner.

Figure 14:
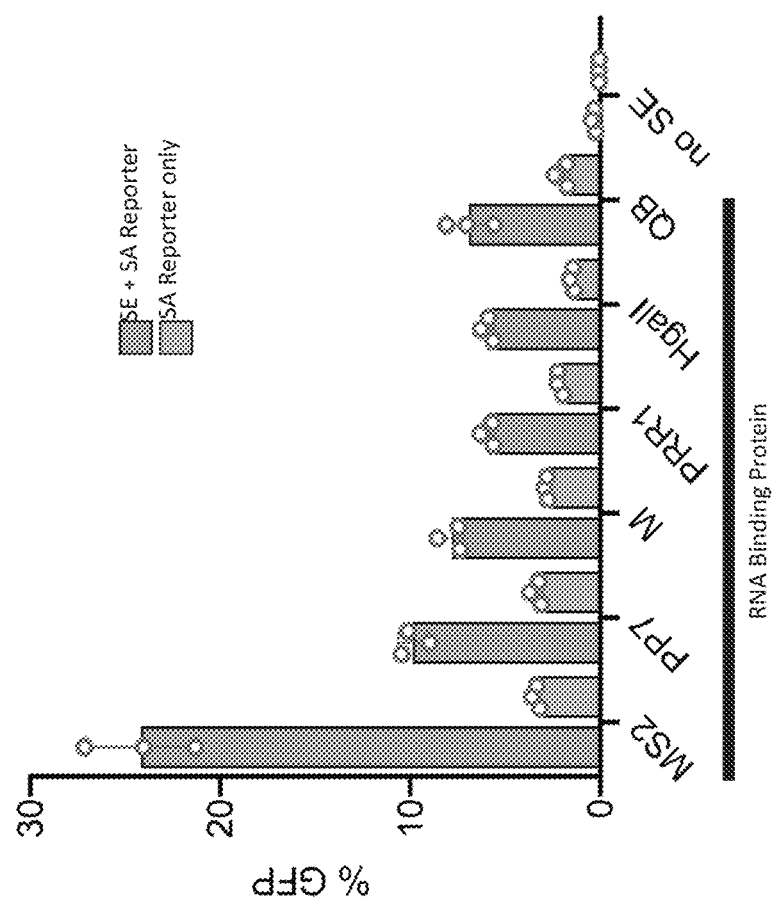

FIG. 14 is a graph showing the percent of GFP positive cells following transfection with an SD reporter encoding the 5'end of GFP and (i) an SA reporter having a sequence motif for the indicated RNA binding protein (RBP) and encoding the 3'end of GFP ("SA Reporter only" bars); or (ii) an SA reporter and a splice editor ("SE") that was dPspCas13b fused to the indicated RBP and PspCas13b gRNA targeting the SD reporter ("SE+SA Reporter" bars). Control cells were transfected with SD reporter only or SD reporter and SA reporter only.

FIG. 15A is an image and FIG. 15B is a graph showing AAV delivery of dCas13K2F3 with a targeting (T) or non-targeting (NT) gRNA and a repRNA to facilitate trans-splicing in HEK293T cells.

Figure 16:
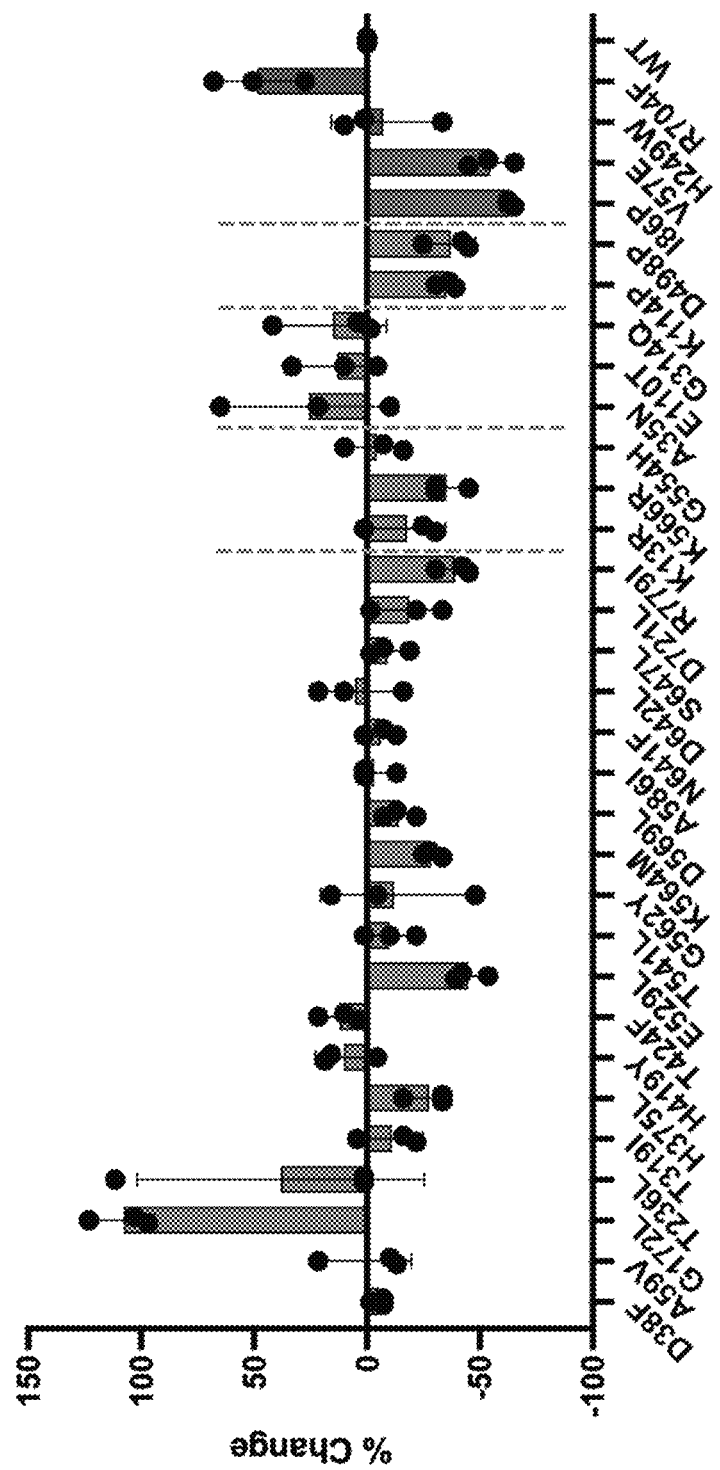

FIG. 16 is a graph showing amino acid substitutions in dCas13K2F3 that enable either improvement or reduction of trans-splicing efficacy in human cells compared to the original (WT) sequence.

Figure 17:
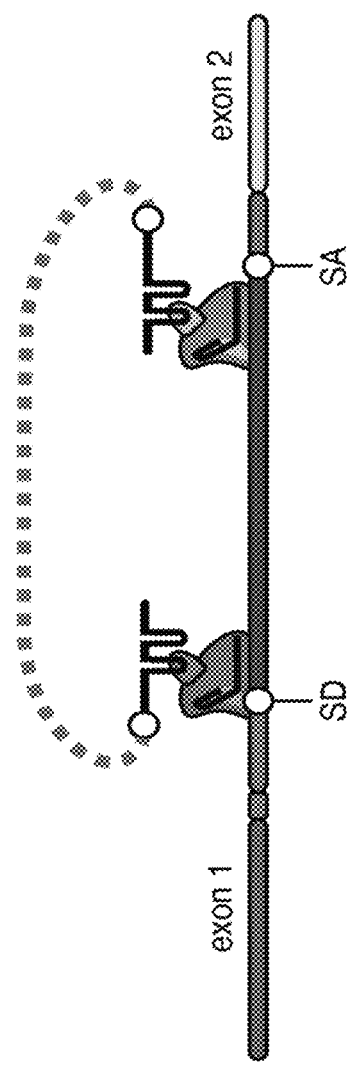

FIG. 17 is an image showing, without wishing to be bound by theory, internal exon replacement using 2 nucleases with 2 separate gRNAs and RBPs, with a repRNA shown in green (directly to the left of the splice donor site in the image).

Figure 18:
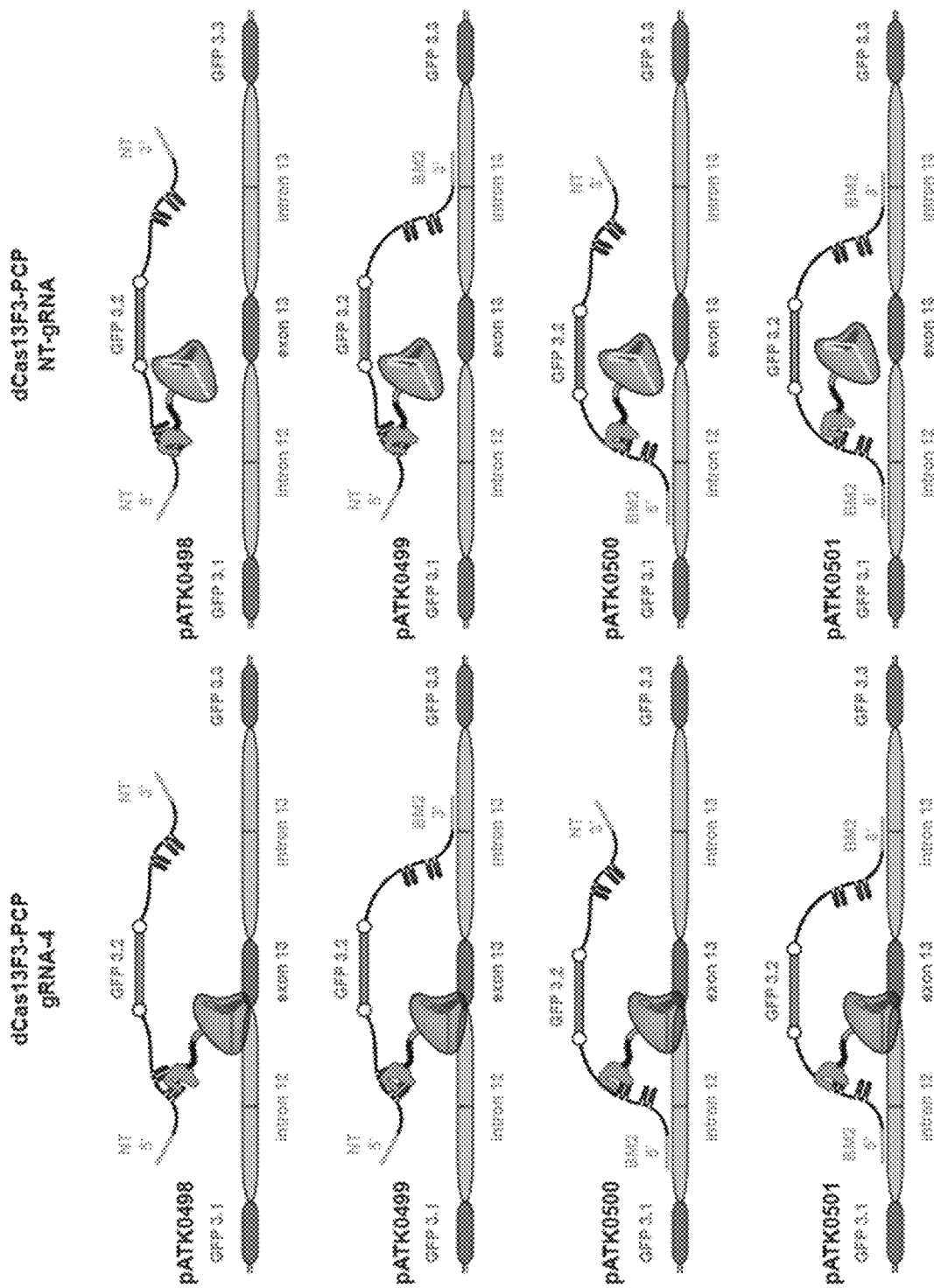

FIG. 18 is an image showing, without wishing to be bound by theory, how internal exon replacement is achieved with a single gRNA, nuclease and an RBP in combination with a binding motif (BM) in the repRNA, shown in orange (and labeled BM2 in the image).

Figure 19:
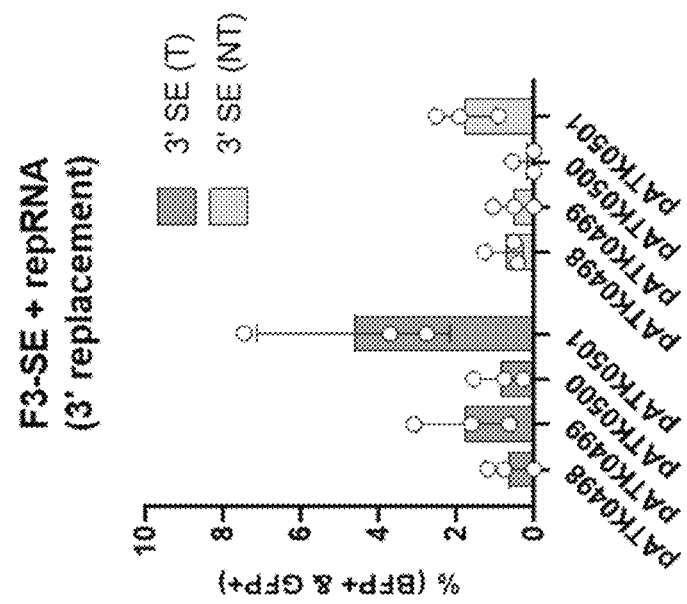

FIG. 19 is a graph showing targeting (T) in the first set of four bars on the left, or non-targeting (NT) in the second set of four bars on the right, of one gRNA, nuclease and RBP (PCP) in combination with a binding motif (BM) (see constructs in FIG. 18) to facilitate internal exon replacement.

Figure 20:
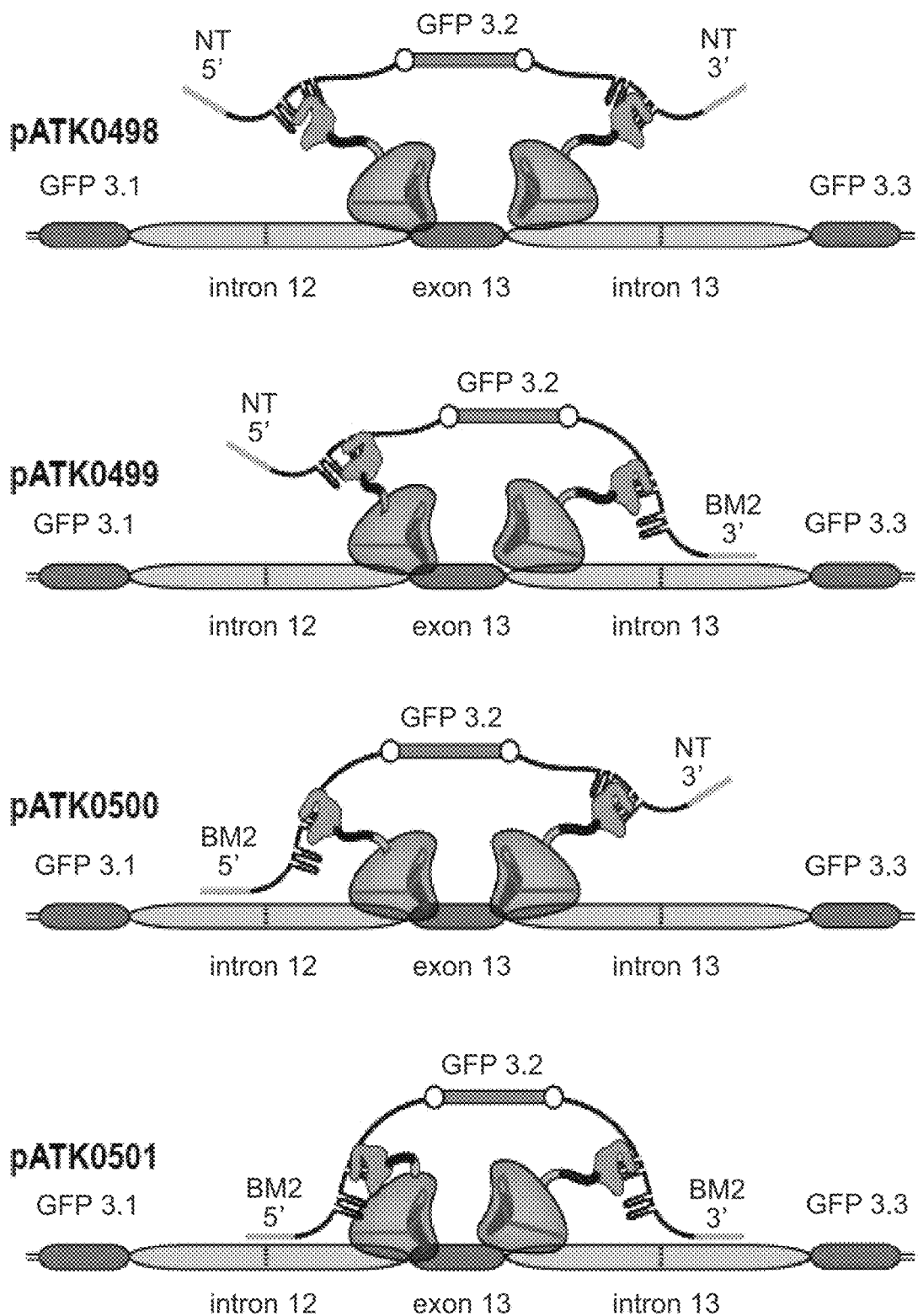

FIG. 20 is an image showing, without wishing to be bound by theory, how internal exon replacement is achieved with two gRNAs, two nucleases and RBPs in combination with, or without, a binding motif (BM) in the repRNA, shown in orange (and labeled BM2 in the image).

Figures 21A, 21B:
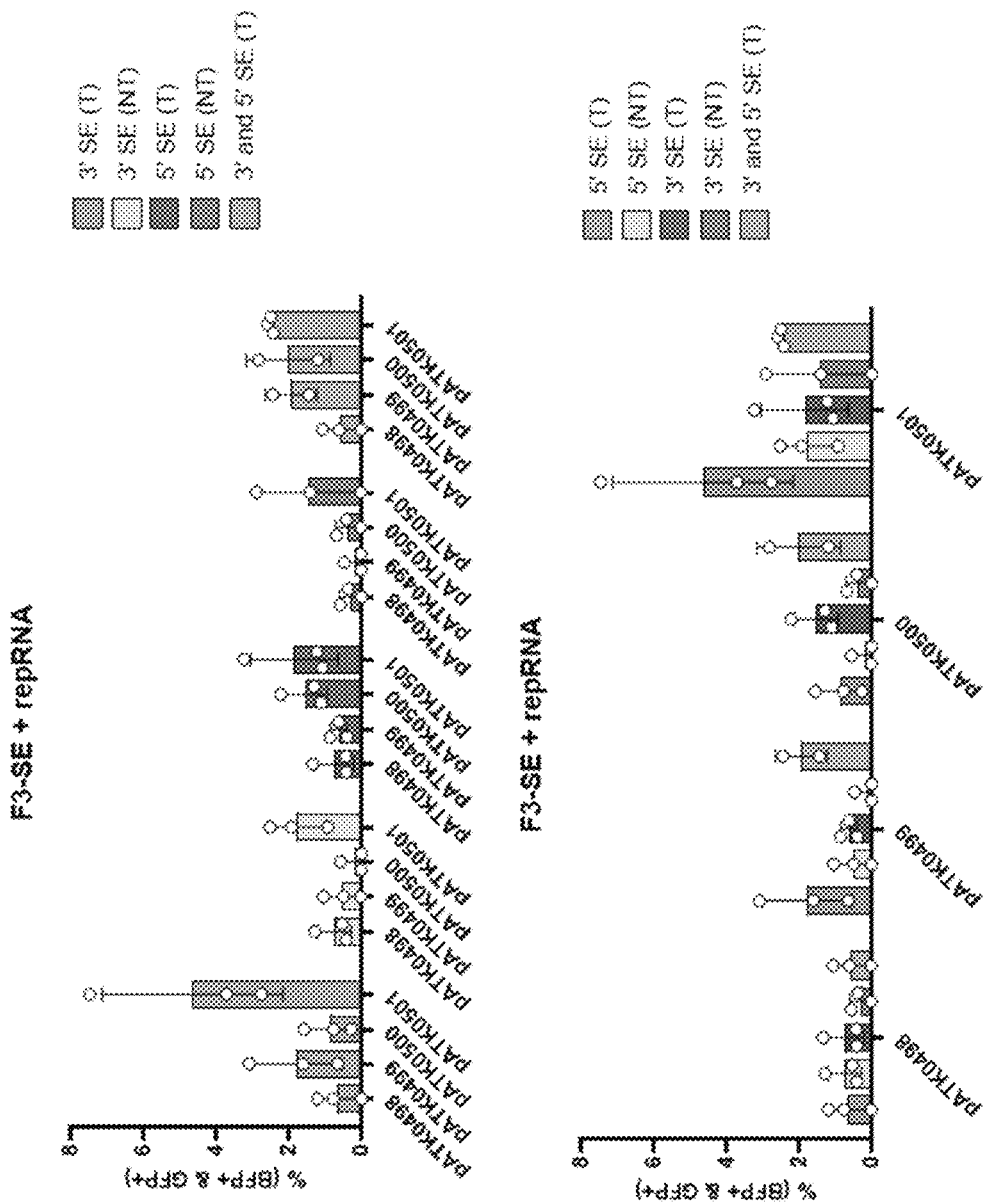

FIG. 21A and FIG. 21B are graphs showing targeting (T) or non-targeting (NT) of two gRNAs, two nucleases and RBPs in combination with, or without, a binding motif (BM) in the repRNA (see constructs in FIG. 20) to facilitate internal exon replacement. In FIG. 21A, the first bar in each set is 3' SE (T) (far left), the next bar in each set is 3' SE (NT) (second from left), the next bar in each set is 5' SE (T)

(middle), the next bar in each set is 5' SE (NT) (second from right), and the last bar in each set is 3' and 5' SE (T) (far right). In FIG. 21B, the first bar in each set is 3' SE (T) (far left), the next bar in each set is 5' SE (NT) (second from left), the next bar in each set is 3' SE (T) (middle), the next bar in each set is 3' SE (NT) (second from right), and the last bar in each set is 3' and 5' SE (T) (far right).

Figure 22A:
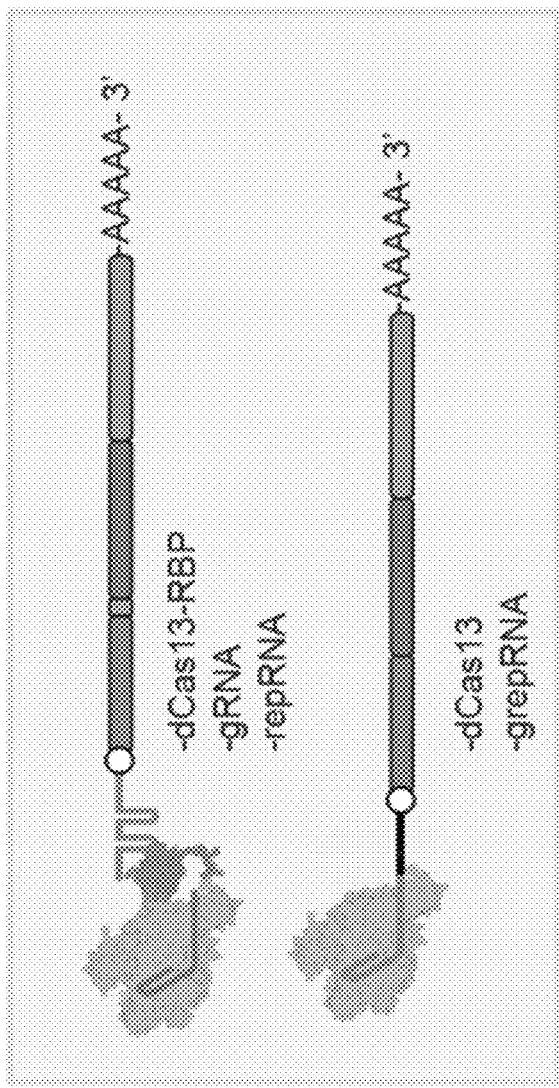
Figure 22B:
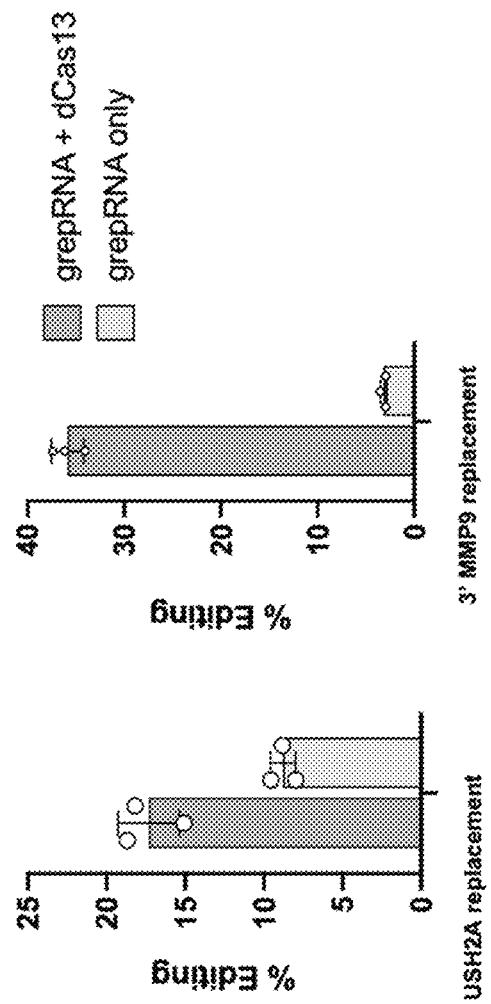

FIG. 22A is an image and FIG. 22B is a graph showing, without wish to be bound by theory, the design of a guide repair RNA ("grepRNA"), which are devoid of an RBP. FIG. 22B shows grepRNA only, or grepRNA and dCas13, for internal exon replacement across two different RNA targets (USH2A, left side of FIG. 22B; and MMP9, right side of FIG. 22B). In the top image of FIG. 22A, from 3' to 5', is the repRNA, gRNA, and dCas13-RBP. In the bottom image of FIG. 22B, from 3' to 5', is the grepRNA, and dCas13.

Figure 23A:
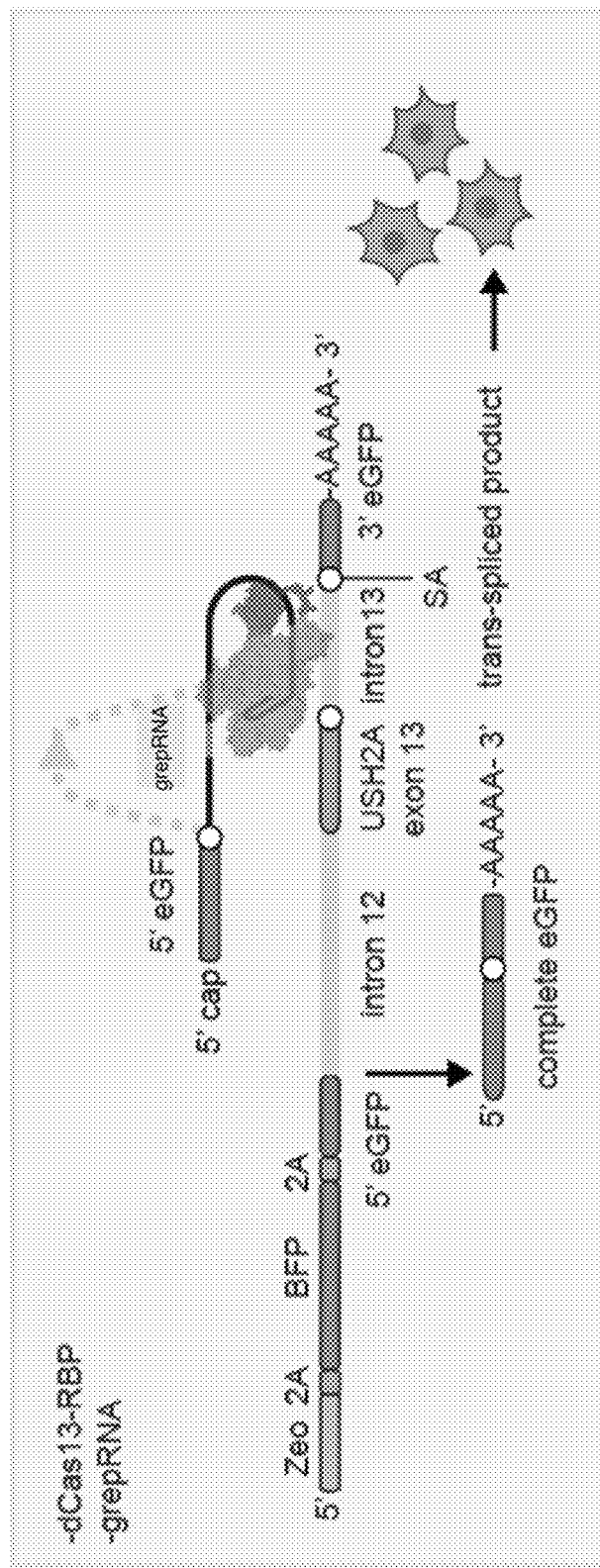
Figure 23B:
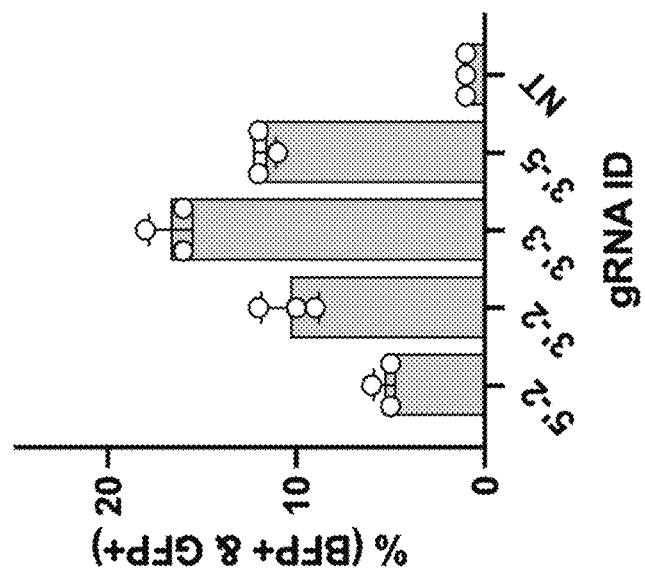

FIG. 23A is an image showing integrated USH2A target for 5' replacement. FIG. 23B is a graph showing targeting (T) or non-targeting (NT) of an integrated 5' USH2A target to facilitate internal exon replacement.

DETAILED DESCRIPTION

The present disclosure provides, inter alia, compositions and methods related to new families of CRISPR-Cas effector proteins, including nucleic acids encoding CRISPR-Cas effector proteins, and RNA components to induce DNA targeting, and methods of use thereof.

The present disclosure is based, in part, on the discovery of compositions and methods related to type VI CRISPR-Cas effector proteins, optionally, complexed with a guide nucleic acid, that are capable of modifying a target nucleic acid. The present disclosure also provides methods of modifying a target nucleic acid using an endonuclease or chimeric protein of the present disclosure and, optionally, a guide RNA.

Belonging to type VI CRISPR-Cas enzymes, Cas13 enzymes were identified as RNA-guided RNA-targeting proteins. While Cas9 cleaves DNA to interrupt DNA replication, Cas13 digests RNA to abate transcription. The CRISPR-Cas13 system can be divided into six subtypes (a, b1, b2, c, d, X, Y). Each subtype carries Cas13, which is a single effector protein. All Cas13 proteins exhibit two distinct RNase activities. One is RNA-targeting degradation, the other is pre-crRNA processing. About six total Cas13 variants have been identified to date.

The present endonucleases (e.g., SEQ ID NO: 1, SEQ ID NO: 2, SEQ ID NO: 3, and SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or fragments or variants thereof), without wishing to be bound by theory, belong to a Cas13K2F system.

Endonucleases (Protein, Nucleic Acid, and System)

The present disclosure provides, in aspects, a composition comprising an endonuclease comprising a sequence, or a fragment or variant thereof, having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications).

The present disclosure provides, in aspects, a composition comprising an endonuclease comprising a sequence, optionally comprising a HEPN domain, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications).

In embodiments, the sequence comprises at least one HEPN domain, or fragments or variants thereof. In embodiments, the sequence comprises at least two HEPN domains, or fragments or variants thereof.

In embodiments, the sequence comprises one or more truncated HEPN domains.

In embodiments, one or more HEPN domains are located according to the positions of the arrows in FIG. 1A, FIG. 1B, FIG. 1C, and FIG. 1D and/or by reference to Table 1 or Table 2.

In embodiments, a polypeptide of the present disclosure, e.g., endonuclease or chimeric protein, is provided as a nucleic acid (e.g., an mRNA, a DNA, a plasmid, an expression vector, a viral vector, and the like) that encodes the endonuclease or chimeric protein. In embodiments, the endonuclease or chimeric protein of the present disclosure is provided directly as a protein (e.g., without an associated guide RNA or with an associate guide RNA, i.e., as a ribonucleoprotein complex). An endonuclease or chimeric protein or nucleic acid of the present disclosure can be introduced into a cell (provided to the cell) by any convenient method; such methods are known to those of ordinary skill in the art.

In embodiments, the endonuclease is suitable for creating a double stranded break in a nucleic acid. In embodiments, the endonuclease is suitable for creating a nick in a nucleic acid. In embodiments, the endonuclease is suitable for nucleic acid modification by HDR. In embodiments, the endonuclease is suitable for nucleic acid modification by NHEJ.

In embodiments, the endonuclease recognizes a PAM. In embodiments, the endonuclease recognizes a plurality of PAMs (e.g., about 2, or about 3, or about 4, or about 5, or about 6, or about 8, or about 10 PAMs). In embodiments, the PAM sequence is about 1 to about 20, or about 2 to about 12, or about 2 to about 6, or about 2, or about 3, or about 4, or about 5, or about 6, or about 8, or about 10 nucleotides in length.

In embodiments, the endonuclease (or chimeric protein) comprises one or more mutations to reduce catalytic activity relative to an unmutated form. In embodiments, the one or more mutations to reduce catalytic activity relative to an unmutated form are in one or more HEPN domains of the present endonucleases. One of skill in the art may select the one or more mutations to reduce catalytic activity relative to an unmutated form by reference, e.g., to FIG. 1A, FIG. 1B, FIG. 1C, and FIG. 1D and/or by reference to Table 1 or Table 2 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, the endonuclease (or chimeric protein) comprises one or more mutations to render the endonuclease substantially catalytically inactive relative to an unmutated form. In embodiments, the one or more mutations to render the endonuclease substantially catalytically inactive relative to an unmutated form are in one or more HEPN domains of the present endonucleases. One of skill in the art may select the one or more mutations to render the endonuclease substantially catalytically inactive relative to an unmutated form by reference, e.g., to FIG. 1A, FIG. 1B, FIG. 1C, and FIG. 1D and/or by reference to Table 1 or Table 2 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, the endonuclease (or chimeric protein) comprises one or more mutations to increase catalytic activity relative to an unmutated form. In embodiments, the one or more mutations to increase catalytic activity relative to an unmutated form are in one or more HEPN domains of the present endonucleases. One of skill in the art may select the one or more mutations to increase catalytic activity relative to an unmutated form by reference, e.g., to FIG. 1 and/or by reference to Table 1 or Table 2 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, the endonuclease (or chimeric protein) comprises one or more mutations to render the endonuclease substantially catalytically hyperactive relative to an unmutated form. In embodiments, the one or more mutations to render the endonuclease substantially catalytically hyperactive relative to an unmutated form are in one or more HEPN domains of the present endonucleases. One of skill in the art may select the one or more mutations to render the endonuclease substantially catalytically hyperactive relative to an unmutated form by reference, e.g., to FIG. 1A, FIG. 1B, FIG. 1C, and FIG. 1D and/or by reference to Table 1 or Table 2 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, the endonuclease has nickase activity. In embodiments, the endonuclease (or chimeric protein) comprises one or more mutations to produce nickase activity. In embodiments, the one or more mutations to produce nickase activity relative to an unmutated form are in one or more HEPN domains of the present endonucleases. One of skill in the art may select the one or more mutations to produce nickase activity relative to an unmutated form by reference, e.g., to FIG. 1A, FIG. 1B, FIG. 1C, and FIG. 1D and/or by reference to Table 1 or Table 2 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, the endonuclease has collateral cleavage activity. In embodiments, the endonuclease (or chimeric protein) comprises one or more mutations to produce, increase, remove, or decrease collateral cleavage activity. In embodiments, the one or more mutations to produce, increase, remove, or decrease collateral cleavage activity relative to an unmutated form are in one or more HEPN domains of the present endonucleases. One of skill in the art may select the one or more mutations to produce, increase, remove, or decrease collateral cleavage activity relative to an unmutated form by reference, e.g., to FIG. 1A, FIG. 1B, FIG. 1C, and FIG. 1D and/or by reference to Table 1 or Table 2 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, one of skill in the art may select residues to alter in light of a desired percent sequence identity and/or select amino acid modifications by reference to the domains of e.g., to FIG. 1A, FIG. 1B, FIG. 1C, and FIG. 1D and/or by reference to Table 1 or Table 2 and/or reference to the alignment information of FIG. 5 and/or the phylogenetic information of FIG. 6 and/or by reference to structural information about other endonucleases known in the art, e.g. Slaymaker, et al., "High-Resolution Structure of Cas13b and Biochemical Characterization of RNA Targeting and Cleavage" 2019, *Cell Reports* 26, 3741-3751, Zhang et al., "Structural Basis for the RNA-Guided Ribonuclease Activity of CRISPR-Cas13d" *Cell* 175(1): 212-22, 2018 (each hereby incorporated by reference in their entireties), and the like.

In embodiments, the amino acid modifications are amino acid mutations or amino acid substitutions. In embodiments, the amino acid substitutions are conservative and/or non-conservative substitutions. In embodiments, the amino acid modifications are amino acid truncations of two or more amino acids (e.g. about to about 100, or about 2 to about 90, or about 2 to about 80, or about 2 to about 70, or about 2 to about 60, or about 2 to about 50, or about 2 to about 40, or about 2 to about 30, or about 2 to about 20, or about 2 to about 10, or about 20 to about 100, or about 50 to about 100, or about 70 to about 100 amino acids).

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In embodiments, the percent sequence identity between a particular nucleic acid or amino acid sequence and a sequence referenced by a particular sequence identification number is determined as follows. A nucleic acid or amino acid sequence is compared to the sequence set forth in a particular sequence identification number using, e.g., the BLAST 2 Sequences (Bl2seq) program from the stand-alone version of BLASTZ containing BLASTN version 2.0.14 and BLASTP version 2.0.14 or the like. This stand-alone version of BLASTZ can be obtained online at or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options may be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -l; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., any of SEQ ID NOs: 1-4, and/or SEQ ID NOs: 80-89), or by an articulated length (e.g., 100 consecutive nucleotides or amino acid residues from a sequence set forth in an identified sequence), followed by multiplying the resulting value by 100. It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

In embodiments, the endonuclease has at least about 75% identity to one or more of SEQ ID NOs: 1-4, and/or SEQ ID NOs: 80-89. In embodiments, the endonuclease has at least about 80% identity to one or more of SEQ ID NOs: 1-4, and/or SEQ ID NOs: 80-89. In embodiments, the endonuclease has at least about 85% identity to one or more of SEQ ID NOs: 1-4, and/or SEQ ID NOs: 80-89. In embodiments, the endonuclease has at least about 90% identity to one or more of SEQ ID NOs: 1-4, and/or SEQ ID NOs: 80-89. In embodiments, the endonuclease has at least about 95% identity to one or more of SEQ ID NOs: 1-4, and/or SEQ ID NOs: 80-89. In embodiments, the endonuclease has at least about 97% identity to one or more of SEQ ID NOs: 1-4, and/or SEQ ID NOs: 80-89. In embodiments, the endonuclease has at least about 99% identity to one or more of SEQ ID NOs: 1-4, and/or SEQ ID NOs: 80-89.

In embodiments, the endonuclease has about 1 to about 15 amino acid modifications. In embodiments, the endonuclease has about 1 to about 10 amino acid modifications. In embodiments, the endonuclease has about 1 to about 5 amino acid modifications. In embodiments, the endonuclease has about 1, or about 2, or about 3, or about 4, or about 5, or about 10, or about 15, or about 20 amino acid modifications. In embodiments, the amino acid modifications are selected from substitutions and deletions.

In embodiments, the endonuclease is selected from Table 1 below.

In embodiments, the sequence comprises at least one HEPN domain, or fragments or variants thereof. In embodiments, the sequence comprises at least two HEPN domains, or fragments or variants thereof. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to one or more of SEQ ID NOs: 1-4, and/or SEQ ID NOs: 80-89. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 1. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 2. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 3. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 4. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 80. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 81. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 82. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 83. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 84. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 85. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 86. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 87. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 88. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 89. In embodiments, the endonuclease comprises about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications) to SEQ ID NOs: 1-4, and/or SEQ ID NOs: 80-89. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 1. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 2. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 3. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 4. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 80. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 81. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 82. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 83. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 84. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 85. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 86. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 87. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 88. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 89.

In aspects, the present disclosure provides a composition comprising a nucleic acid encoding an endonuclease comprising a sequence, optionally comprising a HEPN domain, or a fragment or variant thereof, and having at least about 70% identity to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises at least two HEPN domains, or fragments or variants thereof. In embodiments, the HEPN domain is located according to the positions of the arrows in FIG. 1A, FIG. 1B, FIG. 1C, and FIG. 1D. In embodiments, the endonuclease is selected from Table 1 below. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to one or more of SEQ ID NOs: 1-4, and/or SEQ ID NOs: 80-89. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 1. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 2. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 3. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 4. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 80. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 81. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 82. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 83. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 84. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 85. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 86. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 87. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 88. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 89. In embodiments, the endonuclease comprises about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications) to SEQ ID NOs: 1-4, and/or SEQ ID NOs: 80-89. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 1. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 2. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 3. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 4. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 80. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 81. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 82. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 83. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 84. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 85. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 86. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 87. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 88. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 89.

In aspects, the present disclosure provides a composition comprising a nuclease system, comprising (a) an endonuclease comprising a sequence, optionally comprising a HEPN domain, or a fragment or variant thereof, and having at least about 70% identity to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications); and (b) an RNA molecule comprising a sequence complementary to one strand of a target nucleic acid molecule. In embodiments, the HEPN domain is located according to the positions of the arrows in FIG. 1A, FIG. 1B, FIG. 1C, and FIG. 1D. In embodiments, the sequence comprises at least two HEPN domains, or fragments or variants thereof. In embodiments, the endonuclease is selected from Table 1 below. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to one or more of SEQ ID NOs: 1-4, and/or SEQ ID NOs: 80-89. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 1. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 2. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 3. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 4. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 80. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 81. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 82. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 83. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 84. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 85. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 86. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 87. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 88. In embodiments, the endonuclease comprises a sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO: 89. In embodiments, the endonuclease comprises about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications) to SEQ ID NOs: 1-4, and/or SEQ ID NOs: 80-89. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 1. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 2. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 3. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 4. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 80. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 81. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 82. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 83. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 84. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 85. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 86. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 87. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 88. In embodiments, the endonuclease comprises about 1, about 2, about 3, about 4, about 5, about 6, about 7, about 8, about 9, about 10, about 11, about 12, about 13, about 14, about 15, about 16, about 17, about 18, about 19, or about 20 amino acid modifications to SEQ ID NO: 89.

TABLE 1

Amino Acid Sequences of SEQ ID NOs: 1-4 and SEQ ID NOs: 80-89

| Sequence | SEQ ID NO: |
|---|---|
| MIKKPSNRHALPKVIISEVNSEKILEFKIKYEKLARLDRFEVKAMHYE GKEIVFDEVLVNGGLIDVEYEDEHKTLFVKVGEKSYSIRGQKVGGKQ RLLENRVSKTKVLLELSDGVPDKNAKLRKSRTERELIVVENIKLYSQI VGKEVSTTKEIYLTKRFLSYRSDLLFYYSFVDNFFKVAGNEKELWKIN FDDASSAQFMGYVPFMVNDNLKNDNAYLKDYVSDNEQIKDDLKKV QTMFSTLRHALLHFNYEFLNLLIENIDKLNIDAKKEFIDEEKIKLFGEN LSLAKVYRLYSDICVNRVGFNKFINSMLIKDGVENQALKAEFDRKFF GKAYTIDIHSNQAYKRIYNEHKKLVIKVSTLKDGQAIRRGNKKISELK EQMKSMTKKNSLARLECKMRLAFGFLYGEYNNYNTFKNNFDTNIKN SQFDVNDVEKSKAYFLSTYERRKPRTSEKLEKVAKNIERLELKTVIAN DPLLKFILLMFAFMPQELKGEFLGFVKKYYHDVHSIDDDTKEQEQDV VEAMSTSLKLKILGRNIRSLTLFKYALSSQVNYNSTYNLFYVEGNRYG KIYKKLGISHNQEEFDKTLVVPLLRYYSALFKLMNDFEIYSLAKANPT AVSLQELVDDERSPYKQGRFYNFREVLKQVYLLSDNELTHCKIRITRN KIAHFITEDLLGKPLLGEIKLNLQRKDMVSFMEARGNIKELLDYDAIN DFRMKVIHLRTKMRVNSDKLQTMMDLLSNPKTPNDFYNVYKVKGV EIINKHLLEVLAQTAEERSIEKQIREGNEKYAL | 1 |
| MIKKPSNRHALPKVIISEVNSEKILEFKIKYEKLARLDRFEVKAMHYE GKEIVFDEVLVNGGLIDVEYHDEHKTLFVKVGEKSYSIRGQKVGGKQ RLLENRVSKTKVLLELSDGVEDNKGNLRKSKTERELIVAENIKLYSQI VGREVSTTKEIYLTKRFLSYRSDLLFYYSFVDNFFKVAGNEKELWKIN FDDASSAQFMGYVPFMVNDNLKNDNAYLKDYVSDNEQIKDDLKKV QTMFSTLRHALLHFNYEFFEKLFNGEDVGFDFDIGFLNLLIENIDKLNI DAKKEFIDDEKIKLFGENLSLAKVYRLYSDICVNRVGFNKFINSMLIK DGVENQVLKAEFDRKFGGKAYTVDIHSNQAYKRIYNEHKKLVIKVST LKDGQAIRRGNKKISELKEQMKSMTKKNSLARLECKMRLAFGFLYG EYNNYNAFKNNFDTHIKNSQFDVNDVEKSKAYFLSTYERRKPRTSEK LEKVAKNIESLELKTVIANDPLLKFILLMFVFMPQELKGEFLGFVKKY YHDVHSIDDDTKEQEEDVVEAMSTSLKLKILGRNIRSLTLFKYALSSQ VNYNSTDNLFYVEGNRYGKIYKKLGISHNQEEFDKTLTVPLFRYYSA LFKLMNDFEIYSLAKANPMAVSLQELVDDETSPYKQGDYFNFKNML REIYGLTNDEIKSGKVVFMRNKIAHFDTEVLLSKPLLGQTKMNLQRK DIVSFIEARGNIKELLGYDAINDFRMKVIHLRTKMRVYSDKLQTMMD LLRSAKTPNDFYNVYKVKGVESINKYLLEVLAQTAEERSIEKQIKEGN EKYDL | 2 |
| MDKHPSNRYALPKVIISEVDHERILEFKVKYEKLARLDRFEVKAMHY DGAEIVFDEVVANGGLIEVEYQDNNKTITINLNGKKYTINGRKVGGK RRLLEDRISRGKVCLELHDKIPDEKGNLRSSRTERELITFDSTKLYSQII GRDVASTKEIYLIKRFLAYRSDLLFYYGFIDNFFKVAGNKRELWKIDF SGDKNQELIKYFNFTINDKLKNDKGYLKEYTANDEQIKKDLQNTKEV FTALRHALMHFEYDFFEKLFNNEEIETLSKIHDIELLNTMINKLDKLNI DTRKEYIDDEKITVFGEEISLKTLYGLYAHTAINRVAFNKLINREYMVE NGTENEALKKYFNSKAEGGIAYEIDIHQNSEYKQLYIQHKDLVSKLSA LSDGDEIADTNKKISELKVKMKAITKANSLKRLEHKLRLTFGFIYTEY QDYNAFKNNFDTDIKSGRFIPKDSEGKRRGFDHRELDQLKRYYDATF ADKKPQTKETFDEIDKQIDQLSLKNLIGDDTLLKVILLIYIFLPREIKGE FLGFVKKYYHDTKHIEEDTKDKDEGFDDTFPVGLKLKVLDKNIRALS VLKHSLSYQAKYNKKEEKKEQFYEAGNRHGRFYKKLGISHNQEEFD KSVYAPLLRYHAALFKLLNDFEIYSLAQHIEGKETLAQQIEKPQFSQY EHYNFRKMLSKTYPKSAERGALDNDAFDTVINMRNDIAHLSHEPLFE CPLDGKKSYKLKQGKRTNTINVKPLPISRKMIVDFISSQSDMKKTLGY DAVNDLTMKIIQLRTRLKVYADKSETIKTLVDAAKTPNDFYHIYKVK GVEAINRHLLEVIGETKDEKRIRKRIESGNAIAGRTPADSQEN | 3 |
| MIKKPSNRHALPKVIISEVNSDNILEFKIKYEKLARLDKIEVKAMHYD NRNIVFDEVIVNDGLIELEYRDDHKRLFVKVGDKSYGITGQKVGGKQ RLLENRVSKTKVQLELTDGVLDNKGKHRISRTERELIVATNIALYNQII GREVKTTKEIYLIKRFLGYRSDLLFYYAFVDNFFKVADNEKELWKIDF DANNSTQLIKYISYIVNDNLKNDNAYLKEYVSNVEQIKEDLKKVQTIF SKLRHALLHFNYDFFEKLFNGKDVGFDFDIDFLNLLIENIDKLNIDAK KEFIDDEKIKLFGENLSLAKVYRLYSDICVNRVGFNKFINAMLIKDGV ENQALKEAFDNKLGRKAYTIDIHSNQEYKGLYNRHKKLVIELSTLKN GQAIRKKNAEIAKLKEQMNEMTKKNSLSRLEHKLRLAFGFMYAEYN NHKAFKNNFDTDIKNSKFSENDVEKFKAYFLSTYEGRKRRTSEKLEK VAKNIESLKLKTLIANDPLLKFILLMFVFMPQELKGEFLGFVKKYHD IHSIDEDSKEQENTVLELMPTSLKLKILGRNIRSLTLFKYALSSQVNYN SSDELFYVEGNRYGKIYKKLGISHNQEEFDKTLVVPLFRYYSALFKLM NDFEIYSLAQANPRVLSLQELVDDTTSPYKQGDYYNFKKMLTEIYGV TNDEVNEGKVVFMRNKIAHFETKILLSKPLLGQTKLNLQRKDIVSFIE ARGDIKELLGYDAINDFRMKVIHLRTKMKVYADKLQTMMDLLRNV KTPNDFYNVYKVKGVESINKHLLEVLAQTDQERTIEKQMVEGNKKY KL | 4 |

TABLE 1-continued

Amino Acid Sequences of SEQ ID NOs: 1-4 and SEQ ID NOs: 80-89

| Sequence | SEQ ID NO: |
|---|---|
| MESNKNPSNRHSLPKVIISDVDKDNILEFKVKYEKLGRLDKFKIVSMK YEDRDIVFRDIVSSDKSLEFSLANSNREIIVNLDNKKYTIRGQRVDNNE EKAKKVQLILTDNIKDENGAIRETLTERELIDNSDSIYSKIAGRKINSSK DIYLIKRYLAYRSNLQFFYNFIDKFFKIVDNKELWNIEFGNKHIEYFKF LINDNIKNANGYLYSYLQDNRRVKNDLYKTKDIFSKLRHALMHFDYE FFDKLFNNENLELDLNIEFLNLTIQNIDKLNIDTKKSYIGNQKIKIYSEEI KLDELYNLYNTISINRLGFNRLINSFFMQDGLENRKLKEFFNEEANSEE IYFVDIHQNRDYKKLYIKHKNFVAKLYGNRDGKSIAKLNRDISNIKKQ MQEITDKNSTLRLEYKLRVAFGFIYTNYKNYRHFKNSFDNDLKSGRF NNIDLSQIIEYYKNSYTNKDVLIRVTIKKIDKLNLNALIKDDNLLKIILLI FTFIPNELKGKFLGFIKRYYHDIKHIDEDSKEELEFNDGLSTSLKLKILH KNIRKLTILKYSLATESKYNKKDNYYYEDGHKTKRFLSSLGVSHNIEE FDKTIYTPFFKYYSAMYKLINDFEIFALTQFDSSANLKEITMKEELKQD NEYNFKILLRETNLYDENIVKLRNKISHIDGEFLFSNPLNRRINISSMRE KITNFIDSKNIKKILGYDALNDLSMKIIQQKTKLEANANKDEKINELIK NAQKANDYYSIYKLKAIEGINKRLLKIIGETKQEKYIKDKIIKGNNK | 80 |
| MESNKNPSNRHSLPKVIISDVDKDNILEFKVKYEKLGRLDKFKIVSMK YEDRDIVFRDIVSSDKSLEFSLANSNREIIVNLDNKKYTIRGQRVDNNE EKAKKVQLILTDNIKDENGAIRETLTERELIDNSDSIYSKIAGRKINSSK DIYLIKRYLAYRSNLQFFYNFIDKFFKIVDNKELWNIEFGNKHIEYFKF LINDNIKNANGYLYSYLQDNRRVKNDLYKTKDIFSKLRHALMHFDYE FFDKLFNNENLELDLNIEFLNLTIQNIDKLNIDTKKSYIGNQKIKIYSEEI KLDELYNLYNTISINRLGFNRLINSFFMQDGLENRKLKEFFNEEANSEE IYFVDIHQNRDYKKLYIKHKNFVAKLYGNRDGKTIARLNRDISNIKKQ MQEITDKNSTLRLEYKLRVAFGFIYTNYKNYMHFENSFDNDLKSGRF NNIDLSKIIEYYKNSYTNKDVRIRVTIKKIDKLNLNALIKDDNLLKIILLI FTFIPNELKGEFLGFIKRYYHDIKHIDEDSKEELEFNDGLSTSLKLKILH KNIRKLTILKYSLATESKYNKKDNYYYEDGHKTKRFLSSLGVSHNIEE FDKTIYTPFFKYYSAMYKLINDFEIFALTQFDSSANLKEITMKEELKQD NEYNFKILLRETNLYDENIVKLRNKISHIDGEFLFSNPLNRRINISSMRE KITNFIDSKNIKKILGYDALNDLSMKIIQQKTKLEANANKDEKINELIK NAQKANDYYSIYKLKAIEGINKRLLKIIGETKQEKYIKDKIIKGNNK | 81 |
| MESNKNPSNRHSLPKVIISDVDKDNILEFKVKYEKLGRLDKFKIVSMK YEDRDIVFRDIVSSDKSLEFSLANSNREIIVNLDNKKYTIRGQRVDNNE EKAKKVQLILTDNIKDENGAIRETLTERELIDNSDSIYSKIAGRKINSSK DIYLIKRYLAYRSNLQFFYNFIDKFFKIVDNKELWNIEFDNKHIEYFKF LINDNIKNANGYLYSYLQDNRRVKNDLYKTKDIFSKLRHALMHFDYEF FDKLFNNENLELDLNIEFLNFTIQNIDKLNIDTKKSYIGNQKIKIYSEEI KLDELYNLYNTISINRLGFNRLINSFFMQDGLENRELKKFFNEEANSEE IYFVDIHQNRDYKKLYIKHKNFVAKLYGNRDGKSIAKLNRDISNIKKQ MQEITDKNSTLRLEYKLRVAFGFIYTNYKNYRHFKNSFDNDLKSGRF NNIDLSKIIEYYKNSCTNKDVRIRVTIKKIDKLNLNALIKDDNLLKIILLI FTFIPNELKGEFLGFIKRYYHDIKHIDEDSKEELEFNDGLSKSLKLKILH KNIRKLTILKYSLATESKYNKKDNYYYEDGHKTKRFLSSLGVSHNIEE FDKTIYTPFFKYYSAMYKLINDFEIFALTQFDSSANLKEITMKEELKQD NEYNFKILLRETNLYDENIVKLRNKISHIDGEFLFSNPLNRRINISSMRE KITNFIDSKNIKKILGYDALNDLSMKIIQQKTKLEANANKDEKINELIK NAQKANDYYSIYKLKAIEGINKRLLKIIGETKQEKYIKDKIIKGNNK | 82 |
| MTKKPANRHALPKVIISEVDSEKILEFKIKYEKLARLDRVEVKAMHYE GKSIVFDEVVVNGGLIDVEYQDDHKTLFVKVGEKSYSIRGQKVGGKQ RLREERVSQVKVQLELTDGSSERVSRTERELIVADNIKLYSQIVGREV KTTKEIYLAKRFLGYRSDLLFYYGFVDNFFKVAGNEKELWKIDFEAS ESSQLLAYIPYMVNDNLKNNDAYLKDYIANEEQIKSDLKKVQTIFSEL RHALLHFNYDFFEKLFNGEDVGFDFDIEFLNLLIANIDKLNIDAKKEFI TDEKIKLFGENLSLAKVYKLYSDICVNRVGFNKFINSMLIKDGLENQA LKSEFDRKQGHKAYYIDIHSNEEYKRLYNRHKALVIKVSTLRDGQKIR KGNAEISEFKKQMNSMTTKNSLSHLEHKMRLAFGFMYGEYNHYNAF KNGFDTDVKNRKFDETDVSKSKAYFLSTYERQKPRTREKLERVAKDI ESLKLETLIAHDPLLKFILLMFAFMPREIKGEFLGFVKKYHDVHSIEV DIIEQELDVVESMSTSLKLKNLGRNIRSLTLFKYALSAKVNYNGSDES FYEEGNRYGKIYKKLGISHNQEEFDKTLVVPLFRYYSALFKLMNDFEI YSLAKANPTALNLQMLVDDETSPYKQGNYYNFNKMLREVHGVTND EIKNGQAVFMRNKIAHFDTEVLLSKPLLGQTKMNLQRKIIIEFIKARGE MREILGYDAINDFRMKVVHLRTKMKVYSDKLQTMMDLLRSAKTPN DFYNVYKVKGVESINKQLLEVLAETAEERSIEKQICEGNMKYNS | 83 |
| MSKNPSNRNSLPKVIINKVDENIILEFKIKYEKLARLDRFEVRSMRYDG DGRIIFDEVVANGGLLDVGYEDDNKTIVVKIENKAYKIYGKKVGGKK RLNGKISKAKVQLILTDNIRKNANDTHRQSLTERELIDKNEIDLYSKIA EREISSTKDIYLVKRFLAYRSDLLLYYAFVNDYVKVKGNKEEFWKTPI | 84 |

TABLE 1-continued

Amino Acid Sequences of SEQ ID NOs: 1-4 and SEQ ID NOs: 80-89

| Sequence | SEQ ID NO: |
|---|---|
| DDKIIDYFIYTINDTLKNKEGYLEKYIVDRDQIKKDLEKTKRIFSHLRH KLMHYDFRFFTDLFDGKDVDIKVDNSTQKISELLDIKFLNIVIEELEKL NIDAKKEFIDDEKIPLFRQEIELKKLYSIYAHTAINRVAFNKLINSFLIK DGIENKELKEYFNAQNQGKESYYIDIHQNKEYKKLYIEHKDLLAKLS ATKNGKEIAKINRELADKKEQMKQITKANSLKRLEYKLRLAFGFIYTE YKDYETFKNSFDTDTKNQKFDAIDNAKIIEYFEATNKAKKIEKLEEILK GIDKLSLKTLIQDDILLKFLLLFFTFLPQEIKGEFLGFIRKYYHDITSLDE DTKDKDDEITELSRSLKLKIFAKNIRKLSILKHSLSYQIKYNKKESSYY EVGNAFNKMFKKQAISHNLEEFGKSIYLPMLKYYSALYKLINDFEIYA LYKDMDTSETLSQQVDKQEYERNEYFNFETLLRKKFGNDIEKVLVTY RNKIAHLDFNFLYDKPINKFISLYKSRDKIVNYIKNHDTQAVLKYDAV NDFVMKVIQQRSKLKVYADKEQTIESMIQNAQNPNDFYNIYKVKAVE NINQHLLKVIGYTDSEKAIEEKIRAGNISKS | |
| MLKKPVNRYALPKVIISEVNHEDILEFKIKYEKLGRLDRVAVKKMHY EKENIVFDEVDVNGGLIEVMYKDEHQILLVQAGGKSYSIRGKKIGGK QRKREDRVSQVKIQLELTDGVLDKNEKYRVSQTERELIVNDNIKIYSQ IVGKEVKTTKEIYLIKRFLGYRSDLLFYYGFVDNFFKVVGNKTELWKI NFQDTKNEKLIEYFKFSINDKLKNDETYLKVYSSDNQNIEEDLTKVKN NFSKLRRALMHFDYGFFEKLFNDEDVGFDLDIMFLNVIIKNLDKLNID TRKEFIDDEKIKIFGEELSLKHLGYMYAHIAINRVAFNKLINSFMMQD GVENRSLKEYFNKRAKDGVAYEVDIHQNSQYKELYKQHKNLVSKVS ALSDGVAIAKMNDEIYTLKEKMKQITKPNSLKRLEHKLRLAFGFIYSE YKDYDDFKNNFNDHIIDGRFVPKDEEGKRRAFDSRELARLQGYYDVT LQNKKPQTKEKLGEVSKKIDSLSLATLIDDDKLLKFILLMFTFMPQEL KGEFLGFVKKYYHDTKHIEEDSKDKDKDFADGLSVGLRLKVLDKNIR NLSILKHSLSLQTKYNKKDNYFYEDGNVHGRFFKSLGISHNQEEFSKS VYAPLLKYYSALYKLINDFEIYTLAQYITTEYPTLSKVIDSEKFHLRWD NRSKELVPSDDYVFSTLTNKTYDHEKVKELNFIRNKISHFNSKELFEIP LQGYQMKGKKKLPFFLSKKREEIIDEIELQKDIQKTLGYDAINDFNMK MVQLYTKLKVYANKEETIEKMLEEATTPNDFYNVYKVKGVETINKH LLDVIGETEREKFIRIQIEVNNKRVSNENLDKL | 85 |
| MSKKPANRHALPKVIISEVDSEKILEFKIKYEKLARLDRVEVKAMHYE GKSIVFDEVVVNGGLIDVEYQDNHKTLFVKVGEKSYSIRGKKVGGKQ RLREERVSQVKVQLELSDGSSERVSRTERELIVNENIKLYSQIVGREVK TTKEIYLAKRFLGYRSDLLFYYGFVDNFFKEAKLFNARKNPIELWSEE FYVNDKLSNYTKFMFNDNLKNSESYLKEYIKNNEKENQKIKNDLESA RDIFATLRHNLMHFNYSFFERLFKGKDVKIKNLQTKKFESLSNVLRNI EFLNKVIQSIDKLNIDTRKEFIDKEKIKLFNEDLDLQQLYGFFAHTAIN RVAFNKLINSFIIKDGIENEQLKEYFNQRVDGTAYEIDIHONREYKELY KKHKNLVSKVSTLSDGKEIAKGNSEISALKEQMNKITKANSLKRLEY KLRLAFGFIYTEYGSYKAFVSRFNEDTKRKKIKNVEFEKIGFEKQKEY FKSTFEPLKSKKKDNLEKLIQEYEKLSLNDLIENDTFLKVILLLFIFMPK EVKGDFLGFIKKYYHDTKYIEEDTKEKDEGFTNTLPIGLKLKIVERNIA KLSVLKHSLSLKVKYNRGQYEEDNTYRKVFKKLNISHNQEEFHKSMF SPLLRYYASLYKLINDFEIYTLSHYITDKYSTLNKVIASKQPHYRYVW NRKENKGELVKTDNYTFSTLLSKKYEHKNSQEISEMRNKISHFDEKIL FKFPLEEVNSFFKGKGKNKKEEPVKSLVEKREEIISLMEKQTDMQKIL GYDAINDFRMKTVQFQTKLKEDSKKKEETIKKMIAEAKIPNDFYNIYK VKGVESINKHLLKIIGQTDKEWKIEGDILDGNFKIACKNQRLEEKQQR AKNKQNLDKL | 86 |
| MIKNPSNRHSLPKVIISEVDHEKILEFKIKYEKLARLDRFEVKAMHYE GKEIVFDEVLVNGGLIEVEYQDDNKTLFVKVGEKSYRICGERIGGNYI VTEYKDKNEPKSKKHFRLIEKDGKYFKPNGEEVTKNIRKSSVKVLLTL TDGVEDNNGKLRKSRTERELIVADNIKLYSQIVGREVTTTKEIYLVKR FLGYRSDLLFYYGFVNNFFHVAGKREELWKIDFDTLPSNSPLLEYFKF TINDEKYLKSYSSDIQQIKKDLQNNKYIFLVNGEDIEIKAENYNIKPLSE LLNIEFLNIQIKKDLQNSKYIFSALRHALMHFDYDFFVRLENGEDIEIK AKNGNKKPLSELLNIEFLNIMIENIDKLNIDTRKEFIDDDDVPIKLFGEE MKPKNLYGLYAHTAINRVAFNKLINSFMMENGVENQALKSYFDQKA GGVAYEVDIHQNSNYKKLYVKHKNLVSKVSTLSDGQEIAKVNAKISE LKEQMKKITKANSLKRLEHKFRLAFGFVYSEYKDYEAFKNNFDTDIK KGKFVPKDKEGKRRAFDHRELEQLKGYFDSTFKSKKPNTKEKLGELS KSTGKLSLKALIGDDMFLKFILLMFTFMPQELKGEFLGFVKKYYHDT KHIEEDTKDRDDGFSNERPMGLKLKVLDKNIRSLSILKHSLSFQTKYN KKDKSFYEDGNVHGKFYKKLGISHNQEEFNKSVYAPLFKYYSALSKL | 87 |

TABLE 1-continued

Amino Acid Sequences of SEQ ID NOs: 1-4 and SEQ ID NOs: 80-89

| Sequence | SEQ ID NO: |
|---|---|
| INDFEIYSLTQHVVGSETLAQQVRKRKFIKKGYYNFGNLLKKTDSIIRS SRDNDIFYAVIDMRNTISHLSVEPMFDYPLNGKKFYKLYENKVICVDP LKSRKMIIDFIKRQTEMKKTLGYDAVNDFTMKMVQLQTKLKVYANK EKTIEKMKEEAQTPNDYYNIYKVKGVEAINQYLLEIIGETDDEALIRKL INRGNSINP | |
| MKKIKNPSNRNSLPSIIISRFDDKNIYELKVKYEKLARLDKLEIEDMSL DEESTLLFKKVKFNGIEIEIKNQKLLEFDSYIISGKKQTNTTGKTIISLLK EGKKVTYNVTKKDGKYYKNGKEFIIPQNANKLPDRLINDKFIITIEDK VRDEDTKRKKETQRDILSDDTIETYKRISSYKSIKSEDIYTIKRYITFKS DMMFFYTFVDDFFNPIKKQDLWKVKFGEVENLGKFIEFTLNDTLKNP KGILETYCKDLKTVQADFAKINTIFSKIRHSLVHFDFVFIDKLLSNQKIE EFDFDIKLLNDVIDKTQDLYYEAKKEFIEDEKITILDEKDMEIKKLYTF FSKIDIKQPAFNKLINSFIIKDGIENIELKTYIKEKYKSEYFIDIHANKEY KKIYNEHKKLVGENQFLQLNPKENGQKIKELNDQVEEYKKQMKTITE ANSLKRLEFKLRLAFGFIKVEYGRFDTFKNSFDEDIKKGKFKEISFEKI KGYLDKTYAKEQFFNYGSNKKTKKPYSILDDIENETLKELVQNDNLL KVILLFYIFTPKELKGEFLGFIKKFYHDTKNITKDTKDEEKELENLKLE TPLKLKILEKNLKKITIFNYSIFSNINFDTTNKRFYAEGNRFNRIYKKLN ISHNQDEFDKSLFAPLLQYYMNLYKLIGDFEIYLLLKFDNKKDLSELS NDERLKFRGYYNFTTLLSKWFQFDPKRDKKYEKVLRLRNTISHQDIN NMIINFEKSTILSQRENIVQLIEEQNDLKEILKYDAVNDFTMKTIQLLKS IEIQSDKSKTINELLSNKDISANDFYNIYKVKGVEMIKKELFNRLGKRE IEKKIEEEIAKSTIC | 88 |
| MEKIKKPSNRNSIPSIIISDYDASKIKEIKVKYLKLARLDKITIQDMEIVD NIVEFKKILLNGTEHTIIDNKKIEFDNYEITGCIKPSNKRRDGKISQAKY VVTITDKYLRDNEKEKRFKSTERELPNDILLSRYKQISGFDTLTSKDIY KIKRYIDFKNEMLFYFQFIEEFFNPLLPKGKNFYDLNIEQNKDKVAKFI VYRLNDDFKNQSLNSYIQKTDTIKYDFIKVQKILNDFRHALAHFDFEFI QKFFDNQLDKTRFDINTISLIKTLLQKKEGKHYQEKNNYIDDNDTLTIF DDKDSKFSKLHNFYTKISQKKPAFNKLINSFLSQDGIPNEEFKRYLATK KLDFFEDIHSNKEYKEIYINHKNQVIEKQKEESQEKPDGQKLKNFNDE LQKLKDKMNTITKQNSLNRLEVKLRLAFGFIANEYNYNFKNFNDNFT LDVKNEQKIKAFKNSSNEKLKEYFESTFEAKQFFYYGKNKNIFNSIEN ETLEELVKESPLLQIITFLYLFIPKELQGEFVGFILEIYHHTKNISSDTKE DEISIEDAQNSFSLKLKILAKNLRGLQLFNYSLSHNTLYNNKQDFFYE KGNRWQNIYKNFQISHNQDEFDIHLVIPVIKYYINLNKLIGDFEIYALL KYADQNSITEKLSDITKRDDLKFKGHYNFSTLLNRTFGISVYSDKNPIS IQNIKQIRNDIAHQNIENMLKAFENSEIFAQREEIVNYLQTEHQMQEIL HYNPINDFTMKTVQYLKSLSVHSQKEGKIADIHKKDNLVPNDYYLIY KLKAIEILKQKVIEAIGETKDEKKIKNAIAKEEQIKKGNN | 89 |

In any aspects or embodiments herein, the present endonuclease, or a fragment or variant thereof, having at least about 70% identity to one or more of SEQ ID NOs: 1-4, and/or SEQ ID NOs: 80-89, has the N terminal M residue removed.

In any aspects or embodiments herein, the present endonuclease, or a fragment or variant thereof, having at least about 70% identity to one or more of SEQ ID NOs: 1-4, and/or SEQ ID NOs: 80-89, has the N terminal M residue removed and a SV40 NLS SV40 sequence is added to the N-terminus (MSPKKKRKVEAS (SEQ ID NO: 78)).

In any aspects or embodiments herein, the present endonuclease, or a fragment or variant thereof, having at least about 70% identity to one or more of SEQ ID NOs: 1-4, and/or SEQ ID NOs: 80-89, has the N terminal M residue removed and a SV40 NLS SV40 sequence is added to the N-terminus (MSPKKKRKVEAS (SEQ ID NO: 78)) and a HA tag is added to the C-terminus (GSGPKKKRKVAAAY-PYDVPDYA (SEQ ID NO: 77)).

In embodiments, the catalytic domain is selected from Table 2. In embodiments, a mutation of any of the present endonucleases is of one or more of the residues of Table 2.

TABLE 2

Illustrative Positioning of Catalytic Residues

| Protein | Catalytic Domain Type | Residue | Amino Acid Number |
|---|---|---|---|
| Cas13K2F1 (SEQ ID NO: 1) | HEPN | R | 244 |
| Cas13K2F1 (SEQ ID NO: 1) | HEPN | H | 249 |
| Cas13K2F1 (SEQ ID NO: 1) | HEPN | H | 669 |
| Cas13K2F1 (SEQ ID NO: 1) | HEPN | R | 664 |
| Cas13K2F2 (SEQ ID NO: 2) | HEPN | R | 244 |
| Cas13K2F2 (SEQ ID NO: 2) | HEPN | H | 249 |

TABLE 2-continued

Illustrative Positioning of Catalytic Residues

| Protein | Catalytic Domain Type | Residue | Amino Acid Number |
|---|---|---|---|
| Cas13K2F2 (SEQ ID NO: 2) | HEPN | H | 687 |
| Cas13K2F2 (SEQ ID NO: 2) | HEPN | R | 682 |
| Cas13K2F3 (SEQ ID NO: 3) | HEPN | R | 244 |
| Cas13K2F3 (SEQ ID NO: 3) | HEPN | H | 249 |
| Cas13K2F3 (SEQ ID NO: 3) | HEPN | R | 704 |
| Cas13K2F3 (SEQ ID NO: 3) | HEPN | H | 709 |
| Cas13K2F5 (SEQ ID NO: 4) | HEPN | R | 244 |
| Cas13K2F5 (SEQ ID NO: 4) | HEPN | H | 249 |
| Cas13K2F5 (SEQ ID NO: 4) | HEPN | H | 687 |
| Cas13K2F5 (SEQ ID NO: 4) | HEPN | R | 682 |
| Cas13K2F7 (SEQ ID NO: 80) | HEPN | R | 234 |
| Cas13K2F7 (SEQ ID NO: 80) | HEPN | H | 239 |
| Cas13K2F7 (SEQ ID NO: 80) | HEPN | R | 659 |
| Cas13K2F7 (SEQ ID NO: 80) | HEPN | H | 664 |
| Cas13K2F8 (SEQ ID NO: 81) | HEPN | R | 234 |
| Cas13K2F8 (SEQ ID NO: 81) | HEPN | H | 239 |
| Cas13K2F8 (SEQ ID NO: 81) | HEPN | R | 659 |
| Cas13K2F8 (SEQ ID NO: 81) | HEPN | H | 664 |
| Cas13K2F9 (SEQ ID NO: 82) | HEPN | R | 234 |
| Cas13K2F9 (SEQ ID NO: 82) | HEPN | H | 239 |
| Cas13K2F9 (SEQ ID NO: 82) | HEPN | R | 659 |
| Cas13K2F9 (SEQ ID NO: 82) | HEPN | H | 664 |
| Cas13K2F10 (SEQ ID NO: 83) | HEPN | R | 239 |
| Cas13K2F10 (SEQ ID NO: 83) | HEPN | H | 244 |
| Cas13K2F10 (SEQ ID NO: 83) | HEPN | R | 677 |
| Cas13K2F10 (SEQ ID NO: 83) | HEPN | H | 682 |
| Cas13K2F11 (SEQ ID NO: 84) | HEPN | R | 241 |
| Cas13K2F11 (SEQ ID NO: 84) | HEPN | H | 246 |
| Cas13K2F11 (SEQ ID NO: 84) | HEPN | R | 681 |
| Cas13K2F11 (SEQ ID NO: 84) | HEPN | H | 686 |
| Cas13K2F12 (SEQ ID NO: 85) | HEPN | R | 244 |
| Cas13K2F12 (SEQ ID NO: 85) | HEPN | H | 249 |
| Cas13K2F12 (SEQ ID NO: 85) | HEPN | R | 701 |
| Cas13K2F12 (SEQ ID NO: 85) | HEPN | H | 706 |
| Cas13K2F13 (SEQ ID NO: 86) | HEPN | R | 247 |
| Cas13K2F13 (SEQ ID NO: 86) | HEPN | H | 252 |
| Cas13K2F13 (SEQ ID NO: 86) | HEPN | R | 711 |
| Cas13K2F13 (SEQ ID NO: 86) | HEPN | H | 716 |
| Cas13K2F14 (SEQ ID NO: 87) | HEPN | R | 316 |
| Cas13K2F14 (SEQ ID NO: 87) | HEPN | H | 321 |
| Cas13K2F14 (SEQ ID NO: 87) | HEPN | R | 781 |
| Cas13K2F14 (SEQ ID NO: 87) | HEPN | H | 786 |
| Cas13K2F15 (SEQ ID NO: 88) | HEPN | R | 274 |
| Cas13K2F15 (SEQ ID NO: 88) | HEPN | H | 279 |
| Cas13K2F15 (SEQ ID NO: 88) | HEPN | R | 723 |
| Cas13K2F15 (SEQ ID NO: 88) | HEPN | H | 728 |
| Cas13K2F16 (SEQ ID NO: 89) | HEPN | R | 237 |
| Cas13K2F16 (SEQ ID NO: 89) | HEPN | H | 242 |

TABLE 2-continued

Illustrative Positioning of Catalytic Residues

| Protein | Catalytic Domain Type | Residue | Amino Acid Number |
|---|---|---|---|
| Cas13K2F16 (SEQ ID NO: 89) | HEPN | R | 694 |
| Cas13K2F16 (SEQ ID NO: 89) | HEPN | H | 699 |

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to one of SEQ ID NO: 1, SEQ ID NO: 2, SEQ ID NO: 3, SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, and an amino acid modification one or more positions that have an R or H residue in the wild type sequence.

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to one of SEQ ID NO: 1, SEQ ID NO: 2, SEQ ID NO: 3, SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, and an amino acid modification at one or more positions in a HEPN domain.

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to one of SEQ ID NO: 1, SEQ ID NO: 2, SEQ ID NO: 3, SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, and an amino acid modification at one or more positions in a region of the endonuclease at about 100 to about 300 amino acids, or about 150 to about 300 amino acids, or about 150 to about 250 amino acids, or about 100 to about 300 amino acids, or about 200 to about 250 amino acids, or about 240 to about 250 amino acids from the N-terminus of the endonuclease.

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to one of SEQ ID NO: 1, SEQ ID NO: 2, SEQ ID NO: 3, SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, and an amino acid modification at one or more positions in a region of the endonuclease at about 100 to about 300 amino acids, or about 150 to about 300 amino acids, or about 150 to about 250 amino acids, or about 100 to about 300 amino acids, or about 200 to about 250 amino acids, or about 240 to about 250 amino acids from the C-terminus of the endonuclease.

In embodiments, the amino acid modification is a hydrophilic or hydrophobic amino acid. In embodiments, the amino acid modification is amino acid modification is a hydrophilic amino acid. In embodiments, the amino acid modification is a polar and positively charged hydrophilic amino acid. In embodiments, the amino acid modification is arginine (R) or lysine (K). In embodiments, the amino acid modification is a polar and neutral charged hydrophilic amino acid. In embodiments, the amino acid modification is selected from asparagine (N), glutamine (Q), serine (S), threonine (T), proline (P), and cysteine (C). In embodiments, the amino acid modification is a polar and negatively charged hydrophilic amino acid. In embodiments, the amino acid modification is selected from aspartate (D) or glutamate (E). In embodiments, the amino acid modification is an aromatic, polar and positively charged hydrophilic amino acid. In embodiments, the amino acid modification is histidine (H). In embodiments, the amino acid modification is a hydrophobic amino acid. In embodiments, the amino acid modification is a hydrophobic, aliphatic amino acid. In embodiments, the amino acid modification is selected from glycine (G), alanine (A), leucine (L), isoleucine (I), methionine (M), or valine (V). In embodiments, the amino acid modification is a hydrophobic, aromatic amino acid. In embodiments, the amino acid modification is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 1 and an amino acid modification at position R244. In embodiments, the amino acid modifications are selected from substitutions and deletions. In embodiments, the amino acid modification to SEQ ID NO: 1 at R244 is an essential or non-essential amino acid. In embodiments, the amino acid modification at R244 is a hydrophilic or hydrophobic amino acid. In embodiments, the amino acid modification at R244 is amino acid modification is a hydrophilic amino acid. In embodiments, the amino acid modification at R244 is a polar and positively charged hydrophilic amino acid. In embodiments, the amino acid modification at R244 is lysine (K). In embodiments, the amino acid modification at R244 is a polar and neutral charged hydrophilic amino acid. In embodiments, the amino acid modification at R244 is selected from asparagine (N), glutamine (Q), serine (S), threonine (T), proline (P), and cysteine (C). In embodiments, the amino acid modification at R244 is a polar and negatively charged hydrophilic amino acid. In embodiments, the amino acid modification at R244 is selected from aspartate (D) or glutamate (E). In embodiments, the amino acid modification at R244 is an aromatic, polar and positively charged hydrophilic amino acid. In embodiments, the amino acid modification at R244 is histidine (H). In embodiments, the amino acid modification at R244 is a hydrophobic amino acid. In embodiments, the amino acid modification at R244 is a hydrophobic, aliphatic amino acid. In embodiments, the amino acid modification at R244 is selected from glycine (G), alanine (A), leucine (L), isoleucine (I), methionine (M), or valine (V). In embodiments, the amino acid modification at R244 is a hydrophobic, aromatic amino acid. In embodiments, the amino acid modification at R244 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 1 and an amino acid modification at position H249. In embodiments, the amino acid modifications are selected from substitutions and deletions. In embodiments, the amino acid modification to SEQ ID NO: 1 at H249 is an essential or non-essential amino acid. In embodiments, the amino acid modification at H249 is a hydrophilic or hydrophobic amino acid. In embodiments, the amino acid modification at H249 is amino acid modification is a hydrophilic amino acid. In embodiments, the amino acid modification at H249 is a polar and positively charged hydrophilic amino acid. In embodiments, the amino acid modification at H249 is selected from arginine (R) or lysine (K). In embodiments, the amino acid modification at H249 is a polar and neutral charged hydrophilic amino acid. In embodiments, the amino acid modification at H249 is selected from asparagine (N), glutamine (Q), serine (S), threonine (T), proline (P), and cysteine (C). In embodiments, the amino acid modification at H249 is a polar and negatively charged hydrophilic amino acid. In embodiments, the amino acid modification at H249 is selected from aspartate (D) or glutamate (E). In embodiments, the amino acid modification at H249 is an aromatic, polar and positively charged hydrophilic amino acid. In embodiments, the amino acid modification at H249 is a hydrophobic amino acid. In embodiments, the amino acid modification at H249 is a hydrophobic, aliphatic amino acid. In embodiments, the amino acid modification at H249 is selected from glycine (G), alanine (A), leucine (L), isoleucine (I), methionine (M), or valine (V). In embodiments, the amino acid modification at H249 is a hydrophobic, aromatic amino acid. In embodiments, the amino acid modification at H249 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 1 and an amino acid modification at position H669. In embodiments, the amino acid modifications are selected from substitutions and deletions. In embodiments, the amino acid modification to SEQ ID NO: 1 at H669 is an essential or non-essential amino acid. In embodiments, the amino acid modification at H669 is a hydrophilic or hydrophobic amino acid. In embodiments, the amino acid modification at H669 is amino acid modification is a hydrophilic amino acid. In embodiments, the amino acid modification at H669 is a polar and positively charged hydrophilic amino acid. In embodiments, the amino acid modification at H669 is selected from arginine (R) or lysine (K). In embodiments, the amino acid modification at H669 is a polar and neutral charged hydrophilic amino acid. In embodiments, the amino acid modification at H669 is selected from asparagine (N), glutamine (Q), serine (S), threonine (T), proline (P), and cysteine (C). In embodiments, the amino acid modification at H669 is a polar and negatively charged hydrophilic amino acid. In embodiments, the amino acid modification at H669 is selected from aspartate (D) or glutamate (E). In embodiments, the amino acid modification at H669 is an aromatic, polar and positively charged hydrophilic amino acid. In embodiments, the amino acid modification at H669 is a hydrophobic amino acid. In embodiments, the amino acid modification at H669 is a hydrophobic, aliphatic amino acid. In embodiments, the amino acid modification at H669 is selected from glycine (G), alanine (A), leucine (L), isoleucine (I), methionine (M), or valine (V). In embodiments, the amino acid modification at H669 is a hydrophobic, aromatic amino acid. In embodiments, the amino acid modification at H669 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 1 and an amino acid modification at position R664. In embodiments, the amino acid modifications are selected from substitutions and deletions. In embodiments, the amino acid modification to SEQ ID NO: 1 at R664 is an essential or non-essential amino acid. In embodiments, the amino acid modification at R664 is a hydrophilic or hydrophobic amino acid. In embodiments, the amino acid modification at R664 is amino acid modification is a hydrophilic amino acid. In embodiments, the amino acid modification at R664 is a polar and positively charged hydrophilic amino acid. In embodiments, the amino acid modification at R664 is lysine (K). In embodiments, the amino acid modification at R664 is a polar and neutral charged hydrophilic amino acid. In embodiments, the amino acid modification at R664 is selected from asparagine (N), glutamine (Q), serine (S), threonine (T), proline (P), and cysteine (C). In embodiments, the amino acid modification at R664 is a polar and negatively charged hydrophilic amino acid. In embodiments, the amino acid modification at R664 is selected from aspartate (D) or glutamate (E). In embodiments, the amino acid modification at R664 is an aromatic, polar and positively charged hydrophilic amino acid. In embodiments, the amino acid modification at R664 is histidine (H). In embodiments, the amino acid modification at R664 is a hydrophobic amino acid. In embodiments, the amino acid modification at R664 is a hydrophobic, aliphatic amino acid. In embodiments, the amino acid modification at R664 is selected from glycine (G), alanine (A), leucine (L), isoleucine (I), methionine (M), or valine (V). In embodiments, the amino acid modification at R664 is a hydrophobic, aromatic amino acid. In embodiments, the amino acid modification at R664 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 2 and an amino acid modification at position R244. In embodiments, the amino acid modifications are selected from substitutions and deletions. In embodiments, the amino acid modification to SEQ ID NO: 2 at R244 is an essential or non-essential amino acid. In embodiments, the amino acid modification at R244 is a hydrophilic or hydrophobic amino acid. In embodiments, the amino acid modification at R244 is amino acid modification is a hydrophilic amino acid. In embodiments, the amino acid modification at R244 is a polar and positively charged hydrophilic amino acid. In embodiments, the amino acid modification at R244 is lysine (K). In embodiments, the amino acid modification at R244 is a polar and neutral charged hydrophilic amino acid. In embodiments, the amino acid modification at R244 is selected from asparagine (N), glutamine (Q), serine (S), threonine (T), proline (P), and cysteine (C). In embodiments, the amino acid modification at R244 is a polar and negatively charged hydrophilic amino acid. In embodiments, the amino acid modification at R244 is selected from aspartate (D) or glutamate (E). In embodiments, the amino acid modification at R244 is an aromatic, polar and positively charged hydrophilic amino acid. In embodiments, the amino acid modification at R244 is histidine (H). In embodiments, the amino acid modification at R244 is a hydrophobic amino acid. In embodiments, the amino acid modification at R244 is a hydrophobic, aliphatic amino acid. In embodiments, the amino acid modification at R244 is selected from glycine (G), alanine (A), leucine (L), isoleucine (I), methionine (M), or valine (V). In embodiments, the amino acid modification at R244 is a hydrophobic, aromatic amino acid. In embodiments, the amino acid modification at R244 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 2 and an amino acid modification at position H249. In embodiments, the amino acid modifications are selected from substitutions and deletions. In embodiments, the amino acid modification to SEQ ID NO: 2 at H249 is an essential or non-essential amino acid. In embodiments, the amino acid modification at H249 is a hydrophilic or hydrophobic amino acid. In embodiments, the amino acid modification at H249 is amino acid modification is a hydrophilic amino acid. In embodiments, the amino acid modification at H249 is a polar and positively charged hydrophilic amino acid. In embodiments, the amino acid modification at H249 is selected from arginine (R) or lysine (K). In embodiments, the amino acid modification at H249 is a polar and neutral charged hydrophilic amino acid. In embodiments, the amino acid modification at H249 is selected from asparagine (N), glutamine (Q), serine (S), threonine (T), proline (P), and cysteine (C). In embodiments, the amino acid modification at H249 is a polar and negatively charged hydrophilic amino acid. In embodiments, the amino acid modification at H249 is selected from aspartate (D) or glutamate (E). In embodiments, the amino acid modification at H249 is an aromatic, polar and positively charged hydrophilic amino acid. In embodiments, the amino acid modification at H249 is a hydrophobic amino acid. In embodiments, the amino acid modification at H249 is a hydrophobic, aliphatic amino acid. In embodiments, the amino acid modification at H249 is selected from glycine (G), alanine (A), leucine (L), isoleucine (I), methionine (M), or valine (V). In embodiments, the amino acid modification at H249 is a hydrophobic, aromatic amino acid. In embodiments, the amino acid modification at H249 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 2 and an amino acid modification at position H687. In embodiments, the amino acid modifications are selected from substitutions and deletions. In embodiments, the amino acid modification to SEQ ID NO: 2 at H687 is an essential or non-essential amino acid. In embodiments, the amino acid modification at H687 is a hydrophilic or hydrophobic amino acid. In embodiments, the amino acid modification at H687 is amino acid modification is a hydrophilic amino acid. In embodiments, the amino acid modification at H687 is a polar and positively charged hydrophilic amino acid. In embodiments, the amino acid modification at H687 is selected from arginine (R) or lysine (K). In embodiments, the amino acid modification at H687 is a polar and neutral charged hydrophilic amino acid. In embodiments, the amino acid modification at H687 is selected from asparagine (N), glutamine (Q), serine (S), threonine (T), proline (P), and cysteine (C). In embodiments, the amino acid modification at H687 is a polar and negatively charged hydrophilic amino acid. In embodiments, the amino acid modification at H687 is selected from aspartate (D) or glutamate (E). In embodiments, the amino acid modification at H687 is an aromatic, polar and positively charged hydrophilic amino acid. In embodiments, the amino acid modification at H687 is a hydrophobic amino acid. In embodiments, the amino acid modification at H687 is a hydrophobic, aliphatic amino acid. In embodiments, the amino acid modification at H687 is selected from glycine (G), alanine (A), leucine (L), isoleucine (I), methionine (M), or valine (V). In embodiments, the amino acid modification at H687 is a hydrophobic, aromatic amino acid. In embodiments, the amino acid modification at H687 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 2 and an amino acid modification at position R682. In embodiments, the amino acid modifications are selected from substitutions and deletions. In embodiments, the amino acid modification to SEQ ID NO: 2 at R682 is an essential or non-essential amino acid. In embodiments, the amino acid modification at R682 is a hydrophilic or hydrophobic amino acid. In embodiments, the amino acid modification at R682 is amino acid modification is a hydrophilic amino acid. In embodiments, the amino acid modification at R682 is a polar and positively charged hydrophilic amino acid. In embodiments, the amino acid modification at R682 is lysine (K). In embodiments, the amino acid modification at R682 is a polar and neutral charged hydrophilic amino acid. In embodiments, the amino acid modification at R682 is selected from asparagine (N), glutamine (Q), serine (S), threonine (T), proline (P), and cysteine (C). In embodiments, the amino acid modification at R682 is a polar and negatively charged hydrophilic amino acid. In embodiments, the amino acid modification at R682 is selected from aspartate (D) or glutamate (E). In embodiments, the amino acid modification at R682 is an aromatic, polar and positively charged hydrophilic amino acid. In embodiments, the amino acid modification at R682 is histidine (H). In embodiments, the amino acid modification at R682 is a hydrophobic amino acid. In embodiments, the amino acid modification at R682 is a hydrophobic, aliphatic amino acid. In embodiments, the amino acid modification at R682 is selected from glycine (G), alanine (A), leucine (L), isoleucine (I), methionine (M), or valine (V). In embodiments, the amino acid modification at R682 is a hydrophobic, aromatic amino acid. In embodiments, the amino acid modification at R682 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 3 and an amino acid modification at position R244. In embodiments, the amino acid modifications are selected from substitutions and deletions. In embodiments, the amino acid modification to SEQ ID NO: 3 at R244 is an essential or non-essential amino acid. In embodiments, the amino acid modification at R244 is a hydrophilic or hydrophobic amino acid. In embodiments, the amino acid modification at R244 is amino acid modification is a hydrophilic amino acid. In embodiments, the amino acid modification at R244 is a polar and positively charged hydrophilic amino acid. In embodiments, the amino acid modification at R244 is lysine (K). In embodiments, the amino acid modification at R244 is a polar and neutral charged hydrophilic amino acid. In embodiments, the amino acid modification at R244 is selected from asparagine (N), glutamine (Q), serine (S), threonine (T), proline (P), and cysteine (C). In embodiments, the amino acid modification at R244 is a polar and negatively charged hydrophilic amino acid. In embodiments, the amino acid modification at R244 is selected from aspartate (D) or glutamate (E). In embodiments, the amino acid modification at R244 is an aromatic, polar and positively charged hydrophilic amino acid. In embodiments, the amino acid modification at R244 is histidine (H). In embodiments, the amino acid modification at R244 is a hydrophobic amino acid. In embodiments, the amino acid modification at R244 is a hydrophobic, aliphatic amino acid. In embodiments, the amino acid modification at R244 is selected from glycine (G), alanine (A), leucine (L), isoleucine (I), methionine (M), or valine (V). In embodiments, the amino acid modification at R244 is a hydrophobic, aromatic amino acid. In embodiments, the amino acid modification at R244 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 3 and an amino acid modification at position H249. In embodiments, the amino acid modifications are selected from substitutions and deletions. In embodiments, the amino acid modification to SEQ ID NO: 3 at H249 is an essential or non-essential amino acid. In embodiments, the amino acid modification at H249 is a hydrophilic or hydrophobic amino acid. In embodiments, the amino acid modification at H249 is amino acid modification is a hydrophilic amino acid. In embodiments, the amino acid modification at H249 is a polar and positively charged hydrophilic amino acid. In embodiments, the amino acid modification at H249 is selected from arginine (R) or lysine (K). In embodiments, the amino acid modification at H249 is a polar and neutral charged hydrophilic amino acid. In embodiments, the amino acid modification at H249 is selected from asparagine (N), glutamine (Q), serine (S), threonine (T), proline (P), and cysteine (C). In embodiments, the amino acid modification at H249 is a polar and negatively charged hydrophilic amino acid. In embodiments, the amino acid modification at H249 is selected from aspartate (D) or glutamate (E). In embodiments, the amino acid modification at H249 is an aromatic, polar and positively charged hydrophilic amino acid. In embodiments, the amino acid modification at H249 is a hydrophobic amino acid. In embodiments, the amino acid modification at H249 is a hydrophobic, aliphatic amino acid. In embodiments, the amino acid modification at H249 is selected from glycine (G), alanine (A), leucine (L), isoleucine (I), methionine (M), or valine (V). In embodiments, the amino acid modification at H249 is a hydrophobic, aromatic amino acid. In embodiments, the amino acid modification at H249 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 3 and an amino acid modification at position R704. In embodiments, the amino acid modifications are selected from substitutions and deletions. In embodiments, the amino acid modification to SEQ ID NO: 3 at R704 is an essential or non-essential amino acid. In embodiments, the amino acid modification at R704 is a hydrophilic or hydrophobic amino acid. In embodiments, the amino acid modification at R704 is amino acid modification is a hydrophilic amino acid. In embodiments, the amino acid modification at R704 is a polar and positively charged hydrophilic amino acid. In embodiments, the amino acid modification at R704 is lysine (K). In embodiments, the amino acid modification at R704 is a polar and neutral charged hydrophilic amino acid. In embodiments, the amino acid modification at R704 is selected from asparagine (N), glutamine (Q), serine (S), threonine (T), proline (P), and cysteine (C). In embodiments, the amino acid modification at R704 is a polar and negatively charged hydrophilic amino acid. In embodiments, the amino acid modification at R704 is selected from aspartate (D) or glutamate (E). In embodiments, the amino acid modification at R704 is an aromatic, polar and positively charged hydrophilic amino acid. In embodiments, the amino acid modification at R704 is histidine (H). In embodiments, the amino acid modification at R704 is a hydrophobic amino acid. In embodiments, the amino acid modification at R704 is a hydrophobic, aliphatic amino acid. In embodiments, the amino acid modification at R704 is selected from glycine (G), alanine (A), leucine (L), isoleucine (I), methionine (M), or valine (V). In embodiments, the amino acid modification at R704 is a hydrophobic, aromatic amino acid. In embodiments, the amino acid modification at R704 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 3 and an amino acid modification at position H709. In embodiments, the amino acid modifications are selected from substitutions and deletions. In embodiments, the amino acid modification to SEQ ID NO: 3 at H709 is an essential or non-essential amino acid. In embodiments, the amino acid modification at H709 is a hydrophilic or hydrophobic amino acid. In embodiments, the amino acid modification at H709 is amino acid modification is a hydrophilic amino acid. In embodiments, the amino acid modification at H709 is a polar and positively charged hydrophilic amino acid. In embodiments, the amino acid modification at H709 is selected from arginine (R) or lysine (K). In embodiments, the amino acid modification at H709 is a polar and neutral charged hydrophilic amino acid. In embodiments, the amino acid modification at H709 is selected from asparagine (N), glutamine (Q), serine (S), threonine (T), proline (P), and cysteine (C). In embodiments, the amino acid modification at H709 is a polar and negatively charged hydrophilic amino acid. In embodiments, the amino acid modification at H709 is selected from aspartate (D) or glutamate (E). In embodiments, the amino acid modification at H709 is an aromatic, polar and positively charged hydrophilic amino acid. In embodiments, the amino acid modification at H709 is a hydrophobic amino acid. In embodiments, the amino acid modification at H709 is a hydrophobic, aliphatic amino acid. In embodiments, the amino acid modification at H709 is selected from glycine (G), alanine (A), leucine (L), isoleucine (I), methionine (M), or valine (V). In embodiments, the amino acid modification at H709 is a hydrophobic, aromatic amino acid. In embodiments, the amino acid modification at H709 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 4 and an amino acid modification at position R244. In embodiments, the amino acid modifications are selected from substitutions and deletions. In embodiments, the amino acid modification to SEQ ID NO: 4 at R244 is an essential or non-essential amino acid. In embodiments, the amino acid modification at R244 is a hydrophilic or hydrophobic amino acid. In embodiments, the amino acid modification at R244 is amino acid modification is a hydrophilic amino acid. In embodiments, the amino acid modification at R244 is a polar and positively charged hydrophilic amino acid. In embodiments, the amino acid modification at R244 is lysine (K). In embodiments, the amino acid modification at R244 is a polar and neutral charged hydrophilic amino acid. In embodiments, the amino acid modification at R244 is selected from asparagine (N), glutamine (Q), serine (S), threonine (T), proline (P), and cysteine (C). In embodiments, the amino acid modification at R244 is a polar and negatively charged hydrophilic amino acid. In embodiments, the amino acid modification at R244 is selected from aspartate (D) or glutamate (E). In embodiments, the amino acid modification at R244 is an aromatic, polar and positively charged hydrophilic amino acid. In embodiments, the amino acid modification at R244 is histidine (H). In embodiments, the amino acid modification at R244 is a hydrophobic amino acid. In embodiments, the amino acid modification at R244 is a hydrophobic, aliphatic amino acid. In embodiments, the amino acid modification at R244 is selected from glycine (G), alanine (A), leucine (L), isoleucine (I), methionine (M), or valine (V). In embodiments, the amino acid modification at R244 is a hydrophobic, aromatic amino acid. In embodiments, the amino acid modification at R244 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 4 and an amino acid modification at position H249. In embodiments, the amino acid modifications are selected from substitutions and deletions. In embodiments, the amino acid modification to SEQ ID NO: 4 at H249 is an essential or non-essential amino acid. In embodiments, the amino acid modification at H249 is a hydrophilic or hydrophobic amino acid. In embodiments, the amino acid modification at H249 is amino acid modification is a hydrophilic amino acid. In embodiments, the amino acid modification at H249 is a polar and positively charged hydrophilic amino acid. In embodiments, the amino acid modification at H249 is selected from arginine (R) or lysine (K). In embodiments, the amino acid modification at H249 is a polar and neutral charged hydrophilic amino acid. In embodiments, the amino acid modification at H249 is selected from asparagine (N), glutamine (Q), serine (S), threonine (T), proline (P), and cysteine (C). In embodiments, the amino acid modification at H249 is a polar and negatively charged hydrophilic amino acid. In embodiments, the amino acid modification at H249 is selected from aspartate (D) or glutamate (E). In embodiments, the amino acid modification at H249 is an aromatic, polar and positively charged hydrophilic amino acid. In embodiments, the amino acid modification at H249 is a hydrophobic amino acid. In embodiments, the amino acid modification at H249 is a hydrophobic, aliphatic amino acid. In embodiments, the amino acid modification at H249 is selected from glycine (G), alanine (A), leucine (L), isoleucine (I), methionine (M), or valine (V). In embodiments, the amino acid modification at H249 is a hydrophobic, aromatic amino acid. In embodiments, the amino acid modification at H249 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 4 and an amino acid modification at position H687. In embodiments, the amino acid modifications are selected from substitutions and deletions. In embodiments, the amino acid modification to SEQ ID NO: 4 at H687 is an essential or non-essential amino acid. In embodiments, the amino acid modification at H687 is a hydrophilic or hydrophobic amino acid. In embodiments, the amino acid modification at H687 is amino acid modification is a hydrophilic amino acid. In embodiments, the amino acid modification at H687 is a polar and positively charged hydrophilic amino acid. In embodiments, the amino acid modification at H687 is selected from arginine (R) or lysine (K). In embodiments, the amino acid modification at H687 is a polar and neutral charged hydrophilic amino acid. In embodiments, the amino acid modification at H687 is selected from asparagine (N), glutamine (Q), serine (S), threonine (T), proline (P), and cysteine (C). In embodiments, the amino acid modification at H687 is a polar and negatively charged hydrophilic amino acid. In embodiments, the amino acid modification at H687 is selected from aspartate (D) or glutamate (E). In embodiments, the amino acid modification at H687 is an aromatic, polar and positively charged hydrophilic amino acid. In embodiments, the amino acid modification at H687 is a hydrophobic amino acid. In embodiments, the amino acid modification at H687 is a hydrophobic, aliphatic amino acid. In embodiments, the amino acid modification at H687 is selected from glycine (G), alanine (A), leucine (L), isoleucine (I), methionine (M), or valine (V). In embodiments, the amino acid modification at H687 is a hydrophobic, aromatic amino acid. In embodiments, the amino acid modification at H687 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 4 and an amino acid modification at position R682. In embodiments, the amino acid modifications are selected from substitutions and deletions. In embodiments, the amino acid modification to SEQ ID NO: 4 at R682 is an essential or non-essential amino acid. In embodiments, the amino acid modification at R682 is a hydrophilic or hydrophobic amino acid. In embodiments, the amino acid modification at R682 is amino acid modification is a hydrophilic amino acid. In embodiments, the amino acid modification at R682 is a polar and positively charged hydrophilic amino acid. In embodiments, the amino acid modification at R682 is lysine (K). In embodiments, the amino acid modification at R682 is a polar and neutral charged hydrophilic amino acid. In embodiments, the amino acid modification at R682 is selected from asparagine (N), glutamine (Q), serine (S), threonine (T), proline (P), and cysteine (C). In embodiments, the amino acid modification at R682 is a polar and negatively charged hydrophilic amino acid. In embodiments, the amino acid modification at R682 is selected from aspartate (D) or glutamate (E). In embodiments, the amino acid modification at R682 is an aromatic, polar and positively charged hydrophilic amino acid. In embodiments, the amino acid modification at R682 is histidine (H). In embodiments, the amino acid modification at R682 is a hydrophobic amino acid. In embodiments, the amino acid modification at R682 is a hydrophobic, aliphatic amino acid. In embodiments, the amino acid modification at R682 is selected from glycine (G), alanine (A), leucine (L), isoleucine (I), methionine (M), or valine (V). In embodiments, the amino acid modification at R682 is a hydrophobic, aromatic amino acid. In embodiments, the amino acid modification at R682 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 80 and an amino acid modification at position R234. In embodiments, the amino acid modifications are selected from substitutions and deletions. In embodiments, the amino acid modification to SEQ ID NO: 80 at R234 is an essential or non-essential amino acid. In embodiments, the amino acid modification at R234 is a hydrophilic or hydrophobic amino acid. In embodiments, the amino acid modification at R234 is amino acid modification is a hydrophilic amino acid. In embodiments, the amino acid modification at R234 is a polar and positively charged hydrophilic amino acid. In embodiments, the amino acid modification at R234 is lysine (K). In embodiments, the amino acid modification at R234 is a polar and neutral charged hydrophilic amino acid. In embodiments, the amino acid modification at R234 is selected from asparagine (N), glutamine (Q), serine (S), threonine (T), proline (P), and cysteine (C). In embodiments, the amino acid modification at R234 is a polar and negatively charged hydrophilic amino acid. In embodiments, the amino acid modification at R234 is selected from aspartate (D) or glutamate (E). In embodiments, the amino acid modification at R234 is an aromatic, polar and positively charged hydrophilic amino acid. In embodiments, the amino acid modification at R234 is histidine (H). In embodiments, the amino acid modification at R234 is a hydrophobic amino acid. In embodiments, the amino acid modification at R234 is a hydrophobic, aliphatic amino acid. In embodiments, the amino acid modification at R234 is selected from glycine (G), alanine (A), leucine (L), isoleucine (I), methionine (M), or valine (V). In embodiments, the amino acid modification at R234 is a hydrophobic, aromatic amino acid. In embodiments, the amino acid modification at R234 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 80 and an amino acid modification at position H239. In embodiments, the amino acid modifications are selected from substitutions and deletions. In embodiments, the amino acid modification to SEQ ID NO: 80 at H239 is an essential or non-essential amino acid. In embodiments, the amino acid modification at H239 is a hydrophilic or hydrophobic amino acid. In embodiments, the amino acid modification at H239 is amino acid modification is a hydrophilic amino acid. In embodiments, the amino acid modification at H239 is a polar and positively charged hydrophilic amino acid. In embodiments, the amino acid modification at H239 is selected from arginine (R) or lysine (K). In embodiments, the amino acid modification at H239 is a polar and neutral charged hydrophilic amino acid. In embodiments, the amino acid modification at H239 is selected from asparagine (N), glutamine (Q), serine (S), threonine (T), proline (P), and cysteine (C). In embodiments, the amino acid modification at H239 is a polar and negatively charged hydrophilic amino acid. In embodiments, the amino acid modification at H239 is selected from aspartate (D) or glutamate (E). In embodiments, the amino acid modification at H239 is an aromatic, polar and positively charged hydrophilic amino acid. In embodiments, the amino acid modification at H239 is a hydrophobic amino acid. In embodiments, the amino acid modification at H239 is a hydrophobic, aliphatic amino acid. In embodiments, the amino acid modification at H239 is selected from glycine (G), alanine (A), leucine (L), isoleucine (I), methionine (M), or valine (V). In embodiments, the amino acid modification at H239 is a hydrophobic, aromatic amino acid. In embodiments, the amino acid modification at H239 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 80 and an amino acid modification at position R659. In embodiments, the amino acid modifications are selected from substitutions and deletions. In embodiments, the amino acid modification to SEQ ID NO: 80 at R659 is an essential or non-essential amino acid. In embodiments, the amino acid modification at R659 is a hydrophilic or hydrophobic amino acid. In embodiments, the amino acid modification at R659 is amino acid modification is a hydrophilic amino acid. In embodiments, the amino acid modification at R659 is a polar and positively charged hydrophilic amino acid. In embodiments, the amino acid modification at R659 is lysine (K). In embodiments, the amino acid modification at R659 is a polar and neutral charged hydrophilic amino acid. In embodiments, the amino acid modification at R659 is selected from asparagine (N), glutamine (Q), serine (S), threonine (T), proline (P), and cysteine (C). In embodiments, the amino acid modification at R659 is a polar and negatively charged hydrophilic amino acid. In embodiments, the amino acid modification at R659 is selected from aspartate (D) or glutamate (E). In embodiments, the amino acid modification at R659 is an aromatic, polar and positively charged hydrophilic amino acid. In embodiments, the amino acid modification at R659 is histidine (H). In embodiments, the amino acid modification at R659 is a hydrophobic amino acid. In embodiments, the amino acid modification at R659 is a hydrophobic, aliphatic amino acid. In embodiments, the amino acid modification at R659 is selected from glycine (G), alanine (A), leucine (L), isoleucine (I), methionine (M), or valine (V). In embodiments, the amino acid modification at R659 is a hydrophobic, aromatic amino acid. In embodiments, the amino acid modification at R659 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 80 and an amino acid modification at position H664. In embodiments, the amino acid modifications are selected from substitutions and deletions. In embodiments, the amino acid modification to SEQ ID NO: 80 at H664 is an essential or non-essential amino acid. In embodiments, the amino acid modification at H664 is a hydrophilic or hydrophobic amino acid. In embodiments, the amino acid modification at H664 is amino acid modification is a hydrophilic amino acid. In embodiments, the amino acid modification at H664 is a polar and positively charged hydrophilic amino acid. In embodiments, the amino acid modification at H664 is selected from arginine (R) or lysine (K). In embodiments, the amino acid modification at H664 is a polar and neutral charged hydrophilic amino acid. In embodiments, the amino acid modification at H664 is selected from asparagine (N), glutamine (Q), serine (S), threonine (T), proline (P), and cysteine (C). In embodiments, the amino acid modification at H664 is a polar and negatively charged hydrophilic amino acid. In embodiments, the amino acid modification at H664 is selected from aspartate (D) or glutamate (E). In embodiments, the amino acid modification at H664 is an aromatic, polar and positively charged hydrophilic amino acid. In embodiments, the amino acid modification at H664 is a hydrophobic amino acid. In embodiments, the amino acid modification at H664 is a hydrophobic, aliphatic amino acid. In embodiments, the amino acid modification at H664 is selected from glycine (G), alanine (A), leucine (L), isoleucine (I), methionine (M), or valine (V). In embodiments, the amino acid modification at H664 is a hydrophobic, aromatic amino acid. In embodiments, the amino acid modification at H664 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 81 and an amino acid modification at position R234. In embodiments, the amino acid modifications are selected from substitutions and deletions. In embodiments, the amino acid modification to SEQ ID NO: 81 at R234 is an essential or non-essential amino acid. In embodiments, the amino acid modification at R234 is a hydrophilic or hydrophobic amino acid. In embodiments, the amino acid modification at R234 is amino acid modification is a hydrophilic amino acid. In embodiments, the amino acid modification at R234 is a polar and positively charged hydrophilic amino acid. In embodiments, the amino acid modification at R234 is lysine (K). In embodiments, the amino acid modification at R234 is a polar and neutral charged hydrophilic amino acid. In embodiments, the amino acid modification at R234 is selected from asparagine (N), glutamine (Q), serine (S), threonine (T), proline (P), and cysteine (C). In embodiments, the amino acid modification at R234 is a polar and negatively charged hydrophilic amino acid. In embodiments, the amino acid modification at R234 is selected from aspartate (D) or glutamate (E). In embodiments, the amino acid modification at R234 is an aromatic, polar and positively charged hydrophilic amino acid. In embodiments, the amino acid modification at R234 is histidine (H). In embodiments, the amino acid modification at R234 is a hydrophobic amino acid. In embodiments, the amino acid modification at R234 is a hydrophobic, aliphatic amino acid. In embodiments, the amino acid modification at R234 is selected from glycine (G), alanine (A), leucine (L), isoleucine (I), methionine (M), or valine (V). In embodiments, the amino acid modification at R234 is a hydrophobic, aromatic amino acid. In embodiments, the amino acid modification at R234 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 81 and an amino acid modification at position H239. In embodiments, the amino acid modifications are selected from substitutions and deletions. In embodiments, the amino acid modification to SEQ ID NO: 81 at H239 is an essential or non-essential amino acid. In embodiments, the amino acid modification at H239 is a hydrophilic or hydrophobic amino acid. In embodiments, the amino acid modification at H239 is amino acid modification is a hydrophilic amino acid. In embodiments, the amino acid modification at H239 is a polar and positively charged hydrophilic amino acid. In embodiments, the amino acid modification at H239 is selected from arginine (R) or lysine (K). In embodiments, the amino acid modification at H239 is a polar and neutral charged hydrophilic amino acid. In embodiments, the amino acid modification at H239 is selected from asparagine (N), glutamine (Q), serine (S), threonine (T), proline (P), and cysteine (C). In embodiments, the amino acid modification at H239 is a polar and negatively charged hydrophilic amino acid. In embodiments, the amino acid modification at H239 is selected from aspartate (D) or glutamate (E). In embodiments, the amino acid modification at H239 is an aromatic, polar and positively charged hydrophilic amino acid. In embodiments, the amino acid modification at H239 is a hydrophobic amino acid. In embodiments, the amino acid modification at H239 is a hydrophobic, aliphatic amino acid. In embodiments, the amino acid modification at H239 is selected from glycine (G), alanine (A), leucine (L), isoleucine (I), methionine (M), or valine (V). In embodiments, the amino acid modification at H239 is a hydrophobic, aromatic amino acid. In embodiments, the amino acid modification at H239 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 81 and an amino acid modification at position R659. In embodiments, the amino acid modifications are selected from substitutions and deletions. In embodiments, the amino acid modification to SEQ ID NO: 81 at R659 is an essential or non-essential amino acid. In embodiments, the amino acid modification at R659 is a hydrophilic or hydrophobic amino acid. In embodiments, the amino acid modification at R659 is amino acid modification is a hydrophilic amino acid. In embodiments, the amino acid modification at R659 is a polar and positively charged hydrophilic amino acid. In embodiments, the amino acid modification at R659 is lysine (K). In embodiments, the amino acid modification at R659 is a polar and neutral charged hydrophilic amino acid. In embodiments, the amino acid modification at R659 is selected from asparagine (N), glutamine (Q), serine (S), threonine (T), proline (P), and cysteine (C). In embodiments, the amino acid modification at R659 is a polar and negatively charged hydrophilic amino acid. In embodiments, the amino acid modification at R659 is selected from aspartate (D) or glutamate (E). In embodiments, the amino acid modification at R659 is an aromatic, polar and positively charged hydrophilic amino acid. In embodiments, the amino acid modification at R659 is histidine (H). In embodiments, the amino acid modification at R659 is a hydrophobic amino acid. In embodiments, the amino acid modification at R659 is a hydrophobic, aliphatic amino acid. In embodiments, the amino acid modification at R659 is selected from glycine (G), alanine (A), leucine (L), isoleucine (I), methionine (M), or valine (V). In embodiments, the amino acid modification at R659 is a hydrophobic, aromatic amino acid. In embodiments, the amino acid modification at R659 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 81 and an amino acid modification at position H664. In embodiments, the amino acid modifications are selected from substitutions and deletions. In embodiments, the amino acid modification to SEQ ID NO: 81 at H664 is an essential or non-essential amino acid. In embodiments, the amino acid modification at H664 is a hydrophilic or hydrophobic amino acid. In embodiments, the amino acid modification at H664 is amino acid modification is a hydrophilic amino acid. In embodiments, the amino acid modification at H664 is a polar and positively charged hydrophilic amino acid. In embodiments, the amino acid modification at H664 is selected from arginine (R) or lysine (K). In embodiments, the amino acid modification at H664 is a polar and neutral charged hydrophilic amino acid. In embodiments, the amino acid modification at H664 is selected from asparagine (N), glutamine (Q), serine (S), threonine (T), proline (P), and cysteine (C). In embodiments, the amino acid modification at H664 is a polar and negatively charged hydrophilic amino acid. In embodiments, the amino acid modification at H664 is selected from aspartate (D) or glutamate (E). In embodiments, the amino acid modification at H664 is an aromatic, polar and positively charged hydrophilic amino acid. In embodiments, the amino acid modification at H664 is a hydrophobic amino acid. In embodiments, the amino acid modification at H664 is a hydrophobic, aliphatic amino acid. In embodiments, the amino acid modification at H664 is selected from glycine (G), alanine (A), leucine (L), isoleucine (I), methionine (M), or valine (V). In embodiments, the amino acid modification at H664 is a hydrophobic, aromatic amino acid. In embodiments, the amino acid modification at H664 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 82 and an amino acid modification at position R234. In embodiments, the amino acid modifications are selected from substitutions and deletions. In embodiments, the amino acid modification to SEQ ID NO: 82 at R234 is an essential or non-essential amino acid. In embodiments, the amino acid modification at R234 is a hydrophilic or hydrophobic amino acid. In embodiments, the amino acid modification at R234 is amino acid modification is a hydrophilic amino acid. In embodiments, the amino acid modification at R234 is a polar and positively charged hydrophilic amino acid. In embodiments, the amino acid modification at R234 is lysine (K). In embodiments, the amino acid modification at R234 is a polar and neutral charged hydrophilic amino acid. In embodiments, the amino acid modification at R234 is selected from asparagine (N), glutamine (Q), serine (S), threonine (T), proline (P), and cysteine (C). In embodiments, the amino acid modification at R234 is a polar and negatively charged hydrophilic amino acid. In embodiments, the amino acid modification at R234 is selected from aspartate (D) or glutamate (E). In embodiments, the amino acid modification at R234 is an aromatic, polar and positively charged hydrophilic amino acid. In embodiments, the amino acid modification at R234 is histidine (H). In embodiments, the amino acid modification at R234 is a hydrophobic amino acid. In embodiments, the amino acid modification at R234 is a hydrophobic, aliphatic amino acid. In embodiments, the amino acid modification at R234 is selected from glycine (G), alanine (A), leucine (L), isoleucine (I), methionine (M), or valine (V). In embodiments, the amino acid modification at R234 is a hydrophobic, aromatic amino acid. In embodiments, the amino acid modification at R234 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 82 and an amino acid modification at position H239. In embodiments, the amino acid modifications are selected from substitutions and deletions. In embodiments, the amino acid modification to SEQ ID NO: 82 at H239 is an essential or non-essential amino acid. In embodiments, the amino acid modification at H239 is a hydrophilic or hydrophobic amino acid. In embodiments, the amino acid modification at H239 is amino acid modification is a hydrophilic amino acid. In embodiments, the amino acid modification at H239 is a polar and positively charged hydrophilic amino acid. In embodiments, the amino acid modification at H239 is selected from arginine (R) or lysine (K). In embodiments, the amino acid modification at H239 is a polar and neutral charged hydrophilic amino acid. In embodiments, the amino acid modification at H239 is selected from asparagine (N), glutamine (Q), serine (S), threonine (T), proline (P), and cysteine (C). In embodiments, the amino acid modification at H239 is a polar and negatively charged hydrophilic amino acid. In embodiments, the amino acid modification at H239 is selected from aspartate (D) or glutamate (E). In embodiments, the amino acid modification at H239 is an aromatic, polar and positively charged hydrophilic amino acid. In embodiments, the amino acid modification at H239 is a hydrophobic amino acid. In embodiments, the amino acid modification at H239 is a hydrophobic, aliphatic amino acid. In embodiments, the amino acid modification at H239 is selected from glycine (G), alanine (A), leucine (L), isoleucine (I), methionine (M), or valine (V). In embodiments, the amino acid modification at H239 is a hydrophobic, aromatic amino acid. In embodiments, the amino acid modification at H239 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 82 and an amino acid modification at position R659. In embodiments, the amino acid modifications are selected from substitutions and deletions. In embodiments, the amino acid modification to SEQ ID NO: 82 at R659 is an essential or non-essential amino acid. In embodiments, the amino acid modification at R659 is a hydrophilic or hydrophobic amino acid. In embodiments, the amino acid modification at R659 is amino acid modification is a hydrophilic amino acid. In embodiments, the amino acid modification at R659 is a polar and positively charged hydrophilic amino acid. In embodiments, the amino acid modification at R659 is lysine (K). In embodiments, the amino acid modification at R659 is a polar and neutral charged hydrophilic amino acid. In embodiments, the amino acid modification at R659 is selected from asparagine (N), glutamine (Q), serine (S), threonine (T), proline (P), and cysteine (C). In embodiments, the amino acid modification at R659 is a polar and negatively charged hydrophilic amino acid. In embodiments, the amino acid modification at R659 is selected from aspartate (D) or glutamate (E). In embodiments, the amino acid modification at R659 is an aromatic, polar and positively charged hydrophilic amino acid. In embodiments, the amino acid modification at R659 is histidine (H). In embodiments, the amino acid modification at R659 is a hydrophobic amino acid. In embodiments, the amino acid modification at R659 is a hydrophobic, aliphatic amino acid. In embodiments, the amino acid modification at R659 is selected from glycine (G), alanine (A), leucine (L), isoleucine (I), methionine (M), or valine (V). In embodiments, the amino acid modification at R659 is a hydrophobic, aromatic amino acid. In embodiments, the amino acid modification at R659 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 82 and an amino acid modification at position H664. In embodiments, the amino acid modifications are selected from substitutions and deletions. In embodiments, the amino acid modification to SEQ ID NO: 82 at H664 is an essential or non-essential amino acid. In embodiments, the amino acid modification at H664 is a hydrophilic or hydrophobic amino acid. In embodiments, the amino acid modification at H664 is amino acid modification is a hydrophilic amino acid. In embodiments, the amino acid modification at H664 is a polar and positively charged hydrophilic amino acid. In embodiments, the amino acid modification at H664 is selected from arginine (R) or lysine (K). In embodiments, the amino acid modification at H664 is a polar and neutral charged hydrophilic amino acid. In embodiments, the amino acid modification at H664 is selected from asparagine (N), glutamine (Q), serine (S), threonine (T), proline (P), and cysteine (C). In embodiments, the amino acid modification at H664 is a polar and negatively charged hydrophilic amino acid. In embodiments, the amino acid modification at H664 is selected from aspartate (D) or glutamate (E). In embodiments, the amino acid modification at H664 is an aromatic, polar and positively charged hydrophilic amino acid. In embodiments, the amino acid modification at H664 is a hydrophobic amino acid. In embodiments, the amino acid modification at H664 is a hydrophobic, aliphatic amino acid. In embodiments, the amino acid modification at H664 is selected from glycine (G), alanine (A), leucine (L), isoleucine (I), methionine (M), or valine (V). In embodiments, the amino acid modification at H664 is a hydrophobic, aromatic amino acid. In embodiments, the amino acid modification at H664 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 83 and an amino acid modification at position R239. In embodiments, the amino acid modifications are selected from substitutions and deletions. In embodiments, the amino acid modification to SEQ ID NO: 83 at R239 is an essential or non-essential amino acid. In embodiments, the amino acid modification at R239 is a hydrophilic or hydrophobic amino acid. In embodiments, the amino acid modification at R239 is amino acid modification is a hydrophilic amino acid. In embodiments, the amino acid modification at R239 is a polar and positively charged hydrophilic amino acid. In embodiments, the amino acid modification at R239 is lysine (K). In embodiments, the amino acid modification at R239 is a polar and neutral charged hydrophilic amino acid. In embodiments, the amino acid modification at R239 is selected from asparagine (N), glutamine (Q), serine (S), threonine (T), proline (P), and cysteine (C). In embodiments, the amino acid modification at R239 is a polar and negatively charged hydrophilic amino acid. In embodiments, the amino acid modification at R239 is selected from aspartate (D) or glutamate (E). In embodiments, the amino acid modification at R239 is an aromatic, polar and positively charged hydrophilic amino acid. In embodiments, the amino acid modification at R239 is histidine (H). In embodiments, the amino acid modification at R239 is a hydrophobic amino acid. In embodiments, the amino acid modification at R239 is a hydrophobic, aliphatic amino acid. In embodiments, the amino acid modification at R239 is selected from glycine (G), alanine (A), leucine (L), isoleucine (I), methionine (M), or valine (V). In embodiments, the amino acid modification at R239 is a hydrophobic, aromatic amino acid. In embodiments, the amino acid modification at R239 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 83 and an amino acid modification at position H244. In embodiments, the amino acid modifications are selected from substitutions and deletions. In embodiments, the amino acid modification to SEQ ID NO: 83 at H244 is an essential or non-essential amino acid. In embodiments, the amino acid modification at H244 is a hydrophilic or hydrophobic amino acid. In embodiments, the amino acid modification at H244 is amino acid modification is a hydrophilic amino acid. In embodiments, the amino acid modification at H244 is a polar and positively charged hydrophilic amino acid. In embodiments, the amino acid modification at H244 is selected from arginine (R) or lysine (K). In embodiments, the amino acid modification at H244 is a polar and neutral charged hydrophilic amino acid. In embodiments, the amino acid modification at H244 is selected from asparagine (N), glutamine (Q), serine (S), threonine (T), proline (P), and cysteine (C). In embodiments, the amino acid modification at H244 is a polar and negatively charged hydrophilic amino acid. In embodiments, the amino acid modification at H244 is selected from aspartate (D) or glutamate (E). In embodiments, the amino acid modification at H244 is an aromatic, polar and positively charged hydrophilic amino acid. In embodiments, the amino acid modification at H244 is a hydrophobic amino acid. In embodiments, the amino acid modification at H244 is a hydrophobic, aliphatic amino acid. In embodiments, the amino acid modification at H244 is selected from glycine (G), alanine (A), leucine (L), isoleucine (I), methionine (M), or valine (V). In embodiments, the amino acid modification at H244 is a hydrophobic, aromatic amino acid. In embodiments, the amino acid modification at H244 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 83 and an amino acid modification at position R677. In embodiments, the amino acid modifications are selected from substitutions and deletions. In embodiments, the amino acid modification to SEQ ID NO: 83 at R677 is an essential or non-essential amino acid. In embodiments, the amino acid modification at R677 is a hydrophilic or hydrophobic amino acid. In embodiments, the amino acid modification at R677 is amino acid modification is a hydrophilic amino acid. In embodiments, the amino acid modification at R677 is a polar and positively charged hydrophilic amino acid. In embodiments, the amino acid modification at R677 is lysine (K). In embodiments, the amino acid modification at R677 is a polar and neutral charged hydrophilic amino acid. In embodiments, the amino acid modification at R677 is selected from asparagine (N), glutamine (Q), serine (S), threonine (T), proline (P), and cysteine (C). In embodiments, the amino acid modification at R677 is a polar and negatively charged hydrophilic amino acid. In embodiments, the amino acid modification at R677 is selected from aspartate (D) or glutamate (E). In embodiments, the amino acid modification at R677 is an aromatic, polar and positively charged hydrophilic amino acid. In embodiments, the amino acid modification at R677 is histidine (H). In embodiments, the amino acid modification at R677 is a hydrophobic amino acid. In embodiments, the amino acid modification at R677 is a hydrophobic, aliphatic amino acid. In embodiments, the amino acid modification at R677 is selected from glycine (G), alanine (A), leucine (L), isoleucine (I), methionine (M), or valine (V). In embodiments, the amino acid modification at R677 is a hydrophobic, aromatic amino acid. In embodiments, the amino acid modification at R677 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 83 and an amino acid modification at position H682. In embodiments, the amino acid modifications are selected from substitutions and deletions. In embodiments, the amino acid modification to SEQ ID NO: 83 at H682 is an essential or non-essential amino acid. In embodiments, the amino acid modification at H682 is a hydrophilic or hydrophobic amino acid. In embodiments, the amino acid modification at H682 is amino acid modification is a hydrophilic amino acid. In embodiments, the amino acid modification at H682 is a polar and positively charged hydrophilic amino acid. In embodiments, the amino acid modification at H682 is selected from arginine (R) or lysine (K). In embodiments, the amino acid modification at H682 is a polar and neutral charged hydrophilic amino acid. In embodiments, the amino acid modification at H682 is selected from asparagine (N), glutamine (Q), serine (S), threonine (T), proline (P), and cysteine (C). In embodiments, the amino acid modification at H682 is a polar and negatively charged hydrophilic amino acid. In embodiments, the amino acid modification at H682 is selected from aspartate (D) or glutamate (E). In embodiments, the amino acid modification at H682 is an aromatic, polar and positively charged hydrophilic amino acid. In embodiments, the amino acid modification at H682 is a hydrophobic amino acid. In embodiments, the amino acid modification at H682 is a hydrophobic, aliphatic amino acid. In embodiments, the amino acid modification at H682 is selected from glycine (G), alanine (A), leucine (L), isoleucine (I), methionine (M), or valine (V). In embodiments, the amino acid modification at H682 is a hydrophobic, aromatic amino acid. In embodiments, the amino acid modification at H682 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 84 and an amino acid modification at position R241. In embodiments, the amino acid modifications are selected from substitutions and deletions. In embodiments, the amino acid modification to SEQ ID NO: 84 at R241 is an essential or non-essential amino acid. In embodiments, the amino acid modification at R241 is a hydrophilic or hydrophobic amino acid. In embodiments, the amino acid modification at R241 is amino acid modification is a hydrophilic amino acid. In embodiments, the amino acid modification at R241 is a polar and positively charged hydrophilic amino acid. In embodiments, the amino acid modification at R241 is lysine (K). In embodiments, the amino acid modification at R241 is a polar and neutral charged hydrophilic amino acid. In embodiments, the amino acid modification at R241 is selected from asparagine (N), glutamine (Q), serine (S), threonine (T), proline (P), and cysteine (C). In embodiments, the amino acid modification at R241 is a polar and negatively charged hydrophilic amino acid. In embodiments, the amino acid modification at R241 is selected from aspartate (D) or glutamate (E). In embodiments, the amino acid modification at R241 is an aromatic, polar and positively charged hydrophilic amino acid. In embodiments, the amino acid modification at R241 is histidine (H). In embodiments, the amino acid modification at R241 is a hydrophobic amino acid. In embodiments, the amino acid modification at R241 is a hydrophobic, aliphatic amino acid. In embodiments, the amino acid modification at R241 is selected from glycine (G), alanine (A), leucine (L), isoleucine (I), methionine (M), or valine (V). In embodiments, the amino acid modification at R241 is a hydrophobic, aromatic amino acid. In embodiments, the amino acid modification at R241 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 84 and an amino acid modification at position H246. In embodiments, the amino acid modifications are selected from substitutions and deletions. In embodiments, the amino acid modification to SEQ ID NO: 84 at H246 is an essential or non-essential amino acid. In embodiments, the amino acid modification at H246 is a hydrophilic or hydrophobic amino acid. In embodiments, the amino acid modification at H246 is amino acid modification is a hydrophilic amino acid. In embodiments, the amino acid modification at H246 is a polar and positively charged hydrophilic amino acid. In embodiments, the amino acid modification at H246 is selected from arginine (R) or lysine (K). In embodiments, the amino acid modification at H246 is a polar and neutral charged hydrophilic amino acid. In embodiments, the amino acid modification at H246 is selected from asparagine (N), glutamine (Q), serine (S), threonine (T), proline (P), and cysteine (C). In embodiments, the amino acid modification at H246 is a polar and negatively charged hydrophilic amino acid. In embodiments, the amino acid modification at H246 is selected from aspartate (D) or glutamate (E). In embodiments, the amino acid modification at H246 is an aromatic, polar and positively charged hydrophilic amino acid. In embodiments, the amino acid modification at H246 is a hydrophobic amino acid. In embodiments, the amino acid modification at H246 is a hydrophobic, aliphatic amino acid. In embodiments, the amino acid modification at H246 is selected from glycine (G), alanine (A), leucine (L), isoleucine (I), methionine (M), or valine (V). In embodiments, the amino acid modification at H246 is a hydrophobic, aromatic amino acid. In embodiments, the amino acid modification at H246 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 84 and an amino acid modification at position R681. In embodiments, the amino acid modifications are selected from substitutions and deletions. In embodiments, the amino acid modification to SEQ ID NO: 84 at R681 is an essential or non-essential amino acid. In embodiments, the amino acid modification at R681 is a hydrophilic or hydrophobic amino acid. In embodiments, the amino acid modification at R681 is amino acid modification is a hydrophilic amino acid. In embodiments, the amino acid modification at R681 is a polar and positively charged hydrophilic amino acid. In embodiments, the amino acid modification at R681 is lysine (K). In embodiments, the amino acid modification at R681 is a polar and neutral charged hydrophilic amino acid. In embodiments, the amino acid modification at R681 is selected from asparagine (N), glutamine (Q), serine (S), threonine (T), proline (P), and cysteine (C). In embodiments, the amino acid modification at R681 is a polar and negatively charged hydrophilic amino acid. In embodiments, the amino acid modification at R681 is selected from aspartate (D) or glutamate (E). In embodiments, the amino acid modification at R681 is an aromatic, polar and positively charged hydrophilic amino acid. In embodiments, the amino acid modification at R681 is histidine (H). In embodiments, the amino acid modification at R681 is a hydrophobic amino acid. In embodiments, the amino acid modification at R681 is a hydrophobic, aliphatic amino acid. In embodiments, the amino acid modification at R681 is selected from glycine (G), alanine (A), leucine (L), isoleucine (I), methionine (M), or valine (V). In embodiments, the amino acid modification at R681 is a hydrophobic, aromatic amino acid. In embodiments, the amino acid modification at R681 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 84 and an amino acid modification at position H686. In embodiments, the amino acid modifications are selected from substitutions and deletions. In embodiments, the amino acid modification to SEQ ID NO: 84 at H686 is an essential or non-essential amino acid. In embodiments, the amino acid modification at H686 is a hydrophilic or hydrophobic amino acid. In embodiments, the amino acid modification at H686 is amino acid modification is a hydrophilic amino acid. In embodiments, the amino acid modification at H686 is a polar and positively charged hydrophilic amino acid. In embodiments, the amino acid modification at H686 is selected from arginine (R) or lysine (K). In embodiments, the amino acid modification at H686 is a polar and neutral charged hydrophilic amino acid. In embodiments, the amino acid modification at H686 is selected from asparagine (N), glutamine (Q), serine (S), threonine (T), proline (P), and cysteine (C). In embodiments, the amino acid modification at H686 is a polar and negatively charged hydrophilic amino acid. In embodiments, the amino acid modification at H686 is selected from aspartate (D) or glutamate (E). In embodiments, the amino acid modification at H686 is an aromatic, polar and positively charged hydrophilic amino acid. In embodiments, the amino acid modification at H686 is a hydrophobic amino acid. In embodiments, the amino acid modification at H686 is a hydrophobic, aliphatic amino acid. In embodiments, the amino acid modification at H686 is selected from glycine (G), alanine (A), leucine (L), isoleucine (I), methionine (M), or valine (V). In embodiments, the amino acid modification at H686 is a hydrophobic, aromatic amino acid. In embodiments, the amino acid modification at H686 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 85 and an amino acid modification at position R244. In embodiments, the amino acid modifications are selected from substitutions and deletions. In embodiments, the amino acid modification to SEQ ID NO: 85 at R244 is an essential or non-essential amino acid. In embodiments, the amino acid modification at R244 is a hydrophilic or hydrophobic amino acid. In embodiments, the amino acid modification at R244 is amino acid modification is a hydrophilic amino acid. In embodiments, the amino acid modification at R244 is a polar and positively charged hydrophilic amino acid. In embodiments, the amino acid modification at R244 is lysine (K). In embodiments, the amino acid modification at R244 is a polar and neutral charged hydrophilic amino acid. In embodiments, the amino acid modification at R244 is selected from asparagine (N), glutamine (Q), serine (S), threonine (T), proline (P), and cysteine (C). In embodiments, the amino acid modification at R244 is a polar and negatively charged hydrophilic amino acid. In embodiments, the amino acid modification at R244 is selected from aspartate (D) or glutamate (E). In embodiments, the amino acid modification at R244 is an aromatic, polar and positively charged hydrophilic amino acid. In embodiments, the amino acid modification at R244 is histidine (H). In embodiments, the amino acid modification at R244 is a hydrophobic amino acid. In embodiments, the amino acid modification at R244 is a hydrophobic, aliphatic amino acid. In embodiments, the amino acid modification at R244 is selected from glycine (G), alanine (A), leucine (L), isoleucine (I), methionine (M), or valine (V). In embodiments, the amino acid modification at R244 is a hydrophobic, aromatic amino acid. In embodiments, the amino acid modification at R244 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 85 and an amino acid modification at position H249. In embodiments, the amino acid modifications are selected from substitutions and deletions. In embodiments, the amino acid modification to SEQ ID NO: 85 at H249 is an essential or non-essential amino acid. In embodiments, the amino acid modification at H249 is a hydrophilic or hydrophobic amino acid. In embodiments, the amino acid modification at H249 is amino acid modification is a hydrophilic amino acid. In embodiments, the amino acid modification at H249 is a polar and positively charged hydrophilic amino acid. In embodiments, the amino acid modification at H249 is selected from arginine (R) or lysine (K). In embodiments, the amino acid modification at H249 is a polar and neutral charged hydrophilic amino acid. In embodiments, the amino acid modification at H249 is selected from asparagine (N), glutamine (Q), serine (S), threonine (T), proline (P), and cysteine (C). In embodiments, the amino acid modification at H249 is a polar and negatively charged hydrophilic amino acid. In embodiments, the amino acid modification at H249 is selected from aspartate (D) or glutamate (E). In embodiments, the amino acid modification at H249 is an aromatic, polar and positively charged hydrophilic amino acid. In embodiments, the amino acid modification at H249 is a hydrophobic amino acid. In embodiments, the amino acid modification at H249 is a hydrophobic, aliphatic amino acid. In embodiments, the amino acid modification at H249 is selected from glycine (G), alanine (A), leucine (L), isoleucine (I), methionine (M), or valine (V). In embodiments, the amino acid modification at H249 is a hydrophobic, aromatic amino acid. In embodiments, the amino acid modification at H249 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 85 and an amino acid modification at position R701. In embodiments, the amino acid modifications are selected from substitutions and deletions. In embodiments, the amino acid modification to SEQ ID NO: 85 at R701 is an essential or non-essential amino acid. In embodiments, the amino acid modification at R701 is a hydrophilic or hydrophobic amino acid. In embodiments, the amino acid modification at R701 is amino acid modification is a hydrophilic amino acid. In embodiments, the amino acid modification at R701 is a polar and positively charged hydrophilic amino acid. In embodiments, the amino acid modification at R701 is lysine (K). In embodiments, the amino acid modification at R701 is a polar and neutral charged hydrophilic amino acid. In embodiments, the amino acid modification at R701 is selected from asparagine (N), glutamine (Q), serine (S), threonine (T), proline (P), and cysteine (C). In embodiments, the amino acid modification at R701 is a polar and negatively charged hydrophilic amino acid. In embodiments, the amino acid modification at R701 is selected from aspartate (D) or glutamate (E). In embodiments, the amino acid modification at R701 is an aromatic, polar and positively charged hydrophilic amino acid. In embodiments, the amino acid modification at R701 is histidine (H). In embodiments, the amino acid modification at R701 is a hydrophobic amino acid. In embodiments, the amino acid modification at R701 is a hydrophobic, aliphatic amino acid. In embodiments, the amino acid modification at R701 is selected from glycine (G), alanine (A), leucine (L), isoleucine (I), methionine (M), or valine (V). In embodiments, the amino acid modification at R701 is a hydrophobic, aromatic amino acid. In embodiments, the amino acid modification at R701 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 85 and an amino acid modification at position H706. In embodiments, the amino acid modifications are selected from substitutions and deletions. In embodiments, the amino acid modification to SEQ ID NO: 85 at H706 is an essential or non-essential amino acid. In embodiments, the amino acid modification at H706 is a hydrophilic or hydrophobic amino acid. In embodiments, the amino acid modification at H706 is amino acid modification is a hydrophilic amino acid. In embodiments, the amino acid modification at H706 is a polar and positively charged hydrophilic amino acid. In embodiments, the amino acid modification at H706 is selected from arginine (R) or lysine (K). In embodiments, the amino acid modification at H706 is a polar and neutral charged hydrophilic amino acid. In embodiments, the amino acid modification at H706 is selected from asparagine (N), glutamine (Q), serine (S), threonine (T), proline (P), and cysteine (C). In embodiments, the amino acid modification at H706 is a polar and negatively charged hydrophilic amino acid. In embodiments, the amino acid modification at H706 is selected from aspartate (D) or glutamate (E). In embodiments, the amino acid modification at H706 is an aromatic, polar and positively charged hydrophilic amino acid. In embodiments, the amino acid modification at H706 is a hydrophobic amino acid. In embodiments, the amino acid modification at H706 is a hydrophobic, aliphatic amino acid. In embodiments, the amino acid modification at H706 is selected from glycine (G), alanine (A), leucine (L), isoleucine (I), methionine (M), or valine (V). In embodiments, the amino acid modification at H706 is a hydrophobic, aromatic amino acid. In embodiments, the amino acid modification at H706 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 86 and an amino acid modification at position R247. In embodiments, the amino acid modifications are selected from substitutions and deletions. In embodiments, the amino acid modification to SEQ ID NO: 86 at R247 is an essential or non-essential amino acid. In embodiments, the amino acid modification at R247 is a hydrophilic or hydrophobic amino acid. In embodiments, the amino acid modification at R247 is amino acid modification is a hydrophilic amino acid. In embodiments, the amino acid modification at R247 is a polar and positively charged hydrophilic amino acid. In embodiments, the amino acid modification at R247 is lysine (K). In embodiments, the amino acid modification at R247 is a polar and neutral charged hydrophilic amino acid. In embodiments, the amino acid modification at R247 is selected from asparagine (N), glutamine (Q), serine (S), threonine (T), proline (P), and cysteine (C). In embodiments, the amino acid modification at R247 is a polar and negatively charged hydrophilic amino acid. In embodiments, the amino acid modification at R247 is selected from aspartate (D) or glutamate (E). In embodiments, the amino acid modification at R247 is an aromatic, polar and positively charged hydrophilic amino acid. In embodiments, the amino acid modification at R247 is histidine (H). In embodiments, the amino acid modification at R247 is a hydrophobic amino acid. In embodiments, the amino acid modification at R247 is a hydrophobic, aliphatic amino acid. In embodiments, the amino acid modification at R247 is selected from glycine (G), alanine (A), leucine (L), isoleucine (I), methionine (M), or valine (V). In embodiments, the amino acid modification at R247 is a hydrophobic, aromatic amino acid. In embodiments, the amino acid modification at R247 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 86 and an amino acid modification at position H252. In embodiments, the amino acid modifications are selected from substitutions and deletions. In embodiments, the amino acid modification to SEQ ID NO: 86 at H252 is an essential or non-essential amino acid. In embodiments, the amino acid modification at H252 is a hydrophilic or hydrophobic amino acid. In embodiments, the amino acid modification at H252 is amino acid modification is a hydrophilic amino acid. In embodiments, the amino acid modification at H252 is a polar and positively charged hydrophilic amino acid. In embodiments, the amino acid modification at H252 is selected from arginine (R) or lysine (K). In embodiments, the amino acid modification at H252 is a polar and neutral charged hydrophilic amino acid. In embodiments, the amino acid modification at H252 is selected from asparagine (N), glutamine (Q), serine (S), threonine (T), proline (P), and cysteine (C). In embodiments, the amino acid modification at H252 is a polar and negatively charged hydrophilic amino acid. In embodiments, the amino acid modification at H252 is selected from aspartate (D) or glutamate (E). In embodiments, the amino acid modification at H252 is an aromatic, polar and positively charged hydrophilic amino acid. In embodiments, the amino acid modification at H252 is a hydrophobic amino acid. In embodiments, the amino acid modification at H252 is a hydrophobic, aliphatic amino acid. In embodiments, the amino acid modification at H252 is selected from glycine (G), alanine (A), leucine (L), isoleucine (I), methionine (M), or valine (V). In embodiments, the amino acid modification at H252 is a hydrophobic, aromatic amino acid. In embodiments, the amino acid modification at H252 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 86 and an amino acid modification at position R711. In embodiments, the amino acid modifications are selected from substitutions and deletions. In embodiments, the amino acid modification to SEQ ID NO: 86 at R711 is an essential or non-essential amino acid. In embodiments, the amino acid modification at R711 is a hydrophilic or hydrophobic amino acid. In embodiments, the amino acid modification at R711 is amino acid modification is a hydrophilic amino acid. In embodiments, the amino acid modification at R711 is a polar and positively charged hydrophilic amino acid. In embodiments, the amino acid modification at R711 is lysine (K). In embodiments, the amino acid modification at R711 is a polar and neutral charged hydrophilic amino acid. In embodiments, the amino acid modification at R711 is selected from asparagine (N), glutamine (Q), serine (S), threonine (T), proline (P), and cysteine (C). In embodiments, the amino acid modification at R711 is a polar and negatively charged hydrophilic amino acid. In embodiments, the amino acid modification at R711 is selected from aspartate (D) or glutamate (E). In embodiments, the amino acid modification at R711 is an aromatic, polar and positively charged hydrophilic amino acid. In embodiments, the amino acid modification at R711 is histidine (H). In embodiments, the amino acid modification at R711 is a hydrophobic amino acid. In embodiments, the amino acid modification at R711 is a hydrophobic, aliphatic amino acid. In embodiments, the amino acid modification at R711 is selected from glycine (G), alanine (A), leucine (L), isoleucine (I), methionine (M), or valine (V). In embodiments, the amino acid modification at R711 is a hydrophobic, aromatic amino acid. In embodiments, the amino acid modification at R711 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 86 and an amino acid modification at position H716. In embodiments, the amino acid modifications are selected from substitutions and deletions. In embodiments, the amino acid modification to SEQ ID NO: 86 at H716 is an essential or non-essential amino acid. In embodiments, the amino acid modification at H716 is a hydrophilic or hydrophobic amino acid. In embodiments, the amino acid modification at H716 is amino acid modification is a hydrophilic amino acid. In embodiments, the amino acid modification at H716 is a polar and positively charged hydrophilic amino acid. In embodiments, the amino acid modification at H716 is selected from arginine (R) or lysine (K). In embodiments, the amino acid modification at H716 is a polar and neutral charged hydrophilic amino acid. In embodiments, the amino acid modification at H716 is selected from asparagine (N), glutamine (Q), serine (S), threonine (T), proline (P), and cysteine (C). In embodiments, the amino acid modification at H716 is a polar and negatively charged hydrophilic amino acid. In embodiments, the amino acid modification at H716 is selected from aspartate (D) or glutamate (E). In embodiments, the amino acid modification at H716 is an aromatic, polar and positively charged hydrophilic amino acid. In embodiments, the amino acid modification at H716 is a hydrophobic amino acid. In embodiments, the amino acid modification at H716 is a hydrophobic, aliphatic amino acid. In embodiments, the amino acid modification at H716 is selected from glycine (G), alanine (A), leucine (L), isoleucine (I), methionine (M), or valine (V). In embodiments, the amino acid modification at H716 is a hydrophobic, aromatic amino acid. In embodiments, the amino acid modification at H716 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 87 and an amino acid modification at position R316. In embodiments, the amino acid modifications are selected from substitutions and deletions. In embodiments, the amino acid modification to SEQ ID NO: 87 at R316 is an essential or non-essential amino acid. In embodiments, the amino acid modification at R316 is a hydrophilic or hydrophobic amino acid. In embodiments, the amino acid modification at R316 is amino acid modification is a hydrophilic amino acid. In embodiments, the amino acid modification at R316 is a polar and positively charged hydrophilic amino acid. In embodiments, the amino acid modification at R316 is lysine (K). In embodiments, the amino acid modification at R316 is a polar and neutral charged hydrophilic amino acid. In embodiments, the amino acid modification at R316 is selected from asparagine (N), glutamine (Q), serine (S), threonine (T), proline (P), and cysteine (C). In embodiments, the amino acid modification at R316 is a polar and negatively charged hydrophilic amino acid. In embodiments, the amino acid modification at R316 is selected from aspartate (D) or glutamate (E). In embodiments, the amino acid modification at R316 is an aromatic, polar and positively charged hydrophilic amino acid. In embodiments, the amino acid modification at R316 is histidine (H). In embodiments, the amino acid modification at R316 is a hydrophobic amino acid. In embodiments, the amino acid modification at R316 is a hydrophobic, aliphatic amino acid. In embodiments, the amino acid modification at R316 is selected from glycine (G), alanine (A), leucine (L), isoleucine (I), methionine (M), or valine (V). In embodiments, the amino acid modification at R316 is a hydrophobic, aromatic amino acid. In embodiments, the amino acid modification at R316 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 87 and an amino acid modification at position H321. In embodiments, the amino acid modifications are selected from substitutions and deletions. In embodiments, the amino acid modification to SEQ ID NO: 87 at H321 is an essential or non-essential amino acid. In embodiments, the amino acid modification at H321 is a hydrophilic or hydrophobic amino acid. In embodiments, the amino acid modification at H321 is amino acid modification is a hydrophilic amino acid. In embodiments, the amino acid modification at H321 is a polar and positively charged hydrophilic amino acid. In embodiments, the amino acid modification at H321 is selected from arginine (R) or lysine (K). In embodiments, the amino acid modification at H321 is a polar and neutral charged hydrophilic amino acid. In embodiments, the amino acid modification at H321 is selected from asparagine (N), glutamine (Q), serine (S), threonine (T), proline (P), and cysteine (C). In embodiments, the amino acid modification at H321 is a polar and negatively charged hydrophilic amino acid. In embodiments, the amino acid modification at H321 is selected from aspartate (D) or glutamate (E). In embodiments, the amino acid modification at H321 is an aromatic, polar and positively charged hydrophilic amino acid. In embodiments, the amino acid modification at H321 is a hydrophobic amino acid. In embodiments, the amino acid modification at H321 is a hydrophobic, aliphatic amino acid. In embodiments, the amino acid modification at H321 is selected from glycine (G), alanine (A), leucine (L), isoleucine (I), methionine (M), or valine (V). In embodiments, the amino acid modification at H321 is a hydrophobic, aromatic amino acid. In embodiments, the amino acid modification at H321 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 87 and an amino acid modification at position R781. In embodiments, the amino acid modifications are selected from substitutions and deletions. In embodiments, the amino acid modification to SEQ ID NO: 87 at R781 is an essential or non-essential amino acid. In embodiments, the amino acid modification at R781 is a hydrophilic or hydrophobic amino acid. In embodiments, the amino acid modification at R781 is amino acid modification is a hydrophilic amino acid. In embodiments, the amino acid modification at R781 is a polar and positively charged hydrophilic amino acid. In embodiments, the amino acid modification at R781 is lysine (K). In embodiments, the amino acid modification at R781 is a polar and neutral charged hydrophilic amino acid. In embodiments, the amino acid modification at R781 is selected from asparagine (N), glutamine (Q), serine (S), threonine (T), proline (P), and cysteine (C). In embodiments, the amino acid modification at R781 is a polar and negatively charged hydrophilic amino acid. In embodiments, the amino acid modification at R781 is selected from aspartate (D) or glutamate (E). In embodiments, the amino acid modification at R781 is an aromatic, polar and positively charged hydrophilic amino acid. In embodiments, the amino acid modification at R781 is histidine (H). In embodiments, the amino acid modification at R781 is a hydrophobic amino acid. In embodiments, the amino acid modification at R781 is a hydrophobic, aliphatic amino acid. In embodiments, the amino acid modification at R781 is selected from glycine (G), alanine (A), leucine (L), isoleucine (I), methionine (M), or valine (V). In embodiments, the amino acid modification at R781 is a hydrophobic, aromatic amino acid. In embodiments, the amino acid modification at R781 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 87 and an amino acid modification at position H786. In embodiments, the amino acid modifications are selected from substitutions and deletions. In embodiments, the amino acid modification to SEQ ID NO: 87 at H786 is an essential or non-essential amino acid. In embodiments, the amino acid modification at H786 is a hydrophilic or hydrophobic amino acid. In embodiments, the amino acid modification at H786 is amino acid modification is a hydrophilic amino acid. In embodiments, the amino acid modification at H786 is a polar and positively charged hydrophilic amino acid. In embodiments, the amino acid modification at H786 is selected from arginine (R) or lysine (K). In embodiments, the amino acid modification at H786 is a polar and neutral charged hydrophilic amino acid. In embodiments, the amino acid modification at H786 is selected from asparagine (N), glutamine (Q), serine (S), threonine (T), proline (P), and cysteine (C). In embodiments, the amino acid modification at H786 is a polar and negatively charged hydrophilic amino acid. In embodiments, the amino acid modification at H786 is selected from aspartate (D) or glutamate (E). In embodiments, the amino acid modification at H786 is an aromatic, polar and positively charged hydrophilic amino acid. In embodiments, the amino acid modification at H786 is a hydrophobic amino acid. In embodiments, the amino acid modification at H786 is a hydrophobic, aliphatic amino acid. In embodiments, the amino acid modification at H786 is selected from glycine (G), alanine (A), leucine (L), isoleucine (I), methionine (M), or valine (V). In embodiments, the amino acid modification at H786 is a hydrophobic, aromatic amino acid. In embodiments, the amino acid modification at H786 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 88 and an amino acid modification at position R274. In embodiments, the amino acid modifications are selected from substitutions and deletions. In embodiments, the amino acid modification to SEQ ID NO: 88 at R274 is an essential or non-essential amino acid. In embodiments, the amino acid modification at R274 is a hydrophilic or hydrophobic amino acid. In embodiments, the amino acid modification at R274 is amino acid modification is a hydrophilic amino acid. In embodiments, the amino acid modification at R274 is a polar and positively charged hydrophilic amino acid. In embodiments, the amino acid modification at R274 is lysine (K). In embodiments, the amino acid modification at R274 is a polar and neutral charged hydrophilic amino acid. In embodiments, the amino acid modification at R274 is selected from asparagine (N), glutamine (Q), serine (S), threonine (T), proline (P), and cysteine (C). In embodiments, the amino acid modification at R274 is a polar and negatively charged hydrophilic amino acid. In embodiments, the amino acid modification at R274 is selected from aspartate (D) or glutamate (E). In embodiments, the amino acid modification at R274 is an aromatic, polar and positively charged hydrophilic amino acid. In embodiments, the amino acid modification at R274 is histidine (H). In embodiments, the amino acid modification at R274 is a hydrophobic amino acid. In embodiments, the amino acid modification at R274 is a hydrophobic, aliphatic amino acid. In embodiments, the amino acid modification at R274 is selected from glycine (G), alanine (A), leucine (L), isoleucine (I), methionine (M), or valine (V). In embodiments, the amino acid modification at R274 is a hydrophobic, aromatic amino acid. In embodiments, the amino acid modification at R274 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 88 and an amino acid modification at position H279. In embodiments, the amino acid modifications are selected from substitutions and deletions. In embodiments, the amino acid modification to SEQ ID NO: 88 at H279 is an essential or non-essential amino acid. In embodiments, the amino acid modification at H279 is a hydrophilic or hydrophobic amino acid. In embodiments, the amino acid modification at H279 is amino acid modification is a hydrophilic amino acid. In embodiments, the amino acid modification at H279 is a polar and positively charged hydrophilic amino acid. In embodiments, the amino acid modification at H279 is selected from arginine (R) or lysine (K). In embodiments, the amino acid modification at H279 is a polar and neutral charged hydrophilic amino acid. In embodiments, the amino acid modification at H279 is selected from asparagine (N), glutamine (Q), serine (S), threonine (T), proline (P), and cysteine (C). In embodiments, the amino acid modification at H279 is a polar and negatively charged hydrophilic amino acid. In embodiments, the amino acid modification at H279 is selected from aspartate (D) or glutamate (E). In embodiments, the amino acid modification at H279 is an aromatic, polar and positively charged hydrophilic amino acid. In embodiments, the amino acid modification at H279 is a hydrophobic amino acid. In embodiments, the amino acid modification at H279 is a hydrophobic, aliphatic amino acid. In embodiments, the amino acid modification at H279 is selected from glycine (G), alanine (A), leucine (L), isoleucine (I), methionine (M), or valine (V). In embodiments, the amino acid modification at H279 is a hydrophobic, aromatic amino acid. In embodiments, the amino acid modification at H279 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 88 and an amino acid modification at position R723. In embodiments, the amino acid modifications are selected from substitutions and deletions. In embodiments, the amino acid modification to SEQ ID NO: 88 at R723 is an essential or non-essential amino acid. In embodiments, the amino acid modification at R723 is a hydrophilic or hydrophobic amino acid. In embodiments, the amino acid modification at R723 is amino acid modification is a hydrophilic amino acid. In embodiments, the amino acid modification at R723 is a polar and positively charged hydrophilic amino acid. In embodiments, the amino acid modification at R723 is lysine (K). In embodiments, the amino acid modification at R723 is a polar and neutral charged hydrophilic amino acid. In embodiments, the amino acid modification at R723 is selected from asparagine (N), glutamine (Q), serine (S), threonine (T), proline (P), and cysteine (C). In embodiments, the amino acid modification at R723 is a polar and negatively charged hydrophilic amino acid. In embodiments, the amino acid modification at R723 is selected from aspartate (D) or glutamate (E). In embodiments, the amino acid modification at R723 is an aromatic, polar and positively charged hydrophilic amino acid. In embodiments, the amino acid modification at R723 is histidine (H). In embodiments, the amino acid modification at R723 is a hydrophobic amino acid. In embodiments, the amino acid modification at R723 is a hydrophobic, aliphatic amino acid. In embodiments, the amino acid modification at R723 is selected from glycine (G), alanine (A), leucine (L), isoleucine (I), methionine (M), or valine (V). In embodiments, the amino acid modification at R723 is a hydrophobic, aromatic amino acid. In embodiments, the amino acid modification at R723 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 88 and an amino acid modification at position H728. In embodiments, the amino acid modifications are selected from substitutions and deletions. In embodiments, the amino acid modification to SEQ ID NO: 88 at H728 is an essential or non-essential amino acid. In embodiments, the amino acid modification at H728 is a hydrophilic or hydrophobic amino acid. In embodiments, the amino acid modification at H728 is amino acid modification is a hydrophilic amino acid. In embodiments, the amino acid modification at H728 is a polar and positively charged hydrophilic amino acid. In embodiments, the amino acid modification at H728 is selected from arginine (R) or lysine (K). In embodiments, the amino acid modification at H728 is a polar and neutral charged hydrophilic amino acid. In embodiments, the amino acid modification at H728 is selected from asparagine (N), glutamine (Q), serine (S), threonine (T), proline (P), and cysteine (C). In embodiments, the amino acid modification at H728 is a polar and negatively charged hydrophilic amino acid. In embodiments, the amino acid modification at H728 is selected from aspartate (D) or glutamate (E). In embodiments, the amino acid modification at H728 is an aromatic, polar and positively charged hydrophilic amino acid. In embodiments, the amino acid modification at H728 is a hydrophobic amino acid. In embodiments, the amino acid modification at H728 is a hydrophobic, aliphatic amino acid. In embodiments, the amino acid modification at H728 is selected from glycine (G), alanine (A), leucine (L), isoleucine (I), methionine (M), or valine (V). In embodiments, the amino acid modification at H728 is a hydrophobic, aromatic amino acid. In embodiments, the amino acid modification at H728 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position R237. In embodiments, the amino acid modifications are selected from substitutions and deletions. In embodiments, the amino acid modification to SEQ ID NO: 89 at R237 is an essential or non-essential amino acid. In embodiments, the amino acid modification at R237 is a hydrophilic or hydrophobic amino acid. In embodiments, the amino acid modification at R237 is amino acid modification is a hydrophilic amino acid. In embodiments, the amino acid modification at R237 is a polar and positively charged hydrophilic amino acid. In embodiments, the amino acid modification at R237 is lysine (K). In embodiments, the amino acid modification at R237 is a polar and neutral charged hydrophilic amino acid. In embodiments, the amino acid modification at R237 is selected from asparagine (N), glutamine (Q), serine (S), threonine (T), proline (P), and cysteine (C). In embodiments, the amino acid modification at R237 is a polar and negatively charged hydrophilic amino acid. In embodiments, the amino acid modification at R237 is selected from aspartate (D) or glutamate (E). In embodiments, the amino acid modification at R237 is an aromatic, polar and positively charged hydrophilic amino acid. In embodiments, the amino acid modification at R237 is histidine (H). In embodiments, the amino acid modification at R237 is a hydrophobic amino acid. In embodiments, the amino acid modification at R237 is a hydrophobic, aliphatic amino acid. In embodiments, the amino acid modification at R237 is selected from glycine (G), alanine (A), leucine (L), isoleucine (I), methionine (M), or valine (V). In embodiments, the amino acid modification at R237 is a hydrophobic, aromatic amino acid. In embodiments, the amino acid modification at R237 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position H242. In embodiments, the amino acid modifications are selected from substitutions and deletions. In embodiments, the amino acid modification to SEQ ID NO: 89 at H242 is an essential or non-essential amino acid. In embodiments, the amino acid modification at H242 is a hydrophilic or hydrophobic amino acid. In embodiments, the amino acid modification at H242 is amino acid modification is a hydrophilic amino acid. In embodiments, the amino acid modification at H242 is a polar and positively charged hydrophilic amino acid. In embodiments, the amino acid modification at H242 is selected from arginine (R) or lysine (K). In embodiments, the amino acid modification at H242 is a polar and neutral charged hydrophilic amino acid. In embodiments, the amino acid modification at H242 is selected from asparagine (N), glutamine (Q), serine (S), threonine (T), proline (P), and cysteine (C). In embodiments, the amino acid modification at H242 is a polar and negatively charged hydrophilic amino acid. In embodiments, the amino acid modification at H242 is selected from aspartate (D) or glutamate (E). In embodiments, the amino acid modification at H242 is an aromatic, polar and positively charged hydrophilic amino acid. In embodiments, the amino acid modification at H242 is a hydrophobic amino acid. In embodiments, the amino acid modification at H242 is a hydrophobic, aliphatic amino acid. In embodiments, the amino acid modification at H242 is selected from glycine (G), alanine (A), leucine (L), isoleucine (I), methionine (M), or valine (V). In embodiments, the amino acid modification at H242 is a hydrophobic, aromatic amino acid. In embodiments, the amino acid modification at H242 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position R694. In embodiments, the amino acid modifications are selected from substitutions and deletions. In embodiments, the amino acid modification to SEQ ID NO: 89 at R694 is an essential or non-essential amino acid. In embodiments, the amino acid modification at R694 is a hydrophilic or hydrophobic amino acid. In embodiments, the amino acid modification at R694 is amino acid modification is a hydrophilic amino acid. In embodiments, the amino acid modification at R694 is a polar and positively charged hydrophilic amino acid. In embodiments, the amino acid modification at R694 is lysine (K). In embodiments, the amino acid modification at R694 is a polar and neutral charged hydrophilic amino acid. In embodiments, the amino acid modification at R694 is selected from asparagine (N), glutamine (Q), serine (S), threonine (T), proline (P), and cysteine (C). In embodiments, the amino acid modification at R694 is a polar and negatively charged hydrophilic amino acid. In embodiments, the amino acid modification at R694 is selected from aspartate (D) or glutamate (E). In embodiments, the amino acid modification at R694 is an aromatic, polar and positively charged hydrophilic amino acid. In embodiments, the amino acid modification at R694 is histidine (H). In embodiments, the amino acid modification at R694 is a hydrophobic amino acid. In embodiments, the amino acid modification at R694 is a hydrophobic, aliphatic amino acid. In embodiments, the amino acid modification at R694 is selected from glycine (G), alanine (A), leucine (L), isoleucine (I), methionine (M), or valine (V). In embodiments, the amino acid modification at R694 is a hydrophobic, aromatic amino acid. In embodiments, the amino acid modification at R694 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position H699. In embodiments, the amino acid modifications are selected from substitutions and deletions. In embodiments, the amino acid modification to SEQ ID NO: 89 at H699 is an essential or non-essential amino acid. In embodiments, the amino acid modification at H699 is a hydrophilic or hydrophobic amino acid. In embodiments, the amino acid modification at H699 is amino acid modification is a hydrophilic amino acid. In embodiments, the amino acid modification at H699 is a polar and positively charged hydrophilic amino acid. In embodiments, the amino acid modification at H699 is selected from arginine (R) or lysine (K). In embodiments, the amino acid modification at H699 is a polar and neutral charged hydrophilic amino acid. In embodiments, the amino acid modification at H699 is selected from asparagine (N), glutamine (Q), serine (S), threonine (T), proline (P), and cysteine (C). In embodiments, the amino acid modification at H699 is a polar and negatively charged hydrophilic amino acid. In embodiments, the amino acid modification at H699 is selected from aspartate (D) or glutamate (E). In embodiments, the amino acid modification at H699 is an aromatic, polar and positively charged hydrophilic amino acid. In embodiments, the amino acid modification at H699 is a hydrophobic amino acid. In embodiments, the amino acid modification at H699 is a hydrophobic, aliphatic amino acid. In embodiments, the amino acid modification at H699 is selected from glycine (G), alanine (A), leucine (L), isoleu-cine (I), methionine (M), or valine (V). In embodiments, the amino acid modification at H699 is a hydrophobic, aromatic amino acid. In embodiments, the amino acid modification at H699 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position R237. In embodiments, the amino acid modifications are selected from substitutions and deletions. In embodiments, the amino acid modification to SEQ ID NO: 89 at R237 is an essential or non-essential amino acid. In embodiments, the amino acid modification at R237 is a hydrophilic or hydrophobic amino acid. In embodiments, the amino acid modification at R237 is amino acid modification is a hydrophilic amino acid. In embodiments, the amino acid modification at R237 is a polar and positively charged hydrophilic amino acid. In embodiments, the amino acid modification at R237 is lysine (K). In embodiments, the amino acid modification at R237 is a polar and neutral charged hydrophilic amino acid. In embodiments, the amino acid modification at R237 is selected from asparagine (N), glutamine (Q), serine (S), threonine (T), proline (P), and cysteine (C). In embodiments, the amino acid modification at R237 is a polar and negatively charged hydrophilic amino acid. In embodiments, the amino acid modification at R237 is selected from aspartate (D) or glutamate (E). In embodiments, the amino acid modification at R237 is an aromatic, polar and positively charged hydrophilic amino acid. In embodiments, the amino acid modification at R237 is histidine (H). In embodiments, the amino acid modification at R237 is a hydrophobic amino acid. In embodiments, the amino acid modification at R237 is a hydrophobic, aliphatic amino acid. In embodiments, the amino acid modification at R237 is selected from glycine (G), alanine (A), leucine (L), isoleucine (I), methionine (M), or valine (V). In embodiments, the amino acid modification at R237 is a hydrophobic, aromatic amino acid. In embodiments, the amino acid modification at R237 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position H242. In embodiments, the amino acid modifications are selected from substitutions and deletions. In embodiments, the amino acid modification to SEQ ID NO: 89 at H242 is an essential or non-essential amino acid. In embodiments, the amino acid modification at H242 is a hydrophilic or hydrophobic amino acid. In embodiments, the amino acid modification at H242 is amino acid modification is a hydrophilic amino acid. In embodiments, the amino acid modification at H242 is a polar and positively charged hydrophilic amino acid. In embodiments, the amino acid modification at H242 is selected from arginine (R) or lysine (K). In embodiments, the amino acid modification at H242 is a polar and neutral charged hydrophilic amino acid. In embodiments, the amino acid modification at H242 is selected from asparagine (N), glutamine (Q), serine (S), threonine (T), proline (P), and cysteine (C). In embodiments, the amino acid modification at H242 is a polar and negatively charged hydrophilic amino acid. In embodiments, the amino acid modification at H242 is selected from aspartate (D) or glutamate (E). In embodiments, the amino acid modification at H242 is an aromatic, polar and positively charged hydrophilic amino acid. In embodiments, the amino acid modification at H242 is a hydrophobic amino acid. In embodiments, the amino acid modification at H242 is a hydrophobic, aliphatic amino acid. In embodiments, the amino acid modification at H242 is selected from glycine (G), alanine (A), leucine (L), isoleucine (I), methionine (M), or valine (V). In embodiments, the amino acid modification at H242 is a hydrophobic, aromatic amino acid. In embodiments, the amino acid modification at H242 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position R694. In embodiments, the amino acid modifications are selected from substitutions and deletions. In embodiments, the amino acid modification to SEQ ID NO: 89 at R694 is an essential or non-essential amino acid. In embodiments, the amino acid modification at R694 is a hydrophilic or hydrophobic amino acid. In embodiments, the amino acid modification at R694 is amino acid modification is a hydrophilic amino acid. In embodiments, the amino acid modification at R694 is a polar and positively charged hydrophilic amino acid. In embodiments, the amino acid modification at R694 is lysine (K). In embodiments, the amino acid modification at R694 is a polar and neutral charged hydrophilic amino acid. In embodiments, the amino acid modification at R694 is selected from asparagine (N), glutamine (Q), serine (S), threonine (T), proline (P), and cysteine (C). In embodiments, the amino acid modification at R694 is a polar and negatively charged hydrophilic amino acid. In embodiments, the amino acid modification at R694 is selected from aspartate (D) or glutamate (E). In embodiments, the amino acid modification at R694 is an aromatic, polar and positively charged hydrophilic amino acid. In embodiments, the amino acid modification at R694 is histidine (H). In embodiments, the amino acid modification at R694 is a hydrophobic amino acid. In embodiments, the amino acid modification at R694 is a hydrophobic, aliphatic amino acid. In embodiments, the amino acid modification at R694 is selected from glycine (G), alanine (A), leucine (L), isoleucine (I), methionine (M), or valine (V). In embodiments, the amino acid modification at R694 is a hydrophobic, aromatic amino acid. In embodiments, the amino acid modification at R694 is selected from phenylalanine (F), tryptophan (W), or tyrosine (Y).

In embodiments, the endonuclease has at least about 70%, at least about 80%, at least about 85%, at least about 90%, at least about 91%, at least about 91%, at least about 92%, at least about 93%, at least about 94%, at least about 95%, at least about 96%, at least about 97%, at least about 98%, or at least about 99% identity to SEQ ID NO: 89 and an amino acid modification at position H699. In embodiments, the amino acid modifications are selected from substitutions and deletions. In embodiments, the amino acid modification to SEQ ID NO: 89 at H699 is an essential or non-essential amino acid. In embodiments, the amino acid modification at H699 is a hydrophilic or hydrophobic amino acid. In embodiments, the amino acid modification at H699 is amino acid modification is a hydrophilic amino acid. In embodiments, the amino acid modification at H699 is a polar and positively charged hydrophilic amino acid. In embodiments, the amino acid modification at H699 is selected from arginine (R) or lysine (K). In embodiments, the amino acid modification at H699 is a polar and neutral charged hydrophilic amino acid. In embodiments, the amino acid modification at H699 is selected from asparagine (N), glutamine (Q), serine (S), threonine (T), proline (P), and cysteine (C). In embodiments, the amino acid modification at H699 is a polar and negatively charged hydrophilic amino acid. In embodiments, the amino acid modification at H699 is selected from aspartate (D) or glutamate (E). In embodiments, the amino acid modification at H699 is an aromatic, polar and positively charged hydrophilic amino acid. In embodiments, the amino acid modification at H699 is a hydrophobic amino acid. In embodiments, the amino acid modification at H699 is a hydrophobic, aliphatic amino acid. In embodiments, the amino acid modification at H699 is selected from glycine (G), alanine (A), leucine (L), isoleucine (I), methionine (M), or valine (V). In embodiments, the amino acid modification at H699 is a hydrophobic, aromatic amino acid. In embodiments, the amino acid modification at H699 is selected from phenylalanine (F), tryptophan (W), or tyrosine (Y).

In embodiments, disclosed herein is a composition comprising an endonuclease and having an amino acid sequence of least 90%, or at least 95%, or at least 98%, or at least 99% identity to SEQ ID NO: 3. In embodiments, substitutions are made to SEQ ID NO: 3:

```
Met Asp Lys His Pro Ser Asn Arg Tyr Ala Leu Pro Lys Val Ile Ile Ser Glu Val

Asp His Glu Arg Ile Leu Glu Phe Lys Val Lys Tyr Glu Lys Leu Ala Arg Leu

Asp Arg Phe Glu Val Lys Ala Met His Tyr Asp Gly Ala Glu Ile Val Phe Asp

Glu Val Val Ala Asn Gly Gly Leu Ile Glu Val Glu Tyr Gln Asp Asn Lys

Thr Ile Thr Ile Asn Leu Asn Gly Lys Lys Tyr Thr Ile Asn Gly Arg Lys Val Gly

Gly Lys Arg Arg Leu Leu Glu Asp Arg Ile Ser Arg Gly Lys Val Cys Leu Glu

Leu His Asp Lys Ile Pro Asp Glu Lys Gly Asn Leu Arg Ser Ser Arg Thr Glu

Arg Glu Leu Ile Thr Phe Asp Ser Thr Lys Leu Tyr Ser Gln Ile Ile Gly Arg Asp

Val Ala Ser Thr Lys Glu Ile Tyr Leu Ile Lys Arg Phe Leu Ala Tyr Arg Ser Asp

Leu Leu Phe Tyr Tyr Gly Phe Ile Asp Asn Phe Phe Lys Val Ala Gly Asn Lys

Arg Glu Leu Trp Lys Ile Asp Phe Ser Gly Asp Lys Asn Gln Glu Leu Ile Lys
```

-continued

```
Tyr Phe Asn Phe Thr Ile Asn Asp Lys Leu Lys Asn Asp Lys Gly Tyr Leu Lys

Glu Tyr Thr Ala Asn Asp Glu Gln Ile Lys Lys Asp Leu Gln Asn Thr Lys Glu

Val Phe Thr Ala Leu Arg His Ala Leu Met His Phe Glu Tyr Asp Phe Phe Glu

Lys Leu Phe Asn Asn Glu Glu Ile Glu Thr Leu Ser Lys Ile His Asp Ile Glu Leu

Leu Asn Thr Met Ile Asn Lys Leu Asp Lys Leu Asn Ile Asp Thr Arg Lys Glu

Tyr Ile Asp Asp Glu Lys Ile Thr Val Phe Gly Glu Glu Ile Ser Leu Lys Thr Leu

Tyr Gly Leu Tyr Ala His Thr Ala Ile Asn Arg Val Ala Phe Asn Lys Leu Ile Asn

Arg Phe Met Val Glu Asn Gly Thr Glu Asn Glu Ala Leu Lys Lys Tyr Phe Asn

Ser Lys Ala Glu Gly Gly Ile Ala Tyr Glu Ile Asp Ile His Gln Asn Ser Glu Tyr

Lys Gln Leu Tyr Ile Gln His Lys Asp Leu Val Ser Lys Leu Ser Ala Leu Ser Asp

Gly Asp Glu Ile Ala Asp Thr Asn Lys Lys Ile Ser Glu Leu Lys Val Lys Met

Lys Ala Ile Thr Lys Ala Asn Ser Leu Lys Arg Leu Glu His Lys Leu Arg Leu

Thr Phe Gly Phe Ile Tyr Thr Glu Tyr Gln Asp Tyr Asn Ala Phe Lys Asn Asn

Phe Asp Thr Asp Ile Lys Ser Gly Arg Phe Ile Pro Lys Asp Ser Glu Gly Lys Arg

Arg Gly Phe Asp His Arg Glu Leu Asp Gln Leu Lys Arg Tyr Tyr Asp Ala Thr

Phe Ala Asp Lys Lys Pro Gln Thr Lys Glu Thr Phe Asp Glu Ile Asp Lys Gln

Ile Asp Gln Leu Ser Leu Lys Asn Leu Ile Gly Asp Asp Thr Leu Leu Lys Val

Ile Leu Leu Ile Tyr Ile Phe Leu Pro Arg Glu Ile Lys Gly Glu Phe Leu Gly Phe

Val Lys Lys Tyr Tyr His Asp Thr Lys His Ile Glu Glu Asp Thr Lys Asp Lys

Asp Glu Gly Phe Asp Asp Thr Phe Pro Val Gly Leu Lys Leu Lys Val Leu Asp

Lys Asn Ile Arg Ala Leu Ser Val Leu Lys His Ser Leu Ser Tyr Gln Ala Lys Tyr

Asn Lys Lys Glu Glu Lys Lys Glu Gln Phe Tyr Glu Ala Gly Asn Arg His Gly

Arg Phe Tyr Lys Lys Leu Gly Ile Ser His Asn Gln Glu Glu Phe Asp Lys Ser

Val Tyr Ala Pro Leu Leu Arg Tyr His Ala Ala Leu Phe Lys Leu Leu Asn Asp

Phe Glu Ile Tyr Ser Leu Ala Gln His Ile Glu Gly Lys Glu Thr Leu Ala Gln Gln

Ile Glu Lys Pro Gln Phe Ser Gln Tyr Glu His Tyr Asn Phe Arg Lys Met Leu

Ser Lys Thr Tyr Pro Lys Ser Ala Glu Arg Gly Ala Leu Asp Asn Asp Ala Phe

Asp Thr Val Ile Asn Met Arg Asn Asp Ile Ala His Leu Ser His Glu Pro Leu Phe

Glu Cys Pro Leu Asp Gly Lys Lys Ser Tyr Lys Leu Lys Gln Gly Lys Arg Thr

Asn Thr Ile Asn Val Lys Pro Leu Pro Ile Ser Arg Lys Met Ile Val Asp Phe Ile

Ser Ser Gln Ser Asp Met Lys Lys Thr Leu Gly Tyr Asp Ala Val Asn Asp Leu

Thr Met Lys Ile Ile Gln Leu Arg Thr Arg Leu Lys Val Tyr Ala Asp Lys Ser Glu

Thr Ile Lys Thr Leu Val Asp Ala Ala Lys Thr Pro Asn Asp Phe Tyr His Ile Tyr

Lys Val Lys Gly Val Glu Ala Ile Asn Arg His Leu Leu Glu Val Ile Gly Glu Thr

Lys Asp Glu Lys Arg Ile Arg Lys Arg Ile Glu Ser Gly Asn Ala Ile Ala Gly Arg

Thr Pro Ala Asp Ser Gln Glu Asn
```

As described herein, substitutions may be made to this sequence to generate the inventive endonuclease (including, taking into account degeneracy of the genetic code).

In some embodiments, the endonuclease has one or more substitutions at positions corresponding to D38X, A59X, G172X, T236X, T319X, H375X, H419X, T424X, E529X, T541X, G562X, K564X, D569X, A586X, N641X, D642X, S647X, D721X, R779X, K13X, K566X, G554X, A35X, E110X, G314X, K114X, D498X, I86X, V57X, H249X, R704X of SEQ ID NO: 3, wherein the substitution is defined by X and wherein X is any amino acid. In some embodiments, X is an essential or non-essential amino acid.

In some embodiments, X is a hydrophilic or hydrophobic amino acid.

In some embodiments, X is a hydrophilic amino acid.

In some embodiments, X is a polar and positively charged hydrophilic amino acid. In some embodiments, X is selected from arginine I or lysine (K).

In some embodiments, X is a polar and neutral charged hydrophilic amino acid. In some embodiments, X is selected from asparagine (N), glutamine (Q), serine (S), threonine (T), proline (P), and cysteiI (C).

In some embodiments, X is a polar and negatively charged hydrophilic amino acid. In some embodiments, X is selected from aspartate (D) or glutIte (E).

In some embodiments, wherein X is an aromatic, polar and positively charged hydrophilic amino acid. In some embodiments, wherein X is histidine (H).

In some embodiments, X is a hydrophobic amino acid.

In some embodiments, X is a hydrophobic, aliphatic amino acid. In some embodiments, X is selected from glycine (G), alanine (A), leucine (L), isoleucine (I), methionine (M), or valine (V).

In some embodiments, X is a hydrophobic, aromatic amino acid. In some embodiments, wherein X is selected from phenylalanine (F), tryptophan (W), or tyrosine (Y).

In some embodiments, the endonuclease of SEQ ID NO: 3 comprises one or more of the following substitutions:
 a hydrophilic residue other than aspartate (D) at a position corresponding to 38;
 a hydrophobic residue other than alanine (A) at a position corresponding to 59;
 a hydrophobic residue other than glycine (G) at a position corresponding to 172;
 a hydrophilic residue other than threonine (T) at a position corresponding to 236;
 a hydrophilic residue other than threonine (T) at a position corresponding to 319;
 a hydrophilic residue other than histidine (H) at a position corresponding to 375;
 a hydrophilic residue other than histidine (H) at a position corresponding to 419;
 a hydrophilic residue other than threonine (T) at a position corresponding to 424;
 a hydrophilic residue other than gIamate (E) at a position corresponding to 529;
 a hydrophilic residue other than threonine (T) at a position corresponding to 541;
 a hydrophobic residue other than glycine (G) at a position corresponding to 562;
 a hydrophilic residue other than lysine (K) at a position corresponding to 564;
 a hydrophilic residue other than aspartate (D) at a position corresponding to 569;
 a hydrophobic residue other than alanine (A) at a position corresponding to 586;
 a hydrophilic residue other than asparagine (N) at a position corresponding to 641;
 a hydrophilic residue other than aspartate (D) at a position corresponding to 642;
 a hydrophilic residue other than serine (S) at a position corresponding to 647;
 a hydrophilic residue other than aspartate (D) at a position corresponding to 721;
 a hydrophilic residue other thIarginine (R) at a position corresponding to 779;
 a hydrophilic residue other than lysine (K) at a position corresponding to 13;
 a hydrophilic residue other than lysine (K) at a position corresponding to 566;
 a hydrophobic residue other than glycine (G) at a position corresponding to 554;
 a hydrophobic residue other than alanine (A) at a position corresponding to 35;
 a hydrophilic residue other In glutamate (E) at a position corresponding to 110;
 a hydrophobic residue other than glycine (G) at a position corresponding to 314;
 a hydrophilic residue other than lysine (K) at a position corresponding to 114;
 a hydrophilic residue other than aspartate (D) at a position corresponding to 498;
 a hydrophobic residue other than isoleucine (I) at a position corresponding to 86;
 a hydrophobic residue other than valine (V) at a position corresponding to 57;
 a hydrophilic residue other than histidine (H) at a position corresponding to 249; and
 a hydrophilic residue otI than arginine (R) at a position corresponding to 704.

In some embodiments, the endonuclease of SEQ ID NO: 3 comprises D38F. In some embodiments, the endonuclease of SEQ ID NO: 3 comprises A59V. In some embodiments, the endonuclease of SEQ ID NO: 3 comprises G172L. In some embodiments, the endonuclease of SEQ ID NO: 3 comprises T236L. In some embodiments, the endonuclease of SEQ ID NO: 3 comprises T319I. In some embodiments, the endonuclease of SEQ ID NO: 3 comprises H375L. In some embodiments, the endonuclease of SEQ ID NO: 3 comprises H419Y. In some embodiments, the endonuclease of SEQ ID NO: 3 comprises T424F. In some embodiments, the endonuclease of SEQ ID NO: 3 comprises E529L. In some embodiments, the endonuclease of SEQ ID NO: 3 comprises T541L. In some embodiments, the endonuclease of SEQ ID NO: 3 comprises G562Y. In some embodiments, the endonuclease of SEQ ID NO: 3 comprises K564M. In some embodiments, the endonuclease of SEQ ID NO: 3 comprises D569L. In some embodiments, the endonuclease of SEQ ID NO: 3 comprises A586I. In some embodiments, the endonuclease of SEQ ID NO: 3 comprises N641F. In some embodiments, the endonuclease of SEQ ID NO: 3 comprises D642L. In some embodiments, the endonuclease of SEQ ID NO: 3 comprises S647L. In some embodiments, the endonuclease of SEQ ID NO: 3 comprises D721L. In some embodiments, the endonuclease of SEQ ID NO: 3 comprises R779I. In some embodiments, the endonuclease of SEQ ID NO: 3 comprises K13R. In some embodiments, the endonuclease of SEQ ID NO: 3 comprises K566R. In some embodiments, the endonuclease of SEQ ID NO: 3 comprises G554H. In some embodiments, the endonuclease of SEQ ID NO: 3 comprises A35N. In some embodiments, the endonuclease of SEQ ID NO: 3 comprises E110T. In some embodiments, the endonuclease of SEQ ID NO: 3 comprises G314Q. In some embodiments, the endonuclease of SEQ ID NO: 3 comprises K114P. In some embodiments, the endonuclease of SEQ ID NO: 3 comprises D498P. In some embodiments, the endonuclease of SEQ ID NO: 3 comprises I86P. In some embodiments, the endonuclease of SEQ ID NO: 3 comprises V57E. In some embodiments, the endonuclease of SEQ ID NO: 3 comprises H249W. In some embodiments, the endonuclease of SEQ ID NO: 3 comprises R704F.

In some embodiments, the endonuclease of SEQ ID NO: 3 comprises D38F and A59V. In some embodiments, the endonuclease of SEQ ID NO: 3 comprises D38F, A59V, and G172L. In some embodiments, the endonuclease of SEQ ID NO: 3 comprises D38F, A59V, G172L, and T236L. In some embodiments, the endonuclease of SEQ ID NO: 3 comprises D38F, A59V, G172L, T236L, and T319I. In some embodiments, the endonuclease of SEQ ID NO: 3 comprises D38F, A59V, G172L, T236L, T319I, and H375L. In some embodiments, the endonuclease of SEQ ID NO: 3 comprises D38F, A59V, G172L, T236L, T319I, H375L, and H419Y. In some embodiments, the endonuclease of SEQ ID NO: 3 comprises D38F, A59V, G172L, T236L, T319I, H375L, H419Y, and T424F. In some embodiments, the endonuclease of SEQ ID NO: 3 comprises D38F, A59V, G172L, T236L, T319I, H375L, H419Y, T424F, and E529L. In some embodiments, the endonuclease of SEQ ID NO: 3 comprises D38F, A59V, G172L, T236L, T319I, H375L, H419Y, T424F, E529L, and T541L. In some embodiments, the endonuclease of SEQ ID NO: 3 comprises D38F, A59V, G172L, T236L, T319I, H375L, H419Y, T424F, E529L, T541L, and G562X. In some embodiments, the endonuclease of SEQ ID NO: 3 comprises D38F, A59V, G172L, T236L, T319I, H375L, H419Y, T424F, E529L, T541I, G562X, and K564M. In some embodiments, thI endonuclease of SEQ ID NO: 3 comprises D38F, A59V, G172L, T236L, T319I, H375L, H419Y, T424F, E529L, T541L, G562X, K564M, and D569L. In some embodiments, the endonuclease of SEQ ID NO: 3 comprises D38F, A59V, G172L, T236L, T319I, H375L, H419Y, T424F, E529L, T541L, G562X, K564M, D569L, and A586I. In some embodiments, the endonuclease of SEQ ID NO: 3 comprises D38F, A59V, G172L, T236L, T319I, H375L, H419Y, T424F, E529L, T541L, G562X, K564M, D569L, A586I, and N641F. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, and D642L. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, and S647L. In some embodiments, the endonuclease of SEQ ID NO: 3 comprises D38F, A59V, G172L, T236L, T319I, H375L, H419Y, T424F, E529L, T541L, G562X, aK564M, D569L, A586I, N641F, D642L, S647L, and D721L. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, and R779I. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, and K13R. In some embodiments, the endonuclease of SEQ ID NO: 3 comprises D38F, A59V, G172L, T236L, T319I, H375L, H419Y, T424F, E529L, T541L, G562X, aK564M, D569L, A586I, N641F, D642L, S647L, D721L, R779I, K13R, and K566R. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, and G554H. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, and A35N. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, and E110T. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, and G314Q. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, and K114P. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, and D498P. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, and I86P. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, and V57E. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, V57E, and H249W. In some embodiments, the endonuclease of SEQ ID NO: 3 comprises D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, V57E, H249W, and R704F.

In some embodiments, the disclosed herein are one or more (e.g. about 1, or about 2, or about 3, or about 4, or about 5, or about 6, or about 7, or about 8, or about 9, or about 10, or about 15, or about 20, or about 30) substitutions to SEQ ID NO: 3 or a sequence with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 3 (or about 70%, or about 75%, or about 80%, or about 85%, or about 90, or about 95%, or about 96%, or about 97%, or about 98%, or about 99% identity to SEQ ID NO: 3). In various embodiments, one or more amino acids of SEQ ID NO: 3 is substituted with a naturally occurring amino acid, such as a hydrophilic amino acid (e.g. a polar and positively charged hydrophilic amino Id, such as arginine (R) or lysine (K); a polar and neutral of charge hydrophilic amino acid, such as asparagine (N), glutamine (Q), serine (S), threonine (T), Iline (P), and cysteine (C), a polar and negatively charged hydrophilic amino acid, such alspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In illustrative embodiments, inventive substitutions include, but are not limited to one or more (e.g. about 1, or about 2, or about 3, or about 4, or about 5, or about 6, or about 7, or about 8, or about 9, or about 10, or about 15, or about 20, or about 30) substitutions to SEQ ID NO: 3, or a sequence with at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 3: D38F, A59V, G172L, T236L, T319I, H375L, H419Y, T424F, E529L, T541L, G562X, K564M, D569L, A586I, N641F, D642L, S647L, D721L, R779I, K13R, K566R, G554H, A35N, E110T, G314Q, K114P, D498P, I86P, V57E, H249W, and R704F.

In embodiments, the endonuclease disclosed herein (e.g., SEQ ID NO: 1, SEQ ID NO: 2, SEQ ID NO: 3, and SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or fragments or variants thereof), comprises a bi-lobed structure. In embodiments, the endonuclease comprises two HEPN domains in the Nuclease (NUC) lobe for cleavage of RNA targets, and a Recognition (REC) lobe comprising α-helical domains and an N-terminal domain (NTD). In embodiments, the REC lobe binds the CRISPR repeat of the gRNA. In embodiments, the NTD comprises one or more β sheets.

In embodiments, the endonuclease comprises a C-terminal domain (CTD) in an NUC lobe.

In embodiments, the endonuclease and/or system for targeting a nucleic acid for trans-splicing comprises an inactive endonuclease (dCas). In embodiments, the dCas is a variant of Cas13e3. In embodiments, the Cas13e3 comprises R244A/H249A/R704A/H709A mutations in the HEPN domains or mutations corresponding thereto relative to SEQ ID NO: 3.

In embodiments, disclosed herein is a miniature splice editor. In embodiments, the miniature splice editor is based on dCas13e3. In embodiments, the miniature splice editor is at least about 5%, at least about 10%, at least about 15%, at least about 20%, or at least about 25% shorter in sequence length compared to SE1 (SE1 is fused, linked or associated with dPspCas13b-MCP).

In embodiments, the endonuclease (or chimeric protein) comprises a domain from a different endonuclease. In embodiments, the different endonuclease is a Cas endonuclease. In embodiments, the domain is one or more of a PAM-interacting domain. In embodiments, the domain is derived from one or more of Cas9, Cas12a (Cpf1), Cas12e (CasX), Cas12d (CasY), Cas12b (C2c1), Cas13a (C2c2), Cas13b, Cas13c, Cas13d, Cas13X/Cas13bt, Cas13Y, Cas12c (C2c3), GeoCas9, CjCas9, NmeCas9, Cas12J (CasPhi), Cas12L (CasLambda), Cas12f (Cas14), Cas12g, Cas12h, Cas12i, Cas12k, NmeCas9, Nme2Cas9, CjCas9, GeoCas9, BlatCas9, PpCas9, and Cas14. In embodiments, the domain is derived from a Cas from one or more of *Streptococcus pyogenes, Staphylococcus aureus, Neisseria meningitis, Streptococcus thermophilis,* or *Treponema denticola.*

In embodiments, the composition further comprises one or more donor polynucleotides. In embodiments, the endonuclease is suitable for introducing one or more donor polynucleotides into a target nucleic acid molecule. In embodiments, the donor polynucleotide comprises a transgene. In embodiments, the donor polynucleotide comprises a sequence which corrects a mutation. In embodiments, a donor polynucleotide is of any length, for example between about 2 and about 10000 nucleotides in length (or any integer value therebetween or thereabove), for instance, between about 100 and about 1000 nucleotides in length (or any integer therebetween), or between about 200 and about 500 nucleotides in length.

In embodiments, the endonuclease (or chimeric protein) comprises a nuclear localization signal (NLS). Examples of NLSs are provided in Kosugi et al. (*J. Biol. Chem.* (2009) 284:478-485; hereby incorporated by reference herein). In embodiments, the NLS comprises the consensus sequence K(K/R)X(K/R) (SEQ ID NO: 32). In embodiments, the NLS comprises the consensus sequence (K/R)(K/R)$X_{10-12}$(K/R)$_{3/5}$ (SEQ ID NO: 33), where (K/R)$_{3/5}$ represents at least three of the five amino acids is either lysine or arginine. In embodiments, the NLS comprises the c-myc NLS. In embodiments, the c-myc NLS comprises the sequlnce PAAKRVKLD (SEQ ID NO: 34). In embodiments, tle NLS is the nucleoplasmin NLS. In embodiments, the nucleoplasmin NLS comprises the sequence KRPAATKK-AGQAKKKK (SEQ ID NO: 35). In embodiments, the NLS comprises the SV40 Large T-antigen NLS. In embodiments, the SV40 Large T-antigen NLS comprises the sequence PKKKRKV (SEQ ID NO: 36). In a particular embodiment, the NLS comprises three SV40 Large T-antigen NLSs (e.g., DPKKKRKVDPKKKRKVDPKKKRKV (SEQ ID NO: 37)). In embodiments, the NLS is or comprises SEQ ID NO: 72. In embodiments, the NLS comprises mutations/variations in the above sequences such that they contain 1 or more substitutions, additions, or deletions (e.g., about 1, or about 2, or about 3, or about 4, or about 5, or about 10 substitutions, additions, or deletions).

In embodiments, the endonuclease (or chimeric protein) comprises a polypeptide permeant domain to promote uptake by a cell. In embodiments, the permeant domain is a peptide, peptidomimetic, or non-peptide carrier. In embodiments, the permeant peptide is derived from the third alpha helix of *Drosophila melanogaster* transcription factor Antennapaedia, referred to as penetratin, which comprises the amino acid sequence RQIKIWFQNRRMKWKK (SEQ ID NO: 38). In embodiments, the permeant peptide comprises the HIV-1 tat basic region amino acid sequence, which may include, for example, amino acids 49-57 of naturally occurring tat protein. In embodiments, the permeant peptide is a poly-arginine motif, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A. 2000 Nov. 21; 97(24):13003-8; U.S. Patent Pub. 2003/0220334; 2003/0083256; 2003/0032593; and 2003/0022831, herein incorporated by reference in their entireties).

In embodiments, the endonuclease (or chimeric protein) comprises a polypeptide that promotes or is suitable for VLP delivery, including, without limitation, a retroviral gag polyprotein comprising a matrix polypeptide, a capsid polypeptide, and a nucleocapsid polypeptide (optionally with one or more heterologous protease cleavage sites (e.g. TEV cleavage site, a PreScission (fusion protein of glutathione S-transferase (GST) and human rhinovirus (HRV) type 14 3C protease) cleavage site, a human rhinovirus 3C protease cleavage site, an enterokinase cleavage site, an Epstein-Barr virus protease cleavage site, a cathepsin D cleavage site, and/or a thrombin cleavage site) between one or both of: the matrix polypeptide and the capsid polypeptide; and the capsid polypeptide and the nucleocapsid polypeptide, e.g., a lentiviral gag polyprotein, e.g., a bovine immunodeficiency virus gag polyprotein, a murine leukemia virus (MLV) a gag protein, a simian immunodeficiency virus gag polyprotein, a feline immunodeficiency virus gag polyprotein, a human immunodeficiency virus gag polyprotein, an equine infection anemia virus gag polyprotein, and a caprine arthritis encephalitis virus gag polyprotein or a gag polyprotein of an alpha retrovirus, a beta retrovirus, a gamma retrovirus, a delta retrovirus, an epsilon retrovirus, or a spumavirus. In embodiments, the polypeptide that promotes or is suitable for VLP delivery is co-delivered with a protease to promote cleavage of the chimeric protein. In embodiments, the cleavage of the chimeric protein occurs between the endonuclease and the polypeptide that promotes or is suitable for VLP delivery. In embodiments, the protease is fused to a polypeptide that promotes or is suitable for VLP delivery.

In embodiments, the endonuclease (or chimeric protein) or a delivery vehicle, e.g. one or more lipids, associated therewith comprises a polypeptide or other moiety that interacts with an targeting moiety, e.g. an antibody or antibody-like molecule, a ligand to bind a receptor or a receptor (or fragment thereof) to bind a ligand, aptamer, and the like, for targeted delivery. In embodiments, the endonuclease (or chimeric protein) or a delivery vehicle, e.g. one or more lipids, associated therewith comprises a targeting moiety, e.g., an antibody or antibody-like molecule, a ligand to bind a receptor or a receptor (or fragment thereof) to bind a ligand, aptamer, and the like, for targeted delivery.

In embodiments, the endonuclease is suitable for introducing one or more excisions into a target nucleic acid molecule. In embodiments, the excision is a double-strand DNA break in two strands of the target nucleic acid molecule. In embodiments, the excision is a nick in one or more strands of the target nucleic acid molecule.

Chimeric Constructs/Nucleic Acid Modulating/Modifying Domains

In aspects, the present disclosure provides a composition comprising a chimeric protein comprising: an endonuclease comprising a sequence, optionally comprising a HEPN domain, or a fragment or variant thereof, and having at least about 70% (or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%) to one or more of SEQ ID NOs: 1-4, and/or SEQ ID NOs: 80-89, or having about 1 to about 20 amino acid modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications); and a nucleic acid-modulating domain or a nucleic acid-modifying domain comprising a sequence comprising a catalytic domain, or a fragment or variant thereof, wherein (a) and (b) do not naturally occur together in a same reading frame.

In embodiments, the endonuclease reduces or enhances non-specific degradation of transcripts. In embodiments, the endonuclease reduces or enhances collateral activity, e.g., for use in nucleic acid detection. In embodiments, the endonuclease reduces or enhances collateral activity, e.g. for use in nucleic acid detection using an electrochemical method.

In embodiments, the nucleic acid-modulating domain or the nucleic acid-modifying domain has one or more of nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, debranching activity, transesterification activity, photolyase activity and glycosylase activity. In embodiments, the nucleic acid-modulating domain or the nucleic acid-modifying domain is a METTL3 methyltransferase domain, a METTL3: METTL1 fusion domain, or a fragment or variant thereof.

In embodiments, the nucleic acid-modulating domain or the nucleic acid-modifying domain is a nucleic acid interacting/binding domain. Non-limiting examples of nucleic acid interacting/binding domains are MCP, lambdaN, PP7, QBeta, SLBP, and TBP/TAR.

In embodiments, the nucleic acid-modulating domain or the nucleic acid-modifying domain is a splice-modulating domain. In embodiments, the splice-modulating domain is the RS-rich domain of SRSF1, the Gly-rich domain of hnRNP A1, the alanine-rich motif of RBM4, or the proline-rich motif of DAZAP1. In embodiments, the endonuclease (or chimeric protein) induces exon skipping. In embodiments, the endonuclease (or chimeric protein) induces exon inclusion.

In embodiments, the nucleic acid-modulating domain or the nucleic acid-modifying domain is a degradation domain. In embodiments, the degradation domain is a E2 ubiquitin or ubiquitin-like domain. In embodiments, the degradation domain comprises a ubiquitin core catalytic (UBC) domain. In embodiments, the degradation domain is SUMO, NEDD8, ATG8, ATG12, ISG15, UFM1, FAT10, URM1, or FUB1, or a fragment or variant thereof. In embodiments, the degradation domain is UBE2A (hHR6A), UBE2B (hHR6B), UBE2C (UbcH10), UBE2D1 (UbcH5A), UBE2D2 (UbcH5B), UBE2D3 (UbcH5C), UBE2D4 (HBUCEl), UBE2E1 (UbcH6), UBE2E2, UBE2E3 (UbcH9), UBE2F (NCE2), UBE2G1 (UBE2G), UBE2G2 (UBC7), UBE2H (UBCH), UBE2I (Ubc9), UBE2J1 (NCUBE1), UBE2J2 (NCUBE2), UBE2K (HIP2), UBE2L3 (UbcH7), UBE2L6 (UbcH8), UBE2M (Ubcl2), UBE2N (Ubcl3), UBE2NL, UBE2O (E2-230K), UBE2Q1 (NICE-5), UBE2Q2, UBE2QL, UBE2R1 (CDC34), UBE2R2 (CDC34B), UBE2S (E2-EPF), UBE2T (HSPC150), UBE2U, UBE2V1 (UEV-1A), UBE2V2 (MMS2), UBE2W, UBE2Z (Use1), UVELD (UEV3), BIRC6 (apollon), FTS (AKTIP), TSG101, or UFC1, or a fragment or variant thereof. In embodiments, the degradation domain is cereblon (CRBN) E3 ligase. In embodiments, the degradation domain is modulated by a proteolysis-targeting chimeras (PROTAC).

In embodiments, the degradation domain is a protease, e.g. a protease that is conditionally modulated by another molecule, e.g. a protease inhibitor, e.g. a matrix metalloprotease (MMP) and TIMP-1, TIMP-2, TIMP-3, or TIMP-4.

In embodiments, the degradation domain is modulated by a small molecule. In embodiments, the degradation domain is active in the presence of a small molecule. In embodiments, the degradation domain is inactive in the presence of a small molecule. In embodiments the small molecule is an antiviral drug. In embodiments the small molecule is one or more of abscisic acid (ABA), rapamycin (or rapalog), FK506, Cyclosporine A, FK1012, Gibberellin3-AM, FKCsA, AP1903/AP20187, and auxin.

In embodiments, the nucleic acid-modulating domain or the nucleic acid-modifying domain has nuclease activity, such as that provided by a restriction enzyme (e.g., FokI nuclease).

In embodiments, the nucleic acid-modulating domain or the nucleic acid-modifying domain has methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (e.g. plants), ZMET2, CMT1, CMT2 (e.g. plants), and the like).

In embodiments, the nucleic acid-modulating domain or the nucleic acid-modifying domain has demethylase activity such as that provided by a demethylase (e.g., Ten-Eleven Translocation (TET) dioxygenase 1 (TET1CD), TET1, DME, DML1, DML2, ROS1, and the like).

In embodiments, the nucleic acid-modulating domain or the nucleic acid-modifying domain has deamination activity such as that provided by a deaminase (e.g., a cytosine deaminase enzyme such as rat APOBEC1).

In embodiments, the nucleic acid-modulating domain or the nucleic acid-modifying domain has integrase and/or resolvase activity (e.g., Gin invertase such as the hyperactive mutant of the Gin invertase, GinH106Y; human immunodeficiency virus type 1 integrase (IN); Tn3 resolvase; and the like).

In embodiments, the nucleic acid-modulating domain or the nucleic acid-modifying domain has recombinase activity such as that provided by a recombinase (e.g., catalytic domain of Gin recombinase).

In embodiments, the nucleic acid-modulating domain or the nucleic acid-modifying domain is selected from a deaminase, reverse transcriptase, transposase, integrase, and recombinase. In embodiments, the deaminase is a cytidine or cytosine deaminase, or a fragment or variant thereof. In embodiments, the cytidine or cytosine deaminase is selected from AID, CDA1, and APOBEC, or a fragment or variant thereof. In embodiments, the APOBEC is selected from A3A, AB33, APOBEC1, APOBEC3C, APOBEC31D, APOBEC31F, APOBEC3G, and APOBEC3H, or a fragment or variant thereof. In embodiments, the APOBEC has an amino acid sequence of one of SEQ ID NO: 39 [A3A], SEQ ID NO: 40 [AB3], SEQ ID NO: 41 [APOBEC1], SEQ ID NO: 42 [APOBEC3C], SEQ ID NO: 43 [APOBEC3D], SEQ ID NO: 44 [APOBEC3F], SEQ ID NO: 45 [APOBEC3G], and SEQ ID NO: 46 [APOBEC3H], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the APOBEC has an amino acid sequence selected from one of SEQ ID NOs: 32-39 as shown in Table 5 below.

TABLE 5

APOBEC amino acid sequences

| Sequence | SEQ ID NO: |
|---|---|
| MDPHIFTSNFNNGIGRHKTYLCYEVERLDNGTSVKMDQHRG FLHNQAKNLLCGFYGRHAELRFLDLVPSLQLDPAQIYRVTW FISWSPCFSWGCAGEVRAFLQENTHVRLRIFAARIYDYDPL YKEALQMLRDAGAQVSIMTYDEFKHCWDTFVDHQGCPFQPW DGLDEHSQALSGRLRAILQNQGN | 39 |
| MDPDTFTFNFNNDPLVLRRRQTYLCYEVERLDNGTWVLMDQ HMGFLCNEAKNLLCGFYGRHAELRFLDLVPSLQLDPAQIYR VTWFISWSPCFSWGCAGEVRAFLQENTHVRLRIFAARIYDY DPLYKEALQMLRDAGAQVSIMTYDEFEYCWDTFVYRQGCPF QPWDGLEEHSQALSGRLRAILQNQGN | 40 |
| MTSEKGPSTGDPTLRRRIEPWEFDVFYDPRELRKEACLLYE IKWGMSRKIWRSSGKNTTNHVEVNFIKKFTSERDFHPSMSC SITWFLSWSPCWECSQAIREFLSRHPGVTLVIYVARLFWHM DQQNRQGLRDLVNSGVTIQIMRASEYYHCWRNFVNYPPGDE AHWPQYPPLWMMLYALELHCIILSLPPCLKISRRWQNHLTF FRLHLQNCHYQTIPPHILLATGLIHPSVAWR | 41 |
| MNPQIRNPMKAMYPGTFYFQFKNLWEANDRNETWLCFTVEG IKRRSVVSWKTGVFRNQVDSETHCHAERCFLSWFCDDILSP NTKYQVTWYTSWSPCPDCAGEVAEFLARHSNVNLTIFTARL YYFQYPCYQEGLRSLSQEGVAVEIMDYEDFKYCWENFVYND NEPFKPWKGLKTNFRLLKRRLRESLQ | 42 |
| MNPQIRNPMERMYRDTFYDNFENEPILYGRSYTWLCYEVKI KRGRSNLLWDTGVFRGPVLPKRQSNHRQEVYFRFENHAEMC FLSWFCGNRLPANRRFQITWFVSWNPCLPCVVKVTKFLAEH PNVTLTISAARLYYYRDRDWRWVLLRLHKAGARVKIMDYED FAYCWENFVCNEGQPFMPWYKFDDNYASLHRTLKEILRNPM EAMYPHIFYFHFKNLLKACGRNESWLCFTMEVTKHHSAVFR KRGVFRNQVDPETHCHAERCFLSWFCDDILSPNTNYEVTWY TSWSPCPECAGEVAEFLARHSNVNLTIFTARLCYFWDTDYQ EGLCSLSQEGASVKIMGYKDFVSCWKNFVYSDDEPFKPWKG LQTNFRLLKRRLREILQ | 43 |
| MKPHFRNTVERMYRDTFSYNFYNRPILSRRNTVWLCYEVKT KGPSRPRLDAKIFRGQVYSQPEHHAEMCFLSWFCGNQLPAY KCFQITWFVSWTPCPDCVAKLAEFLAEHPNVTLTISAARLY YYWERDYRRALCRLSQAGARVKIMDDEEFAYCWENFVYSEG QPFMPWYKFDDNYAFLHRTLKEILRNPMEAMYPHIFYFHFK NLRKAYGRNESWLCFTMEVVKHHSPVSWKRGVFRNQVDPET HCHAERCFLSWFCDDILSPNTNYEVTWYTSWSPCPECAGEV AEFLARHSNVNLTIFTARLYYFWDTDYQEGLRSLSQEGASV EIMGYKDFKYCWENFVYNDDEPFKPWKGLKYNFLFLDSKLQ EILE | 44 |
| MKPHFRNTVERMYRDTFSYNFYNRPILSRRNTVWLCYEVKT KGPSRPPLDAKIFRGQVYSELKYHPEMRFFHWFSKWRKLHR DQEYEVTWYISWSPCTKCTRDMATFLAEDPKVTLTIFVARL YYFWDPDYQEALRSLCQKRDGPRATMKIMNYDEFQHCWSKF VYSQRELFEPWNNLPKYYILLHIMLGEILRHSMDPPTFTFN FNNEPWVRGRHETYLCYEVERMHNDTWVLLNQRRGFLCNQA PHKHGFLEGRHAELCFLDVIPFWKLDLDQDYRVTCFTSWSP CFSCAQEMAKFISKNKHVSLCIFTARIYDDQGRCQEGLRTL AEAGAKISIMTYSEFKHCWDTFVDHQGCPFQPWDGLDEHSQ DLSGRLRAILQNQEN | 45 |
| MALLTAETFRLQFNNKRRLRRPYYPRKALLCYQLTPQNGST PTRGYFENKKKCHAEICFINEIKSMGLDETQCYQVTCYLTW SPCSSCAWELVDFIKAHDHLNLGIFASRLYYHWCKPQQKGL RLLCGSQVPVEVMGFPEFADCWENFVDHEKPLSFNPYKMLE ELDKNSRAIKRRLERIKQS | 46 |

In embodiments, the deaminase is a DNA-specific adenine or adenosine deaminase or adenosine base editor (ABE), or a fragment or variant thereof.

In embodiments, the ABE is generated by replacing APOBEC1 component of BE3 with natural or engineered E. coli TadA, human ADAR2, mouse ADA, or human ADAT2. In embodiments, ABE comprises an evolved TadA variant. In embodiments, the ABE is ABE 1.2 (TadA*-XTEN-nCas9-NLS). In some embodiments, TadA* comprises A106V and D108N mutations. In embodiments, the ABE is a second-generation ABE. In embodiments, the ABE is ABE2.1, which comprises additional mutations D147Y and E155V in TadA* (TadA*2.1). In embodiments, the ABE is ABE2.2, ABE2.1 fused to catalytically inactivated version of human alkyl adenine DNA glycosylase (AAG with E125Q mutation). In embodiments, the ABE is ABE2.3, ABE2.1 fused to catalytically inactivated version of E. coli Endo V (inactivated with D35A mutation). In embodiments, the ABE is ABE2.6 which has a linker twice as long (32 amino acids, (SGGS)₂-XTEN-(SGGS)₂ ("(SGGS)₂" disclosed as SEQ ID NO: 47)) as the linker in ABE2.1. In embodiments, the ABE is ABE2.7, which is ABE2.1 tethered with an additional wild-type TadA monomer. In embodiments, the ABE is ABE2.8, which is ABE2.1 tethered with an additional TadA*2.1 monomer. In embodiments, the ABE is ABE2.9, which is a direct fusion of evolved TadA (TadA*2.1) to the N-terminus of ABE2.1. In embodiments, the ABE is ABE2.10, which is a direct fusion of wild type TadA to the N-terminus of ABE2.1. In embodiments, the ABE is ABE2.11, which is ABE2.9 with an inactivating E59A mutation at the N-terminus of TadA* monomer. In embodiments, the ABE is ABE2.12, which is ABE2.9 with an inactivating E59A mutation in the internal TadA* monomer. In embodiments, the ABE is a third generation ABE. In embodiments, the ABE is ABE3.1, which is ABE2.3 with three additional TadA mutations (L84F, H123Y, and I156F). In embodiments, the ABE is a fourth generation ABE. In embodiments, the ABE is ABE4.3, which is ABE3.1 with an additional TadA mutation A142N (TadA*4.3). In embodiments, the ABE is a fifth generation ABE. In embodiments, the ABE is ABE5.1, which is generated by importing a consensus set of mutations from surviving clones (H36L, R51L, S146C, and K157N) into ABE3.1. In embodiments, the ABE is ABE5.3, which has a heterodimeric construct containing wild-type E. coli TadA fused to an internal evolved TadA*. In embodiments, the ABE is ABE5.2, ABE5.4, ABE5.5, ABE5.6, ABE5.7, ABE5.8, ABE5.9, ABE5.10, ABE5.11, ABE5.12, ABE5.13, or ABE5.14, as shown in Table 6 of U.S. Pat. No. 11,142,760 (herein incorporated herein by reference). In embodiments, the ABE is a sixth generation ABE. In embodiments, the ABE is ABE6.1, ABE6.2, ABE6.3, ABI6.4, ABE6.5, or ABE6.6, as shown in below Table 6 of U.S. Pat. No. 11,142,760 (herein incorporated herein by reference). In embodiments, the ABE is a seventh generation ABE. In embodiments, the ABE is ABE7.1, ABE7.2, ABE7.3, ABE7.4, ABE7.5, ABE7.6, ABE7.7, ABE7.8, ABE 7.9, or ABE7.10, as shown in Table 6 of U.S. Pat. No. 11,142,760 (herein incorporated herein by reference). In embodiments, the base editor is an eighth generation ABE (ABE8). In s embodiments, the ABE8 contains a TadA*8 variant. In embodiments, the ABE8 has a monomeric construct containing a TadA*8 variant (ABE8.x-m).

In embodiments, the DNA-specific adenine or adenosine deaminase is selected from tRNA-specific adenosine deaminase 7.10 (TadA 7.10), tRNA-specific adenosine deaminase 6.3 (TadA 6.3), tRNA-specific adenosine deaminase 7.8 (TadA 7.8), tRNA-specific adenosine deaminase 7.9 (TadA 7.9), and tRNA-specific adenosine deaminase 8e (TadA8e (TadA-8e V106W)) or a fragment or variant thereof. In embodiments, the TadA has an amino acid sequence of one of SEQ ID NO: 48 [TadA 7.10], SEQ ID NO: 49 [TadA 6.3], SEQ ID NO: 50 [TadA 7.8], SEQ ID NO: 51 [TadA 7.9], and SEQ ID NO: 52 [TadA 8e], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the TadA has an amino acid sequence selected from one of SEQ ID NOs: 48-52 as shown in Table 6 below.

TABLE 6

TadA amino acid sequences

| Sequence | SEQ ID NO: |
|---|---|
| SEVEFSHEYWMRHALTLAKRARDEREVPVGAVLVLNNRVIG EGWNRAIGLHDPTAHAEIMALRQGGLVMQNYRLIDATLYVT FEPCVMCAGAMIHSRIGRVVFGVRNAKTGAAGSLMDVLHYP GMNHRVEITEGILADECAALLCYFFRMPRQVFNAQKKAQSS TD | 48 |
| MSEVEFSHEYWMRHALTLAKRAWDEREVPVGAVLVLNNRVI GEGWNRSIGLHDPTAHAEIMALRQGGLVMQNYRLIDATLYV TFEPCVMCAGAMIHSRIGRVVFGVRNAKTGAAGSLMDVLHY PGMNHRVEITEGILADECAALLCYFFRMRRQVFNAQKKAQS STD | 49 |
| MSEVEFSHEYWMRHALTLAKRALDEREVPVGAVLVLNNRVI GEGWNRAIGLHDPTAHAEIMALRQGGLVMQNYRLIDATLYV TFEPCVMCAGAMIHSRIGRVVFGVRNAKTGAAGSLMDVLHY PGMNHRVEITEGILADECNALLCYFFRMRRQVFNAQKKAQS STD | 50 |
| MSEVEFSHEYWMRHALTLAKRALDEREVPVGAVLVLNNRVI GEGWNRAIGLHDPTAHAEIMALRQGGLVMQNYRLIDATLYV TFEPCVMCAGAMIHSRIGRVVFGVRNAKTGAAGSLMDVLHY PGMNHRVEITEGILADECNALLCYFFRMPRQVFNAQKKAQS STD | 51 |
| MSEVEFSHEYWMRHALTLAKRARDEREVPVGAVLVLNNRVI GEGWNRAIGLHDPTAHAEIMALRQGGLVMQNYRLIDATLYV TFEPCVMCAGAMIHSRIGRVVFGVRNSKRGAAGSLMNVLNY PGMNHRVEITEGILADECAALLCDFYRMPRQVFNAQKKAQS SIN | 52 |

In embodiments, the deaminase is a RNA-specific adenine or adenosine deaminase, or a fragment or variant thereof. In embodiments, the RNA-specific adenine or adenosine deaminase is an adenosine deaminases acting on RNA (ADAR) enzyme, or a fragment or variant thereof. In embodiments, the ADAR is selected from ADAR1, ADAR2, and ADAR3, or a fragment or variant thereof. In embodiments, the ADAR has an amino acid sequence of one of SEQ ID NO: 53 [ADAR1] and SEQ ID NO: 54 [ADAR2], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the ADAR has an amino acid sequence of any one of SEQ ID NOs 53-54 as shown in Table 7. In embodiments, and as a non-limiting example, the catalytic deaminase domain of ADAR1 comprises amino acids 833-1226 of SEQ ID NO: 53. As another non-limiting example the catalytic deaminase domain of ADAR2 comprises amino acids 299-701 of SEQ ID NO: 54.

TABLE 7

ADAR amino acid sequences

| Sequence | SEQ ID NO: |
|---|---|
| MNPRQGYSLSGYYTHPFQGYEHRQLRYQQPGPGSSPSSFLLK<br>QIEFLKGQLPEAPVIGKQTPSLPPSLPGLRPRFPVLLASSTR<br>GRQVDIRGVPRGVHLRSQGLQRGFQHPSPRGRSLPQRGVDCL<br>SSHFQELSIYQDQEQRILKFLEELGEGKATTAHDLSGKLGTP<br>KKEINRVLYSLAKKGKLQKEAGTPPLWKIAVSTQAWNQHSGV<br>VRPDGHSQGAPNSDPSLEPEDRNSTSVSEDLLEPFIAVSAQA<br>WNQHSGVVRPDSHSQGSPNSDPGLEPEDSNSTSALEDPLEFL<br>DMAEIKEKICDYLFNVSDSSALNLAKNIGLTKARDINAVLID<br>MERQGDVYRQGTTPPIWHLTDKKRERMQIKRNTNSVPETAPA<br>AIPETKRNAEFLTCNIPTSNASNNMVTTEKVENGQEPVIKLE<br>NRQEARPEPARLKPPVHYNGPSKAGYVDFENGQWATDDIPDD<br>LNSIRAAPGEFRAIMEMPSFYSHGLPRCSPYKKLTECQLKNP<br>ISGLLEYAQFASQTCEFNMIEQSGPPHEPRFKFQVVINGREF<br>PPAEAGSKKVAKQDAAMKAMTILLEEAKAKDSGKSEESSHYS<br>TEKESEKTAESQTPTPSATSFFSGKSPVTTLLECMHKLGNSC<br>EFRLLSKEGPAHEPKFQYCVAVGAQTFPSVSAPSKKVAKQMA<br>AEEAMKALHGEATNSMASDNQPEGMISESLDNLESMMPNKVR<br>KIGELVRYLNTNPVGGLLEYARSHGFAAEFKLVDQSGPPHEP<br>KFVYQAKVGGRWFPAVCAHSKKQGKQEAADAALRVLIGENEK<br>AERMGFTEVTPVTGASLRRTMLLLSRSPEAQPKTLPLTGSTF<br>HDQIAMLSHRCFNTLTNSFQPSLLGRKILAAIIMKKDSEDMG<br>VVVSLGTGNRCVKGDSLSLKGETVNDCHAEIISRRGFIRFLY<br>SELMKYNSQTAKDSIFEPAKGGEKLQIKKTVSFHLYISTAPC<br>GDGALFDKSCSDRAMESTESRHYPVFENPKQGKLRTKVENGE<br>GTIPVESSDIVPTWDGIRLGERLRTMSCSDKILRWNVLGLQG<br>ALLTHFLQPIYLKSVTLGYLFSQGHLTRAICCRVTRDGSAFE<br>DGLRHPFIVNHPKVGRVSIYDSKRQSGKTKETSVNWCLADGY<br>DLEILDGTRGTVDGPRNELSRVSKKNIFLLFKKLCSFRYRRD<br>LLRLSYGEAKKAARDYETAKNYFKKGLKDMGYGNWISKPQEE<br>KNFYLCPV | 53 |
| MDIEDEENMSSSSTDVKENRNLDNVSPKDGSTPGPGEGSQLS<br>NGGGGGPGRKRPLEEGSNGHSKYRLKKRRKTPGPVLPKNALM<br>QLNEIKPGLQYTLLSQTGPVHAPLFVMSVEVNGQVFEGSGPT<br>KKKAKLHAAEKALRSFVQFPNASEAHLAMGRTLSVNTDFTSD<br>QADFPDTLFNGFETPDKAEPPFYVGSNGDDSFSSSGDLSLSA<br>SPVPASLAQPPLPVLPPFPPPSGKNPVMILNELRPGLKYDFL<br>SESGESHAKSFVMSVVVDGQFFEGSGRNKKLAKARAAQSALA<br>AIFNLHLDQTPSRQPIPSEGLQLHLPQVLADAVSRLVLGKFG<br>DLTDNFSSPHARRKVLAGVVMTTGTDVKDAKVISVSTGTKCI<br>NGEYMSDRGLALNDCHAEIISRRSLLRFLYTQLELYLNNKDD<br>QKRSIFQKSERGGFRLKENVQFHLYISTSPCGDARIFSPHEP<br>ILEEPADRHPNRKARGQLRTKIESGEGTIPVRSNASIQTWDG<br>VLQGERLLTMSCSDKIARWNVVGIQGSLLSIFVEPIYFSSII<br>LGSLYHGDHLSRAMYQRISNIEDLPPLYTLNKPLLSGISNAE<br>ARQPGKAPNFSVNWTVGDSAIEVINATTGKDELGRASRLCKH<br>ALYCRWMRVHGKVPSHLLRSKITKPNVYHESKLAAKEYQAAK<br>ARLFTAFIKAGLGAWVEKPTEQDQFSLTP | 54 |

In embodiments, the deaminase further comprises a nuclear localization signal (NLS). Examples of NLSs are provided in Kosugi et al. (*J. Biol. Chem.* (2009) 284:478-485; herein incorporated by reference herein in its entirety). In embodiments, the NLS comprises the consensus sequence K(K/R)X(K/R) (SEQ ID NO: 32). In embodiments, the NLS comprises the consensus sequence (K/R)(K/R)$X_{10-12}$(K/R)$_{3/5}$ (SEQ ID NO: 33), where (K/R)$_{3/5}$ represents at least three of the five amino acids is either lysine or arginine. In embodiments, the NLS comprises the c-myc NLS. In embodiments, the c-myc NLS comprises the sequence PAAKRVKLD (SEQ ID NO: 34). In embodiments, the NLS is the nucleoplasmin NLS. In embodiments, the nucleoplasmin NLS comprises the sequence KRPAATKK-AGQAKKKK (SEQ ID NO: 35). In embodiments, the NLS comprises the SV40 Large T-antigen NLS. In embodiments, the SV40 Large T-antigen NLS comprises the sequence PKiKKRKV (SEQ ID NO: 36). In a particular embodiment, the NLS comprises three SV40 Large T-antigen NLSs (e.g., DPKKKRKVDPKKKRKVDPKKKRKV (SEQ ID NO: 37)). In embodiments, the NLS may comprise mutations/variations in the above sequences such that they contain 1 or more substitutions, additions or deletions (e.g., about 1, or about 2, or about 3, or about 4, or about 5, or about 10 substitutions, additions, or deletions).

In embodiments, the endonuclease further comprises a UGI, or a fragment or variant thereof. In embodiments, the endonuclease (or chimeric protein) comprises 1, or 2, or 3, or UGIs. In embodiments, the endonuclease (or chimeric protein) comprises a UGI at the N- and/or C-terminus. Illustrative UGI proteins for use in the present disclosure include, for example, those published in Wang et al., *J Biol. Chem.* 264:1163-1171(1989); Lundquist et al., *J Biol. Chem.* 272:21408-21419(1997); Ravishankar et al., *Nucleic Acids Res.* 26:4880-4887(1998); and Putnam et al., *J. Mol. Biol.* 287:331-346(1999), each of which is incorporated herein by reference in their entirety.

In embodiments, the RNA molecule is a gRNA. In embodiments, the gRNA comprises a sequence that interacts with the endonuclease. In embodiments, the endonuclease forms a complex with the gRNA.

In embodiments, the composition is suitable for base editing, see, e.g., Rees, H. A., and Liu, D. R. (2018). Base editing: precision chemistry on the genome and transcriptome of living cells. *Nat. Rev. Genet.* 19, 770-788. doi: 10.1038/s41576-018-0059-1, hereby incorporated by reference in its entirety. In embodiments, the composition is suitable for DNA base editing. In embodiments, the composition is suitable for RNA base editing. In embodiments, the composition is suitable for catalyzing C>T nucleotide conversions or A>G nucleotide conversions in a target nucleic acid.

In embodiments, the composition comprises both an adenosine deaminase and a cytidine deaminase.

In embodiments, the composition is suitable for dual base editing, see, e.g., *Nature Biotechnology* volume 38, 856-860 (2020), hereby incorporated by reference in its entirety.

In embodiments, the reverse transcriptase is Moloney murine leukemia virus reverse transcriptase (M-MLV RT) or M-MLV RT(D200N/L603W/T330P/T306K/W313F), or a fragment or variant thereof. In embodiments, the M-MLV RT has an amino acid sequence of SEQ ID NO: 55 [M-MLV RT] or SEQ ID NO 56 [M-MLV RT(D200N/L603W/T330P/T306K/W313F)] or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the Moloney murine leukemia virus reverse transcriptase (M-MLV RT) or M-MLV RT(D200N/L603W/T330P/T306K/W313F) is selected from SEQ ID NO: 55 or SEQ ID NO: 56, as shown in Table 8 below.

TABLE 8

Moloney murine leukemia virus reverse transcriptase sequences

| Sequence | SEQ ID NO: |
|---|---|
| TLNIEDEYRLHETSKEPDVSLGSTWLSDFPQAWAETGGMGLA<br>VRQAPLIIPLKATSTPVSIKQYPMSQEARLGIKPHIQRLLDQ<br>GILVPCQSPWNTPLLPVKKPGTNDYRPVQDLREVNKRVEDIH<br>PTVPNPYNLLSGLPPSHQWYTVLDLKDAFFCLRLHPTSQPLF<br>AFEWRDPEMGISGQLTWTRLPQGFKNSPTLFDEALHRDLADF<br>RIQHPDLILLQYVDDLLLAATSELDCQQGTRALLQTLGNLGY | 55 |

TABLE 8-continued

Moloney murine leukemia virus reverse transcriptase sequences

| Sequence | SEQ ID NO: |
|---|---|
| RASAKKAQICQKQVKYLGYLLKEGQRWLTEARKETVMGQPTP KTPRQLREFLGTAGFCRLWIPGFAEMAAPLYPLTKTGTLFNW GPDQQKAYQEIKQALLTAPALGLPDLTKPFELFVDEKQGYAK GVLTQKLGPWRRPVAYLSKKLDPVAAGWPPCLRMVAAIAVLT KDAGKLTMGQPLVILAPHAVEALVKQPPDRWLSNARMTHYQA LLLDTDRVQFGPVVALNPATLLPLPEEGLQHNCLDILAEAHG TRPDLTDQPLPDADHTWYTDGSSLLQEGQRKAGAAVTTETEV IWAKALPAGTSAQRAELIALTQALKMAEGKKLNVYTDSRYAF ATAHIHGEIYRRRGLLTSEGKEIKNKDEILALLKALFLPKRL SIIHCPGHQKGHSAEARGNRMADQAARKAAITETPDTSTLLI ENSSP | |
| AFPLERPDWDYTTQAGRNHLVHYRQLLLAGLQNAGRSPTNLA KVKGITQGPNESPSAFLERLKEAYRRYTPYDPEDPGQETNVS MSFIWQSAPDIGRKLGRLEDLKSKTLGDLVREAEKIFNKRET PEEREERIRRETEEKEERRRTVDEQKEKERDRRRHREMSKLL ATVVIGQEQDRQEGERKRPQLDKDQCAYCKEKGHWAKDCPKK PRGPRGPRPQTSLLTLGDXGGQGQDPPPEPRITLKVGGQPVT FLVDTGAQHSVLTQNPGPLSDKSAWVQGATGGKRYRWTTDRK VHLATGKVTHSFLHVPDCPYPLLGRDLLTKLKAQIHFEGSGA QVVGPMGQPLQVLTLNIEDEYRLHETSKEPDVSLGFTWLSDF PQAWAESGGMGLAVRQAPLIIPLKATSTPVSIKQYPMSQEAR LGIKPHIQRLLDQGILVPCQSPWNTPLLPVKKPGTNDYRPVQ DLREVNKRVEDIHPTVPNPYNLLSGLPPSHQWYTVLDLKDAF FCLRLHPTSQPLFAFEWRDPEMGISGQLTWTRLPQGFKNSPT LFDEALHRDLADFR | 56 |

In embodiments, the composition further comprises a dominant negative human MutL homolog (MLH1). In embodiments, the composition is suitable for use with a dominant negative MLH1.

In embodiments, the RNA molecule is or comprises a prime editing guide RNA (pegRNA). In embodiments, the endonuclease forms a complex with the pegRNA. In embodiments, the pegRNA serves as a template for transcription of a new DNA sequence. In embodiments, the pegRNA binds to a DNA strand opposite from a typical gRNA binding site. In embodiments, the pegRNA comprises a gRNA containing a primer binding site (PBS) and a reverse transcriptase (RT) template sequence. In embodiments, the RNA molecule is or comprises a gRNA. In embodiments, the gRNA comprises a sequence that interacts with the endonuclease. In embodiments, the endonuclease forms a complex with the gRNA. In embodiments, the composition comprises both a gRNA and a pegRNA.

In embodiments, the composition is suitable for prime editing see, e.g., Nature 576, 149-157 (2019), hereby incorporated by reference in its entirety.

In embodiments, the transposase is selected from Tn1, Tn2, Tn3, Tn5, Tn7, Tn9, Tn10, Tn552, Tn903, Tn1000/Gamma-delta, Tn/O, tnsA, tnsB, tnsC, tniQ, IS10, ISS, IS911, Minos, Sleeping beauty, piggyBac, Tol2, Mos1, Himar1, Hermes, Tol2, Minos, Tel, P-element, MuA, Ty1, Chapaev, transib, Tc1/mariner, and Tc3 donor DNA system.

In embodiments, the transposase is a transposon 7-like (Tn7-like) transposon system, or a fragment or variant thereof. In embodiments, the transposase is one or more of transposon 7 protein A (TnsA), transposon 7 protein B (Tns B), transposon 7 protein C (Tns C), and transposition of integron protein Q (TniQ), or a fragment or variant thereof. In embodiments, the Tn7-like transposon system is derived from *Vibrio cholerae* Tn6677.

In embodiments, the transposase has an amino acid sequence of one or more of SEQ ID NO: 57 [TnsA], SEQ ID NO: 58 [TnsB], SEQ ID NO: 59 [TnsC], and SEQ ID NO: 60 [TniQ], or a fragment or variant thereof, or an amino acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the transposase has an amino acid sequence of one or more of SEQ ID NOs 57-60, as shown in Table 9 below.

TABLE 9

Transposase sequences

| Sequence | SEQ ID NO: |
|---|---|
| MYRRHLKHSRVKNLFKFVSAKMNTVFTVESALEFDTCFHLE YSPSVKFYEAQPEGFYYEFAGRQCPYTPDFRLVDQNDSVSF LEIKPSDKVADPDFLHRFPLKQQRAIELSSPLKLVTEKQIR IDPILGNLKLLHRYSGFQSFTPLHMQLLGLVQKLGRVSLLR LSDSIDAPPEEVLASALSLIARGIMQSDLTVQKIGISSFVW AGGHSGIDHG | 57 |
| MDKHNGGLFEDEFVIPQPSTSTSPIDAIQAVLPATVDSFPY VLKVEALHRRDYILWVEKNLAGGWTEKNLTPLLADAALVLP PPTPNWRTLARWRKIYIQHGRKLVSLIPKHQAKGNARSRLP PSDELFFEQAVHRYLVGEQPSIASAFQLYSDSIRIENLGVV ENSIKTISYMAFYNRIKKLPAYQVMKSRKGSYIADVEFKAI ASHKPPSRIMERVEIDHTPLDLLLLDDDLLVPLGRPSLTLL IDAYSHCVVGFNLNFNQPSYESVRNALLSSISKKDYVKNKY PSIEHEWPCYGKPETLVVDNGVEFWSASLAQSCLELGINIQ YNPVRKPWLKPMIERMFGIINRKLLEPIPGKTFSNIQEKGD YDPQKDAVMRFSTFLEIFHHWVIDVYHYEPDSRYRYIPIIS WQHGNKDAPPAPIIGDDLTKLEVILSLSLHCTHRRGGIQRY HLRYDSDELASYRMNYPDQTRGKRKVLVKLNPRDISYVYVF LEDLGSYIRVPCIDPIGYTKGLSLQEHQINVKLHRDFINEQ MDVVSLSKARIYLNDRIKNELIEVRRNIRQRNVKGVNKIAK YRNVGSHAETSIVHELNHPATNEVISKMESASQPEHCDDWD NFTSGLEPY | 58 |
| MDLSCHDADKLRSFIECYVETPLLRAIQEDFDRLRFNKQFA GEPQCMLLTGDTGTGKSSLIRHYAAKHPEQVRHGFIHKPLL VSRIPSRPTLESTMVELLKDLGQFGSSDRIHKSSAESLTEA LIKCLKRCETELIIIDAFQELIENKTREKRNQIANRLKYIS ETAKIPIVLVGMPWATKIAEEPQWSSRLLIRRSIPYFKLSD DRENFIRLIMGLANRMPFETQARLETKHTIYALFAACYGSL RALKQLLDESVKQALAAHAETLKHEHIAVAYALFYPDQVNP FLQPIDEIKACEVKQYSRYEIDAAGKEEVLNPLQFTDKIPI SQLLKKR | 59 |
| MIEAPDVKPWLFLIKPYEGESLSHFLGRFRRANHLSASGLG TLAGIGAIVARWERFHFNPRPSQQELEAIASVVEVDAQRLA QMLPPAGVGMQHEPIRLCGACYAESPCHRIEWQYKSVWKCD RHQLKILAKCPNCQAPFKMPALWEDGCCHRCRMPFAEMAKL QKV | 60 |

In embodiments, the integrase is a serine-recombinase, or a fragment or variant thereof.

In embodiments, the serine-recombinase is Bxb1, or a fragment or variant thereof. In embodiments, the recombinase is a Gin invertase or Tn3 resolvase, or a fragment or variant thereof.

In embodiments, the nucleic acid-modulating domain or the nucleic acid-modifying domain can increase transcription, e.g. transcriptional activators such as VP16, VP64, VP48, VP160, p65 subdomain (e.g., from NFkB), and the activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

In embodiments, the nucleic acid-modulating domain or the nucleic acid-modifying domain can decrease transcription, e.g. transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In embodiments, the nucleic acid-modulating domain or the nucleic acid-modifying domain has enzymatic activity that modifies a target nucleic acid (e.g., ssRNA, dsRNA, ssDNA, dsDNA). Examples of enzymatic activity that can be provided include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (e.g. plants), ZMET2, CMT1, CMT2 (e.g. plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In embodiments, the nucleic acid-modulating domain or the nucleic acid-modifying domain has debranching activity, including, for example, lariat debranching enzyme or DBR1.

In embodiments, the nucleic acid-modulating domain or the nucleic acid-modifying domain has transesterification activity, including, for example, a relaxase or SpoII.

In embodiments, the nucleic acid-modulating domain or the nucleic acid-modifying domain has activity that modifies a protein associated with a target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by ahistone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity. In embodiments, the nucleic acid-modulating domain or the nucleic acid-modifying domain is one or more effector domains, including proteins and/or enzymes, such that those can cleave RNA (e.g., a PIN endonuclease domain, an NYN domain, an SMR domain from SOT1, or an RNase domain from Staphylococcal nuclease), those that can affect RNA stability (e.g., tristetraprolin (TTP) or domains from UPF1, EXOSC5, and STAU1), those that can edit a nucleotide or ribonucleotide (e.g., a cytidine deaminase, PPR protein, adenosine deaminase, ADAR family protein, or APOBEC family protein), those that can activate translation (e.g., eIF4E and other translation initiation factors, a domain of the yeast poly(A)-binding protein or GLD2), those that can repress translation (e.g., *Pumilio* or FBF PUF proteins, deadenylases, CAF1, Argonaute proteins), those that can methylate RNA (e.g., domains from m6A methyltransferase factors such as METTL14, METTL3, or WTAP), those that can demethylate RNA (e.g., human alkylation repair homolog 5 or Alkbh5), those that can affect splicing (e.g., the RS-rich domain of SRSF1, the Gly-rich domain of hnRNP A1, the alanine-rich motif of RBM4, or the proline-rich motif of DAZAP1), those that can enable affinity purification or immunoprecipitation (e.g., FLAG, HA, biotin, or HALO tags), and those that can enable proximity-based protein labeling and identification (e.g., a biotin ligase (such as BirA) or a peroxidase (such as APEX2) in order to biotinylate proteins that interact with the target RNA). In embodiments, the endonuclease (or chimeric protein) induces exon skipping. In embodiments, the endonuclease (or chimeric protein) induces exon inclusion.

In embodiments, the nucleic acid-modulating domain or the nucleic acid-modifying domain comprises one or more mutations to reduce activity relative to an unmutated form.

In embodiments, the nucleic acid-modulating domain or the nucleic acid-modifying domain comprises one or more mutations to increase activity relative to an unmutated form.

Chimeric Protein Design/Linkers

In embodiments, the sequence of (a) is disposed at the N-terminus of the chimeric protein and the sequence of (b) is disposed at the C-terminus of the chimeric protein.

In embodiments, the sequence of (a) is disposed at the C-terminus of the chimeric protein and the sequence of (b) is disposed at the N-terminus of the chimeric protein.

In embodiments, the composition further comprises a linker that joins the sequence of (a) and the sequence of (b). In embodiments, the linker is between about 4 and about 40 amino acids, or about 10 and about 40 amino acids, or about 20 and about 40 amino acids, or about 30 and about 40 amino acids, or about 4 and about 30 amino acids, or about 4 and about 20 amino acids, or about 4 and about 10 amino acids, or about 5 amino acids, or about 10 amino acids, or about 15 amino acids, or about 20 amino acids, or about 25 amino acids, or about 30 amino acids, or about 35 amino acids, or about 40 amino acids. In embodiments, the linker is substantially comprised of glycine and serine residues. In embodiments, the linker is $(GGS)_n$, wherein $n$ is 1, or 2, or 3, or 4, or 5. In embodiments, the linker is GGSGGSGGSG (SEQ ID NO: 61), GGSGGSGGGGSGGGS (SEQ ID NO: 62), GGGGS (SEQ ID NO: 63), GGS (SEQ ID NO: 64), $(GGGGS)_n$(n=1-4) (SEQ ID NO: 65), $(Gly)_8$ (SEQ ID NO: 66), $(Gly)_6$ (SEQ ID NO: 67), $(EAAAK)_n$(n=1-3) (SEQ ID NO: 68), $A(EAAAK)_nA$ (n=2-5) (SEQ ID NO: 69), AEAAAKEAAAKA (SEQ ID NO: 70), $A(EAAAK)_4ALEA(EAAAK)_4A$ (SEQ ID NO: 71), PAPAP (SEQ ID NO: 72), KESGSVSSEQLAQFRSLD (SEQ ID NO: 73), EGKSSGSGSESKST (SEQ ID NO: 74), and GSAGSAAGSGEF (SEQ ID NO: 75), or a variant thereof, wherein the variant comprises about 1, or about 2, or about 3, or about 4, or about 5 mutations, the mutations selected from substitutions or deletions.

Target Nucleic Acid

In embodiments, the target nucleic acid is referred to as a target sequence. In embodiments, the target nucleic acid is or comprises a sequence of contiguous nucleotides present in a target RNA or target DNA. In embodiments, a stretch of contiguous nucleotides refers to a string of nucleotides that are covalently linked and immediately adjacent to one another. In embodiments, the target nucleic acid is or comprises at least about 4, 5, 6, 7, 8, 9, 10, 11, 12, 13, 14, 15, 16, 17, 18, 19, or 20 nucleotides in length. In embodiments, the target nucleic acid is or comprises less than about 300, 250, 200, 100, 150, or 50 nucleotides in length. In embodiments, the target nucleic acid is or comprises about 5-10, about 5-15, about 5-20, about 10-20, about 10-30, about 10-40, about 10-50, about 10-60, about 10-70, about 10-80, about 10-90, about 10-100, about 50-100, about 50-150, about 50-200, about 50-250, about 50-300, about 100-200, about 100-300, or about 200-300 nucleotides in length.

In embodiments, the target nucleic acid is 10-50 nucleotides in length, e.g., 10-45, 10-40, 10-35, 10-30, 10-20, 11-45, 11-40, 11-35, 11-30, 11-20, 12-45, 12-40, 12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In embodiments, the target nucleic acid is or comprises ssRNA. In embodiments, the target nucleic acid is or comprises dsRNA. In embodiments, the target nucleic acid is or comprises ssDNA. In embodiments, the target nucleic acid is or comprises dsDNA. In embodiments, the target nucleic acid is about 2 to about 6 nucleotides upstream of a PAM sequence.

In embodiments, the target nucleic acid is proximal to an exon. In embodiments, the target nucleic acid is upstream of an exon. In embodiments, the target nucleic acid is downstream of an exon. In embodiments, the target nucleic acid overlaps with an exon.

In embodiments, the target nucleic acid is proximal to an intron. In embodiments, the target nucleic acid is upstream of an intron. In embodiments, the target nucleic acid is downstream of an intron. In embodiments, the target nucleic acid overlaps with an intron.

General Features of the Compositions

In embodiments, the composition further comprises a viral vector. In embodiments, the viral vector is or comprises an AAV. In embodiments, the AAV is or comprises one or more of AAV1, AAV2, AAV3, AAV4, AAV5, AAV6, AAV7, AAV8, AAV9, AAV10, AAV11, AAV12, AAV13, AAV2/1, AAV2/5, AAV2/8, AAV2/9, AAV3/1, AAV3/5, AAV3/8, and AAV3/9. In embodiments, the composition further comprises a non-viral vector.

In embodiments, the present compositions take the form of, or delivery of the present compositions is effected using, a nanoparticle, e.g., any particle having a diameter of less than about 1000 nm. In embodiments, nanoparticles suitable for use in delivering the present compositions to a target cell have a diameter of about 500 nm or less, e.g., from about 25 nm to about 35 nm, from about 35 nm to about 50 nm, from about 50 nm to about 75 nm, from about 75 nm to about 100 nm, from about 100 nm to about 150 nm, from about 150 nm to about 200 nm, from about 200 nm to about 300 nm, from about 300 nm to about 400 nm, or from about 400 nm to about 500 nm. In embodiments, nanoparticles suitable for use in delivering the present compositions to a target cell have a diameter of from about 25 nm to about 200 nm. In embodiments, nanoparticles suitable for use in delivery have a diameter of about 100 nm or less. In embodiments, nanoparticles suitable for use in delivery have a diameter of from about 35 nm to about 60 nm.

In embodiments, the composition further comprises a lipid nanoparticle (LNP) liposomes, lipoplexes or polymeric nanoparticle. In embodiments, the LNP comprises one or more of ionizable lipids, amino lipids, anionic lipids, neutral lipids, amphipathic lipids, helper lipids, structural lipids, PEG lipids, and lipoids.

In embodiments there is provided a particle, e.g., a delivery particle comprising lipid or lipidoid and hydrophilic polymer, e.g., a cationic lipid and a hydrophilic polymer, for instance where the cationic lipid comprises 1,2-dioleoyl-3-trimethylammonium-propane (DOTAP) or 1,2-ditetradecanoyl-sn-glycero-3-phosphocholine (DMPC) and/or where the hydrophilic polymer comprises ethylene glycol or polyethylene glycol (PEG); and/or where the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5).

In embodiments, a liposome is used to deliver a composition of the present disclosure to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

In embodiments, the composition is in the form of a lipoplex. Lipoplexes that utilize cationic lipids have proven utility for gene transfer. Cationic lipids, due to their positive charge, naturally complex with the negatively charged DNA. Also, as a result of their charge, they interact with the cell membrane. Endocytosis of the lipoplex then occurs, and the DNA is released into the cytoplasm. The cationic lipids also protect against degradation of the DNA by the cell.

In embodiments, the composition is in the form of a polyplex. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

In embodiments, the composition is in the form of a dendrimer, a highly branched macromolecule with a spherical shape may be also be used to genetically modify stem cells. The surface of the dendrimer particle may be functionalized to alter its properties. In particular, it is possible to construct a cationic dendrimer (e.g., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In aspects, the present disclosure provides a nucleic acid encoding the endonuclease or chimeric protein of any one of the embodiments and/or aspects disclosed herein. In embodiments, the nucleic acid is or comprises a DNA molecule or an RNA molecule. In embodiments, the RNA is or comprises mRNA or modified mRNA (mmRNA). In embodiments, the DNA is or comprises a vector or plasmid. In embodiments, the nucleic acid comprises a codon optimized sequence. In embodiments, the nucleic acid comprises one or more modifications. In embodiments, the modifications are one or more of base modifications and backbone modifications.

In embodiments, sugar-based particles may be used, for example GalNAc, can be used to deliver a composition of the present disclosure to a target cell.

In aspects, the present disclosure provides a viral vector comprising the nucleic acid of any one of the embodiments and/or aspects disclosed herein. In aspects, the present disclosure provides an expression vector comprising the nucleic acid of any one of the embodiments and/or aspects disclosed herein.

In embodiments, the expression vector is selected from viral expression vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In embodiments, a recombinant expression vector of the present disclosure is a recombinant adeno-associated virus (AAV) vector. In embodiments, a recombinant expression vector of the present disclosure is a recombinant lentivirus vector. In embodiments, a recombinant expression vector of the present disclosure is a recombinant retroviral vector.

In embodiments, the viral vector is or comprises an AAV. In embodiments, the AAV is or comprises one or more of AAV1, AAV2, AAV3, AAV4, AAV5, AAV6, AAV7, AAV8, AAV9, AAV10, AAV11, AAV12, AAV13, AAV2/1, AAV2/5, AAV2/8, AAV2/9, AAV3/1, AAV3/5, AAV3/8, and AAV3/9.

In embodiments, the composition further comprises a VLP, e.g. a structure that in at least one attribute resembles a virus, but which has not been demonstrated to be infectious. In embodiments, the VLP is a nonreplicating, noninfectious viral shell that contains a viral capsid but lacks all or part of the viral genome, in particular, the replicative components of the viral genome. In embodiments, the VLP is composed of one or more viral proteins, such as, but not limited to those proteins referred to as capsid, coat, shell, surface, and structural proteins (e.g., VP1, VP2). In embodiments, the VLP resembles the structure of a bacteriophage, being non-replicative and noninfectious, and lacking at least the gene or genes coding for the replication machinery of the bacteriophage, and also lacking the gene or genes encoding the protein or proteins responsible for viral attachment to or entry into the host. In embodiments, the VLP comprises a polypeptide that promotes or is suitable for VLP delivery, including, without limitation, a retroviral gag polyprotein comprising a matrix polypeptide, a capsid polypeptide, and a nucleocapsid polypeptide (optionally with one or more heterologous protease cleavage sites (e.g. TEV cleavage site, a PreScission (fusion protein of glutathione S-transferase (GST) and human rhinovirus (HRV) type 14 3C protease) cleavage site, a human rhinovirus 3C protease cleavage site, an enterokinase cleavage site, an Epstein-Barr virus protease cleavage site, a cathepsin D cleavage site, and/or a thrombin cleavage site) between one or both of: the matrix polypeptide and the capsid polypeptide; and the capsid polypeptide and the nucleocapsid polypeptide, e.g., a lentiviral gag polyprotein, e.g., a bovine immunodeficiency virus gag polyprotein, a murine leukemia virus (MLV) a gag protein, a simian immunodeficiency virus gag polyprotein, a feline immunodeficiency virus gag polyprotein, a human immunodeficiency virus gag polyprotein, an equine infection anemia virus gag polyprotein, and a caprine arthritis encephalitis virus gag polyprotein or a gag polyprotein of an alpha retrovirus, a beta retrovirus, a gamma retrovirus, a delta retrovirus, an epsilon retrovirus, or a spumavirus. In embodiments, the polypeptide that promotes or is suitable for VLP delivery is co-delivered with a protease to promote cleavage of the chimeric protein. In embodiments, the cleavage of the chimeric protein occurs between the endonuclease and the polypeptide that promotes or is suitable for VLP delivery. In embodiments, the protease is fused to a polypeptide that promotes or is suitable for VLP delivery.

Depending on the host/vector system utilized, in embodiments, any of a number of transcription and/or translation control elements, including constitutive and inducible promoters, transcription enhancer elements, transcription terminators, and the like may be used in the expression vector. In embodiments, a nucleotide sequence encoding a present RNA is operably linked to a control element, e.g., a transcriptional control element, such as a promoter. In embodiments, a nucleotide sequence encoding a present protein, or a present fusion polypeptide is operably linked to a control element, e.g., a transcriptional control element, such as a promoter. In embodiments, the transcriptional control element is a promoter. In embodiments, the promoter is a constitutively active promoter. In embodiments, the promoter is a regulatable promoter. In embodiments, the promoter is an inducible promoter. In embodiments, the promoter is a tissue-specific promoter. In embodiments, the promoter is a cell type-specific promoter. In embodiments, the transcriptional control element (e.g., the promoter) is functional in a targeted cell type or targeted cell population. For example, in embodiments, the transcriptional control element is functional in eukaryotic cells, e.g., hematopoietic stem cells (e.g., mobilized peripheral blood (mPB) CD34(+) cell, bone marrow (BM) CD34(+) cell, and the like). In embodiments, eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art.

In embodiments, a nucleotide sequence encoding a present RNA and/or a present fusion polypeptide is operably linked to an inducible promoter. In embodiments, a nucleotide sequence encoding a present RNA and/or a present chimeric protein is operably linked to a constitutive promoter.

In embodiments, the promoter is derived from viruses and can therefore be referred to as viral promoters, or they are derived from any organism, including prokaryotic or eukaryotic organisms. In embodiments, the promoter is used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter (e.g. is or comprising SEQ ID NO: 76, or a variant thereof) such as the CMV immediate early promoter region (CMVIE), a rous sarcoma virus (RSV) promoter, a human U6 small nuclear promoter (U6) (Miyagishi et-al., Nature Biotechnology 20, 497-500 (2002)), an enhanced U6 promoter (e.g., Xia et al., Nucleic Acids Res. 2003 Sep. 1; 31 (17)), a human H1 promoter (H1), and the like.

In embodiments, a nucleotide sequence encoding a present RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., about 5 Ts) in DNA can act as a terminator for polymerase III (PolIII). Thus, in order to ensure transcription of an RNA in a eukaryotic cell it may be desirable to modify the sequence encoding the RNA to eliminate runs of Ts. In embodiments, a nucleotide sequence encoding a present protein (e.g., a disclosed protein or chimeric protein) is operably linked to a promoter operable in a eukaryotic cell (e.g., a CMV promoter, an EF1α promoter, an estrogen receptor-regulated promoter, and the like).

In embodiments, the inducible promoter includes, but are not limited to, one of T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, and the like. Inducible promoters can therefore be regulated by molecules including, but not limited to, doxycycline; estrogen and/or an estrogen analog; IPTG; and the like. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In embodiments, the promoter is a spatially restricted promoter (e.g., cell type specific promoter, tissue specific promoter, and the like) such that in a multi-cellular organism, the promoter is active (e.g., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In embodiments, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), and the like), tetracycline regulated promoters, (e.g., promoter systems including TetActivators, TetON, TetOFF, and the like), steroid regulated promoters (e.g., rat glucocorticoid receptor promoter systems, human estrogen receptor promoter systems, retinoid promoter systems, thyroid promoter systems, ecdysone promoter systems, mifepristone promoter systems, and the like), metal regulated promoters (e.g., metallothionein promoter systems, and the like), pathogenesis-related regulated promoters (e.g., salicylic acid regulated promoters, ethylene regulated promoters, benzothiadiazole regulated promoters, and the like), temperature regulated promoters (e.g., heat shock inducible promoters (e.g., HSP-70, HSP-90, soybean heat shock promoter, and the like), light regulated promoters, synthetic inducible promoters, and the like.

In embodiments, the vector contains a ribosome binding site for translation initiation and a transcription terminator. In embodiments, the vector includes appropriate sequences for amplifying expression. In embodiments, the vector includes nucleotide sequences encoding protein tags (e.g., 6xHis tag, hemagglutinin tag (e.g., GSGPKKKRKVAAAYPYDVPDYA (SEQ ID NO: 77)), fluorescent protein, and the like) that are fused to the present protein, e.g., at the N- or C-terminus or between the N- or C-terminus, thus resulting in a fusion present polypeptide.

In embodiments, methods of introducing a nucleic acid (e.g., a nucleic acid comprising a donor polynucleotide sequence, one or more nucleic acids encoding a present protein and/or a present RNA, and the like) into a host cell are known in the art, and any convenient method is used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

In embodiments, introducing the recombinant expression vector into cells can occur in any culture media and under any culture conditions that promote the survival of the cells. In embodiments, introducing the recombinant expression vector into a target cell is carried out in vivo or ex vivo. In embodiments, introducing the recombinant expression vector into a target cell is carried out in vitro.

In embodiments, the present protein (e.g., endonuclease, chimeric protein) is provided as a nucleic acid. In embodiments, the present protein (e.g., endonuclease, chimeric protein) is provided as RNA. In embodiments, the present protein (e.g., endonuclease, chimeric protein) is provided as DNA. In embodiments, the RNA is generated by direct chemical synthesis or may be transcribed in vitro from a DNA (e.g., encoding the present protein). Once synthesized, the RNA may be introduced into a cell by any of the well-known techniques for introducing nucleic acids into cells (e.g., microinjection, electroporation, transfection, and the like).

Methods of introducing a nucleic acid into a host cell are known in the art, and any convenient method can be used to introduce a present composition into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like.

In embodiments, nucleic acids may be provided to the cells using well-developed transfection techniques; see, e.g., Angel and Yanik (2010) PLoS ONE 5(7): e11756, and the commercially available TRANSMESSENGER reagents from Qiagen, STEMFECT RNA Transfection Kit from Stemgent, and TRANSIT-mRNA Transfection Kit from Mirus Bio LLC. See also Beumer et al. (2008) PNAS 105(50):19821-19826.

In aspects, the present disclosure provides a lipid nanoparticle comprising the nucleic acid of any one of the embodiments and/or aspects disclosed herein.

In aspects, the present disclosure provides a cell comprising a nucleic acid of any one of the embodiments and/or aspects disclosed herein, the viral vector of any one of the embodiments and/or aspects disclosed herein, or the lipid nanoparticle of any one of the embodiments and/or aspects disclosed herein.

In embodiments, the cell is a prokaryotic cell. In embodiments, the cell is a eukaryotic cell. In embodiments, the cell is a mammalian cell. In embodiments, the cell is a human cell. In embodiments, the cell is an immortalized cell. In embodiments, the cell is harvested from a subject.

In embodiments, the cell derived from the subject is derived from a biological sample. In embodiments, biological sample comprises a biopsy, tissue or bodily fluid. In embodiments, the biological sample comprises one or more of tumor cells, cultured cells, stem cells, and differentiated cells. In embodiments, biological sample refers to a sample obtained or derived from a source of interest (e.g., a cell), as described herein. In embodiments, a source of interest comprises an organism, such as an animal or human. In embodiments, a biological sample is a biological tissue or fluid. Non-limiting examples of biological samples include bone marrow, blood, blood cells, ascites, (tissue or fine needle) biopsy samples, cell-containing body fluids, free floating nucleic acids, sputum, saliva, urine, cerebrospinal fluid, peritoneal fluid, pleural fluid, feces, lymph, gynecological fluids, swabs (e.g., skin swabs, vaginal swabs, oral swabs, and nasal swabs), washings or lavages such as a ductal lavages or broncheoalveolar lavages, aspirates, scrapings, specimens (e.g., bone marrow specimens, tissue biopsy specimens, and surgical specimens), feces, other body fluids, secretions, and/or excretions, and cells therefrom, and the like.

In embodiments, the present disclosure provides a modified cell comprising a composition of the present disclosure. In embodiments, the present disclosure provides a modified cell comprising a composition of the present disclosure, where the modified cell is a cell that does not normally comprise a composition of the present disclosure. In embodiments, the present disclosure provides a modified cell (e.g., a genetically modified cell) comprising nucleic acid comprising a nucleotide sequence encoding a composition of the present disclosure. In embodiments, there is provided a genetically modified cell that is genetically modified with an mRNA comprising a nucleotide sequence encoding a composition of the present disclosure. In embodiments, there is provided a genetically modified cell that is genetically modified with a recombinant expression vector comprising a composition of the present disclosure.

In embodiments, the cells are primary cells; cancer cells; animal cells; plant cells; algal cells; fungal cells; and the like. In embodiments, a cell that serves as a recipient for a composition of the present disclosure is referred to as a "host cell" or a "target cell." In embodiments, the host cell or a target cell can be a recipient of a composition or system of the present disclosure. A host cell or a target cell can be a recipient of a RNP of the present disclosure. A host cell or a target cell can be a recipient of a single component of a k system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, angiosperms, ferns, clubmosses, hornworts, liverworts, mosses, dicotyledons, monocotyledons, and the like), an algal cell, (e.g., *Botryococcus braunii, Chlamydomonas reinhardtii, Nannochloropsis gaditana, Chlorella pyrenoidosa, Sargassum patens*, C. agardh, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, and the like), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); and the like), and the like. In embodiments, the cell is a cell that does not originate from a natural organism (e.g., the cell can be a synthetically made cell; also referred to as an artificial cell).

In embodiments, the cell is an in vitro cell (e.g., established cultured cell line). A cell can be an ex vivo cell (cultured cell from an individual). In embodiments, the cell is in vivo cell (e.g., a cell in an individual). In embodiments, the cell is an isolated cell. In embodiments, the cell is a cell inside of an organism. In embodiments, the cell is an organism. In embodiments, the cell is a cell in a cell culture (e.g., in vitro cell culture). In embodiments, the cell is cell in a collection of cells. In embodiments, the cell is a prokaryotic cell or derived from a prokaryotic cell. cell culture (e.g., in vitro cell culture). In embodiments, the cell is cell in a collection of cells. In embodiments, the cell is a bacterial cell or can be derived from a bacterial cell. In embodiments, the cell is an archaeal cell or derived from an archaeal cell. In embodiments, the cell is an eukaryotic cell or derived from a eukaryotic cell. In embodiments, the cell is a plant cell or derived from a plant cell. In embodiments, the cell is an animal cell or derived from an animal cell. In embodiments, the cell is an invertebrate cell or derived from an invertebrate cell. In embodiments, the cell is a vertebrate cell or derived from a vertebrate cell. In embodiments, the cell is a mammalian cell or derived from a mammalian cell. In embodiments, the cell is a rodent cell or derived from a rodent cell. In embodiments, the cell is a human cell or derived from a human cell. In embodiments, the cell is a microbe cell or derived from a microbe cell. In embodiments, the cell is a fungal cell or derived from a fungal cell. In embodiments, the cell is an insect cell. In embodiments, the cell is an arthropod cell. In embodiments, the cell is a protozoan cell.

In embodiments, the suitable cells include a stem cell (e.g., an embryonic stem (ES) cell, an induced pluripotent stem (iPS) cell; a germ cell (e.g., an oocyte, a sperm, an oogonia, a spermatogonia, and the like); a somatic cell, e.g., a fibroblast, an oligodendrocyte, a glial cell, a hematopoietic cell, a neuron, a muscle cell, a bone cell, a hepatocyte, a pancreatic cell, and the like.

In embodiments, the suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and postnatal stem cells.

In embodiments, the cell is an immune cell, a neuron, an epithelial cell, and endothelial cell, or a stem cell. In embodiments, the immune cell is a T cell, a B cell, a monocyte, a natural killer cell, a dendritic cell, or a macrophage. In embodiments, the immune cell is a cytotoxic T cell. In embodiments, the immune cell is a helper T cell. In embodiments, the immune cell is a regulatory T cell (Treg).

In embodiments, the cell is a stem cell. Stem cells include adult stem cells. Adult stem cells are also referred to as somatic stem cells. Adult stem cells are resident in differentiated tissue but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like. Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In embodiments, the stem cell is a human stem cell. In embodiments, the stem cell is a rodent (e.g., a mouse; a rat) stem cell. In embodiments, the stem cell is a non-human primate stem cell.

In embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

In embodiments, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, Chinese artichoke (crosnes), Chinese cabbage, Chinese celery, Chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (Chinese mustard), gailon, galanga (siam, Thai ginger), garlic, ginger root, gobo, greens, Hanover salad greens, huauzontle, Jerusalem artichokes, jicama, kale greens, kohlrabi, lamb's quarters (quilete), lettuce (bibb), lettuce (Boston), lettuce (Boston red), lettuce (green leaf), lettuce (iceberg), lettuc— (lolla rossa), lettuce (oa—leaf-green), lettuce (oak leaf-red), lettuce (processed), lettuce (red leaf), lettuce (romaine), lettuce (ruby romaine), lettuce (Russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicomia (sea bean), sinqua (angled/ridged luffa), spinach, squash, straw bales, sugarcane, sweet potatoes, Swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

In embodiments, the cell is an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera*.

In embodiments, the cell is an insect cell. For example, in embodiments, the cell is a cell of a mosquito, a grasshopper, a true bug, a fly, a flea, a bee, a wasp, an ant, a louse, a moth, or a beetle.

In aspects, the present disclosure provides a pharmaceutical composition comprising the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, or the cell of any one of the embodiments and/or aspects disclosed herein, and a pharmaceutically acceptable carrier.

The compositions described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis, or tris-(2-hydroxyethyl)amine, 2-hydroxy-tert-butylamine, or tris-(hydroxymethyl)methylamine, N,N-dilower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In embodiments, the compositions described herein are in the form of a pharmaceutically acceptable salt.

In various embodiments, the present invention pertains to pharmaceutical compositions comprising the compositions described herein and a pharmaceutically acceptable carrier or excipient. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In embodiments, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 144$^7$-1676 (Alfonso R. Gennaro eds., 19th ed. 1995), incorporated herein by reference. The present $^{in}$vention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In embodiments, the composition is in the form of a capsule. In another embodiment, the composition is in the form of a tablet. In embodiments, the pharmaceutical composition is formulated in the form of a soft-gel capsule. In a further embodiment, the pharmaceutical composition is formulated in the form of a gelatin capsule. In embodiments, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In embodiments, the administration is by parenteral injection. The mode of administration can be left to the discretion of the practitioner and depends in-part upon the site of the medical condition. In most instances, administration results in the release of any agent described herein into the bloodstream.

In embodiments, the compositions described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any compositions described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In embodiments, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage and should be preserved against microorganisms. The carrier can be a solvent or dispersion medium containing, for example, water, ethanol, polyol (for example, glycerol, propylene glycol, and liquid polyethelene glycol), and suitable mixtures thereof.

The compositions provided herein, alone or in combination with other suitable components, can be made into aerosol formulations (e.g., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release, supra*, vol. 2, pp. 115-138 (1984)). Other controlled-release systems discussed in the review by Langer, 1990, *Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Trans-Splicing System

In embodiments, there is provided a trans-splicing system comprising the compositions or systems of the present disclosure.

In embodiments, the trans-splicing system comprises a splice donor and a splice acceptor. In embodiments, the trans-splicing system comprises a splice donor, a splice acceptor, and the trans-splicing system is suitable for replacing an internal exon in a gene.

In embodiments, the trans-splicing system comprises a repair template comprising a splice donor and/or a splice acceptor. In embodiments, the trans-splicing system comprises a repair template comprising a splice donor and a splice acceptor. In embodiments, the trans-splicing system comprises a repair template comprising a splice donor and a splice acceptor, and the trans-splicing system and/or repair template is suitable for replacing an internal exon in a gene. In embodiments, there is provided a method of trans-splicing an exon in a target nucleic acid, e.g. a pre-mRNA in a cell, the method comprising contacting the cell with the trans-splicing system disclosed herein, wherein the trans-splicing system comprises a repair template comprising a splice donor and a splice acceptor. In embodiments, the present disclosure provides a method of trans-splicing an exon in a target nucleic acid, e.g. a pre-mRNA in a cell in a subject in need thereof, comprising administering an effective amount of the trans-splicing system disclosed herein, wherein the trans-splicing system comprises a repair template comprising a splice donor and a splice acceptor.

In embodiments, the trans-splicing system further comprises a repair template lacking a splice donor and/or a splice acceptor. In embodiments, the trans-splicing system is suitable for splicing of a target nucleic acid comprising a splice donor or a splice acceptor site. In embodiments, the trans-splicing system comprises an RNA molecule, e.g. gRNA that targets a splice acceptor site. In embodiments, the trans-splicing system comprises an RNA molecule, e.g. gRNA that targets a splice donor site. In embodiments, the trans-splicing system comprises is regulated or regulatable by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and auxin. In embodiments, the pre-mRNA is at an intron-exon junction or exon-intron junctions.

In embodiments, the trans-splicing system comprises a pre-trans-splicing (PTS) molecule, wherein the PTS molecule comprises: i) one or more guideRNAs (gRNAs) that target a pre-mRNA; ii) an intronic sequence having a splice signal; and iii) a donor sequence encoding a gene product of a gene of interest, or portion thereof. In embodiments, the gRNA or gRNAs are within the PTS and processed by the endonuclease. In embodiments, the gRNA or gRNAs are within the PTS and are not processed by the endonuclease. In embodiments, the gRNA or gRNAs are not within the PTS. In embodiments, the PTS is the repRNA.

In embodiments, the trans-splicing system comprises a repair RNA (repRNA) sequence, comprising: (a) one or more exons and/or introns; (b) a splice donor and/or splice acceptor, wherein the repRNA is suitable for trans-splicing. In embodiments, the trans-splicing system comprises a system for trans-splicing a target nucleic acid comprising a repRNA, the repRNA comprising: (a) one or more exons and/or introns; and (b) a splice donor and/or splice acceptor. In embodiments, the repRNA comprises one or more binding motifs that direct, and/or hybridizes, the repRNA to a target nucleic acid molecule. In embodiments, the repRNA further comprises a guide RNA (gRNA). In embodiments, the gRNA hybridizes to the target nucleic acid molecule. In embodiments, the gRNA directs the repRNA to a target nucleic acid molecule.

In embodiments, the repRNA is operably linked to one or more sequences that are antisense to the target nucleic acid molecule. In embodiments, the repRNA is provided in cis to one or more sequences that bind to, and/or hybridize to, the target nucleic acid molecule. In embodiments, the repRNA is not operably linked to one or more sequences that bind to, and/or hybridize to, the target nucleic acid molecule. In embodiments, the repRNA is provided in trans to one or more sequences that bind to, and/or hybridize to, the target nucleic acid molecule. In embodiments, the repRNA is operably linked to one or more sequences that bind to, and/or hybridize to, an RNA-binding polypeptide. In embodiments, the repRNA is provided in cis to one or more sequences that bind to, and/or hybridize to, a RNA-binding polypeptide.

In embodiments, the repRNA is not operably to one or more sequences that bind to, and/or hybridize to, a RNA-binding polypeptide, which is herein described as a "grepRNA".

In embodiments, the grepRNA comprises a repair RNA and a gRNA. In embodiments, "grepRNA" is used interchangeably with "PTS".

In embodiments, there is provided a method of trans-splicing a target nucleic acid, e.g. a pre-mRNA in a cell, the method comprising contacting the cell with the trans-splicing system disclosed herein, wherein the trans-splicing system is substantially devoid of an RNA binding protein. In embodiments the present disclosure provides a method of trans-splicing a target nucleic acid, e.g. a pre-mRNA in a cell in a subject in need thereof, comprising administering an effective amount of the trans-splicing system disclosed herein, wherein the trans-splicing system is substantially devoid of an RNA binding protein.

In embodiments, there is provided a method of trans-splicing a target nucleic acid, e.g. a pre-mRNA in a cell, the method comprising contacting the cell with the trans-splicing system disclosed herein, wherein the trans-splicing system comprises a repair template operably linked to a guideRNA. In embodiments the present disclosure provides a method of trans-splicing a target nucleic acid, e.g. a pre-mRNA in a cell in a subject in need thereof, comprising administering an effective amount of the trans-splicing system disclosed herein, wherein the trans-splicing system comprises a repair template operably linked to a guideRNA and the trans-splicing system is substantially devoid of an RNA binding protein.

In embodiments, there is provided a method of trans-splicing a target nucleic acid, e.g. a pre-mRNA in a cell, the method comprising contacting the cell with the trans-splicing system disclosed herein, wherein the trans-splicing system comprises a repair template operably linked to a guideRNA. In embodiments the present disclosure provides a method of trans-splicing a target nucleic acid, e.g. a pre-mRNA in a cell in a subject in need thereof, comprising administering an effective amount of the trans-splicing system disclosed herein, wherein the trans-splicing system comprises a repair template operably linked to a guideRNA and the trans-splicing system is substantially devoid of an RNA binding protein.

In embodiments, the endonuclease is fused to a nucleic acid-interacting domain (e.g. MCP) and the PTS is tethered by the nuclease by interacting with the nucleic acid-interacting domain. In embodiments, one or more gRNAs hybridize to one or more pre-mRNAs. In embodiments, the endonuclease is catalytically active. In embodiments the endonuclease is catalytically inactive. In embodiments the endonuclease (or chimera) is delivered to a cell with viral methods. In embodiments the endonuclease (or chimera), and gRNA(s) or PTS are delivered or deliverable with viral methods. In embodiments the endonuclease (or chimera), gRNA(s), and PTS are delivered or deliverable with viral methods. In embodiments the endonuclease (or chimera) is delivered or deliverable to a cell with non-viral methods. In embodiments the endonuclease (or chimera), and gRNA(s) or PTS are delivered or deliverable with non-viral methods. In embodiments the endonuclease (or chimera), gRNA(s), and PTS are delivered or deliverable with non-viral methods. In embodiments, the endonuclease (or chimera) is delivered or deliverable to a cell implicated in disease. In embodiments, the endonuclease (or chimera) mediates trans-splicing of a pre-mRNA implicated in disease.

In embodiments, the system for targeting a nucleic acid for trans-splicing comprises an endonuclease disclosed herein (e.g., SEQ ID NO: 1, SEQ ID NO: 2, SEQ ID NO: 3, and SEQ ID NO: 4, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, or fragments or variants thereof), linked, associated, and/or fused to an RNA binding protein (RBP) selected from an MS binding protein, MS2 (MCP), PP7 coat protein, PRR1, HgaII, a Qbeta coat protein, the IN protein, or M protein.

In embodiments, the system for targeting a nucleic acid for trans-splicing comprises dPspCas13b linked, associated, and/or fused to an RBP. In embodiments, the system for targeting a nucleic acid for trans-splicing comprises dPspCas13b fused to MS2 ("dPspCas13b-MS2"). In embodiments, the system for targeting a nucleic acid for trans-splicing comprises dPspCas13b fused to PP7 ("dPspCas13b-PP7"). In embodiments, the system for targeting a nucleic acid for trans-splicing comprises dPspCas13b linked, associated, and/or fused to one or more of MS2, PRR1, M protein, HgaII, or a Qbeta hairpin and Qbeta coat protein ("QB"). In embodiments, the system for targeting a nucleic acid for trans-splicing comprises an inactive Cas13K2F endonuclease fused to an RBP. In embodiments, the system for targeting a nucleic acid for trans-splicing comprises an inactive Cas13K2F endonuclease fused to MS2 ("dCas13K2F-MS2"). In embodiments, the system for targeting a nucleic acid for trans-splicing comprises an inactive Cas13K2F endonuclease fused to PP7 ("dCas13K2F-PP7").

In embodiments, the system for targeting a nucleic acid for trans-splicing comprises a second target comprising a splice donor sequence, an intron sequence, a splice acceptor sequence, and an exon sequence. In embodiments, the system for targeting a nucleic acid for trans-splicing comprises a trans-splicing template comprising a splice donor and/or splice acceptor, and an RNA sequence that binds to the specific RNA-binding polypeptide. In embodiments, the trans-splicing template comprises two MS2 stem loops.

In embodiments, disclosed herein is a system for targeting a nucleic acid for trans-splicing, the system comprising: (a) an endonuclease of any one the embodiments disclosed herein, and optionally an RNA molecule comprising a sequence complementary to one strand of a target nucleic acid molecule; (b) an RNA-binding polypeptide that associates with the endonuclease; and (c) a trans-splicing nucleic acid template comprising: (i) a splice donor and/or splice acceptor, and (ii) an RNA sequence that binds to the RNA-binding polypeptide. In embodiments, the RNA molecule is a gRNA.

In embodiments, the endonuclease is linked, associated, and/or fused with the RNA binding protein. In embodiments, the RNA binding protein is a viral protein. In embodiments, the RNA binding protein is an MS binding protein. In embodiments, the RNA binding protein is a PP7 coat protein. In embodiments, the RNA binding protein is PRR1. In embodiments, the RNA binding protein is HgaII. In embodiments, the RNA binding protein is a Qbeta coat protein. In embodiments, the RNA binding protein is the IN protein. In embodiments, the RNA binding protein is the M protein.

In embodiments, disclosed herein is a method for targeted trans-splicing of a pre-mRNA in a cell, comprising contacting the cell with the system of any one of the embodiments disclosed herein.

In embodiments, disclosed herein is a system for targeting a nucleic acid for trans-splicing, the system comprising: (a) dPspCas13b and optionally an RNA molecule comprising a sequence complementary to one strand of a target nucleic acid molecule; (b) an RNA-binding polypeptide that associates with the endonuclease, the RNA-binding polypeptide being selected from one or more of PP7, M, PRR1, HgaII, or Qbeta coat protein; and (c) a trans-splicing nucleic acid template comprising: (i) a splice donor and/or splice acceptor, and (ii) an RNA sequence that binds to the RNA-binding polypeptide.

In embodiments, the RNA molecule is a gRNA.

In embodiments, the endonuclease is linked, associated, and/or fused with the RNA binding protein.

In embodiments, disclosed herein is a method for targeted trans-splicing of a pre-mRNA in a cell, comprising contacting the cell with the system of any one of the embodiments disclosed herein.

RNA Molecules

In embodiments, the RNA molecule binds to or interacts with the present endonuclease.

In embodiments, the RNA molecule binds to or interacts with the present chimeric protein.

In embodiments, the RNA molecule binds to or interacts with the present target nucleic acid.

In embodiments, the RNA molecule is or comprises a guide ribonucleic structure configured to form a complex with the endonuclease.

In embodiments, the guide ribonucleic structure (i) comprises (a) a CRISPR RNA (crRNA) suitable for hybridizing to a target nucleic acid molecule and/or (b) a transactivating CRISPR RNA (tracrRNA) suitable for interacting with the endonuclease or (ii) lacks a (a) a crRNA suitable for hybridizing to a target nucleic acid molecule and/or (b) a tracrRNA suitable for interacting with the endonuclease.

In embodiments, the RNA molecule is or comprises a gRNA. In embodiments, the gRNA comprises a sequence that interacts with the endonuclease. In embodiments, the endonuclease forms a complex with the gRNA.

In embodiments, the RNA molecule contains a repeat and spacer. In embodiments, the RNA has a repeat before a spacer. In embodiments the RNA has a spacer before a repeat. In embodiments the RNA has a repeat before a spacer before a repeat. In embodiments, the RNA has multiple spacers separated by multiple repeats. In embodiments, the RNA has multiple gRNAs. In embodiments, the RNA has multiple gRNAs and is cleaved or processed to separate the gRNAs. In embodiments, the RNA has spacers that target different nucleic acid targets. In embodiments, the RNA has spacers that target the same nucleic acid target.

In embodiments, the endonuclease repeat sequences to formulate the guide RNA are selected from Table 3 below.

TABLE 3

Endonuclease repeat sequences to formulate the guide RNA

| Sequence | SEQ ID NO: |
|---|---|
| GTTAGAATATAACCCTGTTTGTAGGGGTAATAAAAC | 28 |
| GTTAGAATATAACCCTGTTTGTAGGGGTAATAAAAC | 29 |
| GTTGGAATATAACCCCGTTTGTAGGGGTAATAAAAC | 30 |
| GTTAGAATATAACCCTGTTTGTAGGGGTAATAAAAC | 31 |
| GTTAGAATATACCCCATTTTGTATGGGGATTAAAAC | 90 |
| GTTGGAATATAGCCCTGTTTGTAGGGGTAATAAAAC | 91 |
| GATGGAATATAACCCCGTTTGTAGGGGTAATAAAAC | 92 |
| AGTAGAATATAACCCTGATATTAGTAGGGGTAATAAAAC | 93 |
| AGTAGAATATAACCCTGTTAGTAGGGGTAATAAAAC | 94 |
| TATTGACTATACCCCTGATTTGTAGGGGTAAAAGAGA | 95 |
| TATTGACTATACCCCTGATTTGTAGGGGTAAAAAAAC | 96 |
| GTCAGACTATACCCTCGTTTGTAGGGGGAATAAAAC | 97 |

In embodiments, the guide RNA is or comprises a sequence of SEQ ID NOs: 28-31, and/or SEQ ID NOs: 90-97, or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 28 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 29 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 30 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 31 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 90 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 91 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 92 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 93 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 94 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 95 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 96 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto. In embodiments, the guide RNA is or comprises a sequence of SEQ ID NO: 97 or a fragment or variant thereof, or a nucleic acid sequence having at least about 70%, or at least about 75%, or at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identity thereto.

In embodiments, the endonuclease is a polypeptide of one of SEQ ID NOs: 1-4, and/or SEQ ID NOs: 80-89, or a fragment or a variant thereof, or a nucleic acid polypeptide of one of SEQ ID NOs: 1-4, and/or SEQ ID NOs: 80-89, or a fragment or variant thereof. In embodiments, the endonuclease is guided to a target nucleic acid using a guide RNA selected from SEQ ID NOs: 28-31, and/or SEQ ID NOs: 90-97, or a fragment or variant thereof, and/or the endonuclease is associated with a guide RNA selected from SEQ ID NOs: 28-31, and/or SEQ ID NOs: 90-97, or a fragment or variant thereof.

In embodiments, the endonuclease is SEQ ID NO: 1, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 2, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 3, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 4, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 80, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 81, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 82, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 83, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 84, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 85, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 86, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 87, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 88, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 89, or a fragment or variant thereof, and the guide RNA is selected from SEQ ID NO: 28, SEQ ID NO: 29, SEQ ID NO: 30, or SEQ ID NO: 31, SEQ ID NO: 90, SEQ ID NO: 91, SEQ ID NO: 92, SEQ ID NO: 93, SEQ ID NO: 94, SEQ ID NO: 95, SEQ ID NO: 96, or SEQ ID NO: 97, or a fragment or variant thereof.

In embodiments, the endonuclease is SEQ ID NO: 1, or a fragment or variant thereof, and the guide RNA is SEQ ID NO: 28.

In embodiments, the endonuclease is SEQ ID NO: 2, or a fragment or variant thereof, and the guide RNA is SEQ ID NO: 29.

In embodiments, the endonuclease is SEQ ID NO: 3, or a fragment or variant thereof, and the guide RNA is SEQ ID NO: 30.

In embodiments, the endonuclease is SEQ ID NO: 4, or a fragment or variant thereof, and the guide RNA is SEQ ID NO: 31.

In embodiments, the endonuclease is SEQ ID NO: 80, or a fragment or variant thereof, and the guide RNA is SEQ ID NO: 90.

In embodiments, the endonuclease is SEQ ID NO: 81, or a fragment or variant thereof, and the guide RNA is SEQ ID NO: 90

In embodiments, the endonuclease is SEQ ID NO: 82, or a fragment or variant thereof, and the guide RNA is SEQ ID NO: 90.

In embodiments, the endonuclease is SEQ ID NO: 83, or a fragment or variant thereof, and the guide RNA is SEQ ID NO: 91.

In embodiments, the endonuclease is SEQ ID NO: 84, or a fragment or variant thereof, and the guide RNA is SEQ ID NO: 92.

In embodiments, the endonuclease is SEQ ID NO: 85, or a fragment or variant thereof, and the guide RNA is SEQ ID NO: 93, or SEQ ID NO: 94.

In embodiments, the endonuclease is SEQ ID NO: 86, or a fragment or variant thereof, and the guide RNA is SEQ ID NO: 28.

In embodiments, the endonuclease is SEQ ID NO: 87, or a fragment or variant thereof, and the guide RNA is SEQ ID NO: 28.

In embodiments, the endonuclease is SEQ ID NO: 88, or a fragment or variant thereof, and the guide RNA is SEQ ID NO: 95, or SEQ ID NO: 96.

In embodiments, the endonuclease is SEQ ID NO: 89, or a fragment or variant thereof, and the guide RNA is SEQ ID NO: 97.

In embodiments, the RNA molecule is or comprises at least about 4, 5, 6, 7, 8, 9, 10, 11, 12, 13, 14, 15, 16, 17, 18, 19, or 20 nucleotides in length. In embodiments, the RNA molecule is or comprises less than about 300, 250, 200, 100, 150, or 50 nucleotides in length. In embodiments, the RNA molecule is or comprises about 5-10, about 5-15, about 5-20, about 10-20, about 10-30, about 10-40, about 10-50, about 10-60, about 10-70, about 10-80, about 10-90, about 10-100, about 50-100, about 50-150, about 50-200, about 50-250, about 50-300, about 100-200, about 100-300, or about 200-300 nucleotides in length.

In embodiments, the RNA molecule is 10-50 nucleotides in length, e.g., 10-45, 10-40, 10-35, 10-30,10-20, 11-45, 11-40, 11-35, 11-30,11-20, 12-45, 12-40,12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In embodiments, the present disclosure provides a composition comprising a nucleic acid encoding an endonuclease comprising a sequence, optionally comprising a HEPN domain, or a fragment or variant thereof, in conjunction with an RNA containing a repeat having at least about 70% identity to one or more of SEQ ID NOs: 28-31, and/or SEQ ID NOs: 90-97. In embodiments, the composition has least about 75%, or at least about 80%, or at least about 85%, or at least about 90%, or at least about 91%, or at least about 92%, or at least about 93%, or at least about 94%, or at least about 95%, or at least about 96%%, or at least about 97%, or at least about 98%, or at least about 99%) identity to SEQ ID NOs: 28-31, and/or SEQ ID NOs: 90-97, or has about 1 to about 20 nucleotide modifications (e.g. about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20 modifications). In embodiments, the sequence comprises at least one HEPN domain, or fragments or variants thereof. In embodiments, the sequence comprises at least two HEPN domains, or fragments or variants thereof.

Nucleic Acid Modifications

In embodiments, a nucleic acid disclosed herein has one or more modifications, e.g., a base modification, a backbone modification, and the like, to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the ph'sphate'roup can b' linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linka'e or'ackbone of RNA and DNA is a 3' to 5' phosphodiester linkage.

In embodiments, a suitable nucleic acid modificatio' include, but are not limited to' 2'O methyl modified nucleotides, 2' Fluoro modified nucleotides, locked nucleic acid (LNA) modified nucleotides, peptide nucleic acid (PNA) modified nucleotides, nucleotides wit' phosphorothioate linkages, and a 5' cap (e.g., a 7-methylguanylate cap (m7G)). A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be'directly synthesized that contain 2'-O-Methyl RNA. Without wishing to be bound by theory, this modification increases Tm of RNA:RNA duplexes but results in only small changes in RNA:DNA stability. It is stabile with respect to attack by single-stranded ribonucleases and is typically about 5 to about 10-fold le's susceptible to DNases than DNA. 2' 'luoro modified nucleotides (e.g., 2' Fluoro bases) have a fluorine modified ribolhich increases binding affinity (Tm) and also confers some relative nuclease resistance when compared to native RNA. LNA bases have a modification to the ribos' backbone that locks the base in the C3'-endo position, which favors RNA A-type helix duplex geometry. Without wishing to be bound by theory, this modification significantly increases Tm and is also very nuclease resistant. Multiple LNA insertions can be placed 'n an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In embodiments, the number of LNAs incorporated into a single oligo is 10 bases or less. The phosphorothioate (PS) bond (e.g., a phosphorothioate linkage) substitutes a sulfur atom for a non-bridging oxygen in the phosphate backbone of a nucleic acid (e.g., an oligo). Without wishing to be bound by theory, this modification renders the internucleotide linkage resistant to nuclease degradation. Phosphorothioate bonds can be introduced b'tween 'he last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

Modified Backbones and Modified Internucleoside Linkages

In embodiments, the present nucleic acids, optionally containing modifications, include nucleic acids containing modified backbones or non-natural internucleoside linkages. In embodiments, nucleic acids having modified backbones include those that retain a phosphorus atom in the backbone and those that do not have a phosphorus atom in the backbone.

In embodiments, oligonucleotide backbones containing a phosphorus atom therein include, for example, phosphorothioates, chiral phosphorothioates, phosphorodithioates, phosphotriesters, aminoalkylphosphotriesters, methyl 'nd other alkyl phosphonat's including 3'-alkylene phosphonates, 5'-alkylene phosphonates and chiral phosphonates, ph'sphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranoph'sp'ates having normal 3'-5' linkages, 2'-5' linked analogs of these, and those having inverted polarity wherein one' or mo'e i'ternu'leoti'e lin'ages is a 3' to 3', 5' to 5' or 2' to 2' linkage. Suitable oligonucleotides havi'g inv'rted polarity com'rise a single 3' to 3' linkage at the 3'-most internucleotide linkage i.e a single inverted nucleoside residue which may be a basic (the nucleobase is missing or has a hydroxyl group in place thereof). Various salts (such as, for example, potassium or sodium), mixed salts and free acid forms are also included.

In embodiments, the present nucleic acids comprise one or more phosphorothioate and/or heteroatom internucleoside linkages, in particular —CH$_2$—NH—O—CH$_2$—, —CH$_2$—N(CH$_3$)—O—CH$_2$-(known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

In embodiments, the present nucleic acid is in the form of or comprises a nucleic acid mimetic. In embodiments, the term "mimetic" as it is applied to polynucleotides is intended to include polynucleotides where only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

In embodiments, the present nucleic acid is or comprises a mimetic based on morpholino units (morpholino nucleic acid), having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

In embodiments, the present nucleic acid is a mimetic is in the form of or comprises cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J Am. Chem. Soc., 2000, 122, 8595-8602, the disclosure of which is incorporated herein by reference in its entirety). In general, the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

In embodiments, the present nucleic acid comprise's Locked Nucleic Acids (LNAs) in w'ich the 2'-hydroxyl group is linked to the 4' carb'n ato' of the sugar ring thereby forming a 2'-C, 4'-C-oxymethylene linkage thereby forming a bicyclic sugar moiety. The linkage can' be a methylene (—$CH_2$—)' group bridging the 2' oxygen atom and the 4' carbon atom wherein n is 1 or 2 (Singh et al., *Chem. Commun.*, 1998, 4, 455-456, the disclosure of which is incorporated herein by reference in its entirety). LNA and LNA analogs display very high duplex thermal stabilities with complementary DNA a'd RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.*, 2000, 97, 5633-5638, the disclosure of which is incorporated herein by reference in its entirety).

Modified Sugar Moieties

In embodiments, the present nucleic acid comprises one or more substituted sugar moieties. Suitable polynucleotides comprise a sugar substituent group selected from: OH; F; O—, S-, or N-alkyl; O—, S-, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON(($CH_2$)$_n$$CH_3$)$_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar p'operties. A suita'le modification includes 2'-met'oxyethoxy (2'-O—$CH_2$ $CH_2$O'H3, also known as 2'-O-(2-methoxyethyl) or 2'-MOE) (Martin et al., *Helv. Chim. Acta*, 1995, 78, 486-504, the disclosure of which is incorporated herein by reference in its entirety) i.e., an alkoxyalkoxy grou'. A further suitable modification includes 2'-dimethylaminooxyethoxy, i'e., a O($CH_2$)$_2$ON($CH_3$)$_2$ group, also known as 2'-DMAOE' as described in examples hereinbelow, and 2'-dimethyl'minoethoxyethoxy (also known in the' art as 2'-O-dimet'yl-amino-ethoxy-ethyl or 2'-DMAEOE), i.e., 2'-O—$CH_2$—O—$CH_2$—N($CH_3$)$_2$.

Other suitable sugar substituent groups include methoxy (—O—$CH_3$), aminopropoxy (—O $CH$—$H_2NH_2$), allyl (—$CH_2$—CH=$CH_2$), 'O-allyl (—O— $CH_2$—CH=$CH_2$) and fluoro (F). 2'-sugar substituent groups may be in the arabino (up) p'sition or ribo (down) posi'ion. A suitable 2'-arabino modification is 2'-F. Similar modifications may also be made at other positions o' the oligomeric compound, parti'ularly the 3' position of th' s'gar on the 3' terminal nucleoside 'r in 2'-5' lin'ed oligonucleotides and the 5' position of 5' terminal nucleotide. Oligomeric compounds may also have sugar mimetics such as cyclobutyl moieties in place of the pentofuranosyl sugar.

Base Modifications and Substitutions

In embodiments, the present nucleic acid comprises one or more nucleobase (often referred to in the art simply as "base") modifications or substitutions. In embodiments, as used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C=C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)in'ol'2-one), pyridoindole cytidine (H-pyrido(3',2':4,5)pyrrolo(2,3-d)pyrimidin-2-one).

In embodiments, heterocyclic base moieties may also include those in which the purine or pyrimidine base is replaced with other heterocycles, for example 7-deazaadenine, 7-deazaguanosine, 2-aminopyridine and 2-pyridone. Certain nucleobases are, without wishing to be bound by theory, useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability and are suitable b'se substitutions, e.g., when combined with 2'-O-methoxyethyl sugar modifications.

Conjugates

In embodiments, the present compositions are chemically linked to one or more moieties or conjugates which enhance the activity, cellular distribution or cellular uptake of the oligonucleotide. In embodiments, the moieties or conjugates include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

In embodiments, the conjugate may include a Protein Transduction Domain or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In emb'diments, a PTD is covalently linked to the 3' end of an exogenous polynucleotide. In emb'diments, a PTD is covalently linked to the 5' end of an exogenous polynucleotide.

Kits

In aspects, the present disclosure provides a kit comprising a container comprising the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein and with instructions for use in modulating and/or modifying a nucleic acid.

In embodiments, the present disclosure provides kits for carrying out the methods described herein. In embodiments, the kit comprises a composition described herein, a recombinant expression vector, a delivery system, and/or a pharmaceutical composition described herein, optionally further with a reagent for reconstitution and/or dilution.

Methods of Use

In aspects, the present disclosure provides a method of modulating and/or modifying a nucleic acid in a cell, comprising contacting the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In aspects, the present disclosure provides a method of modulating and/or modifying a nucleic acid in a subject in need thereof, comprising administering an effective amount of the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein to the subject.

In embodiments, the modulating and/or modifying is selected from one or more of cleaving, nicking, methylating, labeling, and mutating the nucleic acid. In embodiments, the modulating and/or modifying is selected from one or more of cleaving the nucleic acid; inserting a nucleic acid, editing the nucleic acid; modulating transcription from the nucleic acid; isolating the nucleic acid, binding the nucleic acid, and imaging the nucleic acid.

In aspects, the present disclosure provides a method of disrupting, correcting, and/or replacing a gene in a cell, comprising contacting the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In aspects, the present disclosure provides a method of disrupting, correcting, and/or replacing a gene in a subject in need thereof, comprising administering an effective amount of the composition of any one of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein to the subject.

In aspects, the present disclosure provides a method of trans-splicing a nucleic acid, e.g. a pre-mRNA in a cell, the method comprising contacting the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In aspects, the present disclosure provides a method of trans-splicing a nucleic acid, e.g. a pre-mRNA in a cell, in a subject in need thereof, comprising administering an effective amount of the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In embodiments, the trans-splicing method further comprises use of a repair template comprising a splice donor and/or a splice acceptor. In embodiments, the trans-splicing method further comprises use of a repair template lacking a splice donor and/or a splice acceptor. In embodiments, the trans-splicing method provides splicing of a target nucleic acid comprising a splice donor or a splice acceptor site. In embodiments, the trans-splicing method uses an RNA molecule, e.g. gRNA that targets a splice acceptor site. In embodiments, the trans-splicing method uses an RNA molecule, e.g. gRNA that targets a splice donor site. In embodiments, the activity of at least one portion of the system used in the trans-splicilg methods is regulated by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and auxin. In embodiments, the pre-mRNA is at an intron-exon junction or exon-intron junctions. In embodiments, the trans-splicing method further comprises use of a pre-trans-splicing (PTS) molecule, wherein the PTS molecule comprises: i) one or more guid-eRNAs (gRNAs) that target a pre-mRNA; ii) an intronic sequence having a splice signal; and iii) a donor sequence encoding a gene product of a gene of interest, or portion thereof. In embodiments, the gRNA or gRNAs are within the PTS and processed by the endonuclease. In embodiments, the gRNA or gRNAs are within the PTS and are not processed by the endonuclease. In embodiments, the gRNA or gRNAs are not within the PTS. In embodiments, the endonuclease is fused to a nucleic acid-interacting domain (e.g. MCP) and the PTS is tethered by the nuclease by interacting with the nucleic acid-interacting domain. In embodiments, one or more gRNAs hybridize to one or more pre-mRNAs. In embodiments, the endonuclease is catalytically active. In embodiments the endonuclease is catalytically inactive. In embodiments the endonuclease (or chimera) is delivered to a cell with viral methods. In embodiments the endonuclease (or chimera), and gRNA(s) or PTS are delivered with viral methods. In embodiments the endonuclease (or chimera), gRNA(s), and PTS are delivered with viral methods. In embodiments the endonuclease (or chimera) is delivered to a cell with non-viral methods. In embodiments the endonuclease (or chimera), and gRNA(s) or PTS are delivered with non-viral methods. In embodiments the endonuclease (or chimera), gRNA(s), and PTS are delivered with non-viral methods. In embodiments, the endonuclease (or chimera) is delivered to a cell implicated in disease. In embodiments, the endonuclease (or chimera) mediates trans-splicing of a pre-mRNA implicated in disease.

In aspects, the present disclosure provides a method of modifying a nucleic acid in a cell using a method of exon skipping, comprising contacting the cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In aspects, the present disclosure provides a method of modifying a nucleic acid in a cell in a subject in need thereof, using a method of exon skipping, comprising administering an effective amount of the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein.

In embodiments, the cell is induced to skip over faulty sections of pre-mRNA molecules by interfering with mRNA splicing. In embodiments, the methods produce a truncated, but functional, protein despite the presence of a mutation. In embodiments, the method of exon skipping involves binding an oligonucleotide (e.g. without limitation the present RNA molecule) to a splice site in a pre-mRNA molecule. In embodiments, when the pre-mRNA that is bound by the oligonucleotide is processed into a mature mRNA, the corresponding exon is skipped over, which, for example, restores a disrupted reading frame caused by the mutation. In embodiments, the exon skipping allows translation of an internally-deleted, but substantially functional protein.

In embodiments, the present exon skipping methods comprise creating a single-strand or double-strand break in a gene. In embodiments, the single-strand or double-strand break causes persistent altered splicing of the gene. In embodiments, the altered splicing results in expression of a truncated protein which lacks at least the polypeptide sequence corresponding to an exon containing the mutation. In embodiments, the single-strand or double-strand break removes a splice acceptor site or produces a non-functional splice acceptor site in or near an exon of the gene or removes a splice donor site or produces a non-functional splice donor site in or near an exon of the gene.

In aspects, the present disclosure provides a method of treating, ameliorating or preventing a disease or disorder in a subject, comprising (a) contacting a cell with the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein, and (b) administering an effective amount of the cell to the subject.

In aspects, the present disclosure provides a method of treating, ameliorating or preventing a disease or disorder in a subject, comprising administering an effective amount of the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein to the subject.

In embodiments, composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein for use in treating, ameliorating or preventing a patient with a disease or disorder.

In aspects, the present disclosure provides use of the composition of any one of the embodiments and/or aspects disclosed herein, the nucleic acid of any one of the embodiments and/or aspects disclosed herein, the viral vector of any one of the embodiments and/or aspects disclosed herein, the lipid nanoparticle of any one of the embodiments and/or aspects disclosed herein, the cell of any one of the embodiments and/or aspects disclosed herein, or the pharmaceutical composition of any one of the embodiments and/or aspects disclosed herein in the manufacture of a medicament for the treating, ameliorating or preventing of a disease or disorder.

In aspects, the present disclosure provides a method of detecting and/or quantifying a nucleic acid in a sample, comprising contacting the sample with a composition of any one of the embodiments and/or aspects disclosed herein.

In embodiments, the nucleic acid is a target and/or reporter nucleic acid. In embodiments, the method comprises detection of a reporter signal, the reporter signal being generated upon endonuclease cleavage. In embodiments, the reporter signal is a fluorescent signal. In embodiments, the endonuclease has collateral cleavage activity.

In various embodiments, the composition disclosed herein, or the trans-splicing system disclosed herein, further comprises a repair RNA (repRNA) sequence, comprising: (a) one or more exons and/or introns; (b) a splice donor and/or splice acceptor, wherein the repRNA is suitable for trans-splicing. In embodiments, the trans-splicing system comprises a splice donor, a splice acceptor, and replaces an internal exon. In embodiments, repRNA is operably linked to the RNA molecule comprising a sequence complementary to one strand of a target nucleic acid molecule or the gRNA.

In aspects, the present disclosure provides a system for targeting a nucleic acid for trans-splicing, the system comprising: (a) an endonuclease of any one of the embodiments disclosed herein, and optionally an RNA molecule comprising a sequence complementary to one strand of a target nucleic acid molecule; (b) an RNA-binding polypeptide that associates with the endonuclease; and (c) a repair RNA (repRNA) sequence, comprising: (i) one or more exons and/or introns; (ii) a splice donor and/or splice acceptor.

In embodiments, the RNA molecule is a gRNA.

In embodiments, the endonuclease is not linked, associated, and/or fused with an RNA binding protein.

In embodiments, the repRNA is not operably linked to one or more gRNAs. In embodiments, the repRNA is provided in trans to one or more gRNAs.

In embodiments, the repRNA further comprises a ribozyme site. In embodiments, the ribozyme site is a hairpin, hammerhead, hepatitis delta virus (HDV), Varkud satellite (VS), or glmS ribozyme site, or a variant thereof. In embodiments, the ribozyme site is a HDV ribozyme site. In embodiments, the ribozyme site is upstream of the one or more exons and/or introns of the repRNA.

In aspects, the present disclosure provides a system for targeting a nucleic acid for trans-splicing, the system comprising: (a) an endonuclease of any one of the embodiments disclosed herein and an RNA molecule comprising a sequence complementary to one strand of a target nucleic acid molecule; and (b) a repair RNA (repRNA) sequence, comprising: (i) one or more exons and/or introns; (ii) a splice donor and/or splice acceptor.

In embodiments, the RNA molecule is a gRNA. In embodiments, the endonuclease is not linked, associated, and/or fused with an RNA binding protein. In embodiments, the repRNA is operably linked to one or more gRNAs.

In aspects, the present disclosure provides a variety of methods (e.g., with a composition of any one of the embodiments and/or aspects disclosed herein). For example, a composition of any one of the embodiments and/or aspects disclosed herein can be used to (i) modify (e.g., cleave, e.g., nick; methylate; and the like) target nucleic acid (DNA or RNA; single stranded or double stranded); (ii) modulate transcription of a target nucleic acid; (iii) label a target nucleic acid; (iv) bind a target nucleic acid e.g., for purposes of isolation, labeling, imaging, tracking, and the like); (v) modify a polypeptide (e.g., a histone) associated with a target nucleic acid; and the like.

In embodiments, the present disclosure provides a method of modifying a target nucleic acid. In embodiments, a method of the present disclosure for modifying a target nucleic acid comprises contacting the target nucleic acid with (a) a composition of the present disclosure (e.g. an endonuclease and/or a chimeric protein of any one of the embodiments and/or aspects disclosed herein); and (b) one or more (e.g., two) RNAs of any one of the embodiments and/or aspects disclosed herein. In embodiments, a method of the present disclosure for modifying a target nucleic acid comprises contacting the target nucleic acid with: a) a composition of the present disclosure (e.g. an endonuclease and/or a chimeric protein of any one of the embodiments and/or aspects disclosed herein); and b) one or more (e.g., two) RNAs of any one of the embodiments and/or aspects disclosed herein; and c) a donor nucleic acid (e.g., a donor template). In embodiments, the contacting step is carried out in a cell in vitro. In embodiments, the contacting step is carried out in a cell in vivo. In embodiments, the contacting step is carried out in a cell ex vivo.

It is to be understood that, in emboliments, while a method of binding may result in nothing more than binding of the target nucleic acid, in other embodiments, the method can have different final results (e.g., the method can result in modification of the target nucleic acid, e.g., cleavage/methylation/and the like, modulation of transcription from the target nucleic acid; modulation of translation of the target nucleic acid; genome editing; modulation of a protein associated with the target nucleic acid; isolation of the target nucleic acid; and the like).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-

8; Auer et al., Genome Res. 2013 Oct. 31; Chen et al., Nucleic Acids Res. 2013 Nov. 1; 41 (20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41 (20):e187; Hu et al., Cell Res. 2013 November; 23(11):1322-5; Jiang et al., Nucleic Acids Res. 2013 Nov. 1; 41 (20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

In embodiments, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

In embodiments, the terms "contact a target nucleic acid" and "contacting a target nucleic acid", for example, encompass all methods for contacting the target nucleic acid. For example, a present polypeptide (e.g. of the present endonuclease and/or chimeric protein) is provided to a cell as protein, RNA (encoding the present polypeptide), or DNA (encoding the present polypeptide); while a present RNA can be provided as a RNA or as a nucleic acid encoding the RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for a polypeptide; in the form of a protein for a chimeric polypeptide; in the form of an RNA in embodiments for the present RNA), and also encompasses the introduction into the cell of one or more nucleic acids encoding one or more of the components (e.g., nucleic acid(s) comprising nucleotide sequence(s) encoding a present polypeptide or a present chimeric polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, or inside of a cell ex vivo.

In embodiments, the method of the present disclosure for modifying a target nucleic acid comprises introducing into a target cell a present locus, e.g., a nucleic acid comprising a nucleotide sequence encoding a present polypeptide as well as nucleotide sequences of about 1 kilobase (kb) to 5 kb in length surrounding the present-encoding nucleotide sequence from a cell (e.g., in embodiments, a cell that in its natural state (the state in which it occurs in nature) comprises a present locus) comprising a present locus, where the target cell does not normally (in its natural state) comprise a present locus. However, one or more spacer sequences, encoding guide sequences for the encoded crRNA(s), can be modified such that one or more target sequences of interest are targeted. Thus, for example, in embodiments, a method of the present disclosure for modifying a target nucleic acid comprises introducing into a target cell a present locus, e.g., a nucleic acid obtained from a source cell (e.g., in embodiments, a cell that in its natural state (the state in which it occurs in nature) comprises a present locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a present polypeptide. As noted above, in some such embodiments, one or more spacer sequences, encoding guide sequences for the encoded crRNA(s), can be modified such that one or more target sequences of interest are targeted. In embodiments, the method comprises introducing into a target cell: i) a present locus; and ii) a donor DNA template. In embodiments, the target nucleic acid is in a cell-free composition in vitro. In embodiments, the target nucleic acid is present in a target cell. In embodiments, the target nucleic acid is present in a target cell, where the target cell is a prokaryotic cell. In embodiments, the target nucleic acid is present in a target cell, where the target cell is a eukaryotic cell. In embodiments, the target nucleic acid is present in a target cell, where the target cell is a mammalian cell. In embodiments, the target nucleic acid is present in a target cell, where the target cell is a plant cell.

In embodiments, a method of the present disclosure for modifying a target nucleic acid comprises contacting a target nucleic acid with a present polypeptide of the present disclosure, or with a present chimeric polypeptide of the present disclosure. In embodiments, a method of the present disclosure for modifying a target nucleic acid comprises contacting a target nucleic acid with a present polypeptide and a present guide RNA. In embodiments, a method of the present disclosure for modifying a target nucleic acid comprises contacting a target nucleic acid with a present polypeptide, a first present guide RNA, and a second present guide RNA In embodiments, a method of the present disclosure for modifying a target nucleic acid comprises contacting a target nucleic acid with a present polypeptide of the present disclosure and a present guide RNA and a donor DNA template.

Usher Syndrome

Usher syndrome is inherited as an autosomal recessive condition characterized by hearing loss or deafness and progressive vision loss. The loss of vision is caused by retinitis pigmentosa (RP), which affects the layer of light-sensitive tissue at the retina. Without wishing to be bound by theory, vision loss occurs as the light-sensing cells of the retina gradually deteriorate.

Three major types of Usher syndrome, designated as types I (subtypes IA through IG), II (subtypes IIA, IIB, and IIC), and III, have been identified. These types are distinguished by their severity and the age when signs and symptoms appear.

Subjects with Usher Syndrome type I are born profoundly deaf and begin to lose their vision in the first decade of life. They also exhibit balance difficulties and learn to walk slowly as children, due to problems in their vestibular system.

Usher Syndrome type II is a heterogeneous autosomal recessive disorder characterized by progressive retinitis pigmentosa and sensorineural hearing deficiencies, resulting in deaf-blindness in patients. Subjects with Usher II are generally have a reduced ability to hear rather than deaf, and their hearing does not degrade over time. They do not seem to have noticeable problems with balance. They typically begin to lose their vision in the second decade of life, and may preserve some vision into middle age.

Subjects with Usher syndrome III experience a progressive loss of hearing, and roughly half have balance difficulties. Mutations in CLRN1, have been linked to Usher syndrome type III. CLRN1 encodes clarin-1, a protein involved in the development and maintenance of the inner ear and retina.

Several genes have been implicated or associated with Usher syndrome, and mutations in the genese: CDH23, CLRN1, GPR98, MY07A, PCDH15, USH1C, USH1G, USH2A, and ADGRV1, WHRN. Mutations in any one of these genes alters gene expression or protein function and can lead to Usher syndrome. The genes play roles in the development and maintenance of hair cells, which have sensory functionalities in the inner ear that help transmit sound and motion signals to the brain. In the retina, these genes are also involved in determining the structure and function of light-sensing cells called rods and cones. In some cases, the exact role of these genes in hearing and vision is unknown. Most of the mutations responsible for Usher syndrome lead to a loss or reduction of hair cells in the inner ear and a gradual loss or reduction of rods and cones in the retina. Degeneration of these sensory cells causes hearing loss, balance problems, and vision loss characteristic of this condition.

Usher syndrome type II can be caused by mutations in, e.g., USH2A, ADGRV1, WHRN, GPR98 (also called VLGR1) gene, and DFNB31. Usher syndrome type III can be caused by mutations in e.g., CLRN1.

The protein encoded by the USH2A gene, usherin, is located in the supportive tissue in the inner ear and retina. Usherin is involved in the development and maintenance of these structures. WHRN mutations are associated with Usher syndrome type 2D or non-syndromic deafness (DFNB31). The associated phenotypes are dependent on the mutation location within the two predominantly expressed variants (long and short). Variants in ADGRV1 are a cause of Usher syndrome type 2, and the associated phenotype is less known.

In embodiments, the system for targeting a nucleic acid for trans-splicing is for use in treating a disease, such as Usher Syndrome type II.

In embodiments, disclosed herein is a method of treating, ameliorating or preventing Usher syndrome or a symptom thereof in a subject in need thereof, comprising: administering an effective amount of the composition of any one of the embodiments disclosed herein, the nucleic acid of any one of the embodiments disclosed herein, the viral vector of any one of the embodiments disclosed herein, the lipid nanoparticle of any one of the embodiments disclosed herein, the cell of any one of the embodiments disclosed herein, the pharmaceutical composition of any one of the embodiments disclosed herein, or the trans-splicing system any one of any one of the embodiments disclosed herein to the subject.

In embodiments, disclosed herein is a method of treating, ameliorating or preventing Usher syndrome or a symptom thereof in a subject, in need thereof, comprising: (a) contacting a cell with the composition of any one of the embodiments disclosed herein, the nucleic acid of any one of the embodiments disclosed herein, the viral vector of any one of the embodiments disclosed herein, the lipid nanoparticle of any one of the embodiments disclosed herein, the cell of any one of the embodiments disclosed herein, the pharmaceutical composition of any one of the embodiments disclosed herein, or the trans-splicing system any one of any one of the embodiments disclosed herein and (b) administering an effective amount of the cell to the subject.

In embodiments, the cell is derived from the subject.

In embodiments, the Usher syndrome is selected from Usher syndrome type I, Usher syndrome type II, or Usher syndrome type III.

In embodiments, the Usher syndrome is Usher syndrome type I.

In embodiments, the Usher syndrome is Usher syndrome type II.

In embodiments, the Usher syndrome is Usher syndrome type III.

In embodiments, the method targets one or more Usher syndrome-associated gene.

In embodiments, the method targets one or more genes selected from CDH23, MY07A, PCDH15, USH1C, USH1G, USH2A, ADGRV1, WHRN, GPR98, DFNB31, and CLRN1.

In embodiments, the method targets one or more of USH2A, GPR98, and DFNB31.

In embodiments, the method targets USH2A.

In embodiments, the method corrects a mutation or defect in one or more Usher syndrome-associated gene.

In embodiments, the method corrects a mutation or defect in one or more genes selected from USH2A, CDH23, MY07A, PCDH15, USH1C, USH1G, ADGRV1, WHRN, GPR98, DFNB31, and CLRN1.

In embodiments, the method corrects a mutation or defect in one or more of USH2A, GPR98, and DFNB31.

In embodiments, the method corrects a mutation or defect in USH2A.

In embodiments, the method causes trans-splicing of one or more genes selected from USH2A, CDH23, MY07A, PCDH15, USH1C, USH1G, ADGRV1, WHRN, GPR98, DFNB31, and CLRN1.

In embodiments, the method causes trans-splicing of one or more of USH2A, GPR98, and DFNB31.

In embodiments, the method causes trans-splicing of USH2A.

In embodiments, the method treats, ameliorates or prevents one or more symptoms of retinitis pigmentosa.

In embodiments, the method treats, ameliorates or prevents hearing reduction or loss.

In embodiments, the method treats, ameliorates or prevents vision reduction or loss.

In embodiments, the method treats, ameliorates or prevents one or more of night blindness and loss or reduction of peripheral vision.

In various embodiments, the "subject" refers to any animal (e.g., a mammal), including, but not limited to, humans, and non-human animals (including, but not limited to, non-human primates, dogs, cats, rodents, horses, cows, pigs, mice, rats, hamsters, rabbits, and the like (e.g., which is to be the recipient of a particular treatment, or from whom cells are harvested)). In embodiments, the subject is a human.

It will also be understood that, although the terms first, second, etc., may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients. Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

This disclosure is further illustrated by the following non-limiting examples.

EXAMPLES

Example 1: Guide RNA Design

Figure 1B:
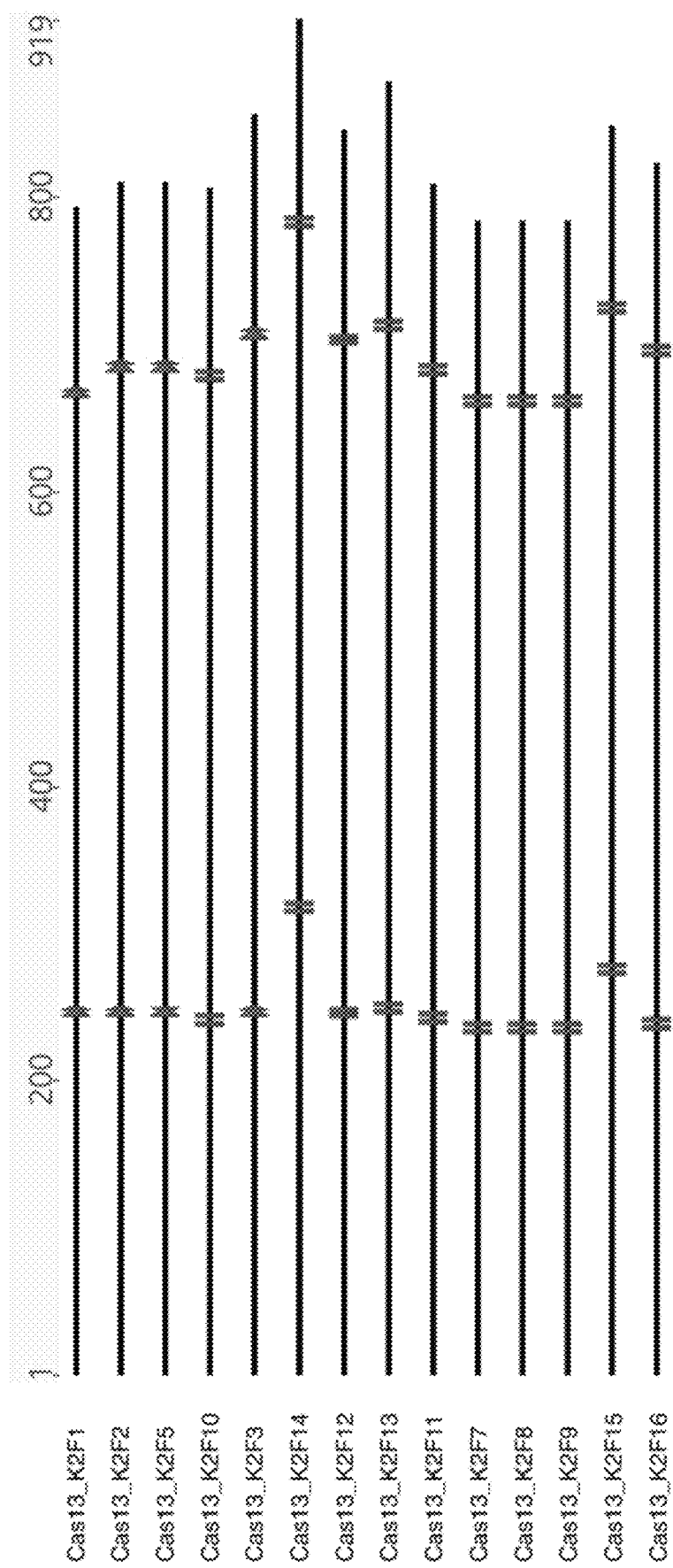
Figure 1C:
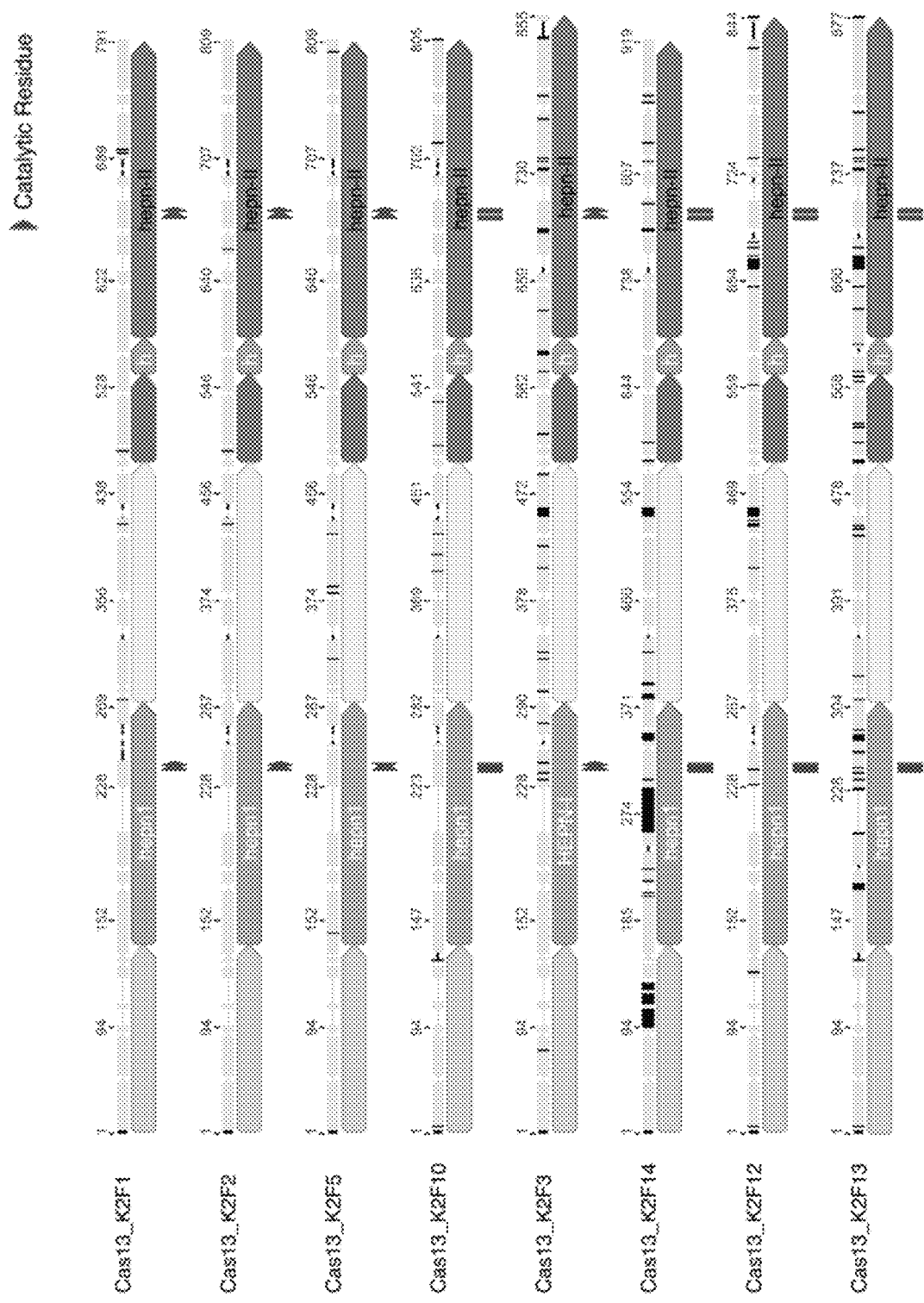
Figure 1D:
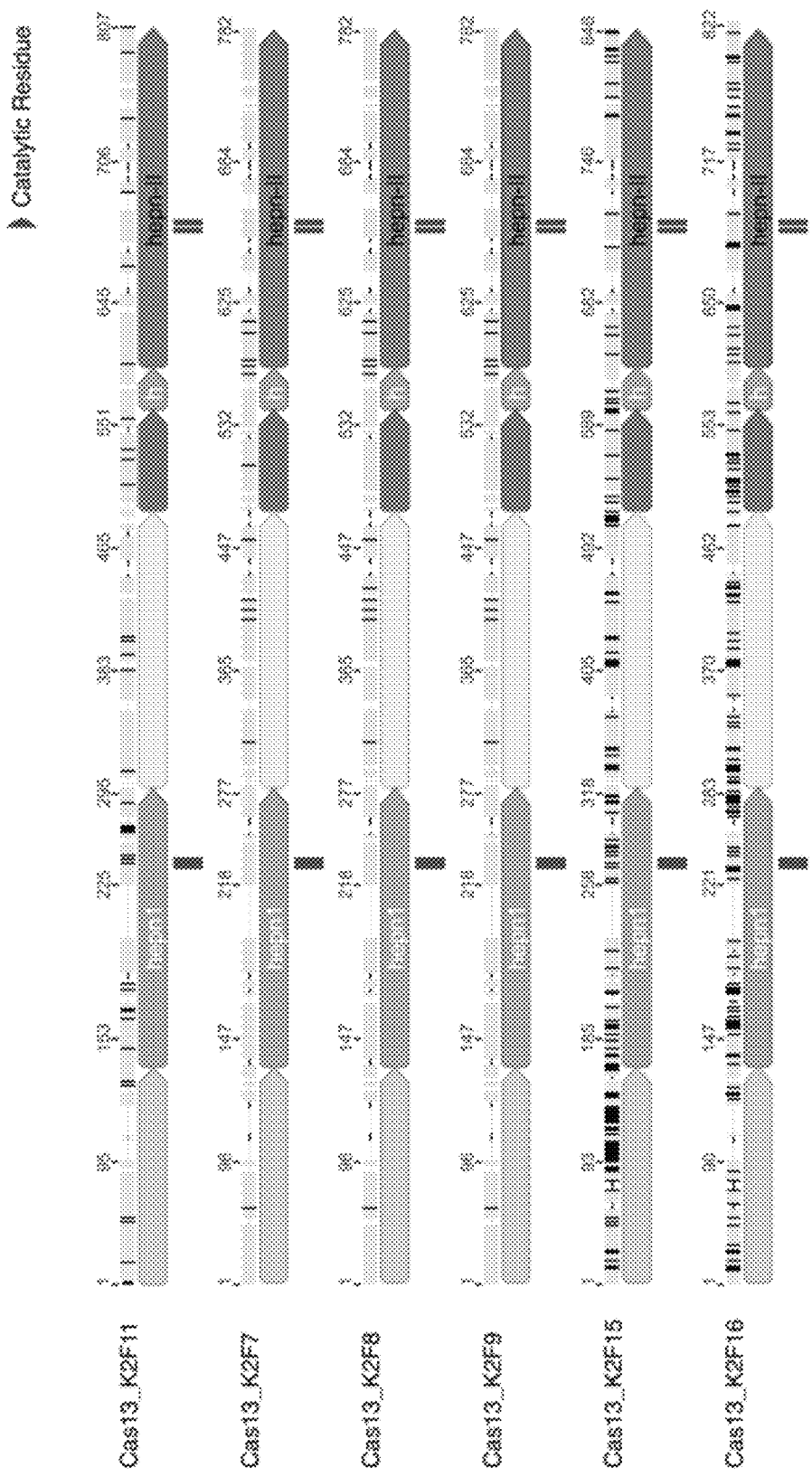
Figure 2:
FIG. 2 is a non-limiting image showing a representative guide RNA structure from the Cas13K2F system (SEQ ID NO: 106).
Figure 3:
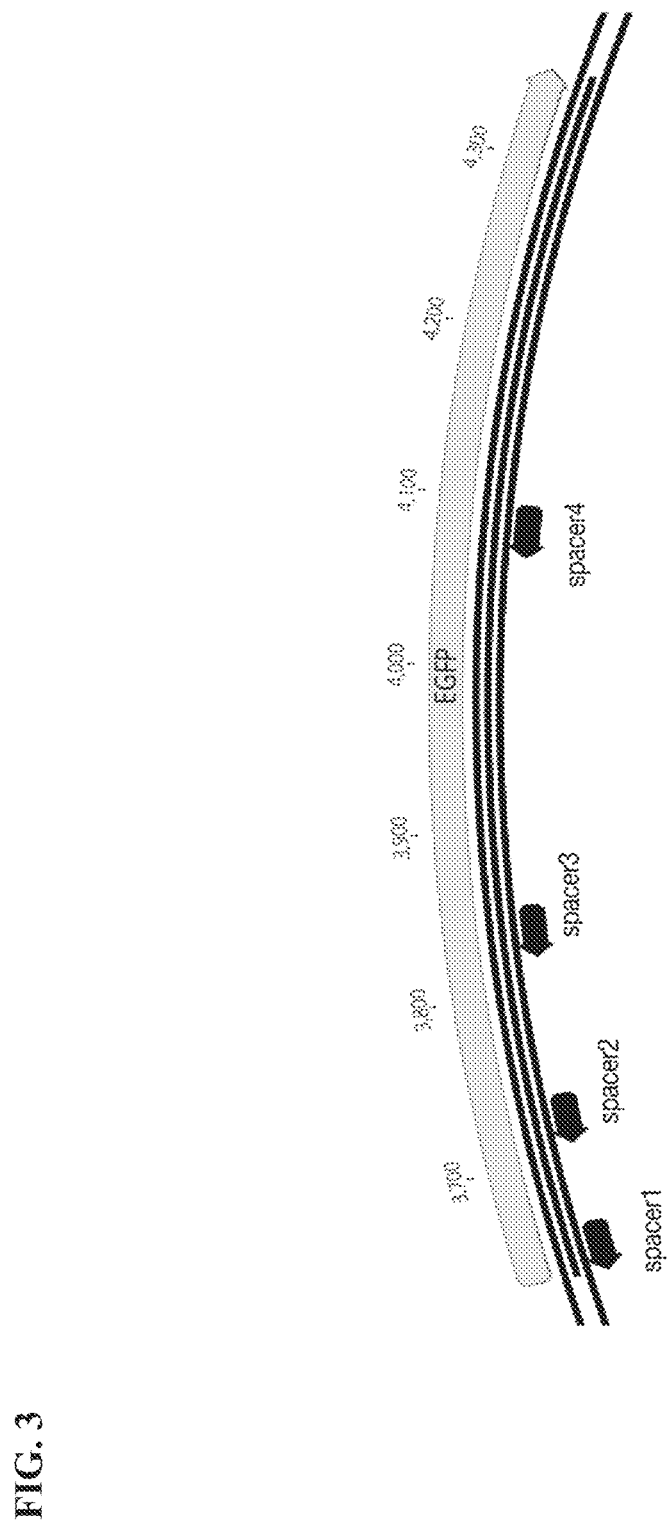
FIG. 3 is an image showing the design of guide RNAs (gRNAs) to target multiple sites across the coding sequence of eGFP in HEK293T cells.

The experiments of this example evaluated the structure of the CRISPR RNA of the Cas13K2F system disclosed herein. In these experiments, gRNAs were designed for the Cas13K2F system disclosed herein to target multiple sites across the coding sequence of eGFP in HEK293T cells (FIG. 3). The gRNAs were tested alongside a scrambled non-targeting guide, demonstrating reprogrammability and specificity of the RNase activity of this CRISPR-Cas system towards different targets.

Figure 4:
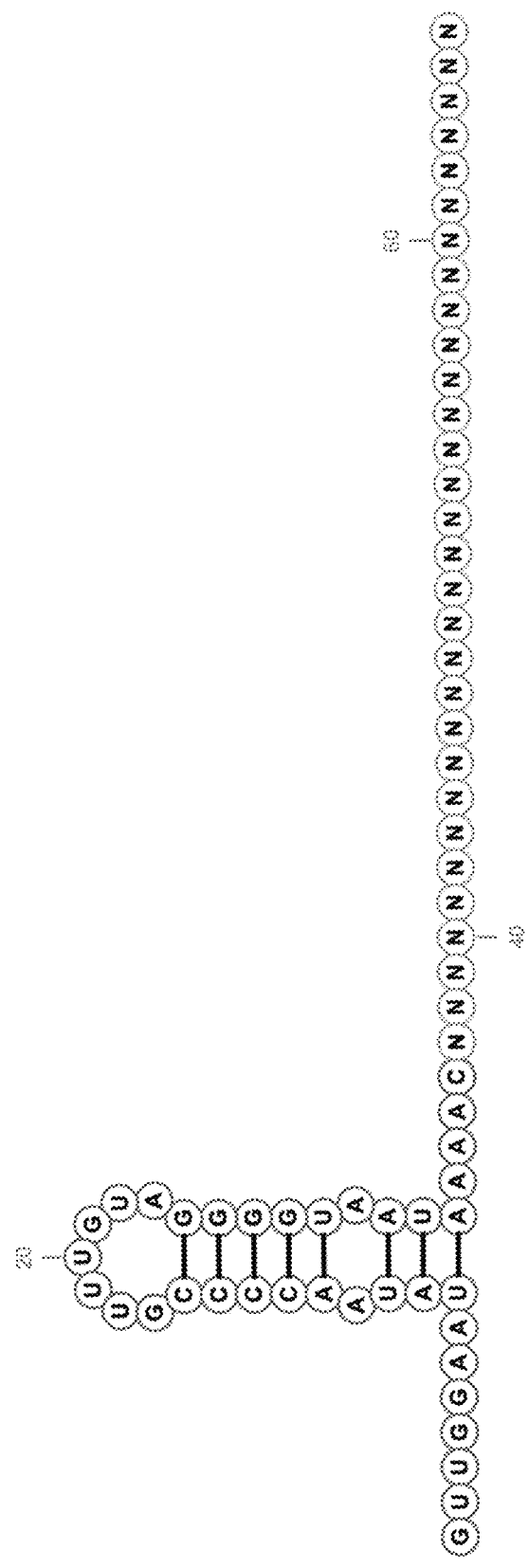
FIG. 4 is an image showing the gRNA structure for the Cas13K2F system (SEQ ID NO: 5).

Several gRNA orientations were tested to evaluate the correct structure of the CRISPR RNA of the Cas13K2F system. The gRNA structure for Cas13K2F system was determined to consist of a CRISPR repeat at the 3' end of the RNA followed by a spacer sequence complementary to the target RNA (see, e.g., FIG. 4).

Example 2: Mammalian Experiments Demonstrating Knockdown of eGFP RNA

The experiments of this example demonstrate the capability of the Cas13K2F system disclosed herein to target and knockdown eGFP RNA. In these experiments, for each Cas open reading frame ("ORF"), an SV40 NLS sequence was added to the N-terminus (MSPKKKRKVEAS (SEQ ID NO: 78)) and an SV40 NLS with an appended HA tag was added to the C-terminus (GSGPKKKRKVAAAYPYDVPDYA (SEQ ID NO: 77)). The resulting ORFs were then mammalian codon optimized and synthesized into mammalian expression vectors. Transcription was driven by a CMV promoter, and an SV40 polyadenylation signal was used to terminate transcription. The sequence of the CMV promoter is the following:

(SEQ ID NO: 76)
CGCCCCATTGACGCAAATGGGCGGTAGGCGTGTACGGTGGGAGGTCTATA

TAAGCAGAGCTGGTTTAGTGAACCGTCAGATC

The sequence of the SV40 polyadenylation signal is the following:

(SEQ ID NO: 79)
CAGCTCACAGACATGATAAGATACATTGATGAGTTTGGACAAACCACAAC

TAGAATGCAGTGAAAAAAATGCTTTATTTGTGAAATTTGTGATGCTATTG

CTTTATTTGTAACCATTATAAGCTGCAATAAACAAGTTAACAACAACAAT

TGCATTCATTTTATGTTTCAGGTTCAGGGGGAGGTGTGGGAGGTTTTTTA

AAGCAAGTAAAACCTCTACAAATGTGGTATTGGC

A plasmid expressing eGFP and plasmids expressing Cas13K2F proteins and gRNAs were co-transfected into HEK293T cells (bio reps n=2) using lipofectamine 2000 per manufacturer's instructions. Protein expression was confirmed by observing fluorescence via fluorescent microscopy on a Bio-Rad ZOE Fluorescent Cell Imager, and flow cytometry was performed 48 hours following transfection on a Sartorius iQue3. Cell and singlet gating was performed with Sartorius iQue3 instrument software, and median GFP intensity of singlets was calculated in python using FlowCytometryTools. Results were plotted using Matplotlib (See FIG. 7A, FIG. 7B, and FIG. 7C).

These experiments further compared the Cas13K2F system disclosed herein to other CAS systems by phylogenetic analysis. FIG. 5 and FIG. 6 each show clear distinction in phylogenetic placement as separate protein families for the Cas13K2F system disclosed herein. Compared to other CAS systems, the Cas13K2F system disclosed herein is novel and shows low sequence similarity to other systems. The results in FIG. 5 are reproduced in Table 4 below.

Accordingly, the results of the experiments of this example demonstrate the Cas13K2F systems disclosed herein is novel and is capable of targeting and knocking down eGFP RNA.

TABLE 4

| Percent Identity Matrix | | | | | |
|---|---|---|---|---|---|
| | Cas13X.1 | Cas13bt3 | Cas13bt2 | Cas13bt1 | Cas13bt8 |
| Cas13X.1 | | 99.5 | 39.8 | 38.3 | 37.4 |
| Cas13bt3 | 99.5 | | 39.3 | 37.8 | 36.9 |
| Cas13bt2 | 39.8 | 39.3 | | 69.3 | 62.5 |
| Cas13bt1 | 38.3 | 37.8 | 69.3 | | 63 |
| Cas13bt8 | 37.4 | 36.9 | 62.5 | 63 | |

TABLE 4-continued

| Percent Identity Matrix | | | | | |
|---|---|---|---|---|---|
| Cas13X.2 | 37.4 | 36.9 | 62.5 | 63 | 100 |
| Cas13bt9 | 37.8 | 37.4 | 43.8 | 43.2 | 49.2 |
| Cas13bt11 | 38 | 37.5 | 43.3 | 42.7 | 48.7 |
| Cas13bt5 | 31.8 | 31.3 | 36.8 | 35.5 | 36.3 |
| Cas13bt10 | 29 | 28.6 | 28.9 | 29.9 | 29.9 |
| Cas13bt15 | 21.9 | 21.4 | 23.3 | 22.2 | 23.5 |
| Cas13bt7 | 19.9 | 19.5 | 21.6 | 21.4 | 21.7 |
| Cas13bt6 | 13.8 | 13.3 | 14.2 | 14.1 | 14.1 |
| Cas13bt14 | 13.6 | 13.2 | 14.6 | 14.5 | 14.6 |
| Cas13Y.3 | 13.6 | 13.2 | 14.6 | 14.5 | 14.6 |
| Cas13bt12 | 14.4 | 13.9 | 15.3 | 14.6 | 14.7 |
| Cas13Y.1 | 14.4 | 13.9 | 15.3 | 14.6 | 14.7 |
| Cas13bt4 | 14.1 | 13.6 | 14.7 | 14.8 | 14.9 |
| Cas13bt16 | 14.3 | 13.8 | 14.7 | 14.7 | 14.9 |
| Cas13Y.5 | 13.9 | 13.4 | 15.6 | 15.9 | 15.8 |
| Cas13Y.4 | 13 | 12.5 | 14.9 | 15.5 | 14.8 |
| Cas13__K2F1 | 9 | 8.7 | 8.4 | 9.2 | 8.6 |
| Cas13__K2F2 | 9.1 | 8.9 | 8.7 | 9.8 | 8.6 |
| Cas13__K2F5 | 9.5 | 9.3 | 9.6 | 9.9 | 9.5 |
| Cas13__K2F3 | 9.4 | 9.4 | 8.9 | 9.1 | 9.2 |

| | Cas13X.2 | Cas13bt9 | Cas13bt11 | Cas13bt5 | Cas13bt10 | Cas13bt15 |
|---|---|---|---|---|---|---|
| Cas13X.1 | 37.4 | 37.8 | 38 | 31.8 | 29 | 21.9 |
| Cas13bt3 | 36.9 | 37.4 | 37.5 | 31.3 | 28.6 | 21.4 |
| Cas13bt2 | 62.5 | 43.8 | 43.3 | 36.8 | 28.9 | 23.3 |
| Cas13bt1 | 63 | 43.2 | 42.7 | 35.5 | 29.9 | 22.2 |
| Cas13bt8 | 100 | 49.2 | 48.7 | 36.3 | 29.9 | 23.5 |
| Cas13X.2 | | 49.2 | 48.7 | 36.3 | 29.9 | 23.5 |
| Cas13bt9 | 49.2 | | 97.9 | 33.1 | 28.7 | 22.6 |
| Cas13bt11 | 48.7 | 97.9 | | 33.2 | 29.2 | 22.5 |
| Cas13bt5 | 36.3 | 33.1 | 33.2 | | 29.1 | 22.2 |
| Cas13bt10 | 29.9 | 28.7 | 29.2 | 29.1 | | 21.2 |
| Cas13bt15 | 23.5 | 22.6 | 22.5 | 22.2 | 21.2 | |
| Cas13bt7 | 21.7 | 22.7 | 22.5 | 20.6 | 20.5 | 44.8 |
| Cas13bt6 | 14.1 | 12.5 | 12.6 | 12.2 | 13.5 | 12 |
| Cas13bt14 | 14.6 | 13 | 13.1 | 12.1 | 14 | 12.1 |
| Cas13Y.3 | 14.6 | 13 | 13.1 | 12.1 | 14 | 12.1 |
| Cas13bt12 | 14.7 | 12.9 | 12.9 | 12.5 | 14 | 13.3 |
| Cas13Y.1 | 14.7 | 12.9 | 12.9 | 12.5 | 14 | 13.3 |
| Cas13bt4 | 14.9 | 13.3 | 13.5 | 12.2 | 13 | 12.3 |
| Cas13bt16 | 14.9 | 13.7 | 13.8 | 11.7 | 13.9 | 12.2 |
| Cas13Y.5 | 15.8 | 14 | 14.1 | 13.6 | 15 | 11.8 |
| Cas13Y.4 | 14.8 | 13.3 | 13.2 | 12.5 | 13.7 | 12.8 |
| Cas13__K2F1 | 8.6 | 8.4 | 8.3 | 9.4 | 9.1 | 7.9 |
| Cas13__K2F2 | 8.6 | 8.4 | 8.3 | 9.9 | 8.9 | 8.5 |
| Cas13__K2F5 | 9.5 | 9.3 | 9.1 | 10.1 | 8.8 | 8.6 |
| Cas13__K2F3 | 9.2 | 8.6 | 8.4 | 8.3 | 8.4 | 8.1 |

| | Cas13bt7 | Cas13bt6 | Cas13bt14 | Cas13Y.3 | Cas13bt12 |
|---|---|---|---|---|---|
| Cas13X.1 | 19.9 | 13.8 | 13.6 | 13.6 | 14.4 |
| Cas13bt3 | 19.5 | 13.3 | 13.2 | 13.2 | 13.9 |
| Cas13bt2 | 21.6 | 14.2 | 14.6 | 14.6 | 15.3 |
| Cas13bt1 | 21.4 | 14.1 | 14.5 | 14.5 | 14.6 |
| Cas13bt8 | 21.7 | 14.1 | 14.6 | 14.6 | 14.7 |
| Cas13X.2 | 21.7 | 14.1 | 14.6 | 14.6 | 14.7 |
| Cas13bt9 | 22.7 | 12.5 | 13 | 13 | 12.9 |
| Cas13bt11 | 22.5 | 12.6 | 13.1 | 13.1 | 12.9 |
| Cas13bt5 | 20.6 | 12.2 | 12.1 | 12.1 | 12.5 |
| Cas13bt10 | 20.5 | 13.5 | 14 | 14 | 14 |
| Cas13bt15 | 44.8 | 12 | 12.1 | 12.1 | 13.3 |
| Cas13bt7 | | 12.1 | 12.2 | 12.2 | 13.3 |
| Cas13bt6 | 12.1 | | 87.2 | 87.2 | 78.1 |
| Cas13bt14 | 12.2 | 87.2 | | 100 | 78.1 |
| Cas13Y.3 | 12.2 | 87.2 | 100 | | 78.1 |
| Cas13bt12 | 13.3 | 78.1 | 78.1 | 78.1 | |
| Cas13Y.1 | 13.3 | 78.1 | 78.1 | 78.1 | 100 |
| Cas13bt4 | 12.4 | 77 | 76.9 | 76.9 | 80.6 |
| Cas13bt16 | 12.7 | 73.2 | 76.8 | 76.8 | 72.7 |
| Cas13Y.5 | 12.3 | 63.8 | 65 | 65 | 64.5 |
| Cas13Y.4 | 13.5 | 62.1 | 62.7 | 62.7 | 62.5 |
| Cas13__K2F1 | 8.3 | 7.5 | 7.4 | 7.4 | 7.7 |
| Cas13__K2F2 | 8.3 | 7.9 | 7.6 | 7.6 | 7.7 |
| Cas13__K2F5 | 8.9 | 7.9 | 7.9 | 7.9 | 7.9 |
| Cas13__K2F3 | 8.3 | 7.9 | 7.4 | 7.4 | 7.7 |

TABLE 4-continued

| Percent Identity Matrix | | | | | |
|---|---|---|---|---|---|
| | Cas13Y.1 | Cas13bt4 | Cas13bt16 | Cas13Y.5 | Cas13Y.4 |
| Cas13X.1 | 14.4 | 14.1 | 14.3 | 13.9 | 13 |
| Cas13bt3 | 13.9 | 13.6 | 13.8 | 13.4 | 12.5 |
| Cas13bt2 | 15.3 | 14.7 | 14.7 | 15.6 | 14.9 |
| Cas13bt1 | 14.6 | 14.8 | 14.7 | 15.9 | 15.5 |
| Cas13bt8 | 14.7 | 14.9 | 14.9 | 15.8 | 14.8 |
| Cas13X.2 | 14.7 | 14.9 | 14.9 | 15.8 | 14.8 |
| Cas13bt9 | 12.9 | 13.3 | 13.7 | 14 | 13.3 |
| Cas13bt11 | 12.9 | 13.5 | 13.8 | 14.1 | 13.2 |
| Cas13bt5 | 12.5 | 12.2 | 11.7 | 13.6 | 12.5 |
| Cas13bt10 | 14 | 13 | 13.9 | 15 | 13.7 |
| Cas13bt15 | 13.3 | 12.3 | 12.2 | 11.8 | 12.8 |
| Cas13bt7 | 13.3 | 12.4 | 12.7 | 12.3 | 13.5 |
| Cas13bt6 | 78.1 | 77 | 73.2 | 63.8 | 62.1 |
| Cas13bt14 | 78.1 | 76.9 | 76.8 | 65 | 62.7 |
| Cas13Y.3 | 78.1 | 76.9 | 76.8 | 65 | 62.7 |
| Cas13bt12 | 100 | 80.6 | 72.7 | 64.5 | 62.5 |
| Cas13Y.1 | | 80.6 | 72.7 | 64.5 | 62.5 |
| Cas13bt4 | 80.6 | | 72.3 | 64.8 | 60.7 |
| Cas13bt16 | 72.7 | 72.3 | | 64.5 | 61.4 |
| Cas13Y.5 | 64.5 | 64.8 | 64.5 | | 64.9 |
| Cas13Y.4 | 62.5 | 60.7 | 61.4 | 64.9 | |
| Cas13_K2F1 | 7.7 | 8 | 7.8 | 8.3 | 8 |
| Cas13_K2F2 | 7.7 | 8.3 | 7.8 | 8.4 | 8.3 |
| Cas13_K2F5 | 7.9 | 8.4 | 7.9 | 7.7 | 8 |
| Cas13_K2F3 | 7.7 | 7.6 | 7.5 | 7.6 | 7.2 |

| | Cas13_K2F1 | Cas13_K2F2 |
|---|---|---|
| Cas13X.1 | 9 | 9.1 |
| Cas13bt3 | 8.7 | 8.9 |
| Cas13bt2 | 8.4 | 8.7 |
| Cas13bt1 | 9.2 | 9.8 |
| Cas13bt8 | 8.6 | 8.6 |
| Cas13X.2 | 8.6 | 8.6 |
| Cas13bt9 | 8.4 | 8.4 |
| Cas13bt11 | 8.3 | 8.3 |
| Cas13bt5 | 9.4 | 9.9 |
| Cas13bt10 | 9.1 | 8.9 |
| Cas13bt15 | 7.9 | 8.5 |
| Cas13bt7 | 8.3 | 8.3 |
| Cas13bt6 | 7.5 | 7.9 |
| Cas13bt14 | 7.4 | 7.6 |
| Cas13Y.3 | 7.4 | 7.6 |
| Cas13bt12 | 7.7 | 7.7 |
| Cas13Y.1 | 7.7 | 7.7 |
| Cas13bt4 | 8 | 8.3 |
| Cas13bt16 | 7.8 | 7.8 |
| Cas13Y.5 | 8.3 | 8.4 |
| A69:B95 | 8 | 8.3 |
| Cas13_K2F1 | | 90.2 |
| Cas13_K2F2 | 90.2 | |
| Cas13_K2F5 | 78 | 83.5 |
| Cas13_K2F3 | 50.2 | 52.4 |

| | Cas13_K2F5 | Cas13_K2F3 |
|---|---|---|
| Cas13X.1 | 9.5 | 9.4 |
| Cas13bt3 | 9.3 | 9.4 |
| Cas13bt2 | 9.6 | 8.9 |
| Cas13bt1 | 9.9 | 9.1 |
| Cas13bt8 | 9.5 | 9.2 |
| Cas13X.2 | 9.5 | 9.2 |
| Cas13bt9 | 9.3 | 8.6 |
| Cas13bt11 | 9.1 | 8.4 |
| Cas13bt5 | 10.1 | 8.3 |
| Cas13bt10 | 8.8 | 8.4 |
| Cas13bt15 | 8.6 | 8.1 |
| Cas13bt7 | 8.9 | 8.3 |
| Cas13bt6 | 7.9 | 7.9 |
| Cas13bt14 | 7.9 | 7.4 |
| Cas13Y.3 | 7.9 | 7.4 |
| Cas13bt12 | 7.9 | 7.7 |
| Cas13Y.1 | 7.9 | 7.7 |
| Cas13bt4 | 8.4 | 7.6 |
| Cas13bt16 | 7.9 | 7.5 |
| Cas13Y.5 | 7.7 | 7.6 |

TABLE 4-continued

| Percent Identity Matrix | | |
|---|---|---|
| A69:B95 | 8 | 7.2 |
| Cas13_K2F1 | 78 | 50.2 |
| Cas13_K2F2 | 83.5 | 52.4 |
| Cas13_K2F5 | | 52 |
| Cas13_K2F3 | 52 | |

Example 3: Targeted Trans-Splicing for Cas13K2F Family and dPspCas13b

In the experiments of this example, the Cas13K2F family was evaluated for targeted trans-splicing using a truncated GFP reporter assay. In this assay, the truncated GFP exons (5' GFP, 3' GFP) introduced by the splice donor and acceptor reporters were spliced together, generating a transcript that contains a complete GFP mRNA sequence capable of creating a functional GFP protein product, and thereby demonstrating successful trans-splicing.

The Cas13 family is highly divergent from Cas13b and Cas13d, as demonstrated by phylogenetic analysis (see FIG. 8A and FIG. 8B). It is also structurally divergent and biochemically distinct from other known Cas13 enzymes.

HEK293 T cells were transfected with either a first or second Cas13K2F gRNA targeting the splice donor (SD) reporter (Cas13K2F gRNA 1 or 2), a fusion of catalytically inactive Cas13K2F orthologue (dCas13K2F) and MS2 (dCas13K2F-MS2), and the splice acceptor (SA) reporter having MS2 stem loops. In these experiments, HEK293FT (Thermo Fisher Scientific Cat. No. R70007) were cultured in a humidified incubator at 5% CO2 at 37° C. using high-glucose DMEM (Invitrogen) complemented with 10% FBS and 1% penicillin/streptomycin. Cell cultures were kept at low passage (<20) and regularly tested for *mycoplasma* contamination. Cells were plated in 96-well format at 15,000 cells per well with 100 uL of media. Cells were transfected 24 hours later with 25 ng gRNA plasmid (U6 driven expression), 25 ng Cas13-RBP plasmid, 25 ng of the SD reporter, and 25 ng of the SA reporter using 0.32 uL lipofectamine and 10 uL of OptiMEM total. Flow cytometry was performed 48 hours after transfection on a Sartorius iQue3 flow cytometer.

For comparison, HEK293T cells were transfected using a dCas13b variant from *Prevotella* sp. ("dPspCas13b"), fused to a panel of RBPs sourced from RNA bacteriophage genomes. As shown in FIG. 8B, more than 30% of cells underwent successful trans-splicing using the Cas13K2F system, which was a level of trans-splicing comparable to that achieved using the dPspCas13b system.

The experiments of this example further evaluated the dPspCas13b systems using different RNA binding proteins. These experiments measured trans-splicing between the SD reporter encoding a 5'GFP upstream of a splice donor, and a SA reporter having two sequence motifs upstream a splice donor and exon encoding 3'GFP. The SA reporters that were tested had sequence motifs recognized by RNA binding proteins (RBPs). The sequence motif and corresponding RBP evaluated included: (i) a MS2 hairpin and a MS2 coat protein ("MS2"); (ii) a PP7 hairpin and a PP7 coat protein ("PP7"); (iii) a M hairpin and a phage M coat protein ("M"); (iv) a PRR1 hairpin and a PRR1 coat protein ("PRR1"); and (v) a Qbeta hairpin and Qbeta coat protein ("QB"). HEK293T cells were transfected with the SD reporter, splice editor (i.e., PspCas13b gRNA and a fusion of dPspCas13b to an RBP), and an SA reporter with the corresponding RBP sequence motif. Control cells were transfected with the SD reporter and SA reporter only. Trans-splicing between the SD reporter and SA reporter yielded a measurable GFP signal. As shown in FIG. 14, each of the splice editors that were evaluated resulted in a level of trans-splicing that was higher than that observed in control cells.

Additionally, the experiments of this example evaluated the Cas13K2F system for trans-splicing using an alternate reporter system having a target nucleic acid containing distinct gene segments from an SD reporter (the target nucleic acid ("target")). In these experiments, the target contained from 5' to 3': the 5' portion of GFP, a first intron from a human protein-coding gene ("gene A"), a splice acceptor, and an exon from gene A. The trans-splicing template (the "template") contained from 5' to 3': an intron containing two MS2 stem loops, a splice acceptor, and the 3' portion of GFP. The constructs were designed such that successful trans-splicing between the splice donor of the target and the splice acceptor of the template would yield a GFP signal. HEK293T cells were transfected using lipofectamine 2000 per manufacturer's instructions in 96-well format. Each plasmid (target, template, Cas13K2F-MCP+gRNA) was one-third (33 ng) of the total DNA transfection. As non-coding dummy DNA was included in conditions where less than four components were delivered, such that there would be a total of 100 ng of DNA in each transfection. Media was changed 12 hours after the transfection. Protein expression was confirmed by observing fluorescence via fluorescent microscopy on a Bio-rad ZOE Fluorescent Cell Imager, and flow cytometry was performed 48 hours following transfection on a Sartorius iQue3. Cell and singlet gating was performed with Sartorius iQue3 instrument software, and the percentage of GFP+ singlets was calculated in python. HEK293T cells were transfected with constructs encoding dCas13K2F fused to a MS2 coat protein, a gRNA directed to the target (gRNA12, gRNA2, gRNA18, or gRNA19), the target, and the template. Control cells were transfected with a non-targeting gRNA or target only. As shown in FIG. 9, the percentage of GFP-positive cells, and the editing performance (FIG. 13A and FIG. 13B) was dramatically increased using the Cas13K2F system, indicating successful trans-splicing of the target. FIG. 13A and FIG. 13B are graphs showing Cas13K2F trans-splicing across two different RNA targets (MMP9 (FIG. 13A) and USH2A (FIG. 13B); USH2A encodes the 5'end of GFP, a splice donor, a gene A intron, a splice acceptor, and a gene A exon) using PP7 (PCP) as the RNA binding partner (RBP) partner.

Example 4: Structural Insights of Novel Miniature CRISPR-Cas Effectors

The experiments of this example produced high-confidence predictions of their structures using ColabFold (FIG. 10A, FIG. 12). As has been reported for other single-effector (Class 2) Cas proteins, the Cas13e (also referred to herein as "Cas13K2F") predicted structure is bi-lobed. Cas13e consists of two HEPN domains in the Nuclease (NUC) lobe for cleavage of RNA targets, and a Recognition (REC) lobe consisting of α-helical domains and an N-terminal domain (NTD) that may be used to bind the CRISPR repeat of the gRNA. As opposed to the NTD comprised of α helices in Cas13a, or short a helices flanking a β sandwich region in Cas13d, the NTD in Cas13e and Cas13c appears to be comprised almost entirely of β sheets. Without wishing to be bound by theory, crRNA and target RNA in the Cas13e RNP would be coordinated within the large, positively charged central channel through the center of the enzyme (FIG. 10A; FIG. 12). Interestingly, the experiments of this example discovered the presence of a novel C-terminal domain (CTD) in the NUC lobe of Cas13c that is not found in previously reported Cas13 systems, and is comprised primarily of β sheets. In addition to the miniaturization of the NTD, HEPN, and helical domains in Cas13e compared to Cas13c, there was no homologous domain structure to the CTD in Cas13e.

Example 5: Miniature Splice Editors Using CRISPR-Cas13e

Given the relatively small size of Cas13e and its sequence divergence from Cas13 systems successfully employed in mammalian cells (<7%), the experiments of this example first sought to define its stability and activity in HEK293 cells. The experiments of this example tested the ability of the native Cas13e enzymes (also referred to as the Cas13K2F family of enzymes disclosed herein) to target and cleave GFP transcripts as compared to RfxCas13d using different guide orientations (FIG. 10B). Cas13e3 exhibited the most robust RNA knockdown activity, with a gRNA orientation that was the reverse of that of Cas13x (Cas13bt) (FIG. 10C; FIG. 12). The experiments of this example thus created nuclease-inactive (dCas) variants of Cas13e3 with R244A/H249A/R704A/H709A mutations in the HEPN domains. Using dCas13e3, a splice editor (SE3; fused, linked, or associated with dCas13K2F3-MCP or dCas13e3-MCP) was created which is 22% smaller than SE1, which allowed for the packaging of the full fusion protein into AAVs for delivery to mammalian cells. The experiments of this example first demonstrated the efficacy of the SE3 system by targeting the MMP9 splice acceptor site, leading to multi-kilobase 3' replacement of RNA, not only via transient delivery (FIG. 10D) but also by packaging the system within AAVs (FIG. 11A). The experiments of this example further demonstrated that Splice Editing is active in a variety of human-derived cell lines beyond HEK293 (FIG. 11B), including in K562 cells (FIG. 11C).

Example 6: Efficient and Programmable 5' RNA Replacement in Alternative Gene Targets USH2A has a gene size of 800 kb and an open reading frame of 15.6 kb (FIG. 11D). USH2A is too heterogeneous to be compatible with existing gene-editing approaches, with many genetic variants spanning missense, nonsense, insertion, deletion, and frame-shift mutations throughout its 72 exons (FIG. 11D). To test splice editing as a corrective approach for USH2A transcripts and demonstrate the possibility of replacement of the 5' end of an RNA target (FIG. 4G), the experiments of this example designed gRNAs to bind intron 12 within an USH2A reporter, and a repRNA that would enable GFP fluorescence upon transcript correction with 5' replacement. Via transient transfection into HEK293 cells, the experiments of this example surprisingly observed splice editing efficiencies up to ~80% (FIG. 11F).

Example 7: Internal Exon Replacement by Trans-Splicing

In the experiments of this example, AAV delivery of dCas13K2F3 with a targeting (T) or non-targeting (NT) gRNA and a repRNA was achieved to facilitate trans-splicing in HEK293T cells. (See FIG. 15A and FIG. 15B) In these experiments, splice editing is achieved by delivering splice editor components based on AAV transduction. In these experiments, a two vector system was used: one AAV with the guide RNA and 'epRNA, and one AAV with the Cas-RBP fusion. 5' trans-splicing of split GFP reporter with USH2A introns and exons, functional GFP was detectable by microscopy and flow cytometry to indicate editing efficiency.

A graph showing amino acid substitutions in dCas13K2F3 that enable either improvement or reduction of trans-splicing efficacy in human cells compared to the original (WT) sequence is shown FIG. 16. In these experiments, 25 ng repRNA, 25 ng gRNA, 50 ng dCas13 variant were transfected into cells with the integrated USH2A reporter and GFP fluorescence measured via flow cytometry to indicate trans-splicing efficiency relative to the wild-type dCas13 sequence.

In these experiments, internal exon replacement was demonstrated using 2 nucleases with 2 separate gRNAs and RBPs, with a repRNA shown in green (directly to the left of the splice donor site in the image) (FIG. 17). In these experiments, internal exon replacement can also be achieved with a single gRNA, nuclease and an RBP (in this case, PCP instead of MCP which is used in the experiments above) in combination with a binding motif (BM) in the repRNA, shown in orange (and labeled BM2 in the image) (FIG. 18). In these experiments, cells were transfected with 25 ng reporter (pA0120), 25 ng repRNA, 25 ng gRNA, 25 ng Cas13. The graph in FIG. 19 shows targeting (T) in the first set of four bars on the left, or non-targeting (NT) in the second set of four bars on the right, of one gRNA, nuclease and RBP (PCP) in combination with a binding motif (BM) (see constructs in FIG. 18) to facilitate internal exon replacement.

Example 8: RNA-Binding Protein-Free Trans-Splicing and repRNA Design

The experiments of this example demonstrate how internal exon replacement is achieved with two gRNAs, two nucleases and RBPs (in this case, PCP and MCP) in combination with, or without, a binding motif (BM) in the repRNA, shown in orange (and labeled BM2 in FIG. 20). The experiments in FIG. 21A and FIG. 21B show targeting (T) or non-targeting (NT) of two gRNAs, two nucleases and RBPs in combination with, or without, a binding motif (BM) in the repRNA (see constructs in FIG. 20) to facilitate internal exon replacement.

The experiments of this example demonstrate the design of a guide repair RNA ("grepRNA"), which is devoid of an RBP (FIG. 22A, bottom image). dCas13 can be used with or without an RBP fusion. FIG. 22B shows grepRNA only, or grepRNA and dCas13, for internal exon replacement across two different RNA targets (USH2A, left side of FIG. 22B; and MMP9, right side of FIG. 22B). In these experiments, HEK293T cells were transfected with pA0120 reporter plasmid (25 ng), grepRNA (50 ng), dCas13F3-MCP (25 ng).

The experiments in FIG. 23A and FIG. 23B show targeting (T) or non-targeting (NT) of an integrated 5' USH2A target to facilitate internal exon replacement. FIG. 23A is an image showing integrated USH2A target for 5' replacement. FIG. 23B is a graph showing targeting (T) or non-targeting (NT) of an integrated 5' USH2A target to facilitate internal exon replacement. Transient transfection of the dCas13F3-MCP, grepRNA (targeting (T) or non-targeting (NT)), and pUC19 in HEK293FT cells with an integrated USH2A target. Each splice editor (SE) component received 25 ng for a total of 100 ng/transfection/well in a 96-well plate.

Materials and Methods

Cell Culture

HEK293FT (Thermo Fisher Scientific Cat. No. R70007) were cultured in a humidified incubator at 5% CO2 at 37C using high-glucose DMEM (Invitrogen) complemented with 10% FBS and 1% penicillin/streptomycin. Cell cultures were kept at low passage (<20) and regularly tested for *mycoplasma* contamination.

Cloning

Plasmids were synthesized, and genes were synthesized. The RBP sequences were synthesized by IDT and inserted with Golden Gate assembly. gRNAs were ordered as oligos from IDT and were hybridized and phosphorylated for golden gate assembly.

Transfections

HEK293FT cells were transfected in a 12-well plate format, with a total of 1250 ng of DNA and 4 µL of Lipofectamine 2000 per condition. Each construct was one fourth (312.5 ng) of the total DNA transfection, with the exception of pUC19, which was used as non-coding dummy DNA in conditions where less than four components were delivered, such that there would be a total of 1250 ng of DNA in each transfection. Media was changed 6 hours after the transfection, and the cells were analyzed via flow cytometry (Beckman Coulter CytoFLEX platform) 48 hours after the transfection.

RNA Knockdown Experiments in Mammalian Cells

For each Cas ORF, an SV40 NLS sequence was added to the N-terminus (MSPKKKRKVEAS (SEQ ID NO: 102)) and an SV40 NLS with an appended HA tag was added to the C-terminus (GSGPKKKRKVAAAYPYDVPDYA (SEQ ID NO: 103)). The resulting ORFs were then mammalian codon-optimized and synthesized into mammalian expression vectors. Transcription was driven by a CMV promoter (CGCCCCAT-TGACGCAAATGGGCGGTAGGCGTGTACGGTGG-GAGGTCTATATAAGCA GAGCTGGTTTAGT-GAACCGTCAGATC (SEQ ID NO: 104)) and an SV40 polyadenylation signal was used to terminate transcription (CAGCTCACAGACATGATAAGATACATTGAT-GAGTTTGGACAAACCACAACTAGAAT GCAGT-GAAAAAAATGCTTTATTTGTGAAATTTGTGATGCT-ATTGCTTTATTTGTAACC
ATTATAAGCTGCAATAAACAAGT-TAACAACAACAATTGCATTCATTTTATGTTTCAG GTTCAGGGGGAGGTGTGGGAGGTTTTT-TAAAGCAAGTAAAACCTCTACAAATGTGG TAT-TGGC (SEQ ID NO: 105)). A plasmid expressing eGFP and plasmids expressing Cas13e proteins and gRNAs were co-transfected into HEK293T cells (bio reps n=2) using lipofectamine 2000. Protein expression was confirmed by observing fluorescence via fluorescent microscopy, and flow cytometry was performed 48 hours following transfection. Cell and singlet gating was performed, and median GFP intensity of singlets was calculated. Results were then plotted. gRNAs were designed for Cas13e systems to target multiple sites across the coding sequence of eGFP in HEK293T cells, to be tested alongside a scrambled non-targeting guide, demonstrating reprogrammability and specificity of the RNase activity of these CRISPR-Cas systems towards different targets. Several gRNA orientations were tested to evaluate the correct structure of the CRISPR RNA of Cas13e systems. gRNA structure for Cas13e systems was determined to consist of a CRISPR repeat at the 5' end of the RNA followed by a spacer sequence complementary to the target RNA. In contrast, the gRNA structure for Cas13e systems was determined to consist of a spacer sequence complementary to the target RNA on the 5' end of the gRNA, followed by a CRISPR repeat at the 3' end.

Metagenome-Assembled Genome Construction, Binning, and Phylogenetic Classification of Cas13 Genomes Briefly, samples were assembled with metaSPAdes v3.15.4. Proteins were identified using Prodigal v2.6.3 and aligned to custom Cas13 profiles. Reference proteins were aligned with Cas13 hits using MAFFT, and phylogenetic trees were built using IQTree. Samples containing one or more significant matches to Cas13 systems were binned into metagenome-assembled genomes (MAGs) using metabat2 v2.16, MaxBin v2.2.7 and CONCOCT v1.1 in parallel. Completeness and contamination were estimated using CheckM v1.2.2 using lineage-specific markers. Bins recovered from all three tools for each sample were refined and merged using DAS Tool v1.1.6. Medium and high-quality MAGs containing Cas13e (≥60% completeness and ≤10% contamination based on essential genes) from all samples were taxonomically classified using GTDB-tk using the "classify_wf" setting. In addition, bin phylogeny was determined by placing these genomes into a phylogenetic tree of existing Epsilonproteobacteria genomes built from a concatenated set of rRNA genes. CRISPR spacers from Cas13 genomes were searched against metagenomes using BLAST, and hits with ≥20nt of matches and ≤4 mismatches were retained for analysis.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A nuclease system, comprising:
   (a) an endonuclease comprising a nucleic acid encoding an endonuclease comprising an endonuclease comprising a sequence, or a fragment or variant thereof, and having at least 90% identity to SEQ ID NO: 3 or having about 1 to about 20 amino acid modifications relative to SEQ ID NO: 3; and (b) an RNA molecule comprising a sequence complementary to one strand of a target nucleic acid molecule, wherein the endonuclease further comprises a nuclear localization signal (NLS).

2. The nuclease system of claim 1, comprising a higher eukaryotes and prokaryotes nucleotide-binding domain (HEPN) domain.

3. The nuclease system of claim 1, further comprising one or more donor polynucleotides.

4. The nuclease system of claim 1, wherein the amino acid modifications are selected from D38F, A59V, G172L, T236L, T319I, H375L, H419Y, T424F, E529L, T541L, G562Y, K564M, D569L, A586I, N641F, D642L, S647L, D721L, R779I, K13R, K566R, G554H, A35N, E110T, G314Q, K114P, D498P, I86P, V57E, H249W, and R704F relative to SEQ ID NO: 3.

5. A chimeric protein comprising:
(a) an endonuclease comprising an endonuclease comprising a sequence, or a fragment or variant thereof, and having at least 90% identity to SEQ ID NO: 3 or having about 1 to about 20 amino acid modifications relative to SEQ ID NO: 3; and
(b) a nucleic acid-modulating domain or a nucleic acid-modifying domain comprising a sequence comprising a catalytic domain, or a fragment or variant thereof,
wherein (a) and (b) do not naturally occur together in a same reading frame.

6. The chimeric protein of claim 5, wherein the nucleic acid-modulating domain or the nucleic acid-modifying domain is selected from MS binding protein (MCP), lambdaN, serine/threonine-protein phosphatase 7 (PP7), QBeta, stem-loop binding protein (SLBP), and TATA-binding protein/TAR DNA Binding Protein (TBP/TAR).

7. The chimeric protein of claim 5, comprising a higher eukaryotes and prokaryotes nucleotide-binding domain (HEPN) domain.

8. The chimeric protein of claim 5, further comprising one or more donor polynucleotides.

9. The chimeric protein of claim 5, wherein the amino acid modifications are selected from D38F, A59V, G172L, T236L, T319I, H375L, H419Y, T424F, E529L, T541L, G562Y, K564M, D569L, A586I, N641F, D642L, S647L, D721L, R779I, K13R, K566R, G554H, A35N, E110T, G314Q, K114P, D498P, I86P, V57E, H249W, and R704F relative to SEQ ID NO: 3.

10. A composition comprising a complex comprising chimeric protein and an RNA molecule, wherein the chimeric protein comprises:
(a) an endonuclease comprising a sequence, or a fragment or variant thereof, and having at least 90% identity to SEQ ID NO: 3 or having about 1 to about 20 amino acid modifications relative to SEQ ID NO: 3; and
(b) a nucleic acid-modulating domain or a nucleic acid-modifying domain comprising a sequence comprising a catalytic domain, or a fragment or variant thereof,
wherein (a) and (b) do not naturally occur together in a same reading frame and the RNA molecule comprises a sequence complementary to one strand of a target nucleic acid molecule.

11. The composition of claim 10, comprising a higher eukaryotes and prokaryotes nucleotide-binding domain (HEPN) domain.

12. The composition of claim 10, further comprising one or more donor polynucleotides.

13. The composition of claim 10, wherein the amino acid modifications are selected from D38F, A59V, G172L, T236L, T319I, H375L, H419Y, T424F, E529L, T541L, G562Y, K564M, D569L, A586I, N641F, D642L, S647L, D721L, R779I, K13R, K566R, G554H, A35N, E110T, G314Q, K114P, D498P, I86P, V57E, H249W, and R704F relative to SEQ ID NO: 3.

14. The chimeric protein of claim 10, wherein the nucleic acid-modulating domain or the nucleic acid-modifying domain is selected from MS binding protein (MCP), lambdaN, serine/threonine-protein phosphatase 7 (PP7), QBeta, stem-loop binding protein (SLBP), and TATA-binding protein/TAR DNA Binding Protein (TBP/TAR).

15. A nuclease system, comprising:
(a) an endonuclease comprising a nucleic acid encoding an endonuclease comprising an endonuclease comprising a sequence, or a fragment or variant thereof, and having at least 90% identity to SEQ ID NO: 3 or having about 1 to about 20 amino acid modifications relative to SEQ ID NO: 3; and
(b) an RNA molecule comprising a sequence complementary to one strand of a target nucleic acid molecule,
wherein the nucleic acid is operably linked to a eukaryotic or viral promoter.

16. A nuclease system, comprising:
(a) an endonuclease comprising a nucleic acid encoding an endonuclease comprising a sequence having at least 90% identity to SEQ ID NO: 3 and having about 1 to about 20 amino acid modifications relative to SEQ ID NO: 3; and
(b) an RNA molecule comprising a sequence complementary to one strand of a target nucleic acid molecule.

17. The nuclease system of claim 16, wherein the amino acid modifications are selected from D38F, A59V, G172L, T236L, T319I, H375L, H419Y, T424F, E529L, T541L, G562Y, K564M, D569L, A586I, N641F, D642L, S647L, D721L, R779I, K13R, K566R, G554H, A35N, E110T, G314Q, K114P, D498P, I86P, V57E, H249W, and R704F relative to SEQ ID NO: 3.

18. A nuclease system, comprising:
(a) an endonuclease comprising a nucleic acid encoding an endonuclease comprising an endonuclease comprising a sequence, or a fragment or variant thereof, and having at least 90% identity to SEQ ID NO: 3 or having about 1 to about 20 amino acid modifications relative to SEQ ID NO: 3; and
(b) an RNA molecule comprising a sequence complementary to one strand of a target nucleic acid molecule,
wherein the target nucleic acid molecule is a eukaryotic nucleic acid molecule.

* * * * *